(12) United States Patent
Praveen et al.

(10) Patent No.: US 11,767,526 B2
(45) Date of Patent: *Sep. 26, 2023

(54) TREATMENT OF OPHTHALMIC CONDITIONS WITH ANGIOPOIETIN-LIKE 7 (ANGPTL7) INHIBITORS

(71) Applicant: Regeneron Pharmaceuticals, Inc., Tarrytown, NY (US)

(72) Inventors: Kavita Praveen, Tarrytown, NY (US); Claudia Schurmann, Tarrytown, NY (US); Lauren Gurski, Tarrytown, NY (US); Tanya Teslovich Dostal, Tarrytown, NY (US); Goncalo Abecasis, Tarrytown, NY (US); Aris Baras, Tarrytown, NY (US); Giovanni Coppola, Tarrytown, NY (US); Carmelo Romano, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 606 days.

This patent is subject to a terminal disclaimer.

(21) Appl. No.: 16/748,006

(22) Filed: Jan. 21, 2020

(65) Prior Publication Data

US 2020/0231965 A1 Jul. 23, 2020

Related U.S. Application Data

(60) Provisional application No. 62/909,573, filed on Oct. 2, 2019, provisional application No. 62/902,683, filed on Sep. 19, 2019, provisional application No. 62/880,609, filed on Jul. 30, 2019, provisional application No. 62/795,665, filed on Jan. 23, 2019.

(51) Int. Cl.
| | |
|---|---|
| *C12N 15/11* | (2006.01) |
| *C12N 9/22* | (2006.01) |
| *C12Q 1/6883* | (2018.01) |
| *C12N 15/113* | (2010.01) |
| *C07K 14/515* | (2006.01) |
| *A61K 31/713* | (2006.01) |
| *A61K 48/00* | (2006.01) |
| *A61P 27/02* | (2006.01) |
| *A61P 27/06* | (2006.01) |

(52) U.S. Cl.
CPC ............ *C12N 15/11* (2013.01); *A61K 31/713* (2013.01); *A61K 48/005* (2013.01); *C07K 14/515* (2013.01); *C12N 9/22* (2013.01); *C12N 15/111* (2013.01); *C12N 15/1136* (2013.01); *C12Q 1/6883* (2013.01); *A61P 27/02* (2018.01); *A61P 27/06* (2018.01); *C12N 2310/14* (2013.01); *C12N 2310/20* (2017.05); *C12N 2800/80* (2013.01); *C12Q 2600/106* (2013.01); *C12Q 2600/156* (2013.01); *C12Q 2600/158* (2013.01); *C12Q 2600/178* (2013.01)

(58) Field of Classification Search
CPC ... A61P 27/02; A61K 48/005; C12N 2310/14; C12N 15/113; C12N 15/111
See application file for complete search history.

(56) References Cited

U.S. PATENT DOCUMENTS

| | | |
|---|---|---|
| 8,637,640 B2 | 1/2014 | Siekmann et al. |
| 8,642,737 B2 | 2/2014 | Siekmann et al. |
| 8,785,139 B2 | 7/2014 | Weber et al. |
| 8,809,501 B2 | 8/2014 | Siekmann et al. |
| 8,945,897 B2 | 2/2015 | Siekmann et al. |
| 8,951,982 B2 | 2/2015 | Jimenez et al. |
| 9,205,064 B2 | 12/2015 | Narain et al. |
| 9,238,837 B2 | 1/2016 | Schmidt-Ott et al. |
| 9,364,542 B2 | 6/2016 | Chang |
| 9,447,431 B2 | 9/2016 | Thess et al. |
| 9,492,555 B2 | 11/2016 | Haider et al. |
| 9,551,034 B2 | 1/2017 | Cowens et al. |
| 9,731,024 B2 | 8/2017 | Siekmann et al. |
| 9,795,683 B2 | 10/2017 | Jain et al. |
| 9,896,731 B2 | 2/2018 | Narain et al. |
| 10,111,968 B2 | 10/2018 | Thess et al. |
| 10,350,301 B2 | 7/2019 | Siekmann et al. |
| 10,351,915 B2 | 7/2019 | Narain et al. |
| 10,370,643 B2 | 8/2019 | Bernstein et al. |
| 10,414,793 B2 | 9/2019 | Haider et al. |
| 10,519,504 B2 | 12/2019 | Narain et al. |

(Continued)

FOREIGN PATENT DOCUMENTS

| | | |
|---|---|---|
| WO | 2012016131 | 2/2012 |
| WO | 2013173543 | 11/2013 |

(Continued)

OTHER PUBLICATIONS

Tanigawa et al., Rare protein-altering variants in ANGPTL7 lower intraocular pressure and protect against glaucoma, PLOS Genetics, vol. 16(5):e1008682, pp. 1-20. (Year: 2020).*

(Continued)

*Primary Examiner* — Dana H Shin

(74) *Attorney, Agent, or Firm* — Armstrong Teasdale LLP

(57) ABSTRACT

The present disclosure provides methods of treating patients having an ophthalmic condition, methods of identifying subjects having an increased risk of developing an ophthalmic condition, methods of detecting human angiopoietin like 7 (ANGPTL7) variant nucleic acid molecules and variant polypeptides, and ANGPTL7 variant nucleic acid molecules and variant polypeptides.

11 Claims, 24 Drawing Sheets
(19 of 24 Drawing Sheet(s) Filed in Color)
Specification includes a Sequence Listing.

(56) References Cited

U.S. PATENT DOCUMENTS

| | | |
|---|---|---|
| 2010/0028875 A1 | 2/2010 | Rhyu et al. |
| 2011/0020312 A1 | 1/2011 | Narain et al. |
| 2011/0027247 A1 | 2/2011 | Narain et al. |
| 2011/0123986 A1 | 5/2011 | Narain et al. |
| 2012/0010230 A1 | 1/2012 | MacDougall et al. |
| 2013/0022983 A1 | 1/2013 | Grifantini et al. |
| 2013/0310546 A1 | 11/2013 | Ray et al. |
| 2014/0107320 A1 | 4/2014 | Haider et al. |
| 2014/0187607 A1 | 7/2014 | Russell et al. |
| 2015/0023940 A1 | 1/2015 | Narain et al. |
| 2015/0025012 A1 | 1/2015 | MacDougall et al. |
| 2015/0174203 A1 | 6/2015 | Chen et al. |
| 2015/0299798 A1 | 10/2015 | de Reynies et al. |
| 2016/0120994 A1 | 5/2016 | Siekmann et al. |
| 2016/0145693 A1 | 5/2016 | Narain et al. |
| 2016/0271253 A1 | 9/2016 | Chang |
| 2017/0121780 A1 | 5/2017 | Cowens et al. |
| 2017/0137879 A1 | 5/2017 | Narain et al. |
| 2017/0368193 A1 | 12/2017 | Siekmann et al. |
| 2018/0177894 A1 | 6/2018 | Thess et al. |
| 2018/0185517 A1 | 7/2018 | Thess et al. |
| 2018/0200380 A1 | 7/2018 | Jain et al. |
| 2018/0237771 A1 | 8/2018 | Kim et al. |
| 2018/0334721 A1 | 11/2018 | Narain et al. |
| 2018/0340153 A1 | 11/2018 | Bean et al. |
| 2018/0340154 A1 | 11/2018 | Bean et al. |
| 2019/0010554 A1 | 1/2019 | Narain et al. |
| 2019/0091335 A1 | 3/2019 | Chang |
| 2019/0177391 A1 | 6/2019 | Chen et al. |
| 2019/0264173 A1 | 8/2019 | Studer et al. |
| 2019/0203186 A1 | 9/2019 | Bean et al. |
| 2019/0314516 A1 | 10/2019 | Siekmann et al. |
| 2019/0322989 A1 | 10/2019 | Bean et al. |
| 2019/0330593 A1 | 10/2019 | Bernstein et al. |
| 2019/0331666 A1 | 10/2019 | Studer et al. |
| 2020/0016202 A1 | 1/2020 | Kuchroo et al. |
| 2020/0017543 A1 | 1/2020 | Haider et al. |
| 2020/0399640 A1 | 12/2020 | Gottesman et al. |

FOREIGN PATENT DOCUMENTS

| | | |
|---|---|---|
| WO | 2013173557 | 11/2013 |
| WO | 2014167529 | 10/2014 |
| WO | 2015132303 | 9/2015 |
| WO | 2018174861 | 9/2018 |
| WO | 2018175630 | 9/2018 |
| WO | 2018218299 | 12/2018 |
| WO | 2019140380 | 7/2019 |
| WO | 2019144052 | 7/2019 |
| WO | 2019197844 | 10/2019 |
| WO | 2020154268 | 7/2020 |
| WO | 2020242896 | 12/2020 |
| WO | 2022072356 | 4/2022 |

OTHER PUBLICATIONS

Charlson et al., "The primary open-angle african american glaucoma genetics study: baseline demographics", Ophthalmology, 2015, 122, pp. 711-720.

Dewey et al., "Distribution and clinical impact of functional variants in 50,726 whole-exome sequences from the DiscovEHR Study", Science, 2016, 354(6319), pp. 1-13.

Van Hout et al., "Whole exome sequencing and characterization of coding variation in 49,960 individuals in the UK Biobank", BioRxiv, 2019, doi: https://doi.org/10.1101/572347.

Borras, "Gene therapy strategies in glaucoma and application for steroid-induced hypertension", Saudi Journal of Opthalmology, 2011, 25(4), pp. 353-362.

Buie et al., "Angiopoietin-like 7 (ANGPTL7) Modulates DEX Induction and Fibronectin (FN1) Fibrils Formation in the Human Trabecular Meshwork (HTM)-ARVO Annual Meeting Abstract", Investigative Ophthalmology & Visual Science, 2011, 52(14), pp. 4622.

Comes et al., "Evidence for a role of angiopoietin-like 7 (ANGPTL7) in extracellular matrix formation of the human trabecular meshwork: implications for glaucoma: ANGPTL7 in the human trabecular meshwork", Genes to Cells, 2010, 16(2), pp. 243-259.

Deboever et al., "Bayesian model comparison for rare variant association studies for multiple phenotypes", BioRxiv, 2018, https://www.biorxiv.org/content/10.1101/257162v5.full.pdf.

Doench et al., "Optimized sgRNA design to maximize activity and minimize off-target effects of CRISPR-Cas9", Nature Biotechnology, 2016, 34(2), pp. 184-191.

Jaru-Ampornpan et al., "Screening Angiopoietin-Like 7 in Primary Congenital Glaucoma Patients—ARVO Annual Meeting Abstract", Investigative Ophthalmology & Visual Science, 2010, 51(13), pp. 2167.

Kuchtey et al., "Angiopoietin-like 7 secretion is induced by glaucoma stimuli and its concentration is elevated in glaucomatous aqueous humor", Investigative Ophthalmology & Visual Science, 2008, 49(8), pp. 3438-3448.

Rozsa et al., "Gene expression profile of human trabecular meshwork cells in response to long-term dexamethasone exposure", Molecular Vision, 2006, 12, pp. 125-141.

Tanigawa et al., "Rare protein-altering variants in ANGPTL7 lower intraocular pressure and protect against glaucoma", BioRxiv, 2019, https://www.biorxiv.org/content/10.1101/677443v2.full.pdf.

Willoughby et al., "Mutational Screening Of The Angiopoietin-like 7 Gene In High-tension Primary Open Angle Glaucoma", Investigative Ophthalmology & Visual Science, 2012, 53, pp. 4504.

Xiao et al., "Loss of Angiopoietin-like 7 diminishes the regeneration capacity of hematopoietic stem and progenitor cells", Journal of Hematology & Oncology, 2015, 8(1), pp. 7.

International Search Report and Written Opinion dated Aug. 11, 2020 for International Patent Application No. PCT/US2020/014373.

Toyono et al., "Angiopoietin-Like 7 Is an Anti-Angiogenic Protein Required to Prevent Vascularization of the Cornea", PLOS ONE, 2015, 10(1), pp. 1-13.

Weinreb et al., "Acute Effects of Dexamethasone on Intraocular Pressure in Glaucoma", Investigative Ophthalmology and Visual Science, 1985, 26, pp. 170-175.

Non-Final Office Action dated Dec. 28, 2021 in related U.S. Appl. No. 17/318,023.

Final Office Action dated Apr. 6, 2022 in related U.S. Appl. No. 17/318,023.

International Search Report and Written Opinion dated Jul. 14, 2022 for International Patent Application No. PCT/US2022/017533.

Karaki et al., "Antisense Oligonucleotides, A Novel Developing Targeting Therapy", Antisense Therapy, 2019, pp. 1-18.

Harborth et al., "Identification of essential genes in cultured mammalian cells using small interfering RNAs", J Cell Sci, 2001, 114(Pt 24), pp. 4557-4565.

Holen T et al., "Positional effects of short interfering RNAs targeting the human coagulation trigger Tissue Factor", Nucleic Acids Res, 2002, 30(8), pp. 1757-1766.

Reynolds et al., "Rational siRNA design for RNA interference", Nat Biotechnol, 2004, 22(3), pp. 326-330.

Ronchetti et al., "Defining the role of glucocorticoids in inflammation", Clinical Science, 2018, 132(14), pp. 1529-1543.

Baudouin et al., "Inflammation in Glaucoma: From the back to the front of the eye and beyond", Progress in Retinal and Eye Research, 2020, 83, pp. 1-26.

Qian et al., "Angiopoietin-Like Protein 7 Promotes an Inflammatory Phenotype in RAW264.7 Macrophages Through the P38 MAPK Signaling Pathway", Inflammation, 2016, 39(3), pp. 974-985.

Roberti et al., "Steroid-induced glaucoma: Epidemiology, pathophysiology, and clinical management", Survey of Ophthalmology, 2020, 65(4), pp. 458-473.

Fukuda et al., "Expression Profiling of Genes in Rheumatoid Fibroblast-like Synoviocytes Regulated by Fas Ligand Using cDNA Microarray Analysis", Arthritis & Rheumatology, 2019, 71(suppl-10), pp. 1.

Notice of Allowance dated Jul. 25, 2022 in related U.S. Appl. No. 17/318,023.

(56) References Cited

OTHER PUBLICATIONS

Non-Final Office Action dated Oct. 6, 2022 in related U.S. Appl. No. 17/031,523.
Non-Final Office Action dated May 12, 2023 in related U.S. Appl. No. 17/678,792.
Elbashir et al., "Functional anatomy of siRNAs for mediating efficient RNAi in Drosophila melanogaster embryo lysate", The EMBO Journal, 2001, 20(23), pp. 6877-6888.
Advisory Action dated May 30, 2023 in related U.S. Appl. No. 17/031,523.
Final Office Action dated Mar. 17, 2023 in related U.S. Appl. No. 17/031,523.
Ozcan et al., "Preclinical and clinical development of siRNA-based therapeutics", Adv Drug Deliv, 2015, 87, pp. 108-119.
Chan et al., "The complexity of antisense transcription revealed by the study of developing male germ cells", Genomics, 2006, 87, pp. 681-692.

\* cited by examiner

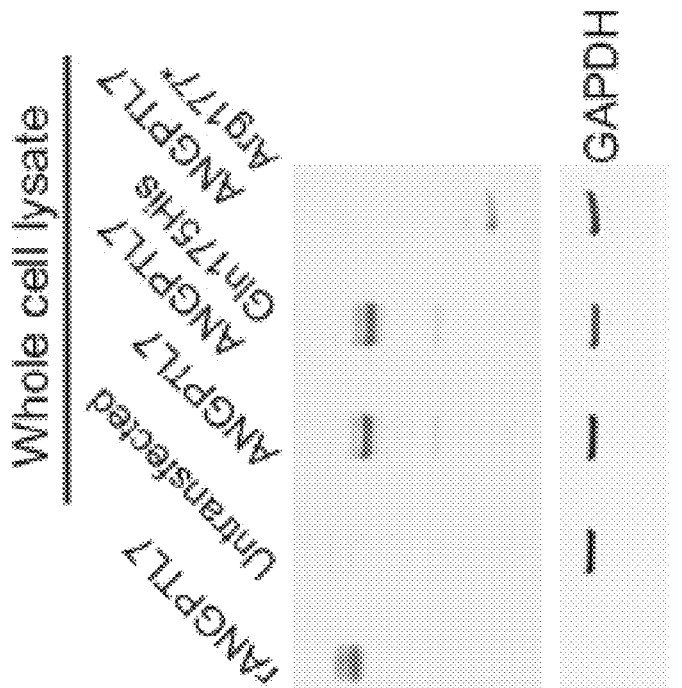
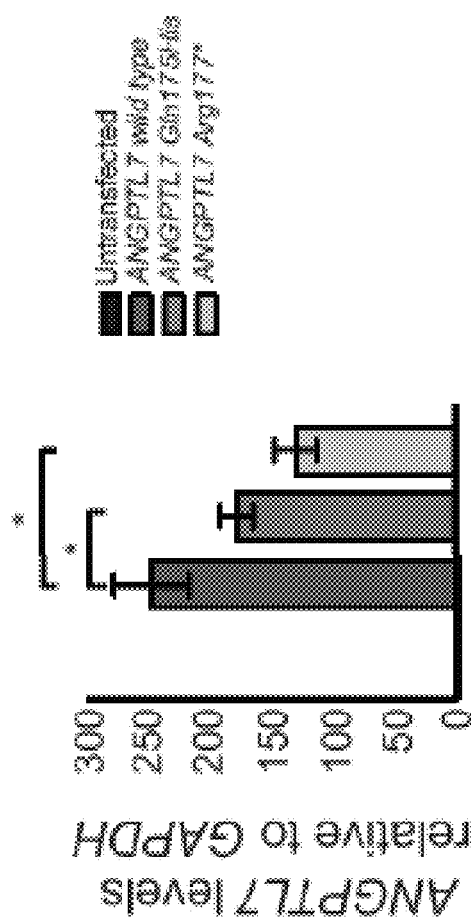
Figure 9A
Figure 9B

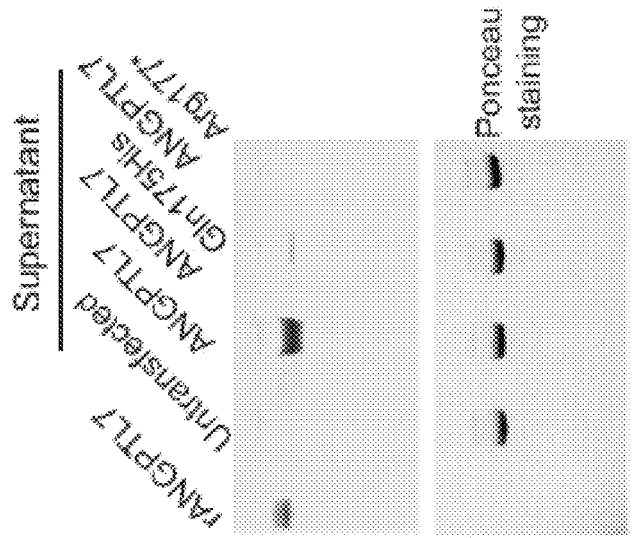
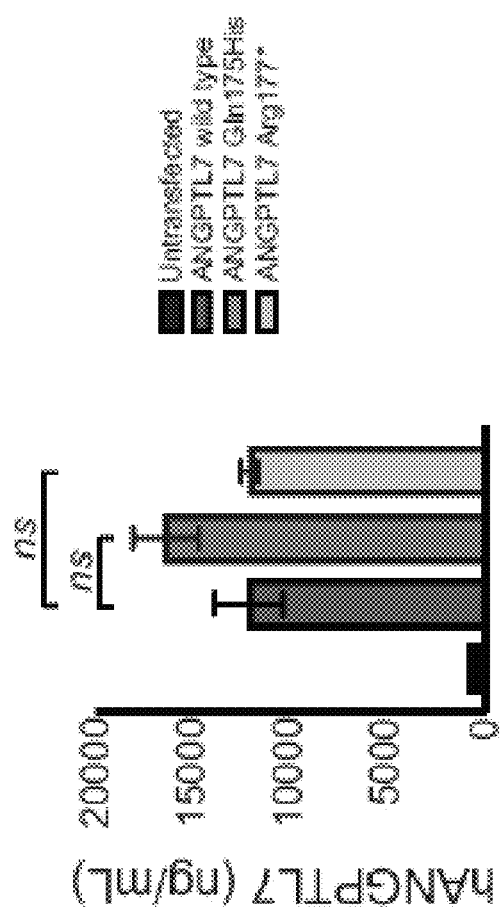
Figure 9C
Figure 9D

US 11,767,526 B2

TREATMENT OF OPHTHALMIC CONDITIONS WITH ANGIOPOIETIN-LIKE 7 (ANGPTL7) INHIBITORS

REFERENCE TO SEQUENCE LISTING

This application includes a Sequence Listing submitted electronically as a text file named 18923801601SEQ, created on Jan. 18, 2020, with a size of 111 kilobytes. The Sequence Listing is incorporated herein by reference.

FIELD

The present disclosure relates generally to the treatment of patients having ophthalmic conditions with angiopoietin like 7 (ANGPTL7) inhibitors, methods of identifying subjects having an increased risk of developing ophthalmic conditions, methods of detecting ANGPTL7 variant nucleic acid molecules and variant polypeptides, and ANGPTL7 variant nucleic acid molecules and ANGPTL7 variant polypeptides.

BACKGROUND

Glaucoma is a collection of disorders that damage the optic nerve of the eye and can result in partial vision loss and blindness. Several types of glaucoma exist, the primary form being open-angle glaucoma, whereby fluid within the eye builds up and increases the pressure inside the eye (intraocular pressure; IOP) to a level that may damage the optic nerve. In low-tension or normal-tension glaucoma, optic nerve damage and narrowed side vision occur in people with normal ocular pressure. In angle-closure glaucoma, the fluid at the front of the eye cannot drain properly, which may lead to a sudden increase in ocular pressure. In congenital glaucoma, children are born with a defect in the eye that slows the normal drainage of fluid. Glaucoma treatments include drug therapy, laser trabeculoplasty, and conventional surgery. While these treatments may save remaining vision, they do not improve sight already lost from glaucoma.

ANGPTL7 is a secreted glycoprotein structurally related to the angiopoietin family of growth factors. ANGPTL7 contains C-terminal (fibrinogen-like) and N-terminal (coiled) domains. ANGPTL7 is predominantly found in the stromal layer of the cornea and the extracellular matrix of the trabecular meshwork.

SUMMARY

The present disclosure provides methods of treating a patient having increased IOP, the method comprising administering an ANGPTL7 inhibitor to the patient.

The present disclosure also provides methods of treating a patient having glaucoma, the method comprising administering an ANGPTL7 inhibitor to the patient.

In some embodiments, the methods further comprise detecting the presence or absence of an ANGPTL7 predicted loss-of-function variant nucleic acid molecule encoding a human ANGPTL7 polypeptide in a biological sample from the patient. In some embodiments, the ANGPTL7 predicted loss-of-function variant nucleic acid molecule is: a genomic nucleic acid molecule having a nucleotide sequence comprising a thymine at a position corresponding to position 4,291 according to SEQ ID NO:2; an mRNA molecule having a nucleotide sequence comprising a uracil at a position corresponding to position 529 according to SEQ ID NO:5; or a cDNA molecule produced from an mRNA molecule, wherein the cDNA molecule has a nucleotide sequence comprising a thymine at a position corresponding to position 529 according to SEQ ID NO:8. In some embodiments, the ANGPTL7 predicted loss-of-function variant nucleic acid molecule is: a genomic nucleic acid molecule having a nucleotide sequence comprising a thymine at a position corresponding to position 4,287 according to SEQ ID NO:3; an mRNA molecule having a nucleotide sequence comprising a uracil at a position corresponding to position 525 according to SEQ ID NO:6; or a cDNA molecule produced from an mRNA molecule, wherein the cDNA molecule has a nucleotide sequence comprising a thymine at a position corresponding to position 525 according to SEQ ID NO:9. In some embodiments, the ANGPTL7 predicted loss-of-function variant nucleic acid molecule is: a genomic nucleic acid molecule having a nucleotide sequence comprising an adenine at a position corresponding to position 4,243 according to SEQ ID NO:132; an mRNA molecule having a nucleotide sequence comprising an adenine at a position corresponding to position 481 according to SEQ ID NO:135; or a cDNA molecule produced from an mRNA molecule, wherein the cDNA molecule has a nucleotide sequence comprising an adenine at a position corresponding to position 481 according to SEQ ID NO:138. In some embodiments, the ANGPTL7 predicted loss-of-function variant nucleic acid molecule is: a genomic nucleic acid molecule having a nucleotide sequence comprising an adenine at a position corresponding to position 4,325 according to SEQ ID NO:133; an mRNA molecule having a nucleotide sequence comprising an adenine at a position corresponding to position 563 according to SEQ ID NO:136; or a cDNA molecule produced from an mRNA molecule, wherein the cDNA molecule has a nucleotide sequence comprising an adenine at a position corresponding to position 563 according to SEQ ID NO:139. In some embodiments, the ANGPTL7 predicted loss-of-function variant nucleic acid molecule is: a genomic nucleic acid molecule having a nucleotide sequence comprising a cytosine at a position corresponding to position 4,336 according to SEQ ID NO:134; an mRNA molecule having a nucleotide sequence comprising a cytosine at a position corresponding to position 574 according to SEQ ID NO:137; or a cDNA molecule produced from an mRNA molecule, wherein the cDNA molecule has a nucleotide sequence comprising a cytosine at a position corresponding to position 574 according to SEQ ID NO:140.

In some embodiments, the detecting step comprises sequencing at least a portion of the nucleotide sequence of the ANGPTL7 genomic nucleic acid molecule in the biological sample, the nucleotide sequence of the ANGPTL7 mRNA molecule in the biological sample, or the nucleotide sequence of the ANGPTL7 cDNA molecule in the biological sample.

In some embodiments, the detecting step comprises: contacting the nucleic acid molecule in the biological sample with an alteration-specific probe comprising a detectable label, and detecting the detectable label.

The present disclosure also provides methods of treating a patient with a therapeutic agent that treats or inhibits an ophthalmic condition, wherein the patient is suffering from an ophthalmic condition, the method comprising the steps of: determining whether the patient has an ANGPTL7 predicted loss-of-function variant nucleic acid molecule encoding a human ANGPTL7 polypeptide by: obtaining or having obtained a biological sample from the patient; and performing or having performed a genotyping assay on the biological sample to determine if the patient has a genotype comprising the ANGPTL7 predicted loss-of-function variant nucleic acid molecule; and when the patient is ANGPTL7 reference, then administering or continuing to administer to the patient the therapeutic agent that treats or inhibits the ophthalmic condition in a standard dosage amount, and administering to the patient an ANGPTL7 inhibitor; and when the patient is heterozygous for an ANGPTL7 predicted loss-of-function variant, then administering or continuing to administer to the patient the therapeutic agent that treats or inhibits the ophthalmic condition in an amount that is the same as or lower than a standard dosage amount, and administering to the patient an ANGPTL7 inhibitor; wherein the presence of a genotype having the ANGPTL7 predicted loss-of-function variant nucleic acid molecule encoding the human ANGPTL7 polypeptide indicates the patient has a reduced risk of developing the ophthalmic condition.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9A shows an RT-PCR analysis of ANGPTL7 wild type and variants at 48 hours from HEK293 transfection. Expression values are calculated relative to GAPDH housekeeping gene.

FIG. 9B shows western blotting showing intracellular protein levels of ANGPTL7 wild type, ANGPTL7 Gln175His and ANGPTL7 Arg177*.

FIG. 9C shows ELISA assay showing intracellular protein levels of ANGPTL7 wild type, ANGPTL7 Gln175His and ANGPTL7 Arg177*. For quantification each cell lysate was diluted 1:1,000.

FIG. 9D shows western blotting showing extracellular protein levels of ANGPTL7 wild type, ANGPTL7 Gln175His and ANGPTL7 Arg177*. The analysis were repeated on three independent biological replicates.

DESCRIPTION

Figure 1:
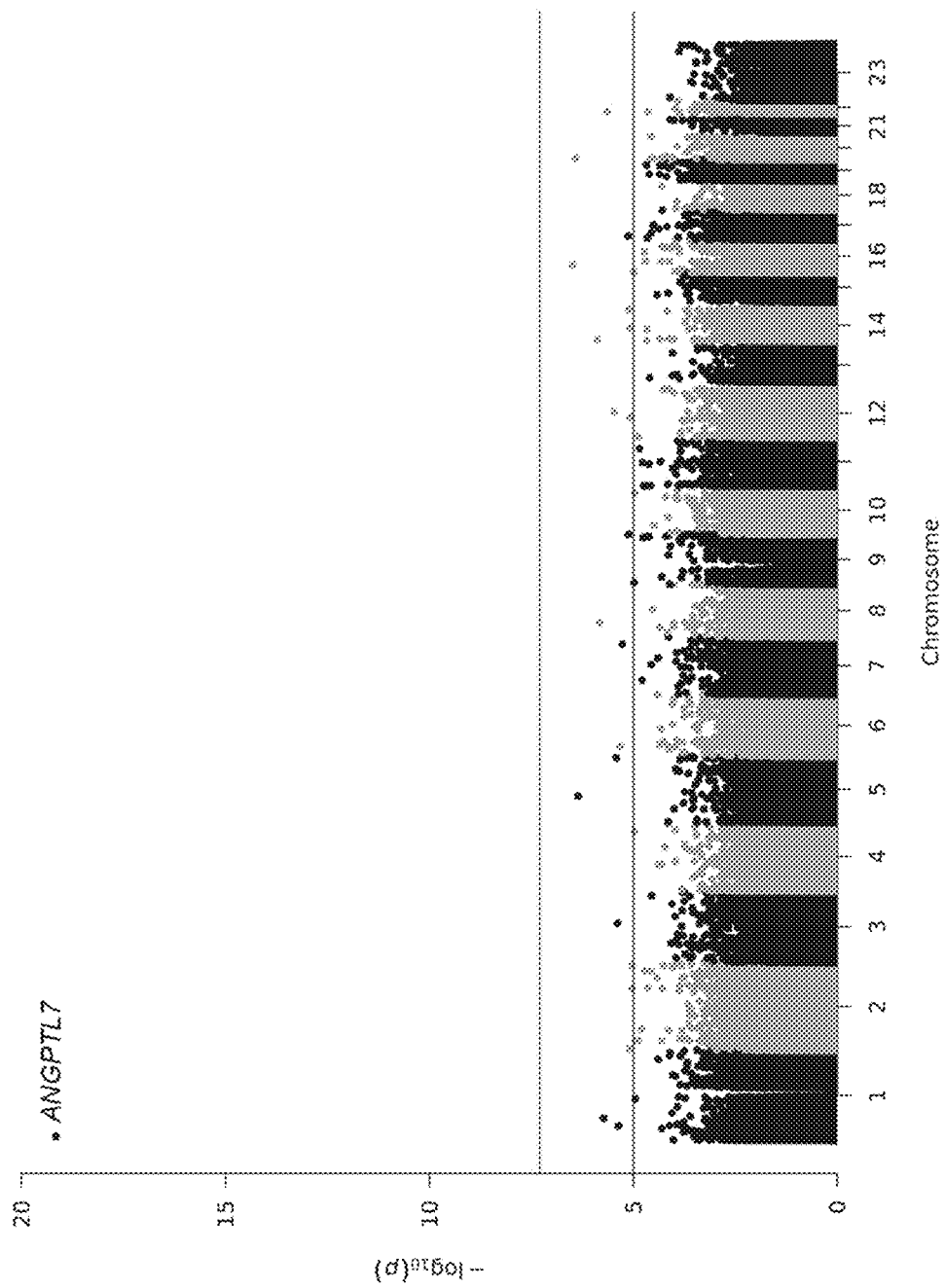
FIG. 1 shows a Manhattan plot depicting association of rare (NAF<0.01), protein-altering variants (including those predicted to affect splicing) with IOP in individuals of European descent in the meta-analysis of the UKB and GHS studies. Significance thresholds: $1\times10^{-5}$ (blue line) and $5\times10^{-8}$ (red line).

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the terms "subject" and "patient" are used interchangeably. A subject may include any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human.

As used herein, a "nucleic acid," a "nucleic acid molecule," a "nucleic acid sequence," a "polynucleotide," or an "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "comprising" may be replaced with "consisting" or "consisting essentially of" in particular embodiments as desired.

An "isolated" nucleic acid molecule is a polynucleotide that is in a condition other than its native environment, such as apart from blood and animal tissue. In a preferred form, the isolated nucleic acid molecule is substantially free of other polynucleotides, particularly other polynucleotides of animal origin. It is preferred to provide the nucleic acid molecule in a highly purified form, i.e., greater than 95% pure, more preferably greater than 99% pure. When used in this context, the term "isolated" does not exclude the presence of the same nucleic acid molecule in alternative physical forms, such as dimers or alternatively phosphorylated or derivatized forms.

Certain variations in the ANGPTL7 gene associate with a decreased risk of developing ophthalmic conditions, such as increased IOP and glaucoma, in human subjects. For example, a genetic alteration that changes the cytosine nucleotide of position 4,291 in the human ANGPTL7 reference (see, SEQ ID NO:1) to thymine or changes the guanine nucleotide of position 4,287 in the human ANGPTL7 reference (see, SEQ ID NO:1) to thymine has been observed to indicate that the human having such an alteration may have a decreased risk of developing ophthalmic conditions, such as increased IOP and glaucoma. Altogether, the genetic analyses described herein indicate that particular variants in the ANGPTL7 gene associate with a decreased risk of developing ophthalmic conditions, such as increased IOP and glaucoma. Therefore, human subjects that are ANGPTL7 reference that have an increased risk of developing an ophthalmic condition, such as increased IOP and glaucoma, may be treated such that the ophthalmic condition is prevented, the symptoms thereof are reduced, and/or development of symptoms is repressed. Accordingly, the present disclosure provides isolated ANGPTL7 variant genomic nucleic acid molecules, variant mRNA molecule, and variant cDNA molecules. Additionally, the disclosure provides methods of leveraging the identification of such variants in subjects to identify or stratify risk in such subjects of developing ophthalmic conditions, such as increased IOP and glaucoma, or to diagnose subjects as having an increased risk of developing ophthalmic conditions, such as increased IOP and glaucoma, such that subjects at risk or subjects with active disease may be treated accordingly. Accordingly, provided herein are ANGPTL7 loss-of-function variant nucleic acid molecules discovered to be associated with a decreased risk of developing ophthalmic conditions, such as increased IOP and glaucoma.

For purposes of the present disclosure, any particular human can be categorized as having one of three ANGPTL7 genotypes: i) ANGPTL7 reference; ii) heterozygous for an ANGPTL7 predicted loss-of-function variant, and iii) homozygous for an ANGPTL7 predicted loss-of-function variant. A human in the ANGPTL7 reference category does not have a copy of an ANGPTL7 predicted loss-of-function variant nucleic acid molecule. A human in the heterozygous ANGPTL7 predicted loss-of-function variant category has a single copy of an ANGPTL7 predicted loss-of-function variant nucleic acid molecule. An ANGPTL7 predicted loss-of-function variant nucleic acid molecule is any ANGPTL7 nucleic acid molecule (such as, a genomic nucleic acid molecule, an mRNA molecule, or a cDNA molecule produced from the mRNA molecule) encoding an ANGPTL7 polypeptide having a partial loss-of-function, a complete loss-of-function, a predicted partial loss-of-function, or a predicted complete loss-of-function. A human who has an ANGPTL7 polypeptide having a partial loss-of-function (or predicted partial loss-of-function) is hypomorphic for ANGPTL7. The ANGPTL7 predicted loss-of-function variant nucleic acid molecule is believed to be any nucleic acid molecule encoding ANGPTL7 Gln175His, Arg177Stop, Lys192Gln, Phe161Ile, Trp188Stop, Arg340His, Arg220His, Asn302Lys, or Arg220Cys. In some embodiments, the ANGPTL7 predicted loss-of-function variant nucleic acid molecule encodes ANGPTL7 Gln175His, Arg177Stop, Lys192Gln, Phe161Ile, or Trp188Stop. In some embodiments, the ANGPTL7 predicted loss-of-function variant nucleic acid molecule encodes ANGPTL7 Gln175His, Arg177Stop, Trp188Stop, Lys192Gln, or Phe161Ile. In some embodiments, the ANGPTL7 predicted loss-of-function variant nucleic acid molecule encodes ANGPTL7 Gln175His, Trp188Stop, or Arg177Stop. In some embodiments, the ANGPTL7 predicted loss-of-function variant nucleic acid molecule encodes ANGPTL7 Gln175His. In some embodiments, the ANGPTL7 predicted loss-of-function variant nucleic acid molecule encodes ANGPTL7 Arg177Stop. In some embodiments, the ANGPTL7 predicted loss-of-function variant nucleic acid molecule encodes ANGPTL7 Trp188Stop. In some embodiments, the ANGPTL7 predicted loss-of-function variant nucleic acid molecule encodes ANGPTL7 Lys192Gln. In some embodiments, the ANGPTL7 predicted loss-of-function variant nucleic acid molecule encodes ANGPTL7 Phe161Ile. A human in the homozygous ANGPTL7 predicted loss-of-function variant category has two copies of an ANGPTL7 predicted loss-of-function variant nucleic acid molecule.

For human subjects or patients that are genotyped or determined to be ANGPTL7 reference, such human subjects or patients have an increased risk of developing ophthalmic conditions, such as increased IOP, pre-glaucoma, glaucoma, and decreased corneal hysteresis. For human subjects or patients that are genotyped or determined to be either ANGPTL7 reference or heterozygous for an ANGPTL7 predicted loss-of-function variant, such human subjects or patients can be treated with an ANGPTL7 inhibitor.

The present disclosure provides methods of treating a patient having glaucoma, the methods comprising administering an ANGPTL7 inhibitor to the patient. In some embodiments, the glaucoma is primary open-angle glaucoma, angle-closure glaucoma, normal-tension glaucoma, congenital glaucoma, neovascular glaucoma, steroid-induced glaucoma, or glaucoma related to ocular trauma.

The present disclosure also provides methods of treating a patient having increased IOP, the methods comprising administering an ANGPTL7 inhibitor to the patient. In some embodiments, the increased IOP is corneal compensated IOP (IOPcc) or Goldmann-correlated IOP (IOPg).

The present disclosure also provides methods of treating a patient having pre-glaucoma, the methods comprising administering an ANGPTL7 inhibitor to the patient.

The present disclosure also provides methods of treating a patient having decreased corneal hysteresis, the methods comprising administering an ANGPTL7 inhibitor to the patient.

In some embodiments, the ANGPTL7 inhibitor comprises an antisense molecule. Examples of antisense molecules include, but are not limited to, antisense nucleic acid molecules, small interfering RNAs (siRNAs), and short hairpin RNAs (shRNAs). Such antisense molecules can be designed to target any region of an ANGPTL7 mRNA. In some embodiments, the antisense RNA, siRNA, or shRNA hybridizes to a sequence within an ANGPTL7 genomic nucleic acid molecule or mRNA molecule and decreases expression of the ANGPTL7 polypeptide in a cell in the subject. In some embodiments, the ANGPTL7 inhibitor comprises an antisense RNA that hybridizes to an ANGPTL7 genomic nucleic acid molecule or mRNA molecule and decreases expression of the ANGPTL7 polypeptide in a cell in the subject. In some embodiments, the ANGPTL7 inhibitor comprises an siRNA that hybridizes to an ANGPTL7 genomic nucleic acid molecule or mRNA molecule and decreases expression of the ANGPTL7 polypeptide in a cell in the subject. In some embodiments, the ANGPTL7 inhibitor comprises an shRNA that hybridizes to an ANGPTL7 genomic nucleic acid molecule or mRNA molecule and decreases expression of the ANGPTL7 polypeptide in a cell in the subject.

In some embodiments, the ANGPTL7 inhibitor comprises a nuclease agent that induces one or more nicks or double-strand breaks at a recognition sequence(s) or a DNA-binding protein that binds to a recognition sequence within an ANGPTL7 genomic nucleic acid molecule. The recognition sequence can be located within a coding region of the ANGPTL7 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the ANGPTL7 gene. For example, the recognition sequence can be located from about 10, 20, 30, 40, 50, 100, 200, 300, 400, 500, or 1,000 nucleotides of the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair (i.e., about 15-18 bp for each ZFN), about 36 bp for a TALE protein or TALEN, and about 20 bp for a CRISPR/Cas guide RNA.

In some embodiments, CRISPR/Cas systems can be used to modify an ANGPTL7 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of ANGPTL7 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in an ANGPTL7 genomic nucleic acid molecule or it can be a nickase that creates a single-strand break in an ANGPTL7 genomic nucleic acid molecule. Additional examples of Cas proteins include, but are not limited to, Cas1, Cas1B, Cast, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (Cas6), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of ANGPTL7 genomic nucleic acid molecules can be generated by contacting a cell with a Cas protein and one or more gRNAs that hybridize to one or more gRNA recognition sequences within a target genomic locus in the ANGPTL7 genomic nucleic acid molecule. For example, a gRNA recognition sequence can be located in a region of SEQ ID NO:1. In some embodiments, the gRNA recognition sequence includes or is proximate to a position corresponding to position 4,291 according to SEQ ID NO:1, position 4,287 according to SEQ ID NO:1, position 4,243 according to SEQ ID NO:1, position 4,325 according to SEQ ID NO:1, or position 4,336 according to SEQ ID NO:1. For example, the gRNA recognition sequence can be located from about 1000, 500, 400, 300, 200, 100, 50, 45, 40, 35, 30, 25, 20, 15, 10, or 5 nucleotides of a position corresponding to position 4,291 according to SEQ ID NO:1. The gRNA recognition sequence can be located from about 1000, 500, 400, 300, 200, 100, 50, 45, 40, 35, 30, 25, 20, 15, 10, or 5 nucleotides of a position corresponding to position 4,287 according to SEQ ID NO:1. The gRNA recognition sequence can be located from about 1000, 500, 400, 300, 200, 100, 50, 45, 40, 35, 30, 25, 20, 15, 10, or 5 nucleotides of a position corresponding to position 4,243 according to SEQ ID NO:1. The gRNA recognition sequence can be located from about 1000, 500, 400, 300, 200, 100, 50, 45, 40, 35, 30, 25, 20, 15, 10, or 5 nucleotides of a position corresponding to position 4,325 according to SEQ ID NO:1. The gRNA recognition sequence can be located from about 1000, 500, 400, 300, 200, 100, 50, 45, 40, 35, 30, 25, 20, 15, 10, or 5 nucleotides of a position corresponding to position 4,336 according to SEQ ID NO:1. As yet another example, a gRNA recognition sequence can include or be proximate to the start codon of an ANGPTL7 genomic nucleic acid molecule or the stop codon of an ANGPTL7 genomic nucleic acid molecule. For example, the gRNA recognition sequence can be located from about 10, 20, 30, 40, 50, 100, 200, 300, 400, 500, or 1,000 nucleotides of the start codon or the stop codon.

The gRNA recognition sequences within a target genomic locus in an ANGPTL7 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within an ANGPTL7 genomic nucleic acid molecule. One exemplary gRNA is a gRNA effective to direct a Cas enzyme to bind to or cleave an ANGPTL7 genomic nucleic acid molecule, wherein the gRNA comprises a DNA-targeting segment that hybridizes to a gRNA recognition sequence within the ANGPTL7 genomic nucleic acid molecule that includes or is proximate to a position corresponding to position 4,291 according to SEQ ID NO:1, or that includes or is proximate to a position corresponding to position 4,287 according to SEQ ID NO:1, or that includes or is proximate to a position corresponding to position 4,243 according to SEQ ID NO:1, or that includes or is proximate to a position corresponding to position 4,325 according to SEQ ID NO:1, or that includes or is proximate to a position corresponding to position 4,336 according to SEQ ID NO:1. For example, a gRNA can be selected such that it hybridizes to a gRNA recognition sequence that is located from about 5, 10, 15, 20, 25, 30, 35, 40, 45, 50, 100, 200, 300, 400, 500, or 1,000 nucleotides of a position corresponding to position 4,291 according to SEQ ID NO:1. A gRNA can also be selected such that it hybridizes to a gRNA recognition sequence that is located from about 5, 10, 15, 20, 25, 30, 35, 40, 45, 50, 100, 200, 300, 400, 500, or 1,000 nucleotides of a position corresponding to position 4,287 according to SEQ ID NO:1. A gRNA can also be selected such that it hybridizes to a gRNA recognition sequence that is located from about 5, 10, 15, 20, 25, 30, 35, 40, 45, 50, 100, 200, 300, 400, 500, or 1,000 nucleotides of a position corresponding to position 4,243 according to SEQ ID NO:1. A gRNA can also be selected such that it hybridizes to a gRNA recognition sequence that is located from about 5, 10, 15, 20, 25, 30, 35, 40, 45, 50, 100, 200, 300, 400, 500, or 1,000 nucleotides of a position corresponding to position 4,325 according to SEQ ID NO:1. A gRNA can also be selected such that it hybridizes to a gRNA recognition sequence that is located from about 5, 10, 15, 20, 25, 30, 35, 40, 45, 50, 100, 200, 300, 400, 500, or 1,000 nucleotides of a position corresponding to position 4,336 according to SEQ ID NO:1. Other exemplary gRNAs comprise a DNA-targeting segment that hybridizes to a gRNA recognition sequence within an ANGPTL7 genomic nucleic acid molecule that is located in a region of SEQ ID NO:1. Other exemplary gRNAs comprise a DNA-targeting segment that hybridizes to a gRNA recognition sequence within an ANGPTL7 genomic nucleic acid molecule that includes or is proximate to the start codon or the stop codon. For example, a gRNA can be selected such that it hybridizes to a gRNA recognition sequence that is located from about 5, 10, 15, 20, 25, 30, 35, 40, 45, 50, 100, 200, 300, 400, 500, or 1,000 nucleotides of the start codon or located from about 5, 10, 15, 20, 25, 30, 35, 40, 45, 50, 100, 200, 300, 400, 500, or 1,000 nucleotides of the start codon or stop codon. The design and synthesis of gRNAs are described in, for example, Mali et al., Science, 2013, 339, 823-826; Jinek et al., Science, 2012, 337, 816-821; Hwang et al., Nat. Biotechnol., 2013, 31, 227-229; Jiang et al., Nat. Biotechnol., 2013, 31, 233-239; and Cong et al., Science, 2013, 339, 819-823. Suitable gRNAs can comprise from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences of the human ANGPTL7 reference gene are set forth in SEQ ID NOS:13-131 and 144-165 (see, Tables 1-9).

TABLE 1

Guide RNA Recognition Sequences Near ANGPTL7 Arg177Stop Variation

| Strand | Guide RNA Recognition Sequence | SEQ ID NO: |
|---|---|---|
| + | CTGCAGGGACAGGAACAGGTTGG | 13 |
| + | CAGAGTATCCCCTCTGCTTCAGG | 14 |
| + | GGCTCTGCAGGGACAGGAACAGG | 15 |
| + | GCTTCAGGTGTTCTGTGACATGG | 16 |
| + | TGCAGGGACAGGAACAGGTTGGG | 17 |
| + | TCTACTGGCTCTGCAGGGACAGG | 18 |
| - | CCTTCTACCGGGACTGGAAGCAG | 19 |
| - | CCGTGGGGACTTCTGGCTGGGGA | 20 |
| - | CCGGGACTGGAAGCAGTACAAGC | 21 |
| - | CCTTGTCTCCTTCTACCGGGACT | 22 |
| - | CCACCGGCTCTCCAGACAGCCAA | 23 |
| - | CCGGCTCTCCAGACAGCCAACCC | 24 |
| + | TGGAGACTTCAGGCGGAGGCTGG | 25 |
| + | TGTGACATGGAGACTTCAGGCGG | 26 |
| + | TTCTGTGACATGGAGACTTCAGG | 27 |
| + | GACATGGAGACTTCAGGCGGAGG | 28 |
| - | CCATGACTGGACCAGTGCCACCA | 29 |
| - | CCCGGCTGCGTGTAGAGATGGAG | 30 |
| - | CCGGCTGCGTGTAGAGATGGAGG | 31 |
| - | CCAACCCGGCTGCGTGTAGAGAT | 32 |
| - | CCAGGGGCCCCATGACTGGACCA | 33 |
| - | CCCCATGACTGGACCAGTGCCAC | 34 |

TABLE 2

Guide RNA Recognition Sequences Near ANGPTL7 Gln175His Variation

| Strand | Guide RNA Recognition Sequence | SEQ ID NO: |
|---|---|---|
| - | CTGCTTCCAGTCCCGGTAGAAGG | 35 |
| + | TTGTCTCCTTCTACCGGGACTGG | 36 |
| + | GCGGGAGTGCACACATCTACTGG | 37 |
| + | GGACTGGAAGCAGTACAAGCAGG | 38 |
| + | GACATGGAGACTTCAGGCGGAGG | 28 |
| + | GTGGCCTTGTCTCCTTCTACCGG | 39 |
| + | TGGAGACTTCAGGCGGAGGCTGG | 25 |
| - | TACTCTGGTGAGGGACTTGCAGG | 40 |
| - | ACTCTGGTGAGGGACTTGCAGGG | 41 |
| - | GCTTGTACTGCTTCCAGTCCCGG | 42 |
| - | AGTCCCGGTAGAAGGAGACAAGG | 43 |
| + | CACACATCTACTGGCTCTGCAGG | 44 |
| - | CAAGGCCACTTTTTCGTCTATGG | 45 |
| + | GACTGGAAGCAGTACAAGCAGGG | 46 |
| - | GCAGAGGGGATACTCTGGTGAGG | 47 |
| + | CAGAGTATCCCCTCTGCTTCAGG | 14 |
| + | TTCTGTGACATGGAGACTTCAGG | 27 |
| - | CTCTGGTGAGGGACTTGCAGGGG | 48 |
| - | CAGAGGGGATACTCTGGTGAGGG | 49 |
| - | ACTTTTTCGTCTATGGATGATGG | 50 |
| + | TGGCCTTGTCTCCTTCTACCGGG | 51 |
| + | AAGCAGTACAAGCAGGGCTTTGG | 52 |
| + | GCTTCAGGTGTTCTGTGACATGG | 16 |
| - | CTGAAGCAGAGGGGATACTCTGG | 53 |
| - | TCACAGAACACCTGAAGCAGAGG | 54 |
| + | ACACATCTACTGGCTCTGCAGGG | 55 |
| + | ATCATCCATAGACGAAAAAGTGG | 56 |
| + | TGTGACATGGAGACTTCAGGCGG | 26 |
| + | TCTACTGGCTCTGCAGGGACAGG | 18 |

TABLE 3

Guide RNA Recognition Sequences Near ANGPTL7 Arg220His Variation

| Strand | Guide RNA Recognition Sequence | SEQ ID NO: |
|---|---|---|
| + | ATGACCGCGTACAACTCCGGGGG | 57 |
| + | CATGACCGCGTACAACTCCGGGG | 58 |
| - | GGCACCCCCGGAGTTGTACGCGG | 59 |

TABLE 3-continued

Guide RNA Recognition Sequences Near ANGPTL7 Arg220His Variation

| Strand | Guide RNA Recognition Sequence | SEQ ID NO: |
|---|---|---|
| - | GAGTTGTACGCGGTCATGTGTGG | 60 |
| + | ACATGACCGCGTACAACTCCGGG | 61 |
| + | CACATGACCGCGTACAACTCCGG | 62 |
| - | TTGTACGCGGTCATGTGTGGTGG | 63 |
| + | TTGTCTCCTTCTACCGGGACTGG | 36 |
| - | CTGCTTCCAGTCCCGGTAGAAGG | 35 |
| + | TGGGGAACGAACACATCCACCGG | 64 |
| + | GGACTGGAAGCAGTACAAGCAGG | 38 |
| - | GGTGGCACTGGTCCAGTCATGGG | 65 |
| - | CAGAATAGGAATGGCACCCCCGG | 66 |
| - | GTGGCACTGGTCCAGTCATGGGG | 67 |
| - | GCGGTCATGTGTGGTGGCACTGG | 68 |
| - | TGGTGGCACTGGTCCAGTCATGG | 69 |
| + | GTGGCCTTGTCTCCTTCTACCGG | 39 |
| + | GCAGCATCCGTGGGGACTTCTGG | 70 |
| + | CATCCGTGGGGACTTCTGGCTGG | 71 |
| - | GCTTGTACTGCTTCCAGTCCCGG | 42 |
| - | AGTCCCGGTAGAAGGAGACAAGG | 43 |
| + | GGCTCTCCAGACAGCCAACCCGG | 72 |
| + | ATCCGTGGGGACTTCTGGCTGGG | 73 |
| + | GACTGGAAGCAGTACAAGCAGGG | 46 |
| - | TTGGCTGTCTGGAGAGCCGGTGG | 74 |
| - | TGGTCCAGTCATGGGCCCCTGG | 75 |
| - | GATTTGTCTTGAATCAGAATAGG | 76 |
| + | AACCCGGCTGCATGTAGAGATGG | 77 |
| - | CTCCATCTCTACATGCAGCCGGG | 78 |
| + | TGGCCTTGTCTCCTTCTACCGGG | 51 |
| + | AAGCAGTACAAGCAGGGCTTTGG | 52 |
| + | TAGAGATGGAGGTAAGCACAAGG | 79 |
| + | TCCGTGGGGACTTCTGGCTGGGG | 80 |

TABLE 4

Guide RNA Recognition Sequences Near ANGPTL7 Arg220Cys Variation

| Strand | Guide RNA Recognition Sequence | SEQ ID NO: |
|---|---|---|
| + | ATGACCGCGTACAACTCCGGGGG | 57 |
| + | CATGACCGCGTACAACTCCGGGG | 58 |
| - | GGCACCCCCGGAGTTGTACGCGG | 59 |
| - | GAGTTGTACGCGGTCATGTGTGG | 60 |
| + | ACATGACCGCGTACAACTCCGGG | 61 |
| + | CACATGACCGCGTACAACTCCGG | 62 |
| - | TTGTACGCGGTCATGTGTGGTGG | 63 |
| + | TTGTCTCCTTCTACCGGGACTGG | 36 |
| - | CTGCTTCCAGTCCCGGTAGAAGG | 35 |
| + | TGGGGAACGAACACATCCACCGG | 64 |
| + | GGACTGGAAGCAGTACAAGCAGG | 38 |
| - | GGTGGCACTGGTCCAGTCATGGG | 65 |
| - | CAGAATAGGAATGGCACCCCCGG | 66 |
| - | GTGGCACTGGTCCAGTCATGGGG | 67 |
| - | GCGGTCATGTGTGGTGGCACTGG | 68 |
| - | TGGTGGCACTGGTCCAGTCATGG | 69 |
| + | CATCCGTGGGGACTTCTGGCTGG | 71 |
| + | GCAGCATCCGTGGGGACTTCTGG | 70 |
| + | GTGGCCTTGTCTCCTTCTACCGG | 39 |
| - | GCTTGTACTGCTTCCAGTCCCGG | 42 |
| + | GGCTCTCCAGACAGCCAACCCGG | 72 |
| - | AGTCCCGGTAGAAGGAGACAAGG | 43 |
| + | ATCCGTGGGGACTTCTGGCTGGG | 73 |
| + | GACTGGAAGCAGTACAAGCAGGG | 46 |
| - | TGGTCCAGTCATGGGCCCCTGG | 75 |
| - | TTGGCTGTCTGGAGAGCCGGTGG | 74 |
| - | GATTTGTCTTGAATCAGAATAGG | 76 |
| - | ATCTCTACACACAGCCGGGTTGG | 81 |
| + | AAGCAGTACAAGCAGGGCTTTGG | 52 |
| + | TGGCCTTGTCTCCTTCTACCGGG | 51 |
| + | TAGAGATGGAGGTAAGCACAAGG | 79 |
| + | TCCGTGGGACTTCTGGCTGGGG | 80 |
| + | AACCCGGCTGTGTGTAGAGATGG | 82 |
| - | CCTCCATCTCTACACACAGCCGG | 83 |

TABLE 5

Guide RNA Recognition Sequences Near ANGPTL7 Asn302Lys Variation

| Strand | Guide RNA Recognition Sequence | SEQ ID NO: |
|---|---|---|
| + | CAATGGAGTGTACTACCGCCTGG | 84 |
| + | AATGGAGTGTACTACCGCCTGGG | 85 |
| + | TACCTACTCCCTCAAACGGGTGG | 86 |
| - | TTTCATCTCCACCCGTTTGAGGG | 87 |
| + | ACAGTCAACTTACTAGCACTGGG | 88 |
| - | TTTTCATCTCCACCCGTTTGAGG | 89 |
| + | GGGTGAGCACAATAAGCACCTGG | 90 |
| + | ATGGCATCACCTGGTATGGCTGG | 91 |
| - | CTCCACCCGTTTGAGGGAGTAGG | 92 |
| - | GGTGCTTATTGTGCTCACCCAGG | 93 |
| + | CTAACTCCTTACCTGATGTCTGG | 94 |
| + | CACAGTCAACTTACTAGCACTGG | 95 |
| - | CAGTTGTACCAGTAGCCACCTGG | 96 |
| - | GATAGACCAGACATCAGGTAAGG | 97 |
| - | TCAGGTAAGGAGTTAGAGCCAGG | 98 |
| + | GATCTACCTACTCCCTCAAACGG | 99 |
| - | AGATCCATGCCAGCCATACCAGG | 100 |
| - | GCTTATTGTGCTCACCCAGGCGG | 101 |
| - | CATACCAGGTGATGCCATCCAGG | 102 |
| + | ATCTACCTACTCCCTCAAACGGG | 103 |
| - | ACTGTGATAGACCAGACATCAGG | 104 |
| + | TTCTCATGCCAGGTGGCTACTGG | 105 |
| + | CTGGATGGCATCACCTGGTATGG | 106 |
| + | AGCACCTGGATGGCATCACCTGG | 107 |
| + | ATCACCTGGTATGGCTGGCATGG | 108 |
| - | GTAGTACACTCCATTGAGTTTGG | 109 |
| + | GAGCACAATAAGCACCTGGATGG | 110 |
| + | CAGGTAAGGAGTTAGAGCCAGGG | 111 |
| + | CTGGGTCTGTTTCTCATGCCAGG | 112 |
| + | TTTGGTATTCTTTCTGACCCTGG | 113 |
| - | GTCAGAAAGAATACCAAAACCGG | 114 |
| + | GGTCTGTTTCTCATGCCAGGTGG | 115 |

TABLE 6

Guide RNA Recognition Sequences Near ANGPTL7 Arg340His Variation

| Strand | Guide RNA Recognition Sequence | SEQ ID NO: |
|---|---|---|
| + | CAATGGAGTGTACTACCGCCTGG | 84 |
| + | AATGGAGTGTACTACCGCCTGGG | 85 |
| - | GGCGGTAGTACACTCCATTGAGG | 116 |
| + | TACCTACTCCCTCAAACGGGTGG | 86 |
| - | GTAGTACACTCCATTGAGGTTGG | 117 |
| - | TTTCATCTCCACCCGTTTGAGGG | 87 |
| - | TTTTCATCTCCACCCGTTTGAGG | 89 |
| + | GGGTGAGCACAATAAGCACCTGG | 90 |
| + | ATGGCATCACCTGGTATGGCTGG | 91 |
| - | GGTGCTTATTGTGCTCACCCAGG | 93 |
| - | CTCCACCCGTTTGAGGGAGTAGG | 92 |
| - | GTTTCTGTATCCGTGCTCCACGG | 118 |
| + | AAACTGAGACACGTGGAGACTGG | 119 |
| - | GCTTATTGTGCTCACCCAGGCGG | 101 |
| + | GATCTACCTACTCCCTCAAACGG | 99 |
| - | AGATCCATGCCAGCCATACCAGG | 100 |
| + | GCCTTAAAAGGAGGCTGCCGTGG | 120 |
| - | CATACCAGGTGATGCCATCCAGG | 102 |
| + | ATCTACCTACTCCCTCAAACGGG | 103 |
| + | GACACGTGGAGACTGGATGAGGG | 121 |
| - | TCCACGGCAGCCTCCTTTTAAGG | 122 |
| + | CTGGATGGCATCACCTGGTATGG | 106 |
| + | AGCACCTGGATGGCATCACCTGG | 107 |
| + | ATCACCTGGTATGGCTGGCATGG | 108 |
| + | TGCACAGACTCCAACCTCAATGG | 123 |
| + | GAGCACAATAAGCACCTGGATGG | 110 |
| + | AGACACGTGGAGACTGGATGAGG | 124 |
| + | AGACTTCAAGCCTTAAAAGGAGG | 125 |
| - | TTTAAGGCTTGAAGTCTTCTGGG | 126 |
| - | AAGGCTTGAAGTCTTCTGGGTGG | 127 |
| - | TTTTAAGGCTTGAAGTCTTCTGG | 128 |
| + | GATACAGAAACTGAGACACGTGG | 129 |
| + | AAGGAGGCTGCCGTGGAGCACGG | 130 |
| + | AGAAGACTTCAAGCCTTAAAAGG | 131 |

TABLE 7

Guide RNA Recognition Sequences Near ANGPTL7 Phe161Ile Variation

| Strand | Guide RNA Recognition Sequence | SEQ ID NO: |
|---|---|---|
| − | ACAGAACACCTGAAGCAGAGGGG | 144 |
| − | ACAGAACACCTGAAGCAGAGGGG | 145 |
| − | CACAGAACACCTGAAGCAGAGGG | 146 |
| + | CAGAGTATCCCCTCTGCTTCAGG | 147 |
| − | ACTCTGGTGAGGGACTTGCAGGG | 148 |
| − | TACTCTGGTGAGGGACTTGCAGG | 149 |
| − | GCAGAGGGGATACTCTGGTGAGG | 150 |
| + | GCTTCAGGTGTTCTGTGACATGG | 151 |
| − | CAGAGGGGATACTCTGGTGAGGG | 152 |

TABLE 8

Guide RNA Recognition Sequences Near ANGPTL7 Trp188STOP Variation

| Strand | Guide RNA Recognition Sequence | SEQ ID NO: |
|---|---|---|
| + | TTGTCTCCTTCTACCGGGACTGG | 153 |
| + | GTGGCCTTGTCTCCTTCTACCG | 154 |
| + | TGGCCTTGTCTCCTTCTACCGGG | 155 |
| + | GACTGGAAGCAGTACAAGCAGGG | 156 |
| + | GGACTGGAAGCAGTACAAGCAGG | 157 |
| − | CTGCTTCCAGTCCCGGTAGAAGG | 158 |
| − | GCTTGTACTGCTTCCAGTCCCGG | 159 |
| − | AGTCCCGGTAGAAGGAGACAAGG | 160 |

TABLE 9

Guide RNA Recognition Sequences Near ANGPTL7 Lys192Gln Variation

| Strand | Guide RNA Recognition Sequence | SEQ ID NO: |
|---|---|---|
| + | GACTGGAAGCAGTACAAGCAGGG | 156 |
| + | GGACTGGAAGCAGTACAAGCAGG | 157 |
| − | GGACTGGAAGCAGTACAAGC | 159 |
| + | AAGCAGTACAAGCAGGGCTTTGG | 161 |
| + | CAGGGCTTTGGCAGCATCCGTGG | 162 |
| + | AGGGCTTTGGCAGCATCCGTGGG | 163 |
| + | GGGCTTTGGCAGCATCCGTGGGG | 164 |
| − | TCCCCAGCCAGAAGTCCCCACGG | 165 |

The Cas protein and the gRNA form a complex, and the Cas protein cleaves the target ANGPTL7 genomic nucleic acid molecule. The Cas protein can cleave the nucleic acid molecule at a site within or outside of the nucleic acid sequence present in the target ANGPTL7 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the ANGPTL7 genomic nucleic acid molecule to which a DNA-targeting segment of a gRNA will bind.

Such methods can result, for example, in an ANGPTL7 genomic nucleic acid molecule in which a region of SEQ ID NO:1 is disrupted, the start codon is disrupted, the stop codon is disrupted, or the coding sequence is deleted. Optionally, the cell can be further contacted with one or more additional gRNAs that hybridize to additional gRNA recognition sequences within the target genomic locus in the ANGPTL7 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In some embodiments, the ANGPTL7 inhibitor comprises a small molecule. In some embodiments, the ANGPTL7 inhibitor is 6,11-dihydro[1]benzothiopyrano[4,3-b]indole (PD146176), 2-bromophenol, 2,4-dibromophenol, 2-(1-thienyl)ethyl-3,4-dihydroxybenzylidenecyanoacetate (TEDC), 4,4'-(2,3-dimethyl-1,4-butanediyl)bis-1,2-benzenediol (nordihydroguaiaretic acid), or cinnamyl-3,4-dihydroxy-a-cyanocinnamate (CDC).

In some embodiments, the methods further comprise detecting the presence or absence of an ANGPTL7 predicted loss-of-function variant nucleic acid molecule encoding a human ANGPTL7 polypeptide in a biological sample from the patient. As used throughout the present disclosure an "ANGPTL7 predicted loss-of-function variant nucleic acid molecule" is any ANGPTL7 nucleic acid molecule (such as, for example, genomic nucleic acid molecule, mRNA molecule, or cDNA molecule) encoding an ANGPTL7 polypeptide having a partial loss-of-function, a complete loss-of-function, a predicted partial loss-of-function, or a predicted complete loss-of-function. For example, the ANGPTL7 predicted loss-of-function variant nucleic acid molecule can be any nucleic acid molecule encoding ANGPTL7 Gln175His, Arg177Stop, Trp188Stop, Lys192Gln, Phe161Ile, Arg340His, Arg220His, Asn302Lys, or Arg220Cys. In some embodiments, the ANGPTL7 predicted loss-of-function variant nucleic acid molecule encodes ANGPTL7 Gln175His, Arg177Stop, Trp188Stop, Lys192Gln, or Phe161Ile. In some embodiments, the ANGPTL7 predicted loss-of-function variant nucleic acid molecule encodes ANGPTL7 Gln175His, Trp188Stop, or Arg177Stop. In some embodiments, the ANGPTL7 predicted loss-of-function variant nucleic acid molecule encodes ANGPTL7 Gln175His. In some embodiments, the ANGPTL7 predicted loss-of-function variant nucleic acid molecule encodes ANGPTL7 Arg177Stop. In some embodiments, the ANGPTL7 predicted loss-of-function variant nucleic acid molecule encodes ANGPTL7 Trp188Stop. In some embodiments, the ANGPTL7 predicted loss-of-function variant nucleic acid molecule encodes ANGPTL7 Lys192Gln. In some embodiments, the ANGPTL7 predicted loss-of-function variant nucleic acid molecule encodes ANGPTL7 Phe161Ile.

In some embodiments, the ANGPTL7 predicted loss-of-function variant nucleic acid molecule is: i) a genomic nucleic acid molecule having a nucleotide sequence comprising a thymine at a position corresponding to position 4,291 according to SEQ ID NO:2; ii) an mRNA molecule having a nucleotide sequence comprising a uracil at a position corresponding to position 529 according to SEQ ID NO:5; or iii) a cDNA molecule produced from an mRNA molecule, wherein the cDNA molecule has a nucleotide sequence comprising a thymine at a position corresponding to position 529 according to SEQ ID NO:8.

In some embodiments, the ANGPTL7 predicted loss-of-function variant nucleic acid molecule is: i) a genomic nucleic acid molecule having a nucleotide sequence comprising a thymine at a position corresponding to position 4,287 according to SEQ ID NO:3; ii) an mRNA molecule having a nucleotide sequence comprising a uracil at a position corresponding to position 525 according to SEQ ID NO:6; or iii) a cDNA molecule produced from an mRNA molecule, wherein the cDNA molecule has a nucleotide sequence comprising a thymine at a position corresponding to position 525 according to SEQ ID NO:9

In some embodiments, the ANGPTL7 predicted loss-of-function variant nucleic acid molecule is: i) a genomic nucleic acid molecule having a nucleotide sequence comprising an adenine at a position corresponding to position 4,243 according to SEQ ID NO:132; ii) an mRNA molecule having a nucleotide sequence comprising an adenine at a position corresponding to position 481 according to SEQ ID NO:135; or iii) a cDNA molecule produced from an mRNA molecule, wherein the cDNA molecule has a nucleotide sequence comprising an adenine at a position corresponding to position 481 according to SEQ ID NO:138.

In some embodiments, the ANGPTL7 predicted loss-of-function variant nucleic acid molecule is: i) a genomic nucleic acid molecule having a nucleotide sequence comprising an adenine at a position corresponding to position 4,325 according to SEQ ID NO:133; ii) an mRNA molecule having a nucleotide sequence comprising an adenine at a position corresponding to position 563 according to SEQ ID NO:136; or iii) a cDNA molecule produced from an mRNA molecule, wherein the cDNA molecule has a nucleotide sequence comprising an adenine at a position corresponding to position 563 according to SEQ ID NO:139.

In some embodiments, the ANGPTL7 predicted loss-of-function variant nucleic acid molecule is: i) a genomic nucleic acid molecule having a nucleotide sequence comprising a cytosine at a position corresponding to position 4,336 according to SEQ ID NO:134; ii) an mRNA molecule having a nucleotide sequence comprising a cytosine at a position corresponding to position 574 according to SEQ ID NO:137; or iii) a cDNA molecule produced from an mRNA molecule, wherein the cDNA molecule has a nucleotide sequence comprising a cytosine at a position corresponding to position 574 according to SEQ ID NO:140.

In some embodiments, when the patient is ANGPTL7 reference, the patient is also administered a therapeutic agent that treats or inhibits an ophthalmic condition in a standard dosage amount. In some embodiments, when the patient is heterozygous for an ANGPTL7 predicted loss-of-function variant, the patient is also administered a therapeutic agent that treats or inhibits an ophthalmic condition in a dosage amount that is the same as or lower than the standard dosage amount.

The present disclosure also provides methods of treating a patient with a therapeutic agent that treats or inhibits an ophthalmic condition, wherein the patient is suffering from an ophthalmic condition, the method comprising the steps of: determining whether the patient has an ANGPTL7 predicted loss-of-function variant nucleic acid molecule encoding a human ANGPTL7 polypeptide by: obtaining or having obtained a biological sample from the patient; and performing or having performed a genotyping assay on the biological sample to determine if the patient has a genotype comprising the ANGPTL7 predicted loss-of-function variant nucleic acid molecule; and when the patient is ANGPTL7 reference, then: i) administering or continuing to administer to the patient the therapeutic agent that treats or inhibits the ophthalmic condition in a standard dosage amount, and administering to the patient an ANGPTL7 inhibitor; and when the patient is heterozygous for an ANGPTL7 predicted loss-of-function variant, then: i) administering or continuing to administer to the patient the therapeutic agent that treats or inhibits the ophthalmic condition in an amount that is the same as or lower than a standard dosage amount, and administering to the patient an ANGPTL7 inhibitor; wherein the presence of a genotype having the ANGPTL7 predicted loss-of-function variant nucleic acid molecule encoding the human ANGPTL7 polypeptide indicates the patient has a reduced risk of developing the ophthalmic condition. In some embodiments, the patient is ANGPTL7 reference. In some embodiments, the patient is heterozygous for an ANGPTL7 predicted loss-of-function variant.

The present disclosure also provides methods of treating a patient with a therapeutic agent that treats or inhibits an ophthalmic condition, wherein the patient is suffering from an ophthalmic condition, the method comprising the steps of: determining whether the patient has an ANGPTL7 predicted loss-of-function variant nucleic acid molecule encoding a human ANGPTL7 polypeptide, wherein the ANGPTL7 predicted loss-of-function variant nucleic acid molecule is: i) a genomic nucleic acid molecule having a nucleotide sequence comprising a thymine at a position corresponding to position 4,291 according to SEQ ID NO:2; ii) an mRNA molecule having a nucleotide sequence comprising a uracil at a position corresponding to position 529 according to SEQ ID NO:5; or iii) a cDNA molecule produced from an mRNA molecule, wherein the cDNA molecule has a nucleotide sequence comprising a thymine at a position corresponding to position 529 according to SEQ ID NO:8; by: obtaining or having obtained a biological sample from the patient; and performing or having performed a genotyping assay on the biological sample to determine if the patient has a genotype comprising the ANGPTL7 predicted loss-of-function variant nucleic acid molecule; and when the patient is ANGPTL7 reference, then administering or continuing to administer to the patient the therapeutic agent that treats or inhibits the ophthalmic condition in a standard dosage amount, and administering to the patient an ANGPTL7 inhibitor; and when the patient is heterozygous for an ANGPTL7 predicted loss-of-function variant, then administering or continuing to administer to the patient the therapeutic agent that treats or inhibits the ophthalmic condition in an amount that is the same as or lower than a standard dosage amount, and administering to the patient an ANGPTL7 inhibitor; wherein the presence of a genotype having the ANGPTL7 predicted loss-of-function variant nucleic acid molecule encoding the human ANGPTL7 polypeptide indicates the patient has a reduced risk of developing the ophthalmic condition. In some embodiments, the patient is ANGPTL7 reference. In some embodiments, the patient is heterozygous for an ANGPTL7 predicted loss-of-function variant.

The present disclosure also provides methods of treating a patient with a therapeutic agent that treats or inhibits an ophthalmic condition, wherein the patient is suffering from an ophthalmic condition, the method comprising the steps of: determining whether the patient has an ANGPTL7 predicted loss-of-function variant nucleic acid molecule encoding a human ANGPTL7 polypeptide, wherein the ANGPTL7 predicted loss-of-function variant nucleic acid molecule is: i) a genomic nucleic acid molecule having a nucleotide sequence comprising a thymine at a position corresponding to position 4,287 according to SEQ ID NO:3; ii) an mRNA molecule having a nucleotide sequence comprising a uracil at a position corresponding to position 525 according to SEQ ID NO:6; or iii) a cDNA molecule produced from an mRNA molecule, wherein the cDNA molecule has a nucleotide sequence comprising a thymine at a position corresponding to position 525 according to SEQ ID NO:9; by: obtaining or having obtained a biological sample from the patient; and performing or having performed a genotyping assay on the biological sample to determine if the patient has a genotype comprising the ANGPTL7 predicted loss-of-function variant nucleic acid molecule; and when the patient is ANGPTL7 reference, then administering or continuing to administer to the patient the therapeutic agent that treats or inhibits the ophthalmic condition in a standard dosage amount, and administering to the patient an ANGPTL7 inhibitor; and when the patient is heterozygous for an ANGPTL7 predicted loss-of-function variant, then administering or continuing to administer to the patient the therapeutic agent that treats or inhibits the ophthalmic condition in an amount that is the same as or lower than a standard dosage amount, and administering to the patient an ANGPTL7 inhibitor; wherein the presence of a genotype having the ANGPTL7 predicted loss-of-function variant nucleic acid molecule encoding the human ANGPTL7 polypeptide indicates the patient has a reduced risk of developing the ophthalmic condition. In some embodiments, the patient is ANGPTL7 reference. In some embodiments, the patient is heterozygous for an ANGPTL7 predicted loss-of-function variant.

The present disclosure also provides methods of treating a patient with a therapeutic agent that treats or inhibits an ophthalmic condition, wherein the patient is suffering from an ophthalmic condition, the method comprising the steps of: determining whether the patient has an ANGPTL7 predicted loss-of-function variant nucleic acid molecule encoding a human ANGPTL7 polypeptide, wherein the ANGPTL7 predicted loss-of-function variant nucleic acid molecule is: i) a genomic nucleic acid molecule having a nucleotide sequence comprising an adenine at a position corresponding to position 4,243 according to SEQ ID NO:132; ii) an mRNA molecule having a nucleotide sequence comprising an adenine at a position corresponding to position 481 according to SEQ ID NO:135; or iii) a cDNA molecule produced from an mRNA molecule, wherein the cDNA molecule has a nucleotide sequence comprising an adenine at a position corresponding to position 481 according to SEQ ID NO:138; by: obtaining or having obtained a biological sample from the patient; and performing or having performed a genotyping assay on the biological sample to determine if the patient has a genotype comprising the ANGPTL7 predicted loss-of-function variant nucleic acid molecule; and when the patient is ANGPTL7 reference, then administering or continuing to administer to the patient the therapeutic agent that treats or inhibits the ophthalmic condition in a standard dosage amount, and administering to the patient an ANGPTL7 inhibitor; and when the patient is heterozygous for an ANGPTL7 predicted loss-of-function variant, then administering or continuing to administer to the patient the therapeutic agent that treats or inhibits the ophthalmic condition in an amount that is the same as or lower than a standard dosage amount, and administering to the patient an ANGPTL7 inhibitor; wherein the presence of a genotype having the ANGPTL7 predicted loss-of-function variant nucleic acid molecule encoding the human ANGPTL7 polypeptide indicates the patient has a reduced risk of developing the ophthalmic condition. In some embodiments, the patient is ANGPTL7 reference. In some embodiments, the patient is heterozygous for an ANGPTL7 predicted loss-of-function variant.

The present disclosure also provides methods of treating a patient with a therapeutic agent that treats or inhibits an ophthalmic condition, wherein the patient is suffering from an ophthalmic condition, the method comprising the steps of: determining whether the patient has an ANGPTL7 predicted loss-of-function variant nucleic acid molecule encoding a human ANGPTL7 polypeptide, wherein the ANGPTL7 predicted loss-of-function variant nucleic acid molecule is: i) a genomic nucleic acid molecule having a nucleotide sequence comprising an adenine at a position corresponding to position 4,325 according to SEQ ID NO:133; ii) an mRNA molecule having a nucleotide sequence comprising an adenine at a position corresponding to position 563 according to SEQ ID NO:136; or iii) a cDNA molecule produced from an mRNA molecule, wherein the cDNA molecule has a nucleotide sequence comprising an adenine at a position corresponding to position 563 according to SEQ ID NO:139; by: obtaining or having obtained a biological sample from the patient; and performing or having performed a genotyping assay on the biological sample to determine if the patient has a genotype comprising the ANGPTL7 predicted loss-of-function variant nucleic acid molecule; and when the patient is ANGPTL7 reference, then administering or continuing to administer to the patient the therapeutic agent that treats or inhibits the ophthalmic condition in a standard dosage amount, and administering to the patient an ANGPTL7 inhibitor; and when the patient is heterozygous for an ANGPTL7 predicted loss-of-function variant, then administering or continuing to administer to the patient the therapeutic agent that treats or inhibits the ophthalmic condition in an amount that is the same as or lower than a standard dosage amount, and administering to the patient an ANGPTL7 inhibitor; wherein the presence of a genotype having the ANGPTL7 predicted loss-of-function variant nucleic acid molecule encoding the human ANGPTL7 polypeptide indicates the patient has a reduced risk of developing the ophthalmic condition. In some embodiments, the patient is ANGPTL7 reference. In some embodiments, the patient is heterozygous for an ANGPTL7 predicted loss-of-function variant.

The present disclosure also provides methods of treating a patient with a therapeutic agent that treats or inhibits an ophthalmic condition, wherein the patient is suffering from an ophthalmic condition, the method comprising the steps of: determining whether the patient has an ANGPTL7 predicted loss-of-function variant nucleic acid molecule encoding a human ANGPTL7 polypeptide, wherein the ANGPTL7 predicted loss-of-function variant nucleic acid molecule is: i) a genomic nucleic acid molecule having a nucleotide sequence comprising a cytosine at a position corresponding to position 4,336 according to SEQ ID NO:134; ii) an mRNA molecule having a nucleotide sequence comprising a cytosine at a position corresponding to position 574 according to SEQ ID NO:137; or iii) a cDNA molecule produced from an mRNA molecule, wherein the cDNA molecule has a nucleotide sequence comprising a cytosine at a position corresponding to position 574 according to SEQ ID NO:140); by: obtaining or having obtained a biological sample from the patient; and performing or having performed a genotyping assay on the biological sample to determine if the patient has a genotype comprising the ANGPTL7 predicted loss-of-function variant nucleic acid molecule; and when the patient is ANGPTL7 reference, then administering or continuing to administer to the patient the therapeutic agent that treats or inhibits the ophthalmic condition in a standard dosage amount, and administering to the patient an ANGPTL7 inhibitor; and when the patient is heterozygous for an ANGPTL7 predicted loss-of-function variant, then administering or continuing to administer to the patient the therapeutic agent that treats or inhibits the ophthalmic condition in an amount that is the same as or lower than a standard dosage amount, and administering to the patient an ANGPTL7 inhibitor; wherein the presence of a genotype having the ANGPTL7 predicted loss-of-function variant nucleic acid molecule encoding the human ANGPTL7 polypeptide indicates the patient has a reduced risk of developing the ophthalmic condition. In some embodiments, the patient is ANGPTL7 reference. In some embodiments, the patient is heterozygous for an ANGPTL7 predicted loss-of-function variant.

The ANGPTL7 predicted loss-of-function variant nucleic acid molecule can be any ANGPTL7 nucleic acid molecule (such as, for example, genomic nucleic acid molecule, mRNA molecule, or cDNA molecule) encoding an ANGPTL7 polypeptide having a partial loss-of-function, a complete loss-of-function, a predicted partial loss-of-function, or a predicted complete loss-of-function. For example, the ANGPTL7 predicted loss-of-function variant nucleic acid molecule can be any nucleic acid molecule encoding ANGPTL7 Gln175His, Arg177Stop, Trp188Stop, Lys192Gln, Phe161Ile, Arg340His, Arg220His, Asn302Lys, or Arg220Cys. In some embodiments, the ANGPTL7 predicted loss-of-function variant nucleic acid molecule encodes ANGPTL7 Gln175His, Trp188Stop, or Arg177Stop. In some embodiments, the ANGPTL7 predicted loss-of-function variant nucleic acid molecule encodes ANGPTL7 Gln175His. In some embodiments, the ANGPTL7 predicted loss-of-function variant nucleic acid molecule encodes ANGPTL7 Arg177Stop. In some embodiments, the ANGPTL7 predicted loss-of-function variant nucleic acid molecule encodes ANGPTL7 Trp188Stop. In some embodiments, the ANGPTL7 predicted loss-of-function variant nucleic acid molecule encodes ANGPTL7 Lys192Gln. In some embodiments, the ANGPTL7 predicted loss-of-function variant nucleic acid molecule encodes ANGPTL7 Phe161Ile.

Detecting the presence or absence of any of the ANGPTL7 predicted loss-of-function variant nucleic acid molecules described herein in a biological sample from a patient and/or determining whether a patient has an ANGPTL7 predicted loss-of-function variant nucleic acid molecule can be carried out by any of the methods described herein. In some embodiments, these methods can be carried out in vitro. In some embodiments, these methods can be carried out in situ. In some embodiments, these methods can be carried out in vivo.

In some embodiments, the determining step, detecting step, or genotyping assay comprises sequencing at least a portion of the nucleotide sequence of the ANGPTL7 genomic nucleic acid molecule, the ANGPTL7 mRNA molecule, or the ANGPTL7 cDNA molecule in the biological sample, wherein the sequenced portion comprises variation(s) that cause a loss-of-function (partial or complete) or are predicted to cause a loss-of-function (partial or complete). For example, in some embodiments, the detection step, detecting step, or genotyping assay comprises sequencing at least a portion of: i) the nucleotide sequence of the ANGPTL7 genomic nucleic acid molecule in the biological sample, wherein the sequenced portion comprises a position corresponding to position 4,291 according to SEQ ID NO:2, or the complement thereof; ii) the nucleotide sequence of the ANGPTL7 mRNA molecule in the biological sample, wherein the sequenced portion comprises a position corresponding to position 529 according to SEQ ID NO:5, or the complement thereof; and/or iii) the nucleotide sequence of the ANGPTL7 cDNA molecule in the biological sample, wherein the sequenced portion comprises a position corresponding to position 529 according to SEQ ID NO:8, or the complement thereof. When the sequenced portion of the ANGPTL7 genomic nucleic acid molecule in the biological sample comprises a thymine at a position corresponding to position 4,291 according to SEQ ID NO:2, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises a uracil at a position corresponding to position 529 according to SEQ ID NO:5, then the ANGPTL7 mRNA molecule in the biological sample is an ANGPTL7 predicted loss-of-function variant mRNA molecule. When the sequenced portion of the ANGPTL7 cDNA molecule in the biological sample comprises a thymine at a position corresponding to position 529 according to SEQ ID NO:8, then the ANGPTL7 cDNA molecule in the biological sample is an ANGPTL7 predicted loss-of-function variant cDNA molecule.

In some embodiments, the determining step, detecting step, or genotyping assay comprises: a) contacting the biological sample with a primer hybridizing to: i) a portion of the nucleotide sequence of the ANGPTL7 genomic nucleic acid molecule that is proximate to a position corresponding to position 4,291 according to SEQ ID NO:2; ii) a portion of the nucleotide sequence of the ANGPTL7 mRNA molecule that is proximate to a position corresponding to position 529 according to SEQ ID NO:5; and/or iii) a portion of the nucleotide sequence of the ANGPTL7 cDNA molecule that is proximate to a position corresponding to position 529 according to SEQ ID NO:8; b) extending the primer at least through: i) the position of the nucleotide sequence of the ANGPTL7 genomic nucleic acid molecule corresponding to position 4,291 according to SEQ ID NO:2; ii) the position of the nucleotide sequence of the ANGPTL7 mRNA molecule corresponding to position 529 according to SEQ ID NO:5; and/or iii) the position of the nucleotide sequence of the ANGPTL7 cDNA molecule corresponding to position 529 according to SEQ ID NO:8; and c) determining whether the extension product of the primer comprises: i) a thymine at a position corresponding to position 4,291 according to SEQ ID NO:2; ii) a uracil at a position corresponding to position 529 according to SEQ ID NO:5; and/or iii) a thymine at a position corresponding to position 529 according to SEQ ID NO:8.

In some embodiments, the determining step, detecting step, or genotyping assay comprises: a) amplifying at least a portion of the nucleic acid molecule that encodes the human ANGPTL7 polypeptide, wherein the portion comprises: i) a thymine at a position corresponding to position 4,291 according to SEQ ID NO:2, or the complement thereof; ii) a uracil at a position corresponding to position 529 according to SEQ ID NO:5, or the complement thereof; and/or iii) a thymine at a position corresponding to position 529 according to SEQ ID NO:8, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a thymine at a position corresponding to position 4,291 according to SEQ ID NO:2, or the complement thereof; ii) the nucleic acid sequence of the amplified nucleic acid molecule comprising a uracil at a position corresponding to position 529 according to SEQ ID NO:5, or the complement thereof; and/or iii) the nucleic acid sequence of the amplified nucleic acid molecule comprising a thymine at a position corresponding to position 529 according to SEQ ID NO:8, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising a thymine at a position corresponding to position 4,291 according to SEQ ID NO:2, or the complement thereof; the nucleotide sequence of the amplified nucleic acid molecule comprising a uracil at a position corresponding to position 529 according to SEQ ID NO:5, or the complement thereof; and/or the nucleotide sequence of the amplified nucleic acid molecule comprising a thymine at a position corresponding to position 529 according to SEQ ID NO:8, or the complement thereof; and detecting the detectable label.

In some embodiments, the determining step, detecting step, or genotyping assay comprises sequencing at least a portion of: i) the nucleotide sequence of the ANGPTL7 genomic nucleic acid molecule in the biological sample, wherein the sequenced portion comprises a position corresponding to position 4,287 according to SEQ ID NO:3, or the complement thereof; ii) the nucleotide sequence of the ANGPTL7 mRNA molecule in the biological sample, wherein the sequenced portion comprises a position corresponding to position 525 according to SEQ ID NO:6, or the complement thereof; and/or iii) the nucleotide sequence of the ANGPTL7 cDNA molecule in the biological sample, wherein the sequenced portion comprises a position corresponding to position 525 according to SEQ ID NO:9, or the complement thereof. When the sequenced portion of the ANGPTL7 genomic nucleic acid molecule in the biological sample comprises a thymine at a position corresponding to position 4,287 according to SEQ ID NO:3, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises a uracil at a position corresponding to position 525 according to SEQ ID NO:6, then the ANGPTL7 mRNA molecule in the biological sample is an ANGPTL7 predicted loss-of-function variant mRNA molecule. When the sequenced portion of the ANGPTL7 cDNA molecule in the biological sample comprises a thymine at a position corresponding to position 525 according to SEQ ID NO:9, then the ANGPTL7 cDNA molecule in the biological sample is an ANGPTL7 predicted loss-of-function variant cDNA molecule.

In some embodiments, the determining step, detecting step, or genotyping assay comprises: a) contacting the biological sample with a primer hybridizing to: i) a portion of the nucleotide sequence of the ANGPTL7 genomic nucleic acid molecule that is proximate to a position corresponding to position 4,287 according to SEQ ID NO:3; ii) a portion of the nucleotide sequence of the ANGPTL7 mRNA molecule that is proximate to a position corresponding to position 525 according to SEQ ID NO:6; and/or iii) a portion of the nucleotide sequence of the ANGPTL7 cDNA molecule that is proximate to a position corresponding to position 525 according to SEQ ID NO:9; b) extending the primer at least through: i) the position of the nucleotide sequence of the ANGPTL7 genomic nucleic acid molecule corresponding to position 4,287 according to SEQ ID NO:3; ii) the position of the nucleotide sequence of the ANGPTL7 mRNA molecule corresponding to position 525 according to SEQ ID NO:6; and/or iii) the position of the nucleotide sequence of the ANGPTL7 cDNA molecule corresponding to position 525 according to SEQ ID NO:9; and c) determining whether the extension product of the primer comprises: i) a thymine at a position corresponding to position 4,287 according to SEQ ID NO:3; ii) a uracil at a position corresponding to position 525 according to SEQ ID NO:6; and/or iii) a thymine at a position corresponding to position 525 according to SEQ ID NO:9.

In some embodiments, the determining step, detecting step, or genotyping assay comprises: a) amplifying at least a portion of the nucleic acid molecule that encodes the human ANGPTL7 polypeptide, wherein the portion comprises: i) a thymine at a position corresponding to position 4,287 according to SEQ ID NO:3, or the complement thereof; ii) a uracil at a position corresponding to position 525 according to SEQ ID NO:6, or the complement thereof; and/or iii) a thymine at a position corresponding to position 525 according to SEQ ID NO:9, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a thymine at a position corresponding to position 4,287 according to SEQ ID NO:3, or the complement thereof; ii) the nucleic acid sequence of the amplified nucleic acid molecule comprising a uracil at a position corresponding to position 525 according to SEQ ID NO:6, or the complement thereof; and/or iii) the nucleic acid sequence of the amplified nucleic acid molecule comprising a thymine at a position corresponding to position 525 according to SEQ ID NO:9, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising a thymine at a position corresponding to position 4,287 according to SEQ ID NO:3, or the complement thereof; the nucleotide sequence of the amplified nucleic acid molecule comprising a uracil at a position corresponding to position 525 according to SEQ ID NO:6, or the complement thereof; and/or the nucleotide sequence of the amplified nucleic acid molecule comprising a thymine at a position corresponding to position 525 according to SEQ ID NO:9, or the complement thereof; and detecting the detectable label.

In some embodiments, the determining step, detecting step, or genotyping assay comprises sequencing at least a portion of: i) the nucleotide sequence of the ANGPTL7 genomic nucleic acid molecule in the biological sample, wherein the sequenced portion comprises a position corresponding to position 4,243 according to SEQ ID NO:132, or the complement thereof; ii) the nucleotide sequence of the ANGPTL7 mRNA molecule in the biological sample, wherein the sequenced portion comprises a position corresponding to position 481 according to SEQ ID NO:135; or the complement thereof; and/or iii) the nucleotide sequence of the ANGPTL7 cDNA molecule in the biological sample, wherein the sequenced portion comprises a position corresponding to position 481 according to SEQ ID NO:138, or the complement thereof. When the sequenced portion of the ANGPTL7 genomic nucleic acid molecule in the biological sample comprises an adenine at a position corresponding to position 4,243 according to SEQ ID NO:132, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises an adenine at a position corresponding to position 481 according to SEQ ID NO:135, then the ANGPTL7 mRNA molecule in the biological sample is an ANGPTL7 predicted loss-of-function variant mRNA molecule. When the sequenced portion of the ANGPTL7 cDNA molecule in the biological sample comprises an adenine at a position corresponding to position 481 according to SEQ ID NO:138, then the ANGPTL7 cDNA molecule in the biological sample is an ANGPTL7 predicted loss-of-function variant cDNA molecule.

In some embodiments, the determining step, detecting step, or genotyping assay comprises: a) contacting the biological sample with a primer hybridizing to: i) a portion of the nucleotide sequence of the ANGPTL7 genomic nucleic acid molecule that is proximate to a position corresponding to position 4,243 according to SEQ ID NO:132; ii) a portion of the nucleotide sequence of the ANGPTL7 mRNA molecule that is proximate to a position corresponding to position 481 according to SEQ ID NO:135; and/or iii) a portion of the nucleotide sequence of the ANGPTL7 cDNA molecule that is proximate to a position corresponding to position 481 according to SEQ ID NO:138; b) extending the primer at least through: i) the position of the nucleotide sequence of the ANGPTL7 genomic nucleic acid molecule corresponding to position 4,243 according to SEQ ID NO:132; ii) the position of the nucleotide sequence of the ANGPTL7 mRNA molecule corresponding to position 481 according to SEQ ID NO:135; and/or iii) the position of the nucleotide sequence of the ANGPTL7 cDNA molecule corresponding to position 481 according to SEQ ID NO:138; and c) determining whether the extension product of the primer comprises: i) an adenine at a position corresponding to position 4,243 according to SEQ ID NO:132; ii) an adenine at a position corresponding to position 481 according to SEQ ID NO:135; and/or iii) adenine at a position corresponding to position 481 according to SEQ ID NO:138.

In some embodiments, the determining step, detecting step, or genotyping assay comprises: a) amplifying at least a portion of the nucleic acid molecule that encodes the human ANGPTL7 polypeptide, wherein the portion comprises: i) an adenine at a position corresponding to position 4,243 according to SEQ ID NO:132, or the complement thereof; ii) an adenine at a position corresponding to position 481 according to SEQ ID NO:135; and/or iii) an adenine at a position corresponding to position 481 according to SEQ ID NO:138, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising an adenine at a position corresponding to position 4,243 according to SEQ ID NO:132, or the complement thereof; ii) the nucleic acid sequence of the amplified nucleic acid molecule comprising an adenine at a position corresponding to position 481 according to SEQ ID NO:135, or the complement thereof; and/or iii) the nucleic acid sequence of the amplified nucleic acid molecule comprising an adenine at a position corresponding to position 481 according to SEQ ID NO:138, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising an adenine at a position corresponding to position 4,243 according to SEQ ID NO:132, or the complement thereof; the nucleotide sequence of the amplified nucleic acid molecule comprising an adenine at a position corresponding to position 481 according to SEQ ID NO:135, or the complement thereof; and/or the nucleotide sequence of the amplified nucleic acid molecule comprising an adenine at a position corresponding to position 481 according to SEQ ID NO:138, or the complement thereof; and detecting the detectable label.

In some embodiments, the determining step, detecting step, or genotyping assay comprises sequencing at least a portion of: i) the nucleotide sequence of the ANGPTL7 genomic nucleic acid molecule in the biological sample, wherein the sequenced portion comprises a position corresponding to position 4,325 according to SEQ ID NO:133, or the complement thereof; ii) the nucleotide sequence of the ANGPTL7 mRNA molecule in the biological sample, wherein the sequenced portion comprises a position corresponding to position 563 according to SEQ ID NO:136, or the complement thereof; and/or iii) the nucleotide sequence of the ANGPTL7 cDNA molecule in the biological sample, wherein the sequenced portion comprises a position corresponding to position 563 according to SEQ ID NO:139, or the complement thereof. When the sequenced portion of the ANGPTL7 genomic nucleic acid molecule in the biological sample comprises an adenine at a position corresponding to position 4,325 according to SEQ ID NO:133, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises an adenine at a position corresponding to position 563 according to SEQ ID NO:136, then the ANGPTL7 mRNA molecule in the biological sample is an ANGPTL7 predicted loss-of-function variant mRNA molecule. When the sequenced portion of the ANGPTL7 cDNA molecule in the biological sample comprises an adenine at a position corresponding to position 563 according to SEQ ID NO:139, then the ANGPTL7 cDNA molecule in the biological sample is an ANGPTL7 predicted loss-of-function variant cDNA molecule.

In some embodiments, the determining step, detecting step, or genotyping assay comprises: a) contacting the biological sample with a primer hybridizing to: i) a portion of the nucleotide sequence of the ANGPTL7 genomic nucleic acid molecule that is proximate to a position corresponding to position 4,325 according to SEQ ID NO:133; ii) a portion of the nucleotide sequence of the ANGPTL7 mRNA molecule that is proximate to a position corresponding to position 563 according to SEQ ID NO:136; and/or iii) a portion of the nucleotide sequence of the ANGPTL7 cDNA molecule that is proximate to a position corresponding to position 563 according to SEQ ID NO:139; b) extending the primer at least through: i) the position of the nucleotide sequence of the ANGPTL7 genomic nucleic acid molecule corresponding to position 4,325 according to SEQ ID NO:133; ii) the position of the nucleotide sequence of the ANGPTL7 mRNA molecule corresponding to position 563 according to SEQ ID NO:136 and/or iii) the position of the nucleotide sequence of the ANGPTL7 cDNA molecule corresponding to position 563 according to SEQ ID NO:139; and c) determining whether the extension product of the primer comprises: i) an adenine at a position corresponding to position 4,325 according to SEQ ID NO:133; ii) an adenine at a position corresponding to position 563 according to SEQ ID NO:136; and/or iii) an adenine at a position corresponding to position 563 according to SEQ ID NO:139.

In some embodiments, the determining step, detecting step, or genotyping assay comprises: a) amplifying at least a portion of the nucleic acid molecule that encodes the human ANGPTL7 polypeptide, wherein the portion comprises: i) an adenine at a position corresponding to position 4,325 according to SEQ ID NO:133, or the complement thereof; ii) an adenine at a position corresponding to position 563 according to SEQ ID NO:136, or the complement thereof; and/or iii) an adenine at a position corresponding to position 563 according to SEQ ID NO:139 or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising an adenine at a position corresponding to position 4,325 according to SEQ ID NO:133, or the complement thereof; ii) the nucleic acid sequence of the amplified nucleic acid molecule comprising an adenine at a position corresponding to position 563 according to SEQ ID NO:136, or the complement thereof; and/or iii) the nucleic acid sequence of the amplified nucleic acid molecule comprising an adenine at a position corresponding to position 563 according to SEQ ID NO:139, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising an adenine at a position corresponding to position 4,325 according to SEQ ID NO:133, or the complement thereof; the nucleotide sequence of the amplified nucleic acid molecule comprising an adenine at a position corresponding to position 563 according to SEQ ID NO:136, or the complement thereof; and/or the nucleotide sequence of the amplified nucleic acid molecule comprising an adenine at a position corresponding to position 563 according to SEQ ID NO:139, or the complement thereof; and detecting the detectable label.

In some embodiments, the determining step, detecting step, or genotyping assay comprises sequencing at least a portion of: i) the nucleotide sequence of the ANGPTL7 genomic nucleic acid molecule in the biological sample, wherein the sequenced portion comprises a position corresponding to position 4,336 according to SEQ ID NO:134, or the complement thereof; ii) the nucleotide sequence of the ANGPTL7 mRNA molecule in the biological sample, wherein the sequenced portion comprises a position corresponding to position 574 according to SEQ ID NO:137; or the complement thereof; and/or iii) the nucleotide sequence of the ANGPTL7 cDNA molecule in the biological sample, wherein the sequenced portion comprises a position corresponding to position 574 according to SEQ ID NO:140, or the complement thereof. When the sequenced portion of the ANGPTL7 genomic nucleic acid molecule in the biological sample comprises a cytosine at a position corresponding to position 4,336 according to SEQ ID NO:134, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises a cytosine at a position corresponding to position 574 according to SEQ ID NO:137, then the ANGPTL7 mRNA molecule in the biological sample is an ANGPTL7 predicted loss-of-function variant mRNA molecule. When the sequenced portion of the ANGPTL7 cDNA molecule in the biological sample comprises a cytosine at a position corresponding to position 574 according to SEQ ID NO:140, then the ANGPTL7 cDNA molecule in the biological sample is an ANGPTL7 predicted loss-of-function variant cDNA molecule.

In some embodiments, the determining step, detecting step, or genotyping assay comprises: a) contacting the biological sample with a primer hybridizing to: i) a portion of the nucleotide sequence of the ANGPTL7 genomic nucleic acid molecule that is proximate to a position corresponding to position 4,336 according to SEQ ID NO:134; ii) a portion of the nucleotide sequence of the ANGPTL7 mRNA molecule that is proximate to a position corresponding to position 574 according to SEQ ID NO:137; and/or iii) a portion of the nucleotide sequence of the ANGPTL7 cDNA molecule that is proximate to a position corresponding to position 574 according to SEQ ID NO:140; b) extending the primer at least through: i) the position of the nucleotide sequence of the ANGPTL7 genomic nucleic acid molecule corresponding to position 4,336 according to SEQ ID NO:134; ii) the position of the nucleotide sequence of the ANGPTL7 mRNA molecule corresponding to position 574 according to SEQ ID NO:137; and/or iii) the position of the nucleotide sequence of the ANGPTL7 cDNA molecule corresponding to position 574 according to SEQ ID NO:140; and c) determining whether the extension product of the primer comprises: i) a cytosine at a position corresponding to position 4,336 according to SEQ ID NO:134; ii) a cytosine at a position corresponding to position 574 according to SEQ ID NO:137; and/or iii) a cytosine at a position corresponding to position 574 according to SEQ ID NO:140.

In some embodiments, the determining step, detecting step, or genotyping assay comprises: a) amplifying at least a portion of the nucleic acid molecule that encodes the human ANGPTL7 polypeptide, wherein the portion comprises: i) a cytosine at a position corresponding to position 4,336 according to SEQ ID NO:134, or the complement thereof; ii) a cytosine at a position corresponding to position 574 according to SEQ ID NO:137; and/or iii) a cytosine at a position corresponding to position 574 according to SEQ ID NO:140, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a cytosine at a position corresponding to position 4,336 according to SEQ ID NO:134, or the complement thereof; ii) the nucleic acid sequence of the amplified nucleic acid molecule comprising a cytosine at a position corresponding to position 574 according to SEQ ID NO:137, or the complement thereof; and/or iii) the nucleic acid sequence of the amplified nucleic acid molecule comprising a cytosine at a position corresponding to position 574 according to SEQ ID NO:140, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising a cytosine at a position corresponding to position 4,336 according to SEQ ID NO:134, or the complement thereof; the nucleotide sequence of the amplified nucleic acid molecule comprising a cytosine at a position corresponding to position 574 according to SEQ ID NO:139, or the complement thereof; and/or the nucleotide sequence of the amplified nucleic acid molecule comprising a cytosine at a position corresponding to position 574 according to SEQ ID NO:140, or the complement thereof; and detecting the detectable label.

In any of these embodiments, the nucleic acid molecule can be present within a cell obtained from the human subject.

In any of the embodiments described herein, the ophthalmic condition is increased IOP, pre-glaucoma, glaucoma, or decreased corneal hysteresis. In some embodiments, the ophthalmic condition is increased IOP. In some embodiments, the increased IOP is IOPcc or IOPg. In some embodiments, the ophthalmic condition is pre-glaucoma. In some embodiments, the ophthalmic condition is glaucoma. In some embodiments, the glaucoma is primary open-angle glaucoma, angle-closure glaucoma, normal-tension glaucoma, congenital glaucoma, neovascular glaucoma, steroid-induced glaucoma, or glaucoma related to ocular trauma. In some embodiments, the ophthalmic condition is decreased corneal hysteresis.

For human subjects or patients that are genotyped or determined to be either ANGPTL7 reference or heterozygous for an ANGPTL7 predicted loss-of-function variant, such human subjects or patients can be treated with an ANGPTL7 inhibitor, as described herein.

Examples of therapeutic agents that treat or inhibit the ophthalmic condition include, but are not limited to: a prostaglandin, a beta blocker, an alpha-adrenergic agonist, a carbonic anhydrase inhibitor, a rho kinase inhibitor, or a miotic or cholinergic agent.

In some embodiments, the therapeutic agent that treats or inhibits the ophthalmic condition is a prostaglandin. In some embodiments, the prostaglandin is Xalatan® (latanoprost), Travatan Z® (travoprost), Zioptan® (tafluprost), Lumigan® (bimatoprost), or Vyzulta® (latanoprostene bunod).

In some embodiments, the therapeutic agent that treats or inhibits the ophthalmic condition is a beta blocker. In some embodiments, the beta blocker is Betimol®, Istalol®, or Timoptic® (timolol) or Betoptic® (betaxolol).

In some embodiments, the therapeutic agent that treats or inhibits the ophthalmic condition is an alpha-adrenergic agonist. In some embodiments, the alpha-adrenergic agonist is Lopidine® (apraclonidine) or Alphagan® or Qoliana® (brimonidine).

In some embodiments, the therapeutic agent that treats or inhibits the ophthalmic condition is a carbonic anhydrase inhibitor. In some embodiments, the carbonic anhydrase inhibitor is Trusopt® (dorzolamide) or Azopt® (brinzolamide).

In some embodiments, the therapeutic agent that treats or inhibits the ophthalmic condition is a rho kinase inhibitor. In some embodiments, the rho kinase inhibitor is Rhopressa® (netarsudil).

In some embodiments, the therapeutic agent that treats or inhibits the ophthalmic condition is a miotic or cholinergic agent. In some embodiments, the miotic or cholinergic agent is Isopto® Carpine (pilocarpine).

In some embodiments, the dose of the therapeutic agents that treat or inhibit the ophthalmic condition can be reduced by about 10%, by about 20%, by about 30%, by about 40%, by about 50%, by about 60%, by about 70%, by about 80%, or by about 90% for patients or human subjects that are heterozygous for an ANGPTL7 predicted loss-of-function variant (i.e., a lower than the standard dosage amount) compared to patients or human subjects that are ANGPTL7 reference (who may receive a standard dosage amount). In some embodiments, the dose of the therapeutic agents that treat or inhibit the ophthalmic condition can be reduced by about 10%, by about 20%, by about 30%, by about 40%, or by about 50%. In addition, the dose of therapeutic agents that treat or inhibit the ophthalmic condition in patients or human subjects that are heterozygous for an ANGPTL7 predicted loss-of-function variant can be administered less frequently compared to patients or human subjects that are ANGPTL7 reference.

Administration of the therapeutic agents that treat or inhibit the ophthalmic condition and/or ANGPTL7 inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a patient can receive therapy for a prolonged period of time such as, for example, 6 months, 1 year, or more.

Administration of the therapeutic agents that treat or inhibit the ophthalmic condition and/or ANGPTL7 inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in an ophthalmic condition, a decrease/reduction in the severity of an ophthalmic condition (such as, for example, a reduction or inhibition of development or an ophthalmic condition), a decrease/reduction in symptoms and ophthalmic condition-related effects, delaying the onset of symptoms and ophthalmic condition-related effects, reducing the severity of symptoms of the ophthalmic condition-related effects, reducing the severity of an acute episode, reducing the number of symptoms and ophthalmic condition-related effects, reducing the latency of symptoms and ophthalmic condition-related effects, an amelioration of symptoms and ophthalmic condition-related effects, reducing secondary symptoms, reducing secondary infections, preventing relapse to an ophthalmic condition, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of ophthalmic condition development/progression (such as, for example, a complete or partial avoidance/inhibition or a delay), and an increased survival time of the affected host animal, following administration of a therapeutic protocol. Treatment of an ophthalmic condition encompasses the treatment of patients already diagnosed as having any form of the ophthalmic condition at any clinical stage or manifestation, the delay of the onset or evolution or aggravation or deterioration of the symptoms or signs of the ophthalmic condition, and/or preventing and/or reducing the severity of the ophthalmic condition.

In some embodiments, the detecting step comprises sequencing at least a portion of the polypeptide that comprises positions corresponding to any positions that are C-terminal to position 176 according to SEQ ID NO:11. In some embodiments, the detecting step comprises sequencing the entire polypeptide. In some embodiments, the detecting step comprises an immunoassay for detecting the presence of a polypeptide that comprises positions corresponding to any positions that are C-terminal to position 176 according to SEQ ID NO:11.

In some embodiments, the detecting step comprises sequencing at least a portion of the polypeptide that comprises a position corresponding to position 175 according to SEQ ID NO:10 or SEQ ID NO:12. In some embodiments, the detecting step comprises sequencing the entire polypeptide. In some embodiments, the detecting step comprises an immunoassay for detecting the presence of a polypeptide that comprises a position corresponding to position 175 according to SEQ ID NO:10 or SEQ ID NO:12.

In some embodiments, the detecting step comprises sequencing at least a portion of the polypeptide that comprises a position corresponding to position 161 according to SEQ ID NO:141 or SEQ ID NO:10. In some embodiments, the detecting step comprises sequencing the entire polypeptide. In some embodiments, the detecting step comprises an immunoassay for detecting the presence of a polypeptide that comprises a position corresponding to position 161 according to SEQ ID NO:141 or SEQ ID NO:10.

In some embodiments, the detecting step comprises sequencing at least a portion of the polypeptide that comprises positions corresponding to any positions that are C-terminal to position 187 according to SEQ ID NO:142. In some embodiments, the detecting step comprises sequencing the entire polypeptide. In some embodiments, the detecting step comprises an immunoassay for detecting the presence of a polypeptide that comprises positions corresponding to any positions that are C-terminal to position 187 according to SEQ ID NO:142.

In some embodiments, the detecting step comprises sequencing at least a portion of the polypeptide that comprises a position corresponding to position 192 according to SEQ ID NO:143 or SEQ ID NO:10. In some embodiments, the detecting step comprises sequencing the entire polypeptide. In some embodiments, the detecting step comprises an immunoassay for detecting the presence of a polypeptide that comprises a position corresponding to position 192 according to SEQ ID NO:143 or SEQ ID NO:10.

The present disclosure also provides methods of identifying a human subject having an increased risk for developing an ophthalmic condition, wherein the method comprises: determining or having determined in a biological sample obtained from the subject the presence or absence of an ANGPTL7 predicted loss-of-function variant nucleic acid molecule (such as a genomic nucleic acid molecule, mRNA molecule, and/or cDNA molecule) encoding a human ANGPTL7 polypeptide; wherein: i) when the human subject lacks an ANGPTL7 predicted loss-of-function variant nucleic acid molecule (i.e., the human subject is genotypically categorized as an ANGPTL7 reference), then the human subject has an increased risk for developing an ophthalmic condition; and ii) when the human subject has an ANGPTL7 predicted loss-of-function variant nucleic acid molecule (i.e., the human subject is categorized as heterozygous for an ANGPTL7 predicted loss-of-function variant or homozygous for an ANGPTL7 predicted loss-of-function variant), then the human subject has a decreased risk for developing an ophthalmic condition. Having a single copy of an ANGPTL7 predicted loss-of-function variant nucleic acid molecule confers protection to a human subject from developing an ophthalmic condition.

Without intending to be limited to any particular theory or mechanism of action, it is believed that a single copy of an ANGPTL7 predicted loss-of-function variant nucleic acid molecule (i.e., heterozygous for an ANGPTL7 predicted loss-of-function variant) confers protection to a human subject from developing an ophthalmic condition, and it is also believed that having two copies of an ANGPTL7 predicted loss-of-function variant nucleic acid molecule (i.e., homozygous for an ANGPTL7 predicted loss-of-function variant) may confer more protection of a human subject from developing an ophthalmic condition, relative to a human subject with a single copy. Thus, in some embodiments, a single copy of an ANGPTL7 predicted loss-of-function variant nucleic acid molecule may not be completely protective, but instead, may be partially or incompletely protective of a human subject from developing an ophthalmic condition. While not desiring to be bound by any particular theory, there may be additional factors or molecules involved in the development of ophthalmic conditions that are still present in a human subject having a single copy of an ANGPTL7 predicted loss-of-function variant nucleic acid molecule, thus resulting in less than complete protection from the development of an ophthalmic condition.

The present disclosure also provides methods of identifying a human subject having an increased risk for developing an ophthalmic condition, wherein the method comprises: detecting the presence or absence of an ANGPTL7 predicted loss-of-function variant nucleic acid molecule encoding a human ANGPTL7 polypeptide in a biological sample from the patient, wherein the ANGPTL7 predicted loss-of-function variant nucleic acid molecule is: i) a genomic nucleic acid molecule having a nucleotide sequence comprising a thymine at a position corresponding to position 4,291 according to SEQ ID NO:2, or the complement thereof; ii) an mRNA molecule having a nucleotide sequence comprising a uracil at a position corresponding to position 529 according to SEQ ID NO:5, or the complement thereof; or iii) a cDNA molecule produced from an mRNA molecule, wherein the cDNA molecule has a nucleotide sequence comprising a thymine at a position corresponding to position 529 according to SEQ ID NO:8, or the complement thereof; wherein: when the human subject is ANGPTL7 reference, then the human subject has an increased risk for developing an ophthalmic condition; and when the human subject is heterozygous for an ANGPTL7 predicted loss-of-function variant or homozygous for an ANGPTL7 predicted loss-of-function variant, then the human subject has a decreased risk for developing an ophthalmic condition. In some embodiments, the patient is ANGPTL7 reference. In some embodiments, the patient is heterozygous for an ANGPTL7 predicted loss-of-function variant.

The present disclosure also provides methods of identifying a human subject having an increased risk for developing an ophthalmic condition, wherein the method comprises: detecting the presence or absence of an ANGPTL7 predicted loss-of-function variant nucleic acid molecule encoding a human ANGPTL7 polypeptide in a biological sample from the patient, wherein the ANGPTL7 predicted loss-of-function variant nucleic acid molecule is: i) a genomic nucleic acid molecule having a nucleotide sequence comprising a thymine at a position corresponding to position 4,287 according to SEQ ID NO:3, or the complement thereof; ii) an mRNA molecule having a nucleotide sequence comprising a uracil at a position corresponding to position 525 according to SEQ ID NO:6, or the complement thereof; or iii) a cDNA molecule produced from an mRNA molecule, wherein the cDNA molecule has a nucleotide sequence comprising a thymine at a position corresponding to position 525 according to SEQ ID NO:9, or the complement thereof; wherein: when the human subject is ANGPTL7 reference, then the human subject has an increased risk for developing an ophthalmic condition; and when the human subject is heterozygous for an ANGPTL7 predicted loss-of-function variant or homozygous for an ANGPTL7 predicted loss-of-function variant, then the human subject has a decreased risk for developing an ophthalmic condition. In some embodiments, the patient is ANGPTL7 reference. In some embodiments, the patient is heterozygous for an ANGPTL7 predicted loss-of-function variant.

The present disclosure also provides methods of identifying a human subject having an increased risk for developing an ophthalmic condition, wherein the method comprises: detecting the presence or absence of an ANGPTL7 predicted loss-of-function variant nucleic acid molecule encoding a human ANGPTL7 polypeptide in a biological sample from the patient, wherein the ANGPTL7 predicted loss-of-function variant nucleic acid molecule is: i) a genomic nucleic acid molecule having a nucleotide sequence comprising an adenine at a position corresponding to position 4,243 according to SEQ ID NO:132, or the complement thereof; ii) an mRNA molecule having a nucleotide sequence comprising an adenine at a position corresponding to position 481 according to SEQ ID NO:135, or the complement thereof; or iii) a cDNA molecule produced from an mRNA molecule, wherein the cDNA molecule has a nucleotide sequence comprising an adenine at a position corresponding to position 481 according to SEQ ID NO:138, or the complement thereof; wherein: when the human subject is ANGPTL7 reference, then the human subject has an increased risk for developing an ophthalmic condition; and when the human subject is heterozygous for an ANGPTL7 predicted loss-of-function variant or homozygous for an ANGPTL7 predicted loss-of-function variant, then the human subject has a decreased risk for developing an ophthalmic condition. In some embodiments, the patient is ANGPTL7 reference. In some embodiments, the patient is heterozygous for an ANGPTL7 predicted loss-of-function variant.

The present disclosure also provides methods of identifying a human subject having an increased risk for developing an ophthalmic condition, wherein the method comprises: detecting the presence or absence of an ANGPTL7 predicted loss-of-function variant nucleic acid molecule encoding a human ANGPTL7 polypeptide in a biological sample from the patient, wherein the ANGPTL7 predicted loss-of-function variant nucleic acid molecule is: i) a genomic nucleic acid molecule having a nucleotide sequence comprising an adenine at a position corresponding to position 4,325 according to SEQ ID NO:133, or the complement thereof; ii) an mRNA molecule having a nucleotide sequence comprising an adenine at a position corresponding to position 563 according to SEQ ID NO:136, or the complement thereof; or iii) a cDNA molecule produced from an mRNA molecule, wherein the cDNA molecule has a nucleotide sequence comprising an adenine at a position corresponding to position 563 according to SEQ ID NO:139, or the complement thereof; wherein: when the human subject is ANGPTL7 reference, then the human subject has an increased risk for developing an ophthalmic condition; and when the human subject is heterozygous for an ANGPTL7 predicted loss-of-function variant or homozygous for an ANGPTL7 predicted loss-of-function variant, then the human subject has a decreased risk for developing an ophthalmic condition. In some embodiments, the patient is ANGPTL7 reference. In some embodiments, the patient is heterozygous for an ANGPTL7 predicted loss-of-function variant.

The present disclosure also provides methods of identifying a human subject having an increased risk for developing an ophthalmic condition, wherein the method comprises: detecting the presence or absence of an ANGPTL7 predicted loss-of-function variant nucleic acid molecule encoding a human ANGPTL7 polypeptide in a biological sample from the patient, wherein the ANGPTL7 predicted loss-of-function variant nucleic acid molecule is: i) a genomic nucleic acid molecule having a nucleotide sequence comprising a cytosine at a position corresponding to position 4,336 according to SEQ ID NO:134, or the complement thereof; ii) an mRNA molecule having a nucleotide sequence comprising a cytosine at a position corresponding to position 574 according to SEQ ID NO:137, or the complement thereof; or iii) a cDNA molecule produced from an mRNA molecule, wherein the cDNA molecule has a nucleotide sequence comprising a cytosine at a position corresponding to position 574 according to SEQ ID NO:140, or the complement thereof; wherein: when the human subject is ANGPTL7 reference, then the human subject has an increased risk for developing an ophthalmic condition; and when the human subject is heterozygous for an ANGPTL7 predicted loss-of-function variant or homozygous for an ANGPTL7 predicted loss-of-function variant, then the human subject has a decreased risk for developing an ophthalmic condition. In some embodiments, the patient is ANGPTL7 reference. In some embodiments, the patient is heterozygous for an ANGPTL7 predicted loss-of-function variant.

The ANGPTL7 predicted loss-of-function variant nucleic acid molecule can be any ANGPTL7 nucleic acid molecule (such as, for example, genomic nucleic acid molecule, mRNA molecule, or cDNA molecule) encoding an ANGPTL7 polypeptide having a partial loss-of-function, a complete loss-of-function, a predicted partial loss-of-function, or a predicted complete loss-of-function. For example, the ANGPTL7 predicted loss-of-function variant nucleic acid molecule can be any nucleic acid molecule encoding ANGPTL7 Gln175His, Arg177Stop, Trp188Stop, Lys192Gln, Phe161Ile, Arg340His, Arg220His, Asn302Lys, or Arg220Cys. In some embodiments, the ANGPTL7 predicted loss-of-function variant nucleic acid molecule encodes ANGPTL7 Gln175His, Arg177Stop, Trp188Stop, Lys192Gln, or Phe161Ile. In some embodiments, the ANGPTL7 predicted loss-of-function variant nucleic acid molecule encodes ANGPTL7 Gln175His, Trp188Stop, or Arg177Stop. In some embodiments, the ANGPTL7 predicted loss-of-function variant nucleic acid molecule encodes ANGPTL7 Gln175His. In some embodiments, the ANGPTL7 predicted loss-of-function variant nucleic acid molecule encodes ANGPTL7 Arg177Stop. In some embodiments, the ANGPTL7 predicted loss-of-function variant nucleic acid molecule encodes ANGPTL7 Trp188Stop. In some embodiments, the ANGPTL7 predicted loss-of-function variant nucleic acid molecule encodes ANGPTL7 Lys192Gln. In some embodiments, the ANGPTL7 predicted loss-of-function variant nucleic acid molecule encodes ANGPTL7 Phe161Ile.

In any of the embodiments described herein, the ophthalmic condition is increased IOP, pre-glaucoma, glaucoma, or decreased corneal hysteresis. In some embodiments, the ophthalmic condition is increased IOP. In some embodiments, the increased IOP is IOPcc or IOPg. In some embodiments, the ophthalmic condition is pre-glaucoma. In some embodiments, the ophthalmic condition is glaucoma. In some embodiments, the glaucoma is primary open-angle glaucoma, angle-closure glaucoma, normal-tension glaucoma, congenital glaucoma, neovascular glaucoma, steroid-induced glaucoma, or glaucoma related to ocular trauma. In some embodiments, the ophthalmic condition is decreased corneal hysteresis.

Determining or having determined in a sample obtained from the subject the presence or absence of the particular nucleic acid molecules can be carried out by any of the methods described herein. In some embodiments, these methods can be carried out in vitro. In some embodiments, these methods can be carried out in situ. In some embodiments, these methods can be carried out in vivo.

In some embodiments, the determining step comprises sequencing at least a portion of: i) the nucleotide sequence of the ANGPTL7 genomic nucleic acid molecule in the biological sample, wherein the sequenced portion comprises a position corresponding to position 4,291 according to SEQ ID NO:2, or the complement thereof; ii) the nucleotide sequence of the ANGPTL7 mRNA molecule in the biological sample, wherein the sequenced portion comprises a position corresponding to position 529 according to SEQ ID NO:5, or the complement thereof; and/or iii) the nucleotide sequence of the ANGPTL7 cDNA molecule in the biological sample, wherein the sequenced portion comprises a position corresponding to position 529 according to SEQ ID NO:8, or the complement thereof. When the sequenced portion of the ANGPTL7 genomic nucleic acid molecule in the biological sample comprises a thymine at a position corresponding to position 4,291 according to SEQ ID NO:2, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises a uracil at a position corresponding to position 529 according to SEQ ID NO:5, then the ANGPTL7 mRNA molecule in the biological sample is an ANGPTL7 predicted loss-of-function variant mRNA molecule. When the sequenced portion of the ANGPTL7 cDNA molecule in the biological sample comprises a thymine at a position corresponding to position 529 according to SEQ ID NO:8, then the ANGPTL7 cDNA molecule in the biological sample is an ANGPTL7 predicted loss-of-function variant cDNA molecule.

In some embodiments, the determining step comprises: a) contacting the biological sample with a primer hybridizing to: i) a portion of the nucleotide sequence of the ANGPTL7 genomic nucleic acid molecule that is proximate to a position corresponding to position 4,291 according to SEQ ID NO:2; ii) a portion of the nucleotide sequence of the ANGPTL7 mRNA molecule that is proximate to a position corresponding to position 529 according to SEQ ID NO:5; and/or iii) a portion of the nucleotide sequence of the ANGPTL7 cDNA molecule that is proximate to a position corresponding to position 529 according to SEQ ID NO:8; b) extending the primer at least through: i) the position of the nucleotide sequence of the ANGPTL7 genomic nucleic acid molecule corresponding to position 4,291 according to SEQ ID NO:2; ii) the position of the nucleotide sequence of the ANGPTL7 mRNA molecule corresponding to position 529 according to SEQ ID NO:5; and/or iii) the position of the nucleotide sequence of the ANGPTL7 cDNA molecule corresponding to position 529 according to SEQ ID NO:8;

and c) determining whether the extension product of the primer comprises: i) a thymine at a position corresponding to position 4,291 according to SEQ ID NO:2; ii) a uracil at a position corresponding to position 529 according to SEQ ID NO:5; and/or iii) a thymine at a position corresponding to position 529 according to SEQ ID NO:8.

In some embodiments, the determining step comprises: a) amplifying at least a portion of the nucleic acid molecule that encodes the human ANGPTL7 polypeptide, wherein the portion comprises: i) a thymine at a position corresponding to position 4,291 according to SEQ ID NO:2, or the complement thereof; ii) a uracil at a position corresponding to position 529 according to SEQ ID NO:5, or the complement thereof; or iii) a thymine at a position corresponding to position 529 according to SEQ ID NO:8, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a thymine at a position corresponding to position 4,291 according to SEQ ID NO:2, or the complement thereof; ii) the nucleic acid sequence of the amplified nucleic acid molecule comprising a uracil at a position corresponding to position 529 according to SEQ ID NO:5, or the complement thereof; or iii) the nucleic acid sequence of the amplified nucleic acid molecule comprising a thymine at a position corresponding to position 529 according to SEQ ID NO:8, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the determining step comprises: contacting the nucleic acid molecule in the biological sample with an alteration-specific probe comprising a detectable label, wherein the alteration-specific probe comprises a nucleotide sequence which hybridizes under stringent conditions to: i) the nucleotide sequence of the amplified nucleic acid molecule comprising a thymine at a position corresponding to position 4,291 according to SEQ ID NO:2, or the complement thereof; ii) the nucleotide sequence of the amplified nucleic acid molecule comprising a uracil at a position corresponding to position 529 according to SEQ ID NO:5, or the complement thereof; or iii) the nucleotide sequence of the amplified nucleic acid molecule comprising a thymine at a position corresponding to position 529 according to SEQ ID NO:8, or the complement thereof; and detecting the detectable label.

In some embodiments, the determining step comprises sequencing at least a portion of: i) the nucleotide sequence of the ANGPTL7 genomic nucleic acid molecule in the biological sample, wherein the sequenced portion comprises a position corresponding to position 4,287 according to SEQ ID NO:3, or the complement thereof; ii) the nucleotide sequence of the ANGPTL7 mRNA molecule in the biological sample, wherein the sequenced portion comprises a position corresponding to position 525 according to SEQ ID NO:6, or the complement thereof; and/or iii) the nucleotide sequence of the ANGPTL7 cDNA molecule in the biological sample, wherein the sequenced portion comprises a position corresponding to position 525 according to SEQ ID NO:9, or the complement thereof. When the sequenced portion of the ANGPTL7 genomic nucleic acid molecule in the biological sample comprises a thymine at a position corresponding to position 4,287 according to SEQ ID NO:3, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises a uracil at a position corresponding to position 525 according to SEQ ID NO:6, then the ANGPTL7 mRNA molecule in the biological sample is an ANGPTL7 predicted loss-of-function variant mRNA molecule. When the sequenced portion of the ANGPTL7 cDNA molecule in the biological sample comprises a thymine at a position corresponding to position 525 according to SEQ ID NO:9, then the ANGPTL7 cDNA molecule in the biological sample is an ANGPTL7 predicted loss-of-function variant cDNA molecule.

In some embodiments, the determining step comprises: a) contacting the biological sample with a primer hybridizing to: i) a portion of the nucleotide sequence of the ANGPTL7 genomic nucleic acid molecule that is proximate to a position corresponding to position 4,287 according to SEQ ID NO:3; ii) a portion of the nucleotide sequence of the ANGPTL7 mRNA molecule that is proximate to a position corresponding to position 525 according to SEQ ID NO:6; and/or iii) a portion of the nucleotide sequence of the ANGPTL7 cDNA molecule that is proximate to a position corresponding to position 525 according to SEQ ID NO:9; b) extending the primer at least through: i) the position of the nucleotide sequence of the ANGPTL7 genomic nucleic acid molecule corresponding to position 4,287 according to SEQ ID NO:3; ii) the position of the nucleotide sequence of the ANGPTL7 mRNA molecule corresponding to position 525 according to SEQ ID NO:6; and/or iii) the position of the nucleotide sequence of the ANGPTL7 cDNA molecule corresponding to position 525 according to SEQ ID NO:9; and c) determining whether the extension product of the primer comprises: i) a thymine at a position corresponding to position 4,287 according to SEQ ID NO:3; ii) a uracil at a position corresponding to position 525 according to SEQ ID NO:6; and/or iii) a thymine at a position corresponding to position 525 according to SEQ ID NO:9.

In some embodiments, the determining step comprises: a) amplifying at least a portion of the nucleic acid molecule that encodes the human ANGPTL7 polypeptide, wherein the portion comprises: i) a thymine at a position corresponding to position 4,287 according to SEQ ID NO:3, or the complement thereof; ii) a uracil at a position corresponding to position 525 according to SEQ ID NO:6, or the complement thereof; or iii) a thymine at a position corresponding to position 525 according to SEQ ID NO:9, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a thymine at a position corresponding to position 4,287 according to SEQ ID NO:3, or the complement thereof; ii) the nucleic acid sequence of the amplified nucleic acid molecule comprising a uracil at a position corresponding to position 525 according to SEQ ID NO:6, or the complement thereof; or iii) the nucleic acid sequence of the amplified nucleic acid molecule comprising a thymine at a position corresponding to position 525 according to SEQ ID NO:9, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the determining step comprises: contacting the nucleic acid molecule in the biological sample with an alteration-specific probe comprising a detectable label, wherein the alteration-specific probe comprises a nucleotide sequence which hybridizes under stringent conditions to: i) the nucleotide sequence of the amplified nucleic acid molecule comprising a thymine at a position corresponding to position 4,287 according to SEQ ID NO:3, or the complement thereof; ii) the nucleotide sequence of the amplified nucleic acid molecule comprising a uracil at a position corresponding to position 525 according to SEQ ID NO:6, or the complement thereof; or iii) the nucleotide sequence of the amplified nucleic acid molecule comprising a thymine at a position corresponding to position 525 according to SEQ ID NO:9, or the complement thereof; and detecting the detectable label.

In some embodiments, determining step comprises sequencing at least a portion of: i) the nucleotide sequence of the ANGPTL7 genomic nucleic acid molecule in the biological sample, wherein the sequenced portion comprises a position corresponding to position 4,243 according to SEQ ID NO:132, or the complement thereof; ii) the nucleotide sequence of the ANGPTL7 mRNA molecule in the biological sample, wherein the sequenced portion comprises a position corresponding to position 481 according to SEQ ID NO:135; or the complement thereof; and/or iii) the nucleotide sequence of the ANGPTL7 cDNA molecule in the biological sample, wherein the sequenced portion comprises a position corresponding to position 481 according to SEQ ID NO:138, or the complement thereof. When the sequenced portion of the ANGPTL7 genomic nucleic acid molecule in the biological sample comprises an adenine at a position corresponding to position 4,243 according to SEQ ID NO:132, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises an adenine at a position corresponding to position 481 according to SEQ ID NO:135, then the ANGPTL7 mRNA molecule in the biological sample is an ANGPTL7 predicted loss-of-function variant mRNA molecule. When the sequenced portion of the ANGPTL7 cDNA molecule in the biological sample comprises an adenine at a position corresponding to position 481 according to SEQ ID NO:138, then the ANGPTL7 cDNA molecule in the biological sample is an ANGPTL7 predicted loss-of-function variant cDNA molecule.

In some embodiments, the determining step comprises: a) contacting the biological sample with a primer hybridizing to i) a portion of the nucleotide sequence of the ANGPTL7 genomic nucleic acid molecule that is proximate to a position corresponding to position 4,243 according to SEQ ID NO:132; ii) a portion of the nucleotide sequence of the ANGPTL7 mRNA molecule that is proximate to a position corresponding to position 481 according to SEQ ID NO:135; and/or iii) a portion of the nucleotide sequence of the ANGPTL7 cDNA molecule that is proximate to a position corresponding to position 481 according to SEQ ID NO:138; b) extending the primer at least through: i) the position of the nucleotide sequence of the ANGPTL7 genomic nucleic acid molecule corresponding to position 4,243 according to SEQ ID NO:132; ii) the position of the nucleotide sequence of the ANGPTL7 mRNA molecule corresponding to position 481 according to SEQ ID NO:135; and/or iii) the position of the nucleotide sequence of the ANGPTL7 cDNA molecule corresponding to position 481 according to SEQ ID NO:138; and c) determining whether the extension product of the primer comprises: i) an adenine at a position corresponding to position 4,243 according to SEQ ID NO:132; ii) an adenine at a position corresponding to position 481 according to SEQ ID NO:135; and/or iii) adenine at a position corresponding to position 481 according to SEQ ID NO:138.

In some embodiments, the determining step comprises: a) amplifying at least a portion of the nucleic acid molecule that encodes the human ANGPTL7 polypeptide, wherein the portion comprises: i) an adenine at a position corresponding to position 4,243 according to SEQ ID NO:132, or the complement thereof; ii) an adenine at a position corresponding to position 481 according to SEQ ID NO:135; and/or iii) an adenine at a position corresponding to position 481 according to SEQ ID NO:138, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising an adenine at a position corresponding to position 4,243 according to SEQ ID NO:132, or the complement thereof; ii) the nucleic acid sequence of the amplified nucleic acid molecule comprising an adenine at a position corresponding to position 481 according to SEQ ID NO:135, or the complement thereof; and/or iii) the nucleic acid sequence of the amplified nucleic acid molecule comprising an adenine at a position corresponding to position 481 according to SEQ ID NO:138, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the determining step comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising an adenine at a position corresponding to position 4,243 according to SEQ ID NO:132, or the complement thereof; the nucleotide sequence of the amplified nucleic acid molecule comprising an adenine at a position corresponding to position 481 according to SEQ ID NO:135, or the complement thereof; and/or the nucleotide sequence of the amplified nucleic acid molecule comprising an adenine at a position corresponding to position 481 according to SEQ ID NO:138, or the complement thereof; and detecting the detectable label.

In some embodiments, the determining step comprises sequencing at least a portion of: i) the nucleotide sequence of the ANGPTL7 genomic nucleic acid molecule in the biological sample, wherein the sequenced portion comprises a position corresponding to position 4,325 according to SEQ ID NO:133, or the complement thereof; ii) the nucleotide sequence of the ANGPTL7 mRNA molecule in the biological sample, wherein the sequenced portion comprises a position corresponding to position 563 according to SEQ ID NO:136, or the complement thereof; and/or iii) the nucleotide sequence of the ANGPTL7 cDNA molecule in the biological sample, wherein the sequenced portion comprises a position corresponding to position 563 according to SEQ ID NO:139, or the complement thereof. When the sequenced portion of the ANGPTL7 genomic nucleic acid molecule in the biological sample comprises an adenine at a position corresponding to position 4,325 according to SEQ ID NO:133, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises an adenine at a position corresponding to position 563 according to SEQ ID NO:136, then the ANGPTL7 mRNA molecule in the biological sample is an ANGPTL7 predicted loss-of-function variant mRNA molecule. When the sequenced portion of the ANGPTL7 cDNA molecule in the biological sample comprises an adenine at a position corresponding to position 563 according to SEQ ID NO:139, then the ANGPTL7 cDNA molecule in the biological sample is an ANGPTL7 predicted loss-of-function variant cDNA molecule.

In some embodiments, the determining step comprises: a) contacting the biological sample with a primer hybridizing to: i) a portion of the nucleotide sequence of the ANGPTL7 genomic nucleic acid molecule that is proximate to a position corresponding to position 4,325 according to SEQ ID NO:133; ii) a portion of the nucleotide sequence of the ANGPTL7 mRNA molecule that is proximate to a position corresponding to position 563 according to SEQ ID NO:136; and/or iii) a portion of the nucleotide sequence of the ANGPTL7 cDNA molecule that is proximate to a position corresponding to position 563 according to SEQ ID NO:139; b) extending the primer at least through: i) the position of the nucleotide sequence of the ANGPTL7 genomic nucleic acid molecule corresponding to position 4,325 according to SEQ ID NO:133; ii) the position of the nucleotide sequence of the ANGPTL7 mRNA molecule corresponding to position 563 according to SEQ ID NO:136 and/or iii) the position of the nucleotide sequence of the ANGPTL7 cDNA molecule corresponding to position 563 according to SEQ ID NO:139; and c) determining whether the extension product of the primer comprises: i) an adenine at a position corresponding to position 4,325 according to SEQ ID NO:133; ii) an adenine at a position corresponding to position 563 according to SEQ ID NO:136; and/or iii) an adenine at a position corresponding to position 563 according to SEQ ID NO:139.

In some embodiments, the determining step comprises: a) amplifying at least a portion of the nucleic acid molecule that encodes the human ANGPTL7 polypeptide, wherein the portion comprises: i) an adenine at a position corresponding to position 4,325 according to SEQ ID NO:133, or the complement thereof; ii) an adenine at a position corresponding to position 563 according to SEQ ID NO:136, or the complement thereof; and/or iii) an adenine at a position corresponding to position 563 according to SEQ ID NO:139 or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising an adenine at a position corresponding to position 4,325 according to SEQ ID NO:133, or the complement thereof; ii) the nucleic acid sequence of the amplified nucleic acid molecule comprising an adenine at a position corresponding to position 563 according to SEQ ID NO:136, or the complement thereof; and/or iii) the nucleic acid sequence of the amplified nucleic acid molecule comprising an adenine at a position corresponding to position 563 according to SEQ ID NO:139, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the determining step comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising an adenine at a position corresponding to position 4,325 according to SEQ ID NO:133, or the complement thereof; the nucleotide sequence of the amplified nucleic acid molecule comprising an adenine at a position corresponding to position 563 according to SEQ ID NO:136, or the complement thereof; and/or the nucleotide sequence of the amplified nucleic acid molecule comprising an adenine at a position corresponding to position 563 according to SEQ ID NO:139, or the complement thereof; and detecting the detectable label.

In some embodiments, the determining step comprises sequencing at least a portion of: i) the nucleotide sequence of the ANGPTL7 genomic nucleic acid molecule in the biological sample, wherein the sequenced portion comprises a position corresponding to position 4,336 according to SEQ ID NO:134, or the complement thereof; ii) the nucleotide sequence of the ANGPTL7 mRNA molecule in the biological sample, wherein the sequenced portion comprises a position corresponding to position 574 according to SEQ ID NO:137; or the complement thereof; and/or iii) the nucleotide sequence of the ANGPTL7 cDNA molecule in the biological sample, wherein the sequenced portion comprises a position corresponding to position 574 according to SEQ ID NO:140, or the complement thereof. When the sequenced portion of the ANGPTL7 genomic nucleic acid molecule in the biological sample comprises a cytosine at a position corresponding to position 4,336 according to SEQ ID NO:134, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises a cytosine at a position corresponding to position 574 according to SEQ ID NO:137, then the ANGPTL7 mRNA molecule in the biological sample is an ANGPTL7 predicted loss-of-function variant mRNA molecule. When the sequenced portion of the ANGPTL7 cDNA molecule in the biological sample comprises a cytosine at a position corresponding to position 574 according to SEQ ID NO:140, then the ANGPTL7 cDNA molecule in the biological sample is an ANGPTL7 predicted loss-of-function variant cDNA molecule.

In some embodiments, the determining step comprises: a) contacting the biological sample with a primer hybridizing to: i) a portion of the nucleotide sequence of the ANGPTL7 genomic nucleic acid molecule that is proximate to a position corresponding to position 4,336 according to SEQ ID NO:134; ii) a portion of the nucleotide sequence of the ANGPTL7 mRNA molecule that is proximate to a position corresponding to position 574 according to SEQ ID NO:137; and/or iii) a portion of the nucleotide sequence of the ANGPTL7 cDNA molecule that is proximate to a position corresponding to position 574 according to SEQ ID NO:140; b) extending the primer at least through: i) the position of the nucleotide sequence of the ANGPTL7 genomic nucleic acid molecule corresponding to position 4,336 according to SEQ ID NO:134; ii) the position of the nucleotide sequence of the ANGPTL7 mRNA molecule corresponding to position 574 according to SEQ ID NO:137; and/or iii) the position of the nucleotide sequence of the ANGPTL7 cDNA molecule corresponding to position 574 according to SEQ ID NO:140; and c) determining whether the extension product of the primer comprises: i) a cytosine at a position corresponding to position 4,336 according to SEQ ID NO:134; ii) a cytosine at a position corresponding to position 574 according to SEQ ID NO:137; and/or iii) a cytosine at a position corresponding to position 574 according to SEQ ID NO:140.

In some embodiments, the determining step comprises: a) amplifying at least a portion of the nucleic acid molecule that encodes the human ANGPTL7 polypeptide, wherein the portion comprises: i) a cytosine at a position corresponding to position 4,336 according to SEQ ID NO:134, or the complement thereof; ii) a cytosine at a position corresponding to position 574 according to SEQ ID NO:137; and/or iii) a cytosine at a position corresponding to position 574 according to SEQ ID NO:140, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a cytosine at a position corresponding to position 4,336 according to SEQ ID NO:134, or the complement thereof; ii) the nucleic acid sequence of the amplified nucleic acid molecule comprising a cytosine at a position corresponding to position 574 according to SEQ ID NO:137, or the complement thereof; and/or iii) the nucleic acid sequence of the amplified nucleic acid molecule comprising a cytosine at a position corresponding to position 574 according to SEQ ID NO:140, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the determining step comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising a cytosine at a position corresponding to position 4,336 according to SEQ ID NO:134, or the complement thereof; the nucleotide sequence of the amplified nucleic acid molecule comprising a cytosine at a position corresponding to position 574 according to SEQ ID NO:137, or the complement thereof; and/or the nucleotide sequence of the amplified nucleic acid molecule comprising a cytosine at a position corresponding to position 574 according to SEQ ID NO:140, or the complement thereof; and detecting the detectable label.

In any of these embodiments, the nucleic acid molecule can be present within a cell obtained from the human subject.

In some embodiments, the human subject is further treated with a therapeutic agent that treats or inhibits the ophthalmic condition and/or an ANGPTL7 inhibitor, as described herein. For example, when the human subject is ANGPTL7 reference, and therefore has an increased risk for developing an ophthalmic condition, the human subject is administered an ANGPTL7 inhibitor. In some embodiments, such a patient is also administered a therapeutic agent that treats or inhibits the ophthalmic condition. In some embodiments, when the patient is heterozygous for an ANGPTL7 predicted loss-of-function variant, the patient is administered the therapeutic agent that treats or inhibits the ophthalmic condition in a dosage amount that is the same as or lower than the standard dosage amount, and is also administered an ANGPTL7 inhibitor. In some embodiments, the patient is ANGPTL7 reference. In some embodiments, the patient is heterozygous for an ANGPTL7 predicted loss-of-function variant.

The present disclosure also provides methods of detecting the presence of an ANGPTL7 predicted loss-of-function variant genomic nucleic acid molecule, an ANGPTL7 predicted loss-of-function variant mRNA molecule, and/or an ANGPTL7 predicted loss-of-function variant cDNA molecule in a biological sample from a subject human. It is understood that gene sequences within a population and mRNA molecules encoded by such genes can vary due to polymorphisms such as single-nucleotide polymorphisms. The sequences provided herein for the ANGPTL7 variant genomic nucleic acid molecule, ANGPTL7 variant mRNA molecule, and ANGPTL7 variant cDNA molecule are only exemplary sequences. Other sequences for the ANGPTL7 variant genomic nucleic acid molecule, variant mRNA molecule, and variant cDNA molecule are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any ANGPTL7 variant nucleic acid molecule, preliminary processing designed to isolate or enrich the sample for the genomic DNA can be employed. A variety of known techniques may be used for this purpose. When detecting the level of any ANGPTL7 variant mRNA, different techniques can be used enrich the biological sample with mRNA. Various methods to detect the presence or level of a mRNA or the presence of a particular variant genomic DNA locus can be used.

In some embodiments, the methods of detecting a human ANGPTL7 predicted loss-of-function variant nucleic acid molecule in a human subject comprise assaying a biological sample obtained from the human subject to determine whether an ANGPTL7 genomic nucleic acid molecule, an ANGPTL7 mRNA molecule, or an ANGPTL7 cDNA molecule in the biological sample comprises one or more variations that cause a loss-of-function (partial or complete) or are predicted to cause a loss-of-function (partial or complete). For example, in some embodiments, the methods of detecting a human ANGPTL7 predicted loss-of-function variant nucleic acid molecule in a human subject comprise assaying a biological sample obtained from the subject to determine whether an ANGPTL7 nucleic acid molecule in the biological sample comprises a nucleotide sequence comprising: i) a thymine at a position corresponding to position 4,291 according to SEQ ID NO:2, or the complement thereof, ii) a uracil at a position corresponding to position 529 according to SEQ ID NO:5, or the complement thereof, or iii) a thymine at a position corresponding to position 529 according to SEQ ID NO:8, or the complement thereof. In some embodiments, the method is an in vitro method.

In some embodiments, the methods of detecting the presence or absence of an ANGPTL7 predicted loss-of-function variant nucleic acid molecule (such as, for example, a genomic nucleic acid molecule, an mRNA molecule, and/or a cDNA molecule) in a human subject, comprise: performing an assay on a biological sample obtained from the human subject, which assay determines whether a nucleic acid molecule in the biological sample comprises a nucleotide sequence that encodes: i) a thymine at a position corresponding to position 4,291 according to SEQ ID NO:2 (genomic nucleic acid molecule), ii) a uracil at a position corresponding to position 529 according to SEQ ID NO:5 (mRNA molecule), or iii) a thymine at a position corresponding to position 529 according to SEQ ID NO:8 (cDNA molecule). In some embodiments, the biological sample comprises a cell or cell lysate. Such methods can further comprise, for example, obtaining a biological sample from the subject comprising an ANGPTL7 genomic nucleic acid molecule or mRNA molecule, and if mRNA, optionally reverse transcribing the mRNA into cDNA, and performing an assay on the biological sample that determines that a position of the ANGPTL7 genomic nucleic acid molecule, mRNA, or cDNA encodes a thymine at a position corresponding to position 4,291 according to SEQ ID NO:2, a uracil at a position corresponding to position 529 according to SEQ ID NO:5, or a thymine at a position corresponding to position 529 according to SEQ ID NO:8, respectively. Such assays can comprise, for example determining the identity of these positions of the particular ANGPTL7 nucleic acid molecule. In some embodiments, the method is an in vitro method.

In some embodiments, the assay comprises sequencing at least a portion of the nucleotide sequence of the ANGPTL7 genomic nucleic acid molecule, the ANGPTL7 mRNA molecule, or the ANGPTL7 cDNA molecule in the biological sample, wherein the sequenced portion comprises one or more variations that cause a loss-of-function (partial or complete). For example, in some embodiments, the assay comprises sequencing at least a portion of: i) the nucleotide sequence of the ANGPTL7 genomic nucleic acid molecule in the biological sample, wherein the sequenced portion comprises a position corresponding to position 4,291 according to SEQ ID NO:2, or the complement thereof; ii) the nucleotide sequence of the ANGPTL7 mRNA molecule in the biological sample, wherein the sequenced portion comprises a position corresponding to position 529 according to SEQ ID NO:5, or the complement thereof; or iii) the nucleotide sequence of the ANGPTL7 cDNA molecule in the biological sample, wherein the sequenced portion comprises a position corresponding to position 529 according to SEQ ID NO:8, or the complement thereof. When the sequenced portion of the ANGPTL7 genomic nucleic acid molecule in the biological sample comprises a thymine at a position corresponding to position 4,291 according to SEQ ID NO:2, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises a uracil at a position corresponding to position 529 according to SEQ ID NO:5, then the ANGPTL7 mRNA molecule in the biological sample is an ANGPTL7 predicted loss-of-function variant mRNA molecule. When the sequenced portion of the ANGPTL7 cDNA molecule in the biological sample comprises a thymine at a position corresponding to position 529 according to SEQ ID NO:8, then the ANGPTL7 cDNA molecule in the biological sample is an ANGPTL7 predicted loss-of-function variant cDNA molecule.

In some embodiments, the assay comprises: a) contacting the biological sample with a primer hybridizing to: i) a portion of the nucleotide sequence of the ANGPTL7 genomic nucleic acid molecule that is proximate to a position corresponding to position 4,291 according to SEQ ID NO:2; ii) a portion of the nucleotide sequence of the ANGPTL7 mRNA molecule that is proximate to a position corresponding to position 529 according to SEQ ID NO:5; or iii) a portion of the nucleotide sequence of the ANGPTL7 cDNA molecule that is proximate to a position corresponding to position 529 according to SEQ ID NO:8; b) extending the primer at least through: i) the position of the nucleotide sequence of the ANGPTL7 genomic nucleic acid molecule corresponding to position 4,291 according to SEQ ID NO:2; ii) the position of the nucleotide sequence of the ANGPTL7 mRNA molecule corresponding to position 529 according to SEQ ID NO:5; or iii) the position of the nucleotide sequence of the ANGPTL7 cDNA molecule corresponding to position 529 according to SEQ ID NO:8; and c) determining whether the extension product of the primer comprises: i) a thymine at a position corresponding to position 4,291 according to SEQ ID NO:2; ii) a uracil at a position corresponding to position 529 according to SEQ ID NO:5; or iii) a thymine at a position corresponding to position 529 according to SEQ ID NO:8. In some embodiments, the assay comprises sequencing the entire nucleic acid molecule. In some embodiments, only an ANGPTL7 genomic nucleic acid molecule is analyzed. In some embodiments, only an ANGPTL7 mRNA is analyzed. In some embodiments, only an ANGPTL7 cDNA obtained from ANGPTL7 mRNA is analyzed.

In some embodiments, the assay comprises: a) amplifying at least a portion of the nucleic acid molecule that encodes the human ANGPTL7 polypeptide, wherein the portion comprises: i) a thymine at a position corresponding to position 4,291 according to SEQ ID NO:2, or the complement thereof; ii) a uracil at a position corresponding to position 529 according to SEQ ID NO:5, or the complement thereof; or iii) a thymine at a position corresponding to position 529 according to SEQ ID NO:8, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a thymine at a position corresponding to position 4,291 according to SEQ ID NO:2, or the complement thereof; ii) the nucleic acid sequence of the amplified nucleic acid molecule comprising a uracil at a position corresponding to position 529 according to SEQ ID NO:5, or the complement thereof; or iii) the nucleic acid sequence of the amplified nucleic acid molecule comprising a thymine at a position corresponding to position 529 according to SEQ ID NO:8, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the assay comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising a thymine at a position corresponding to position 4,291 according to SEQ ID NO:2, or the complement thereof; the nucleotide sequence of the amplified nucleic acid molecule comprising a uracil at a position corresponding to position 529 according to SEQ ID NO:5, or the complement thereof; or the nucleotide sequence of the amplified nucleic acid molecule comprising a thymine at a position corresponding to position 529 according to SEQ ID NO:8, or the complement thereof; and detecting the detectable label. Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the methods of detecting a human ANGPTL7 predicted loss-of-function variant nucleic acid molecule in a human subject comprise assaying a biological sample obtained from the subject to determine whether an ANGPTL7 nucleic acid molecule in the biological sample comprises a nucleotide sequence comprising: i) a thymine at a position corresponding to position 4,287 according to SEQ ID NO:3, or the complement thereof, ii) a uracil at a position corresponding to position 525 according to SEQ ID NO:6, or the complement thereof, or iii) a thymine at a position corresponding to position 525 according to SEQ ID NO:9, or the complement thereof. In some embodiments, the method is an in vitro method.

In some embodiments, the methods of detecting the presence or absence of an ANGPTL7 predicted loss-of-function variant nucleic acid molecule (such as, for example, a genomic nucleic acid molecule, an mRNA molecule, and/or a cDNA molecule) in a human subject, comprise: performing an assay on a biological sample obtained from the human subject, which assay determines whether a nucleic acid molecule in the biological sample comprises a nucleotide sequence that encodes: i) a thymine at a position corresponding to position 4,287 according to SEQ ID NO:3 (genomic nucleic acid molecule), ii) a uracil at a position corresponding to position 525 according to SEQ ID NO:6 (mRNA molecule), or iii) a thymine at a position corresponding to position 525 according to SEQ ID NO:9 (cDNA molecule). In some embodiments, the biological sample comprises a cell or cell lysate. Such methods can further comprise, for example, obtaining a biological sample from the subject comprising an ANGPTL7 genomic nucleic acid molecule or mRNA molecule, and if mRNA, optionally reverse transcribing the mRNA into cDNA, and performing an assay on the biological sample that determines that a position of the ANGPTL7 genomic nucleic acid molecule, mRNA, or cDNA encodes a thymine at a position corresponding to position 4,287 according to SEQ ID NO:3, a uracil at a position corresponding to position 525 according to SEQ ID NO:6, or a thymine at a position corresponding to position 525 according to SEQ ID NO:9, respectively. Such assays can comprise, for example determining the identity of these positions of the particular ANGPTL7 nucleic acid molecule. In some embodiments, the method is an in vitro method.

In some embodiments, the assay comprises sequencing at least a portion of the nucleotide sequence of the ANGPTL7 genomic nucleic acid molecule, the ANGPTL7 mRNA molecule, or the ANGPTL7 cDNA molecule in the biological sample, wherein the sequenced portion comprises one or more variations that cause a loss-of-function (partial or complete). For example, in some embodiments, the assay comprises sequencing at least a portion of: i) the nucleotide sequence of the ANGPTL7 genomic nucleic acid molecule in the biological sample, wherein the sequenced portion comprises a position corresponding to position 4,287 according to SEQ ID NO:3, or the complement thereof; ii) the nucleotide sequence of the ANGPTL7 mRNA molecule in the biological sample, wherein the sequenced portion comprises a position corresponding to position 525 according to SEQ ID NO:6, or the complement thereof; or iii) the nucleotide sequence of the ANGPTL7 cDNA molecule in the biological sample, wherein the sequenced portion comprises a position corresponding to position 525 according to SEQ ID NO:9, or the complement thereof. When the sequenced portion of the ANGPTL7 genomic nucleic acid molecule in the biological sample comprises a thymine at a position corresponding to position 4,287 according to SEQ ID NO:3, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises a uracil at a position corresponding to position 525 according to SEQ ID NO:6, then the ANGPTL7 mRNA molecule in the biological sample is an ANGPTL7 predicted loss-of-function variant mRNA molecule. When the sequenced portion of the ANGPTL7 cDNA molecule in the biological sample comprises a thymine at a position corresponding to position 525 according to SEQ ID NO:9, then the ANGPTL7 cDNA molecule in the biological sample is an ANGPTL7 predicted loss-of-function variant cDNA molecule.

In some embodiments, the assay comprises: a) contacting the biological sample with a primer hybridizing to: i) a portion of the nucleotide sequence of the ANGPTL7 genomic nucleic acid molecule that is proximate to a position corresponding to position 4,287 according to SEQ ID NO:3; ii) a portion of the nucleotide sequence of the ANGPTL7 mRNA molecule that is proximate to a position corresponding to position 525 according to SEQ ID NO:6; or iii) a portion of the nucleotide sequence of the ANGPTL7 cDNA molecule that is proximate to a position corresponding to position 525 according to SEQ ID NO:9; b) extending the primer at least through: i) the position of the nucleotide sequence of the ANGPTL7 genomic nucleic acid molecule corresponding to position 4,287 according to SEQ ID NO:3; ii) the position of the nucleotide sequence of the ANGPTL7 mRNA molecule corresponding to position 525 according to SEQ ID NO:6; or iii) the position of the nucleotide sequence of the ANGPTL7 cDNA molecule corresponding to position 525 according to SEQ ID NO:9; and c) determining whether the extension product of the primer comprises: i) a thymine at a position corresponding to position 4,287 according to SEQ ID NO:3; ii) a uracil at a position corresponding to position 525 according to SEQ ID NO:6; or iii) a thymine at a position corresponding to position 525 according to SEQ ID NO:9. In some embodiments, the assay comprises sequencing the entire nucleic acid molecule. In some embodiments, only an ANGPTL7 genomic nucleic acid molecule is analyzed. In some embodiments, only an ANGPTL7 mRNA is analyzed. In some embodiments, only an ANGPTL7 cDNA obtained from ANGPTL7 mRNA is analyzed.

In some embodiments, the assay comprises: a) amplifying at least a portion of the nucleic acid molecule that encodes the human ANGPTL7 polypeptide, wherein the portion comprises: i) a thymine at a position corresponding to position 4,287 according to SEQ ID NO:3, or the complement thereof; ii) a uracil at a position corresponding to position 525 according to SEQ ID NO:6, or the complement thereof; or iii) a thymine at a position corresponding to position 525 according to SEQ ID NO:9, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a thymine at a position corresponding to position 4,287 according to SEQ ID NO:3, or the complement thereof; ii) the nucleic acid sequence of the amplified nucleic acid molecule comprising a uracil at a position corresponding to position 525 according to SEQ ID NO:6, or the complement thereof; or iii) the nucleic acid sequence of the amplified nucleic acid molecule comprising a thymine at a position corresponding to position 525 according to SEQ ID NO:9, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the assay comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising a thymine at a position corresponding to position 4,287 according to SEQ ID NO:3, or the complement thereof; the nucleotide sequence of the amplified nucleic acid molecule comprising a uracil at a position corresponding to position 525 according to SEQ ID NO:6, or the complement thereof; or the nucleotide sequence of the amplified nucleic acid molecule comprising a thymine at a position corresponding to position 525 according to SEQ ID NO:9, or the complement thereof; and detecting the detectable label. Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the methods of detecting a human ANGPTL7 predicted loss-of-function variant nucleic acid molecule in a human subject comprise assaying a biological sample obtained from the subject to determine whether an ANGPTL7 nucleic acid molecule in the biological sample comprises a nucleotide sequence comprising: i) an adenine at a position corresponding to position 4,243 according to SEQ ID NO:132, or the complement thereof, ii) an adenine at a position corresponding to position 481 according to SEQ ID NO:135, or the complement thereof, or iii) an adenine at a position corresponding to position 481 according to SEQ ID NO:138, or the complement thereof. In some embodiments, the method is an in vitro method.

In some embodiments, the methods of detecting the presence or absence of an ANGPTL7 predicted loss-of-function variant nucleic acid molecule (such as, for example, a genomic nucleic acid molecule, an mRNA molecule, and/or a cDNA molecule) in a human subject, comprise: performing an assay on a biological sample obtained from the human subject, which assay determines whether a nucleic acid molecule in the biological sample comprises a nucleotide sequence that encodes i) an adenine at a position corresponding to position 4,243 according to SEQ ID NO:132, or the complement thereof; ii) an adenine at a position corresponding to position 481 according to SEQ ID NO:135; and/or iii) an adenine at a position corresponding to position 481 according to SEQ ID NO:138. In some embodiments, the biological sample comprises a cell or cell lysate. Such methods can further comprise, for example, obtaining a biological sample from the subject comprising an ANGPTL7 genomic nucleic acid molecule or mRNA molecule, and if mRNA, optionally reverse transcribing the mRNA into cDNA, and performing an assay on the biological sample that determines that a position of the ANGPTL7 genomic nucleic acid molecule, mRNA, or cDNA encodes an adenine at a position corresponding to position 4,243 according to SEQ ID NO:132, an adenine at a position corresponding to position 481 according to SEQ ID NO:135, an adenine at a position corresponding to position 481 according to SEQ ID NO:138, respectively. Such assays can comprise, for example, determining the identity of these positions of the particular ANGPTL7 nucleic acid molecule. In some embodiments, the method is an in vitro method.

In some embodiments, the assay comprises sequencing at least a portion of: i) the nucleotide sequence of the ANGPTL7 genomic nucleic acid molecule in the biological sample, wherein the sequenced portion comprises a position corresponding to position 4,243 according to SEQ ID NO:132, or the complement thereof; ii) the nucleotide sequence of the ANGPTL7 mRNA molecule in the biological sample, wherein the sequenced portion comprises a position corresponding to position 481 according to SEQ ID NO:135; or the complement thereof; and/or iii) the nucleotide sequence of the ANGPTL7 cDNA molecule in the biological sample, wherein the sequenced portion comprises a position corresponding to position 481 according to SEQ ID NO:138, or the complement thereof. When the sequenced portion of the ANGPTL7 genomic nucleic acid molecule in the biological sample comprises an adenine at a position corresponding to position 4,243 according to SEQ ID NO:132, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises an adenine at a position corresponding to position 481 according to SEQ ID NO:135, then the ANGPTL7 mRNA molecule in the biological sample is an ANGPTL7 predicted loss-of-function variant mRNA molecule. When the sequenced portion of the ANGPTL7 cDNA molecule in the biological sample comprises an adenine at a position corresponding to position 481 according to SEQ ID NO:138, then the ANGPTL7 cDNA molecule in the biological sample is an ANGPTL7 predicted loss-of-function variant cDNA molecule.

In some embodiments, the assay comprises: a) contacting the biological sample with a primer hybridizing to i) a portion of the nucleotide sequence of the ANGPTL7 genomic nucleic acid molecule that is proximate to a position corresponding to position 4,243 according to SEQ ID NO:132; ii) a portion of the nucleotide sequence of the ANGPTL7 mRNA molecule that is proximate to a position corresponding to position 481 according to SEQ ID NO:135; and/or iii) a portion of the nucleotide sequence of the ANGPTL7 cDNA molecule that is proximate to a position corresponding to position 481 according to SEQ ID NO:138; b) extending the primer at least through: i) the position of the nucleotide sequence of the ANGPTL7 genomic nucleic acid molecule corresponding to position 4,243 according to SEQ ID NO:132; ii) the position of the nucleotide sequence of the ANGPTL7 mRNA molecule corresponding to position 481 according to SEQ ID NO:135; and/or iii) the position of the nucleotide sequence of the ANGPTL7 cDNA molecule corresponding to position 481 according to SEQ ID NO:138; and c) determining whether the extension product of the primer comprises: i) an adenine at a position corresponding to position 4,243 according to SEQ ID NO:132; ii) an adenine at a position corresponding to position 481 according to SEQ ID NO:135; and/or iii) adenine at a position corresponding to position 481 according to SEQ ID NO:138.

In some embodiments, the assay comprises: a) amplifying at least a portion of the nucleic acid molecule that encodes the human ANGPTL7 polypeptide, wherein the portion comprises: i) an adenine at a position corresponding to position 4,243 according to SEQ ID NO:132, or the complement thereof; ii) an adenine at a position corresponding to position 481 according to SEQ ID NO:135; and/or iii) an adenine at a position corresponding to position 481 according to SEQ ID NO:138, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising an adenine at a position corresponding to position 4,243 according to SEQ ID NO:132, or the complement thereof; ii) the nucleic acid sequence of the amplified nucleic acid molecule comprising an adenine at a position corresponding to position 481 according to SEQ ID NO:135, or the complement thereof; and/or iii) the nucleic acid sequence of the amplified nucleic acid molecule comprising an adenine at a position corresponding to position 481 according to SEQ ID NO:138, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the assay comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising an adenine at a position corresponding to position 4,243 according to SEQ ID NO:132, or the complement thereof; the nucleotide sequence of the amplified nucleic acid molecule comprising an adenine at a position corresponding to position 481 according to SEQ ID NO:135, or the complement thereof; and/or the nucleotide sequence of the amplified nucleic acid molecule comprising an adenine at a position corresponding to position 481 according to SEQ ID NO:138, or the complement thereof; and detecting the detectable label.

In some embodiments, the methods of detecting a human ANGPTL7 predicted loss-of-function variant nucleic acid molecule in a human subject comprise assaying a biological sample obtained from the subject to determine whether an ANGPTL7 nucleic acid molecule in the biological sample comprises a nucleotide sequence comprising: i) an adenine at a position corresponding to position 4,325 according to SEQ ID NO:133, or the complement thereof, ii) an adenine at a position corresponding to position 563 according to SEQ ID NO:136, or the complement thereof, or iii) an adenine at a position corresponding to position 563 according to SEQ ID NO:139, or the complement thereof. In some embodiments, the method is an in vitro method.

In some embodiments, the methods of detecting the presence or absence of an ANGPTL7 predicted loss-of-function variant nucleic acid molecule (such as, for example, a genomic nucleic acid molecule, an mRNA molecule, and/or a cDNA molecule) in a human subject, comprise: performing an assay on a biological sample obtained from the human subject, which assay determines whether a nucleic acid molecule in the biological sample comprises a nucleotide sequence that encodes i) an adenine at a position corresponding to position 4,325 according to SEQ ID NO:133; ii) an adenine at a position corresponding to position 563 according to SEQ ID NO:136; and/or iii) an adenine at a position corresponding to position 563 according to SEQ ID NO:139. In some embodiments, the biological sample comprises a cell or cell lysate. Such methods can further comprise, for example, obtaining a biological sample from the subject comprising an ANGPTL7 genomic nucleic acid molecule or mRNA molecule, and if mRNA, optionally reverse transcribing the mRNA into cDNA, and performing an assay on the biological sample that determines that a position of the ANGPTL7 genomic nucleic acid molecule, mRNA, or cDNA encodes an adenine at a position corresponding to position 4,325 according to SEQ ID NO:133, an adenine at a position corresponding to position 563 according to SEQ ID NO:136, an adenine at a position corresponding to position 563 according to SEQ ID NO:139, respectively. Such assays can comprise, for example determining the identity of these positions of the particular ANGPTL7 nucleic acid molecule. In some embodiments, the method is an in vitro method.

In some embodiments, the assay comprises sequencing at least a portion of: i) the nucleotide sequence of the ANGPTL7 genomic nucleic acid molecule in the biological sample, wherein the sequenced portion comprises a position corresponding to position 4,325 according to SEQ ID NO:133, or the complement thereof; ii) the nucleotide sequence of the ANGPTL7 mRNA molecule in the biological sample, wherein the sequenced portion comprises a position corresponding to position 563 according to SEQ ID NO:136, or the complement thereof; and/or iii) the nucleotide sequence of the ANGPTL7 cDNA molecule in the biological sample, wherein the sequenced portion comprises a position corresponding to position 563 according to SEQ ID NO:139, or the complement thereof. When the sequenced portion of the ANGPTL7 genomic nucleic acid molecule in the biological sample comprises an adenine at a position corresponding to position 4,325 according to SEQ ID NO:133, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises an adenine at a position corresponding to position 563 according to SEQ ID NO:136, then the ANGPTL7 mRNA molecule in the biological sample is an ANGPTL7 predicted loss-of-function variant mRNA molecule. When the sequenced portion of the ANGPTL7 cDNA molecule in the biological sample comprises an adenine at a position corresponding to position 563 according to SEQ ID NO:139, then the ANGPTL7 cDNA molecule in the biological sample is an ANGPTL7 predicted loss-of-function variant cDNA molecule.

In some embodiments, the assay comprises: a) contacting the biological sample with a primer hybridizing to: i) a portion of the nucleotide sequence of the ANGPTL7 genomic nucleic acid molecule that is proximate to a position corresponding to position 4,325 according to SEQ ID NO:133; ii) a portion of the nucleotide sequence of the ANGPTL7 mRNA molecule that is proximate to a position corresponding to position 563 according to SEQ ID NO:136; and/or iii) a portion of the nucleotide sequence of the ANGPTL7 cDNA molecule that is proximate to a position corresponding to position 563 according to SEQ ID NO:139; b) extending the primer at least through: i) the position of the nucleotide sequence of the ANGPTL7 genomic nucleic acid molecule corresponding to position 4,325 according to SEQ ID NO:133; ii) the position of the nucleotide sequence of the ANGPTL7 mRNA molecule corresponding to position 563 according to SEQ ID NO:136 and/or iii) the position of the nucleotide sequence of the ANGPTL7 cDNA molecule corresponding to position 563 according to SEQ ID NO:139; and c) determining whether the extension product of the primer comprises: i) an adenine at a position corresponding to position 4,325 according to SEQ ID NO:133; ii) an adenine at a position corresponding to position 563 according to SEQ ID NO:136; and/or iii) an adenine at a position corresponding to position 563 according to SEQ ID NO:139.

In some embodiments, the assay comprises: a) amplifying at least a portion of the nucleic acid molecule that encodes the human ANGPTL7 polypeptide, wherein the portion comprises: i) an adenine at a position corresponding to position 4,325 according to SEQ ID NO:133, or the complement thereof; ii) an adenine at a position corresponding to position 563 according to SEQ ID NO:136, or the complement thereof; and/or iii) an adenine at a position corresponding to position 563 according to SEQ ID NO:139 or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising an adenine at a position corresponding to position 4,325 according to SEQ ID NO:133, or the complement thereof; ii) the nucleic acid sequence of the amplified nucleic acid molecule comprising an adenine at a position corresponding to position 563 according to SEQ ID NO:136, or the complement thereof; and/or iii) the nucleic acid sequence of the amplified nucleic acid molecule comprising an adenine at a position corresponding to position 563 according to SEQ ID NO:139, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the assay comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising an adenine at a position corresponding to position 4,325 according to SEQ ID NO:133, or the complement thereof; the nucleotide sequence of the amplified nucleic acid molecule comprising an adenine at a position corresponding to position 563 according to SEQ ID NO:136, or the complement thereof; and/or the nucleotide sequence of the amplified nucleic acid molecule comprising an adenine at a position corresponding to position 563 according to SEQ ID NO:139, or the complement thereof; and detecting the detectable label.

In some embodiments, the methods of detecting a human ANGPTL7 predicted loss-of-function variant nucleic acid molecule in a human subject comprise assaying a biological sample obtained from the subject to determine whether an ANGPTL7 nucleic acid molecule in the biological sample comprises a nucleotide sequence comprising: i) a cytosine at a position corresponding to position 4,336 according to SEQ ID NO:134, or the complement thereof, ii) a cytosine at a position corresponding to position 574 according to SEQ ID NO:137, or the complement thereof, or iii) a cytosine at a position corresponding to position 574 according to SEQ ID NO:140, or the complement thereof. In some embodiments, the method is an in vitro method.

In some embodiments, the methods of detecting the presence or absence of an ANGPTL7 predicted loss-of-function variant nucleic acid molecule (such as, for example, a genomic nucleic acid molecule, an mRNA molecule, and/or a cDNA molecule) in a human subject, comprise: performing an assay on a biological sample obtained from the human subject, which assay determines whether a nucleic acid molecule in the biological sample comprises a nucleotide sequence that encodes i) a cytosine at a position corresponding to position 4,336 according to SEQ ID NO:134; ii) a cytosine at a position corresponding to position 574 according to SEQ ID NO:137; and/or iii) a cytosine at a position corresponding to position 574 according to SEQ ID NO:140. In some embodiments, the biological sample comprises a cell or cell lysate. Such methods can further comprise, for example, obtaining a biological sample from the subject comprising an ANGPTL7 genomic nucleic acid molecule or mRNA molecule, and if mRNA, optionally reverse transcribing the mRNA into cDNA, and performing an assay on the biological sample that determines that a position of the ANGPTL7 genomic nucleic acid molecule, mRNA, or cDNA encodes an a cytosine at a position corresponding to position 4,336 according to SEQ ID NO:134, a cytosine at a position corresponding to position 574 according to SEQ ID NO:137, a cytosine at a position corresponding to position 574 according to SEQ ID NO:140, respectively. Such assays can comprise, for example determining the identity of these positions of the particular ANGPTL7 nucleic acid molecule. In some embodiments, the method is an in vitro method.

In some embodiments, the assay comprises sequencing at least a portion of: i) the nucleotide sequence of the ANGPTL7 genomic nucleic acid molecule in the biological sample, wherein the sequenced portion comprises a position corresponding to position 4,336 according to SEQ ID NO:134, or the complement thereof; ii) the nucleotide sequence of the ANGPTL7 mRNA molecule in the biological sample, wherein the sequenced portion comprises a position corresponding to position 574 according to SEQ ID NO:137; or the complement thereof; and/or iii) the nucleotide sequence of the ANGPTL7 cDNA molecule in the biological sample, wherein the sequenced portion comprises a position corresponding to position 574 according to SEQ ID NO:140, or the complement thereof. When the sequenced portion of the ANGPTL7 genomic nucleic acid molecule in the biological sample comprises a cytosine at a position corresponding to position 4,336 according to SEQ ID NO:134, then the ANGPTL7 genomic nucleic acid molecule in the biological sample is an ANGPTL7 predicted loss-of-function variant genomic nucleic acid molecule. When the sequenced portion of the ANGPTL7 mRNA molecule in the biological sample comprises a cytosine at a position corresponding to position 574 according to SEQ ID NO:137, then the ANGPTL7 mRNA molecule in the biological sample is an ANGPTL7 predicted loss-of-function variant mRNA molecule. When the sequenced portion of the ANGPTL7 cDNA molecule in the biological sample comprises a cytosine at a position corresponding to position 574 according to SEQ ID NO:140, then the ANGPTL7 cDNA molecule in the biological sample is an ANGPTL7 predicted loss-of-function variant cDNA molecule.

In some embodiments, the assay comprises: a) contacting the biological sample with a primer hybridizing to: i) a portion of the nucleotide sequence of the ANGPTL7 genomic nucleic acid molecule that is proximate to a position corresponding to position 4,336 according to SEQ ID NO:134; ii) a portion of the nucleotide sequence of the ANGPTL7 mRNA molecule that is proximate to a position corresponding to position 574 according to SEQ ID NO:137;

and/or iii) a portion of the nucleotide sequence of the ANGPTL7 cDNA molecule that is proximate to a position corresponding to position 574 according to SEQ ID NO:140; b) extending the primer at least through: i) the position of the nucleotide sequence of the ANGPTL7 genomic nucleic acid molecule corresponding to position 4,336 according to SEQ ID NO:134; ii) the position of the nucleotide sequence of the ANGPTL7 mRNA molecule corresponding to position 574 according to SEQ ID NO:137; and/or iii) the position of the nucleotide sequence of the ANGPTL7 cDNA molecule corresponding to position 574 according to SEQ ID NO:140; and c) determining whether the extension product of the primer comprises: i) a cytosine at a position corresponding to position 4,336 according to SEQ ID NO:134; ii) a cytosine at a position corresponding to position 574 according to SEQ ID NO:137; and/or iii) a cytosine at a position corresponding to position 574 according to SEQ ID NO:140.

In some embodiments, the assay comprises: a) amplifying at least a portion of the nucleic acid molecule that encodes the human ANGPTL7 polypeptide, wherein the portion comprises: i) a cytosine at a position corresponding to position 4,336 according to SEQ ID NO:134, or the complement thereof; ii) a cytosine at a position corresponding to position 574 according to SEQ ID NO:137; and/or iii) a cytosine at a position corresponding to position 574 according to SEQ ID NO:140, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to: i) the nucleic acid sequence of the amplified nucleic acid molecule comprising a cytosine at a position corresponding to position 4,336 according to SEQ ID NO:134, or the complement thereof; ii) the nucleic acid sequence of the amplified nucleic acid molecule comprising a cytosine at a position corresponding to position 574 according to SEQ ID NO:137, or the complement thereof; and/or iii) the nucleic acid sequence of the amplified nucleic acid molecule comprising a cytosine at a position corresponding to position 574 according to SEQ ID NO:140, or the complement thereof; and d) detecting the detectable label. In some embodiments, the nucleic acid molecule is mRNA and the determining step further comprises reverse-transcribing the mRNA into a cDNA prior to the amplifying step.

In some embodiments, the assay comprises: contacting the nucleic acid molecule in the biological sample with an alteration-specific probe comprising a detectable label, wherein the alteration-specific probe comprises a nucleotide sequence which hybridizes under stringent conditions to: the nucleotide sequence of the amplified nucleic acid molecule comprising a cytosine at a position corresponding to position 4,336 according to SEQ ID NO:134, or the complement thereof; the nucleotide sequence of the amplified nucleic acid molecule comprising a cytosine at a position corresponding to position 574 according to SEQ ID NO:137, or the complement thereof; and/or the nucleotide sequence of the amplified nucleic acid molecule comprising a cytosine at a position corresponding to position 574 according to SEQ ID NO:140, or the complement thereof; and detecting the detectable label.

In some embodiments, the nucleic acid molecule in the sample is mRNA and the mRNA is reverse-transcribed into a cDNA prior to the amplifying step. In some embodiments, the nucleic acid molecule is present within a cell obtained from the human subject.

The ANGPTL7 predicted loss-of-function variant nucleic acid molecule can be any ANGPTL7 nucleic acid molecule (such as, for example, genomic nucleic acid molecule, mRNA molecule, or cDNA molecule) encoding an ANGPTL7 polypeptide having a partial loss-of-function, a complete loss-of-function, a predicted partial loss-of-function, or a predicted complete loss-of-function. For example, the ANGPTL7 predicted loss-of-function variant nucleic acid molecule can be any nucleic acid molecule encoding ANGPTL7 Gln175His, Arg177Stop, Trp188Stop, Lys192Gln, Phe161Ile, Arg340His, Arg220His, Asn302Lys, or Arg220Cys. In some embodiments, the ANGPTL7 predicted loss-of-function variant nucleic acid molecule encodes ANGPTL7 Gln175His, Arg177Stop, Trp188Stop, Lys192Gln, or Phe161Ile. In some embodiments, the ANGPTL7 predicted loss-of-function variant nucleic acid molecule encodes ANGPTL7 Gln175His, Trp188Stop, or Arg177Stop. In some embodiments, the ANGPTL7 predicted loss-of-function variant nucleic acid molecule encodes ANGPTL7 Gln175His. In some embodiments, the ANGPTL7 predicted loss-of-function variant nucleic acid molecule encodes ANGPTL7 Arg177Stop. In some embodiments, the ANGPTL7 predicted loss-of-function variant nucleic acid molecule encodes ANGPTL7 Trp188Stop. In some embodiments, the ANGPTL7 predicted loss-of-function variant nucleic acid molecule encodes ANGPTL7 Lys192Gln. In some embodiments, the ANGPTL7 predicted loss-of-function variant nucleic acid molecule encodes ANGPTL7 Phe161Ile.

In some embodiments, the assay comprises contacting the biological sample with a primer or probe, such as an alteration-specific primer or alteration-specific probe, that specifically hybridizes to an ANGPTL7 variant genomic sequence, variant mRNA sequence, or variant cDNA sequence and not the corresponding ANGPTL7 reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising an ANGPTL7 variant genomic nucleic acid molecule, variant mRNA molecule, or variant cDNA molecule. The hybridization conditions or reaction conditions can be determined by the operator to achieve this result. This nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Accordingly, probes and primers can share about 80%, about 85%, about 90%, about 91%, about 92%, about 93%, about 94%, about 95%, about 96%, about 97%, about 98%, about 99%, or 100% sequence identity or complementarity to the nucleotide sequence of the target nucleic acid molecule.

In some embodiments, to determine whether the ANGPTL7 nucleic acid molecule (genomic nucleic acid molecule, mRNA molecule, or cDNA molecule), or complement thereof, within a biological sample comprises a nucleotide sequence comprising a thymine at a position corresponding to position 4,291 according to SEQ ID NO:2 (genomic nucleic acid molecule), or a uracil at a position corresponding to position 529 according to SEQ ID NO:5 (mRNA molecule), or a thymine at a position corresponding to position 529 according to SEQ ID NO:8 (cDNA molecule), the biological sample may be subjected to an amplification method using a primer pair that includes a first primer derived from the 5' flanking sequence adjacent to a thymine at a position corresponding to position 4,291 according to SEQ ID NO:2, or a uracil at a position corresponding to position 529 according to SEQ ID NO:5, or a thymine at a position corresponding to position 529 according to SEQ ID NO:8, and a second primer derived from the 3' flanking sequence adjacent to a thymine at a position corresponding to position 4,291 according to SEQ ID NO:2, or a uracil at a position corresponding to position 529 according to SEQ ID NO:5, or a thymine at a position corresponding to position 529 according to SEQ ID NO:8 to produce an amplicon that is indicative of the presence of the SNP at positions comprising a thymine at a position corresponding to position 4,291 according to SEQ ID NO:2, or a uracil at a position corresponding to position 529 according to SEQ ID NO:5, or a thymine at a position corresponding to position 529 according to SEQ ID NO:8. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a thymine at a position corresponding to position 4,291 according to SEQ ID NO:2, or a uracil at a position corresponding to position 529 according to SEQ ID NO:5, or a thymine at a position corresponding to position 529 according to SEQ ID NO:8, and at least 1, 2, 3, 4, 5, 6, 7, 8, 9, 10, or more nucleotides on each side of positions comprising a thymine at a position corresponding to position 4,291 according to SEQ ID NO:2, or a uracil at a position corresponding to position 529 according to SEQ ID NO:5, or a thymine at a position corresponding to position 529 according to SEQ ID NO:8.

In some embodiments, to determine whether the ANGPTL7 nucleic acid molecule (genomic nucleic acid molecule, mRNA molecule, or cDNA molecule), or complement thereof, within a biological sample comprises a nucleotide sequence comprising a thymine at a position corresponding to position 4,287 according to SEQ ID NO:3 (genomic nucleic acid molecule), or a uracil at a position corresponding to position 525 according to SEQ ID NO:6 (mRNA molecule), or a thymine at a position corresponding to position 525 according to SEQ ID NO:9 (cDNA molecule), the biological sample may be subjected to an amplification method using a primer pair that includes a first primer derived from the 5' flanking sequence adjacent to a thymine at a position corresponding to position 4,287 according to SEQ ID NO:3, or a uracil at a position corresponding to position 525 according to SEQ ID NO:6, or a thymine at a position corresponding to position 525 according to SEQ ID NO:9, and a second primer derived from the 3' flanking sequence adjacent to a thymine at a position corresponding to position 4,287 according to SEQ ID NO:3, or a uracil at a position corresponding to position 525 according to SEQ ID NO:6, or a thymine at a position corresponding to position 525 according to SEQ ID NO:9 to produce an amplicon that is indicative of the presence of the SNP at positions comprising a thymine at a position corresponding to position 4,287 according to SEQ ID NO:3, or a uracil at a position corresponding to position 525 according to SEQ ID NO:6, or a thymine at a position corresponding to position 525 according to SEQ ID NO:9. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a thymine at a position corresponding to position 4,287 according to SEQ ID NO:3, or a uracil at a position corresponding to position 525 according to SEQ ID NO:6, or a thymine at a position corresponding to position 525 according to SEQ ID NO:9, and at least 1, 2, 3, 4, 5, 6, 7, 8, 9, 10, or more nucleotides on each side of positions comprising a thymine at a position corresponding to position 4,287 according to SEQ ID NO:3, or a uracil at a position corresponding to position 525 according to SEQ ID NO:6, or a thymine at a position corresponding to position 525 according to SEQ ID NO:9.

In some embodiments, to determine whether a ANGPTL7 nucleic acid molecule (genomic nucleic acid molecule, mRNA molecule, or cDNA molecule), or complement thereof, within a biological sample comprises a nucleotide sequence comprising an adenine at a position corresponding to position 4,243 according to SEQ ID NO:132 (genomic nucleic acid molecule), or an adenine at a position corresponding to position 481 according to SEQ ID NO:135 (mRNA molecule), or an adenine at a position corresponding to position 481 according to SEQ ID NO:138 (cDNA molecule), the biological sample can be subjected to an amplification method using a primer pair that includes a first primer derived from the 5' flanking sequence adjacent to an adenine at a position corresponding to position 4,243 according to SEQ ID NO:132, or an adenine at a position corresponding to position 481 according to SEQ ID NO:135, or an adenine at a position corresponding to position 481 according to SEQ ID NO:138, and a second primer derived from the 3' flanking sequence adjacent to an adenine at a position corresponding to position 4,243 according to SEQ ID NO:132, or an adenine at a position corresponding to position 481 according to SEQ ID NO:135, or an adenine at a position corresponding to position 481 according to SEQ ID NO:138 to produce an amplicon that is indicative of the presence of the SNP at positions encoding an adenine at a position corresponding to position 4,243 according to SEQ ID NO:132, or an adenine at a position corresponding to position 481 according to SEQ ID NO:135, or an adenine at a position corresponding to position 481 according to SEQ ID NO:138. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 4,243 according to SEQ ID NO:132, or an adenine at a position corresponding to position 481 according to SEQ ID NO:135, or an adenine at a position corresponding to position 481 according to SEQ ID NO:138, and at least 1, 2, 3, 4, 5, 6, 7, 8, 9, 10, or more nucleotides on each side of positions comprising an adenine at a position corresponding to position 4,243 according to SEQ ID NO:132, or an adenine at a position corresponding to position 481 according to SEQ ID NO:135, or an adenine at a position corresponding to position 481 according to SEQ ID NO:138.

In some embodiments, to determine whether a ANGPTL7 nucleic acid molecule (genomic nucleic acid molecule, mRNA molecule, or cDNA molecule), or complement thereof, within a biological sample comprises a nucleotide sequence comprising an adenine at a position corresponding to position 4,325 according to SEQ ID NO:133 (genomic nucleic acid molecule), or an adenine at a position corresponding to position 563 according to SEQ ID NO:136 (mRNA molecule), or an adenine at a position corresponding to position 563 according to SEQ ID NO:139 (cDNA molecule), the biological sample can be subjected to an amplification method using a primer pair that includes a first primer derived from the 5' flanking sequence adjacent to an adenine at a position corresponding to position 4,325 according to SEQ ID NO:133, or an adenine at a position corresponding to position 563 according to SEQ ID NO:136, or an adenine at a position corresponding to position 563 according to SEQ ID NO:139, and a second primer derived from the 3' flanking sequence adjacent to an adenine at a position corresponding to position 4,325 according to SEQ ID NO:133, or an adenine at a position corresponding to position 563 according to SEQ ID NO:136, or an adenine at a position corresponding to position 563 according to SEQ ID NO:139 to produce an amplicon that is indicative of the presence of the SNP at positions encoding an adenine at a position corresponding to position 4,325 according to SEQ ID NO:133, or an adenine at a position corresponding to position 563 according to SEQ ID NO:136, or an adenine at a position corresponding to position 563 according to SEQ ID NO:139. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 4,325 according to SEQ ID NO:133, or an adenine at a position corresponding to position 563 according to SEQ ID NO:136, or an adenine at a position corresponding to position 563 according to SEQ ID NO:139, and at least 1, 2, 3, 4, 5, 6, 7, 8, 9, 10, or more nucleotides on each side of positions comprising an adenine at a position corresponding to position 4,325 according to SEQ ID NO:133, or an adenine at a position corresponding to position 563 according to SEQ ID NO:136, or an adenine at a position corresponding to position 563 according to SEQ ID NO:139.

In some embodiments, to determine whether a ANGPTL7 nucleic acid molecule (genomic nucleic acid molecule, mRNA molecule, or cDNA molecule), or complement thereof, within a biological sample comprises a nucleotide sequence comprising a cytosine at a position corresponding to position 4,336 according to SEQ ID NO:134 (genomic nucleic acid molecule), or a cytosine at a position corresponding to position 574 according to SEQ ID NO:137 (mRNA molecule), or a cytosine at a position corresponding to position 574 according to SEQ ID NO:140 (cDNA molecule), the biological sample can be subjected to an amplification method using a primer pair that includes a first primer derived from the 5' flanking sequence adjacent to a cytosine at a position corresponding to position 4,336 according to SEQ ID NO:134, or a cytosine at a position corresponding to position 574 according to SEQ ID NO:137, or a cytosine at a position corresponding to position 574 according to SEQ ID NO:140, and a second primer derived from the 3' flanking sequence adjacent to a cytosine at a position corresponding to position 4,336 according to SEQ ID NO:134, or a cytosine at a position corresponding to position 574 according to SEQ ID NO:137, or a cytosine at a position corresponding to position 574 according to SEQ ID NO:140 to produce an amplicon that is indicative of the presence of the SNP at positions encoding a cytosine at a position corresponding to position 4,336 according to SEQ ID NO:134, or a cytosine at a position corresponding to position 574 according to SEQ ID NO:137, or a cytosine at a position corresponding to position 574 according to SEQ ID NO:140. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a cytosine at a position corresponding to position 4,336 according to SEQ ID NO:134, or a cytosine at a position corresponding to position 574 according to SEQ ID NO:137, or a cytosine at a position corresponding to position 574 according to SEQ ID NO:140, and at least 1, 2, 3, 4, 5, 6, 7, 8, 9, 10, or more nucleotides on each side of positions comprising a cytosine at a position corresponding to position 4,336 according to SEQ ID NO:134, or a cytosine at a position corresponding to position 574 according to SEQ ID NO:137, or a cytosine at a position corresponding to position 574 according to SEQ ID NO:140.

PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0©, 1991, Whitehead Institute for Biomedical Research, Cambridge, Mass.). Additionally, the sequence can be visually scanned and primers manually identified using known guidelines.

A variety of techniques are available in the art including, for example, nucleic acid sequencing, nucleic acid hybridization, and nucleic acid amplification. Illustrative examples of nucleic acid sequencing techniques include, but are not limited to, chain terminator (Sanger) sequencing and dye terminator sequencing.

Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a human ANGPTL7 predicted loss-of-function variant polypeptide comprising performing an assay on a sample obtained from a human subject to determine whether an ANGPTL7 polypeptide in the subject contains one or more variations that causes the polypeptide to have a loss-of-function (partial or complete). For example, in some embodiments, the methods detect the presence of a human ANGPTL7 predicted loss-of-function variant polypeptide, such as, for example, the ANGPTL7 Arg177Stop variant polypeptide, and comprise performing an assay on a sample obtained from a human subject to determine whether an ANGPTL7 polypeptide in the sample terminates at a position corresponding to position 176 according to SEQ ID NO:11. In some embodiments, the detecting step comprises sequencing at least a portion of the polypeptide that comprises positions corresponding to any positions that are C-terminal to position 176 according to SEQ ID NO:11 (such polypeptides are reference; an absence of such positions indicates that the polypeptide terminates at least at position 176 and is a predicted loss-of-function variant ANGPTL7 polypeptide). In some embodiments, the detecting step comprises sequencing the entire polypeptide. In some embodiments, the detecting step comprises an immunoassay for detecting the presence of a polypeptide that terminates at a position corresponding to position 176 according to SEQ ID NO:11.

The present disclosure also provides isolated nucleic acid molecules that hybridize to ANGPTL7 variant genomic nucleic acid molecules (such as SEQ ID NO:2), ANGPTL7 variant mRNA molecules (such as SEQ ID NO:5), and/or ANGPTL7 variant cDNA molecules (such as SEQ ID NO:8). In some embodiments, the isolated nucleic acid molecules hybridize to the portion of the ANGPTL7 nucleic acid molecule that includes a position corresponding to position 4,291 according to SEQ ID NO:2, or includes a position corresponding to position 529 according to SEQ ID NO:5 or SEQ ID NO:8.

In some embodiments, the methods detect the presence of a human ANGPTL7 predicted loss-of-function variant polypeptide, such as, for example, the ANGPTL7 Gln175His variant polypeptide, and comprise performing an assay on a sample obtained from a human subject to determine whether an ANGPTL7 polypeptide in the sample comprises a histidine at a position corresponding to position 175 according to SEQ ID NO:12. In some embodiments, the detecting step comprises sequencing at least a portion of the polypeptide that comprises a position corresponding to position 175 according to SEQ ID NO:10 or SEQ ID NO:12. In some embodiments, the detecting step comprises sequencing the entire polypeptide. In some embodiments, the detecting step comprises an immunoassay for detecting the presence of a polypeptide that comprises a position corresponding to position 175 according to SEQ ID NO:10 or SEQ ID NO:12.

The present disclosure also provides isolated nucleic acid molecules that hybridize to ANGPTL7 variant genomic nucleic acid molecules (such as SEQ ID NO:3), ANGPTL7 variant mRNA molecules (such as SEQ ID NO:6), and/or ANGPTL7 variant cDNA molecules (such as SEQ ID NO:9). In some embodiments, the isolated nucleic acid molecules hybridize to the portion of the ANGPTL7 nucleic acid molecule that includes a position corresponding to position 4,287 according to SEQ ID NO:3, or includes a position corresponding to position 525 according to SEQ ID NO:6 or SEQ ID NO:9.

In some embodiments, the methods detect the presence of a human ANGPTL7 predicted loss-of-function variant polypeptide, such as, for example, the ANGPTL7 Phe161Ile variant polypeptide, and comprise performing an assay on a sample obtained from a human subject to determine whether an ANGPTL7 polypeptide in the sample comprises an isoleucine at a position corresponding to position 161 according to SEQ ID NO:141. In some embodiments, the detecting step comprises sequencing at least a portion of the polypeptide that comprises a position corresponding to position 161 according to SEQ ID NO:10 or SEQ ID NO:141. In some embodiments, the detecting step comprises sequencing the entire polypeptide. In some embodiments, the detecting step comprises an immunoassay for detecting the presence of a polypeptide that comprises a position corresponding to position 161 according to SEQ ID NO:10 or SEQ ID NO:141.

The present disclosure also provides isolated nucleic acid molecules that hybridize to ANGPTL7 variant genomic nucleic acid molecules (such as SEQ ID NO:132), ANGPTL7 variant mRNA molecules (such as SEQ ID NO:135), and/or ANGPTL7 variant cDNA molecules (such as SEQ ID NO:138). In some embodiments, the isolated nucleic acid molecules hybridize to the portion of the ANGPTL7 nucleic acid molecule that includes a position corresponding to position 4,243 according to SEQ ID NO:132, or includes a position corresponding to position 481 according to SEQ ID NO:135 or SEQ ID NO:138.

In some embodiments, the methods detect the presence of a human ANGPTL7 predicted loss-of-function variant polypeptide, such as, for example, the ANGPTL7 Trp188Stop variant polypeptide, and comprise performing an assay on a sample obtained from a human subject to determine whether an ANGPTL7 polypeptide in the sample terminates at a position corresponding to position 187 according to SEQ ID NO:142. In some embodiments, the detecting step comprises sequencing at least a portion of the polypeptide that comprises positions corresponding to any positions that are C-terminal to position 187 according to SEQ ID NO:142 (such polypeptides are reference; an absence of such positions indicates that the polypeptide terminates at least at position 187 and is a predicted loss-of-function variant ANGPTL7 polypeptide). In some embodiments, the detecting step comprises sequencing the entire polypeptide. In some embodiments, the detecting step comprises an immunoassay for detecting the presence of a polypeptide that terminates at a position corresponding to position 187 according to SEQ ID NO:142.

The present disclosure also provides isolated nucleic acid molecules that hybridize to ANGPTL7 variant genomic nucleic acid molecules (such as SEQ ID NO:133), ANGPTL7 variant mRNA molecules (such as SEQ ID NO:136), and/or ANGPTL7 variant cDNA molecules (such as SEQ ID NO:139). In some embodiments, the isolated nucleic acid molecules hybridize to the portion of the ANGPTL7 nucleic acid molecule that includes a position corresponding to position 4,325 according to SEQ ID NO:133, or includes a position corresponding to position 563 according to SEQ ID NO:136 or SEQ ID NO:139.

In some embodiments, the methods detect the presence of a human ANGPTL7 predicted loss-of-function variant polypeptide, such as, for example, the ANGPTL7 Lys192Gln variant polypeptide, and comprise performing an assay on a sample obtained from a human subject to determine whether an ANGPTL7 polypeptide in the sample comprises a glutamine at a position corresponding to position 192 according to SEQ ID NO:143. In some embodiments, the detecting step comprises sequencing at least a portion of the polypeptide that comprises a position corresponding to position 192 according to SEQ ID NO:10 or SEQ ID NO:143. In some embodiments, the detecting step comprises sequencing the entire polypeptide. In some embodiments, the detecting step comprises an immunoassay for detecting the presence of a polypeptide that comprises a position corresponding to position 192 according to SEQ ID NO:10 or SEQ ID NO:143.

The present disclosure also provides isolated nucleic acid molecules that hybridize to ANGPTL7 variant genomic nucleic acid molecules (such as SEQ ID NO:134), ANGPTL7 variant mRNA molecules (such as SEQ ID NO:137), and/or ANGPTL7 variant cDNA molecules (such as SEQ ID NO:140). In some embodiments, the isolated nucleic acid molecules hybridize to the portion of the ANGPTL7 nucleic acid molecule that includes a position corresponding to position 4,336 according to SEQ ID NO:134, or includes a position corresponding to position 574 according to SEQ ID NO:137 or SEQ ID NO:140.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In preferred embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules comprise or consist of from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In preferred embodiments, the isolated nucleic acid molecules comprise or consist of from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to ANGPTL7 variant genomic nucleic acid molecules (such as SEQ ID NO:2), ANGPTL7 variant mRNA molecules (such as SEQ ID NO:5), and/or ANGPTL7 variant cDNA molecules (such as SEQ ID NO:8) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to ANGPTL7 variant genomic nucleic acid molecules (such as SEQ ID NO:2), ANGPTL7 variant mRNA molecules (such as SEQ ID NO:5), and/or ANGPTL7 variant cDNA molecules (such as SEQ ID NO:8). In some embodiments, the isolated nucleic acid molecules comprise or consist of from about 15 to about 100 nucleotides, or from about 15 to about 35 nucleotides. In some embodiments, the isolated nucleic acid molecules comprise or consist of from about 15 to about 100 nucleotides. In some embodiments, the isolated nucleic acid molecules comprise or consist of from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human ANGPTL7 polypeptide, wherein the portion comprises a position corresponding to:

position 4,291 according to SEQ ID NO:2, or the complement thereof; position 529 according to SEQ ID NO:5, or the complement thereof; or position 529 according to SEQ ID NO:8, or the complement thereof. In some embodiments, the alteration-specific probe or alteration-specific primer comprises a nucleotide sequence which is complementary to a portion of a nucleotide sequence comprising a position corresponding to position 4,291 according to SEQ ID NO:2, or the complement thereof. In some embodiments, the alteration-specific probe or alteration-specific primer comprises a nucleotide sequence which is complementary to a portion of a nucleotide sequence comprising positions corresponding to positions 4,289 to 4,291 according to SEQ ID NO:2, or the complement thereof. In some embodiments, the alteration-specific probe or alteration-specific primer comprises a nucleotide sequence which is complementary to a portion of a nucleotide sequence comprising a position corresponding to position 529 according to SEQ ID NO:5, or the complement thereof. In some embodiments, the alteration-specific probe or alteration-specific primer comprises a nucleotide sequence which is complementary to a portion of a nucleotide sequence comprising positions corresponding to positions 529 to 531 according to SEQ ID NO:5, or the complement thereof. In some embodiments, the alteration-specific probe or alteration-specific primer comprises a nucleotide sequence which is complementary to a portion of a nucleotide sequence comprising a position corresponding to position 529 according to SEQ ID NO:8, or the complement thereof. In some embodiments, the alteration-specific probe or alteration-specific primer comprises a nucleotide sequence which is complementary to a portion of a nucleotide sequence comprising positions corresponding to positions 529 to 531 according to SEQ ID NO:8, or the complement thereof.

In some embodiments, such isolated nucleic acid molecules hybridize to ANGPTL7 variant genomic nucleic acid molecules (such as SEQ ID NO:3), ANGPTL7 variant mRNA molecules (such as SEQ ID NO:6), and/or ANGPTL7 variant cDNA molecules (such as SEQ ID NO:9) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to ANGPTL7 variant genomic nucleic acid molecules (such as SEQ ID NO:3), ANGPTL7 variant mRNA molecules (such as SEQ ID NO:6), and/or ANGPTL7 variant cDNA molecules (such as SEQ ID NO:9). In some embodiments, the isolated nucleic acid molecules comprise or consist of from about 15 to about 100 nucleotides, or from about 15 to about 35 nucleotides. In some embodiments, the isolated nucleic acid molecules comprise or consist of from about 15 to about 100 nucleotides. In some embodiments, the isolated nucleic acid molecules comprise or consist of from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human ANGPTL7 polypeptide, wherein the portion comprises a position corresponding to: position 4,287 according to SEQ ID NO:3, or the complement thereof; position 525 according to SEQ ID NO:6, or the complement thereof; or position 525 according to SEQ ID NO:9, or the complement thereof. In some embodiments, the alteration-specific probe or alteration-specific primer comprises a nucleotide sequence which is complementary to a portion of a nucleotide sequence comprising a position corresponding to position 4,287 according to SEQ ID NO:3, or the complement thereof. In some embodiments, the alteration-specific probe or alteration-specific primer comprises a nucleotide sequence which is complementary to a portion of a nucleotide sequence comprising positions corresponding to positions 4,285 to 4,287 according to SEQ ID NO:3, or the complement thereof. In some embodiments, the alteration-specific probe or alteration-specific primer comprises a nucleotide sequence which is complementary to a portion of a nucleotide sequence comprising a position corresponding to position 525 according to SEQ ID NO:6, or the complement thereof. In some embodiments, the alteration-specific probe or alteration-specific primer comprises a nucleotide sequence which is complementary to a portion of a nucleotide sequence comprising positions corresponding to positions 523 to 525 according to SEQ ID NO:6, or the complement thereof. In some embodiments, the alteration-specific probe or alteration-specific primer comprises a nucleotide sequence which is complementary to a portion of a nucleotide sequence comprising a position corresponding to position 525 according to SEQ ID NO:9, or the complement thereof. In some embodiments, the alteration-specific probe or alteration-specific primer comprises a nucleotide sequence which is complementary to a portion of a nucleotide sequence comprising positions corresponding to positions 523 to 525 according to SEQ ID NO:9, or the complement thereof.

In some embodiments, such isolated nucleic acid molecules hybridize to ANGPTL7 variant genomic nucleic acid molecules (such as SEQ ID NO:132), ANGPTL7 variant mRNA molecules (such as SEQ ID NO:135), and/or ANGPTL7 variant cDNA molecules (such as SEQ ID NO:138) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to ANGPTL7 variant genomic nucleic acid molecules (such as SEQ ID NO:132), ANGPTL7 variant mRNA molecules (such as SEQ ID NO:135), and/or ANGPTL7 variant cDNA molecules (such as SEQ ID NO:138). In some embodiments, the isolated nucleic acid molecules comprise or consist of from about 15 to about 100 nucleotides, or from about 15 to about 35 nucleotides. In some embodiments, the isolated nucleic acid molecules comprise or consist of from about 15 to about 100 nucleotides. In some embodiments, the isolated nucleic acid molecules comprise or consist of from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human ANGPTL7 polypeptide, wherein the portion comprises a position corresponding to: position 4,243 according to SEQ ID NO:132, or the complement thereof; position 481 according to SEQ ID NO:135, or the complement thereof; or position 481 according to SEQ ID NO:138, or the complement thereof. In some embodiments, the alteration-specific probe or alteration-specific primer comprises a nucleotide sequence which is complementary to a portion of a nucleotide sequence comprising a position corresponding to position 4,243 according to SEQ ID NO:132, or the complement thereof. In some embodiments, the alteration-specific probe or alteration-specific primer comprises a nucleotide sequence which is complementary to a portion of a nucleotide sequence comprising positions corresponding to positions 4,243 to 4,245 according to SEQ ID NO:132, or the complement thereof. In some embodiments, the alteration-specific probe or alteration-specific primer comprises a nucleotide sequence which is complementary to a portion of a nucleotide sequence comprising a position corresponding to position 481 according to SEQ ID NO:135, or the complement thereof. In some embodiments, the alteration-specific probe or alteration-specific primer comprises a nucleotide sequence which is complementary to a portion of a nucleotide sequence comprising positions corresponding to positions 481 to 483 according to SEQ ID NO:135, or the complement thereof. In some embodiments, the alteration-specific probe or alteration-specific primer comprises a nucleotide sequence which is complementary to a portion of a nucleotide sequence comprising a position corresponding to position 481 according to SEQ ID NO:138, or the complement thereof. In some embodiments, the alteration-specific probe or alteration-specific primer comprises a nucleotide sequence which is complementary to a portion of a nucleotide sequence comprising positions corresponding to positions 481 to 483 according to SEQ ID NO:138, or the complement thereof.

In some embodiments, such isolated nucleic acid molecules hybridize to ANGPTL7 variant genomic nucleic acid molecules (such as SEQ ID NO:133), ANGPTL7 variant mRNA molecules (such as SEQ ID NO:136), and/or ANGPTL7 variant cDNA molecules (such as SEQ ID NO:139) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to ANGPTL7 variant genomic nucleic acid molecules (such as SEQ ID NO:133), ANGPTL7 variant mRNA molecules (such as SEQ ID NO:136), and/or ANGPTL7 variant cDNA molecules (such as SEQ ID NO:139). In some embodiments, the isolated nucleic acid molecules comprise or consist of from about 15 to about 100 nucleotides, or from about 15 to about 35 nucleotides. In some embodiments, the isolated nucleic acid molecules comprise or consist of from about 15 to about 100 nucleotides. In some embodiments, the isolated nucleic acid molecules comprise or consist of from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human ANGPTL7 polypeptide, wherein the portion comprises a position corresponding to: position 4,325 according to SEQ ID NO:133, or the complement thereof; position 563 according to SEQ ID NO:136, or the complement thereof; or position 563 according to SEQ ID NO:139, or the complement thereof. In some embodiments, the alteration-specific probe or alteration-specific primer comprises a nucleotide sequence which is complementary to a portion of a nucleotide sequence comprising a position corresponding to position 4,325 according to SEQ ID NO:133, or the complement thereof. In some embodiments, the alteration-specific probe or alteration-specific primer comprises a nucleotide sequence which is complementary to a portion of a nucleotide sequence comprising positions corresponding to positions 4,324 to 4,326 according to SEQ ID NO:133, or the complement thereof. In some embodiments, the alteration-specific probe or alteration-specific primer comprises a nucleotide sequence which is complementary to a portion of a nucleotide sequence comprising a position corresponding to position 563 according to SEQ ID NO:136, or the complement thereof. In some embodiments, the alteration-specific probe or alteration-specific primer comprises a nucleotide sequence which is complementary to a portion of a nucleotide sequence comprising positions corresponding to positions 562 to 564 according to SEQ ID NO:136, or the complement thereof. In some embodiments, the alteration-specific probe or alteration-specific primer comprises a nucleotide sequence which is complementary to a portion of a nucleotide sequence comprising a position corresponding to position 563 according to SEQ ID NO:139, or the complement thereof. In some embodiments, the alteration-specific probe or alteration-specific primer comprises a nucleotide sequence which is complementary to a portion of a nucleotide sequence comprising positions corresponding to positions 562 to 564 according to SEQ ID NO:139, or the complement thereof.

In some embodiments, such isolated nucleic acid molecules hybridize to ANGPTL7 variant genomic nucleic acid molecules (such as SEQ ID NO:134), ANGPTL7 variant mRNA molecules (such as SEQ ID NO:137), and/or ANGPTL7 variant cDNA molecules (such as SEQ ID NO:140) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to ANGPTL7 variant genomic nucleic acid molecules (such as SEQ ID NO:134), ANGPTL7 variant mRNA molecules (such as SEQ ID NO:137), and/or ANGPTL7 variant cDNA molecules (such as SEQ ID NO:140). In some embodiments, the isolated nucleic acid molecules comprise or consist of from about 15 to about 100 nucleotides, or from about 15 to about 35 nucleotides. In some embodiments, the isolated nucleic acid molecules comprise or consist of from about 15 to about 100 nucleotides. In some embodiments, the isolated nucleic acid molecules comprise or consist of from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding a human ANGPTL7 polypeptide, wherein the portion comprises a position corresponding to: position 4,336 according to SEQ ID NO:134, or the complement thereof; position 574 according to SEQ ID NO:137, or the complement thereof; or position 574 according to SEQ ID NO:140, or the complement thereof. In some embodiments, the alteration-specific probe or alteration-specific primer comprises a nucleotide sequence which is complementary to a portion of a nucleotide sequence comprising a position corresponding to position 4,336 according to SEQ ID NO:134, or the complement thereof. In some embodiments, the alteration-specific probe or alteration-specific primer comprises a nucleotide sequence which is complementary to a portion of a nucleotide sequence comprising positions corresponding to positions 4,336 to 4,338 according to SEQ ID NO:134, or the complement thereof. In some embodiments, the alteration-specific probe or alteration-specific primer comprises a nucleotide sequence which is complementary to a portion of a nucleotide sequence comprising a position corresponding to position 574 according to SEQ ID NO:137, or the complement thereof. In some embodiments, the alteration-specific probe or alteration-specific primer comprises a nucleotide sequence which is complementary to a portion of a nucleotide sequence comprising positions corresponding to positions 574 to 576 according to SEQ ID NO:137, or the complement thereof. In some embodiments, the alteration-specific probe or alteration-specific primer comprises a nucleotide sequence which is complementary to a portion of a nucleotide sequence comprising a position corresponding to position 574 according to SEQ ID NO:140, or the complement thereof. In some embodiments, the alteration-specific probe or alteration-specific primer comprises a nucleotide sequence which is complementary to a portion of a nucleotide sequence comprising positions corresponding to positions 574 to 576 according to SEQ ID NO:140, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect the C4,291T variation within the ANGPTL7 variant genomic nucleic acid molecule (such as, for example, according to SEQ ID NO:2), or the C529U variation within the ANGPTL7 variant mRNA molecule (such as, for example, according to SEQ ID NO:5), or the C529T variation within the ANGPTL7 variant cDNA molecule (such as, for example, according to SEQ ID NO:8). For example, the primers can be used to amplify ANGPTL7 variant genomic nucleic acid molecules or a fragment thereof comprising the C4,291T variation. The primers can also be used to amplify ANGPTL7 variant mRNA or a fragment thereof comprising the C529U variation. The primers can also be used to amplify ANGPTL7 variant cDNA or a fragment thereof comprising the C529T variation.

The probes and primers described herein can be used to detect the G4,287T variation within the ANGPTL7 variant genomic nucleic acid molecule (such as, for example, according to SEQ ID NO:3), or the G525U variation within the ANGPTL7 variant mRNA molecule (such as, for example, according to SEQ ID NO:6), or the G525T variation within the ANGPTL7 variant cDNA molecule (such as, for example, according to SEQ ID NO:9). For example, the primers can be used to amplify ANGPTL7 variant genomic nucleic acid molecules or a fragment thereof comprising the G4,287T variation. The primers can also be used to amplify ANGPTL7 variant mRNA or a fragment thereof comprising the G525U variation. The primers can also be used to amplify ANGPTL7 variant cDNA or a fragment thereof comprising the G525T variation.

The probes and primers described herein can be used to detect the T4,243A variation within the ANGPTL7 variant genomic nucleic acid molecule (such as, for example, according to SEQ ID NO:132), or the U481A variation within the ANGPTL7 variant mRNA molecule (such as, for example, according to SEQ ID NO:135), or the T481A variation within the ANGPTL7 variant cDNA molecule (such as, for example, according to SEQ ID NO:138). For example, the primers can be used to amplify ANGPTL7 variant genomic nucleic acid molecules or a fragment thereof comprising the T4,243A variation. The primers can also be used to amplify ANGPTL7 variant mRNA or a fragment thereof comprising the U481A variation. The primers can also be used to amplify ANGPTL7 variant cDNA or a fragment thereof comprising the T481A variation.

The probes and primers described herein can be used to detect the G4,325A variation within the ANGPTL7 variant genomic nucleic acid molecule (such as, for example, according to SEQ ID NO:133), or the G563A variation within the ANGPTL7 variant mRNA molecule (such as, for example, according to SEQ ID NO:136), or the G563A variation within the ANGPTL7 variant cDNA molecule (such as, for example, according to SEQ ID NO:139). For example, the primers can be used to amplify ANGPTL7 variant genomic nucleic acid molecules or a fragment thereof comprising the G4,325A variation. The primers can also be used to amplify ANGPTL7 variant mRNA or a fragment thereof comprising the G563A variation. The primers can also be used to amplify ANGPTL7 variant cDNA or a fragment thereof comprising the G563A variation.

The probes and primers described herein can be used to detect the A4,336C variation within the ANGPTL7 variant genomic nucleic acid molecule (such as, for example, according to SEQ ID NO:134), or the A574C variation within the ANGPTL7 variant mRNA molecule (such as, for example, according to SEQ ID NO:137), or the A574C variation within the ANGPTL7 variant cDNA molecule (such as, for example, according to SEQ ID NO:140). For example, the primers can be used to amplify ANGPTL7 variant genomic nucleic acid molecules or a fragment thereof comprising the A4,336C variation. The primers can also be used to amplify ANGPTL7 variant mRNA or a fragment thereof comprising the A574C variation. The primers can also be used to amplify ANGPTL7 variant cDNA or a fragment thereof comprising the A574C variation.

The present disclosure also provides pairs of primers comprising any of the primers described above. If one of the primers' 3'-ends hybridizes to a cytosine at a position corresponding to position 4,291 (rather than thymine) (comparing SEQ ID NO:1 and SEQ ID NO:2) in a particular ANGPTL7 genomic nucleic acid molecule, then the presence of the amplified fragment would indicate the presence of an ANGPTL7 reference genomic nucleic acid molecule. Conversely, if one of the primers' 3'-ends hybridizes to a thymine at a position corresponding to position 4,291 (rather than cytosine) (comparing SEQ ID NO:1 and SEQ ID NO:2) in a particular ANGPTL7 genomic nucleic acid molecule, then the presence of the amplified fragment would indicate the presence of the ANGPTL7 variant genomic nucleic acid molecule. In some embodiments, the nucleotide of the primer complementary to the thymine at a position corresponding to position 4,291 in SEQ ID NO:2 can be at the 3' end of the primer. In addition, if one of the primers' 3'-ends hybridizes to a cytosine at a position corresponding to position 529 (rather than uracil) (comparing SEQ ID NO:4 and SEQ ID NO:5) in a particular ANGPTL7 mRNA molecule, then the presence of the amplified fragment would indicate the presence of an ANGPTL7 reference mRNA molecule. Conversely, if one of the primers' 3'-ends hybridizes to a uracil at a position corresponding to position 529 (rather than cytosine) (comparing SEQ ID NO:4 and SEQ ID NO:5) in a particular ANGPTL7 mRNA molecule, then the presence of the amplified fragment would indicate the presence of the ANGPTL7 variant mRNA molecule. In some embodiments, the nucleotide of the primer complementary to the uracil at a position corresponding to position 529 in SEQ ID NO:5 can be at the 3' end of the primer. In addition, if one of the primers' 3'-ends hybridizes to a cytosine at a position corresponding to position 529 (rather than thymine) (comparing SEQ ID NO:7 and SEQ ID NO:8) in a particular ANGPTL7 cDNA molecule, then the presence of the amplified fragment would indicate the presence of an ANGPTL7 reference cDNA molecule. Conversely, if one of the primers' 3'-ends hybridizes to a thymine at a position corresponding to position 529 (rather than cytosine) (comparing SEQ ID NO:7 and SEQ ID NO:8) in a particular ANGPTL7 cDNA molecule, then the presence of the amplified fragment would indicate the presence of the ANGPTL7 variant cDNA molecule. In some embodiments, the nucleotide of the primer complementary to the thymine at a position corresponding to position 529 in SEQ ID NO:8 can be at the 3' end of the primer.

In some embodiments, the probes or primers comprise a nucleotide sequence which hybridizes to a portion of an ANGPTL7 genomic nucleic acid molecule, wherein the portion comprises a thymine at a position corresponding to position 4,291 according to SEQ ID NO:2, or which hybridizes to the complement of this nucleic acid molecule. In some embodiments, the probes or primers comprise a nucleotide sequence which hybridizes to an ANGPTL7 genomic nucleic acid molecule comprising SEQ ID NO:2 at a portion comprising a thymine at a position corresponding to position 4,291 according to SEQ ID NO:2, or which hybridizes to the complement of this nucleic acid molecule. In some embodiments, the probes or primers comprise a nucleotide sequence which hybridizes to a portion of an ANGPTL7 mRNA molecule, wherein the portion comprises a uracil at a position corresponding to position 529 according to SEQ ID NO:5, or which hybridizes to the complement of this nucleic acid molecule. In some embodiments, the probes or primers comprise a nucleotide sequence which hybridizes to an ANGPTL7 mRNA molecule comprising SEQ ID NO:5 at a portion comprising a uracil at a position corresponding to position 529 according to SEQ ID NO:5, or which hybridizes to the complement of this nucleic acid molecule. In some embodiments, the probes or primers comprise a nucleotide sequence which hybridizes to a portion of an ANGPTL7 cDNA molecule, wherein the portion comprises a thymine at a position corresponding to position 529 according to SEQ ID NO:8, or which hybridizes to the complement of this nucleic acid molecule. In some embodiments, the probes or primers comprise a nucleotide sequence which hybridizes to an ANGPTL7 cDNA molecule comprising SEQ ID NO:8 at a portion comprising a thymine at a position corresponding to position 529 according to SEQ ID NO:8, or which hybridizes to the complement of this nucleic acid molecule.

If one of the primers' 3'-ends hybridizes to a guanine at a position corresponding to position 4,287 (rather than thymine) (comparing SEQ ID NO:1 and SEQ ID NO:3) in a particular ANGPTL7 genomic nucleic acid molecule, then the presence of the amplified fragment would indicate the presence of an ANGPTL7 reference genomic nucleic acid molecule. Conversely, if one of the primers' 3'-ends hybridizes to a thymine at a position corresponding to position 4,287 (rather than guanine) (comparing SEQ ID NO:1 and SEQ ID NO:3) in a particular ANGPTL7 genomic nucleic acid molecule, then the presence of the amplified fragment would indicate the presence of the ANGPTL7 variant genomic nucleic acid molecule. In some embodiments, the nucleotide of the primer complementary to the thymine at a position corresponding to position 4,287 in SEQ ID NO:3 can be at the 3' end of the primer. In addition, if one of the primers' 3'-ends hybridizes to a guanine at a position corresponding to position 525 (rather than uracil) (comparing SEQ ID NO:4 and SEQ ID NO:6) in a particular ANGPTL7 mRNA molecule, then the presence of the amplified fragment would indicate the presence of an ANGPTL7 reference mRNA molecule. Conversely, if one of the primers' 3'-ends hybridizes to a uracil at a position corresponding to position 525 (rather than guanine) (comparing SEQ ID NO:4 and SEQ ID NO:6) in a particular ANGPTL7 mRNA molecule, then the presence of the amplified fragment would indicate the presence of the ANGPTL7 variant mRNA molecule. In some embodiments, the nucleotide of the primer complementary to the uracil at a position corresponding to position 525 in SEQ ID NO:6 can be at the 3' end of the primer. In addition, if one of the primers' 3'-ends hybridizes to a guanine at a position corresponding to position 525 (rather than thymine) (comparing SEQ ID NO:7 and SEQ ID NO:9) in a particular ANGPTL7 cDNA molecule, then the presence of the amplified fragment would indicate the presence of an ANGPTL7 reference cDNA molecule. Conversely, if one of the primers' 3'-ends hybridizes to a thymine at a position corresponding to position 525 (rather than guanine) (comparing SEQ ID NO:7 and SEQ ID NO:9) in a particular ANGPTL7 cDNA molecule, then the presence of the amplified fragment would indicate the presence of the ANGPTL7 variant cDNA molecule. In some embodiments, the nucleotide of the primer complementary to the thymine at a position corresponding to position 525 in SEQ ID NO:9 can be at the 3' end of the primer.

In some embodiments, the probes or primers comprise a nucleotide sequence which hybridizes to a portion of an ANGPTL7 genomic nucleic acid molecule, wherein the portion comprises a thymine at a position corresponding to position 4,287 according to SEQ ID NO:3, or which hybridizes to the complement of this nucleic acid molecule. In some embodiments, the probes or primers comprise a nucleotide sequence which hybridizes to an ANGPTL7 genomic nucleic acid molecule comprising SEQ ID NO:3 at a portion comprising a thymine at a position corresponding to position 4,287 according to SEQ ID NO:3, or which hybridizes to the complement of this nucleic acid molecule. In some embodiments, the probes or primers comprise a nucleotide sequence which hybridizes to a portion of an ANGPTL7 mRNA molecule, wherein the portion comprises a uracil at a position corresponding to position 525 according to SEQ ID NO:6, or which hybridizes to the complement of this nucleic acid molecule. In some embodiments, the probes or primers comprise a nucleotide sequence which hybridizes to an ANGPTL7 mRNA molecule comprising SEQ ID NO:6 at a portion comprising a uracil at a position corresponding to position 525 according to SEQ ID NO:6, or which hybridizes to the complement of this nucleic acid molecule. In some embodiments, the probes or primers comprise a nucleotide sequence which hybridizes to a portion of an ANGPTL7 cDNA molecule, wherein the portion comprises a thymine at a position corresponding to position 525 according to SEQ ID NO:9, or which hybridizes to the complement of this nucleic acid molecule. In some embodiments, the probes or primers comprise a nucleotide sequence which hybridizes to an ANGPTL7 cDNA molecule comprising SEQ ID NO:9 at a portion comprising a thymine at a position corresponding to position 525 according to SEQ ID NO:9, or which hybridizes to the complement of this nucleic acid molecule.

If one of the primers' 3'-ends hybridizes to a thymine at a position corresponding to position 4,243 (rather than adenine) (comparing SEQ ID NO:1 and SEQ ID NO:132) in a particular ANGPTL7 genomic nucleic acid molecule, then the presence of the amplified fragment would indicate the presence of an ANGPTL7 reference genomic nucleic acid molecule. Conversely, if one of the primers' 3'-ends hybridizes to an adenine at a position corresponding to position 4,243 (rather than thymine) (comparing SEQ ID NO:1 and SEQ ID NO:132) in a particular ANGPTL7 genomic nucleic acid molecule, then the presence of the amplified fragment would indicate the presence of an ANGPTL7 variant genomic nucleic acid molecule. In some embodiments, the nucleotide of the primer complementary to the adenine at a position corresponding to position 4,243 according to SEQ ID NO:132 can be at the 3' end of the primer. In addition, if one of the primers' 3'-ends hybridizes to a uracil at a position corresponding to position 481 (rather than adenine) (comparing SEQ ID NO:4 and SEQ ID NO:135) in a particular ANGPTL7 mRNA molecule, then the presence of the amplified fragment would indicate the presence of an ANGPTL7 reference mRNA molecule. Conversely, if one of the primers' 3'-ends hybridizes to an adenine at a position corresponding to position 481 (rather than uracil) (comparing SEQ ID NO:4 and SEQ ID NO:135) in a particular ANGPTL7 mRNA molecule, then the presence of the amplified fragment would indicate the presence of the ANGPTL7 variant mRNA molecule. In some embodiments, the nucleotide of the primer complementary to the adenine at a position corresponding to position 481 according to SEQ ID NO:135 can be at the 3' end of the primer. In addition, if one of the primers' 3'-ends hybridizes to a thymine at a position corresponding to position 481 (rather than adenine) (comparing SEQ ID NO:7 and SEQ ID NO:138) in a particular ANGPTL7 cDNA molecule, then the presence of the amplified fragment would indicate the presence of an ANGPTL7 reference cDNA molecule. Conversely, if one of the primers' 3'-ends hybridizes to an adenine at a position corresponding to position 481 (rather than thymine) (comparing SEQ ID NO:4 and SEQ ID NO:138) in a particular ANGPTL7 cDNA molecule, then the presence of the amplified fragment would indicate the presence of the ANGPTL7 variant cDNA molecule. In some embodiments, the nucleotide of the primer complementary to the adenine at a position corresponding to position 481 according to SEQ ID NO:138 can be at the 3' end of the primer.

In some embodiments, the probes or primers comprise a nucleotide sequence which hybridizes to a portion of an ANGPTL7 genomic nucleic acid molecule, wherein the portion comprises an adenine at a position corresponding to position 4,243 according to SEQ ID NO:132, or which hybridizes to the complement of this nucleic acid molecule. In some embodiments, the probes or primers comprise a nucleotide sequence which hybridizes to an ANGPTL7 genomic nucleic acid molecule comprising SEQ ID NO:132 at a portion comprising an adenine at a position corresponding to position 4,243 according to SEQ ID NO:132 or which hybridizes to the complement of this nucleic acid molecule. In some embodiments, the probes or primers comprise a nucleotide sequence which hybridizes to a portion of an ANGPTL7 mRNA molecule, wherein the portion comprises an adenine at a position corresponding to position 481 according to SEQ ID NO:135, or which hybridizes to the complement of this nucleic acid molecule. In some embodiments, the probes or primers comprise a nucleotide sequence which hybridizes to an ANGPTL7 mRNA molecule comprising SEQ ID NO:135 at a portion comprising an adenine at a position corresponding to position 481 according to SEQ ID NO:135, or which hybridizes to the complement of this nucleic acid molecule. In some embodiments, the probes or primers comprise a nucleotide sequence which hybridizes to a portion of an ANGPTL7 cDNA molecule, wherein the portion comprises an adenine at a position corresponding to position 481 according to SEQ ID NO:138, or which hybridizes to the complement of this nucleic acid molecule. In some embodiments, the probes or primers comprise a nucleotide sequence which hybridizes to an ANGPTL7 cDNA molecule comprising SEQ ID NO:138 at a portion comprising an adenine at a position corresponding to position 481 according to SEQ ID NO:138, or which hybridizes to the complement of this nucleic acid molecule.

If one of the primers' 3'-ends hybridizes to a guanine at a position corresponding to position 4,325 (rather than adenine) (comparing SEQ ID NO:1 and SEQ ID NO:133) in a particular ANGPTL7 genomic nucleic acid molecule, then the presence of the amplified fragment would indicate the presence of an ANGPTL7 reference genomic nucleic acid molecule. Conversely, if one of the primers' 3'-ends hybridizes to an adenine at a position corresponding to position 4,325 (rather than guanine) (comparing SEQ ID NO:1 and SEQ ID NO:133) in a particular ANGPTL7 genomic nucleic acid molecule, then the presence of the amplified fragment would indicate the presence of the ANGPTL7 variant genomic nucleic acid molecule. In some embodiments, the nucleotide of the primer complementary to the adenine at a position corresponding to position 4,325 according to SEQ ID NO:133 can be at the 3' end of the primer. In addition, if one of the primers' 3'-ends hybridizes to a guanine at a position corresponding to position 563 (rather than adenine) (comparing SEQ ID NO:4 and SEQ ID NO:136) in a particular ANGPTL7 mRNA molecule, then the presence of the amplified fragment would indicate the presence of an ANGPTL7 reference mRNA molecule. Conversely, if one of the primers' 3'-ends hybridizes to an adenine at a position corresponding to position 563 (rather than guanine) (comparing SEQ ID NO:4 and SEQ ID NO:136) in a particular ANGPTL7 mRNA molecule, then the presence of the amplified fragment would indicate the presence of the ANGPTL7 variant mRNA molecule. In some embodiments, the nucleotide of the primer complementary to the adenine at a position corresponding to position 563 according to SEQ ID NO:136 can be at the 3' end of the primer. In addition, if one of the primers' 3'-ends hybridizes to a guanine at a position corresponding to position 563 (rather than adenine) (comparing SEQ ID NO:7 and SEQ ID NO:139) in a particular ANGPTL7 cDNA molecule, then the presence of the amplified fragment would indicate the presence of an ANGPTL7 reference cDNA molecule. Conversely, if one of the primers' 3'-ends hybridizes to an adenine at a position corresponding to position 563 (rather than guanine) (comparing SEQ ID NO:7 and SEQ ID NO:139) in a particular ANGPTL7 cDNA molecule, then the presence of the amplified fragment would indicate the presence of the ANGPTL7 variant cDNA molecule. In some embodiments, the nucleotide of the primer complementary to the adenine at a position corresponding to position 563 according to SEQ ID NO:139 can be at the 3' end of the primer.

In some embodiments, the probes or primers comprise a nucleotide sequence which hybridizes to a portion of an ANGPTL7 genomic nucleic acid molecule, wherein the portion comprises an adenine at a position corresponding to position 4,325 according to SEQ ID NO:133, or which hybridizes to the complement of this nucleic acid molecule. In some embodiments, the probes or primers comprise a nucleotide sequence which hybridizes to an ANGPTL7 genomic nucleic acid molecule comprising SEQ ID NO:133 at a portion comprising an adenine at a position corresponding to position 4,325 according to SEQ ID NO:133 or which hybridizes to the complement of this nucleic acid molecule. In some embodiments, the probes or primers comprise a nucleotide sequence which hybridizes to a portion of an ANGPTL7 mRNA molecule, wherein the portion comprises an adenine at a position corresponding to position 563 according to SEQ ID NO:136, or which hybridizes to the complement of this nucleic acid molecule. In some embodiments, the probes or primers comprise a nucleotide sequence which hybridizes to an ANGPTL7 mRNA molecule comprising SEQ ID NO:136 at a portion comprising an adenine at a position corresponding to position 563 according to SEQ ID NO:136, or which hybridizes to the complement of this nucleic acid molecule. In some embodiments, the probes or primers comprise a nucleotide sequence which hybridizes to a portion of an ANGPTL7 cDNA molecule, wherein the portion comprises an adenine at a position corresponding to position 563 according to SEQ ID NO:139, or which hybridizes to the complement of this nucleic acid molecule. In some embodiments, the probes or primers comprise a nucleotide sequence which hybridizes to an ANGPTL7 cDNA molecule comprising SEQ ID NO:139 at a portion comprising an adenine at a position corresponding to position 563 according to SEQ ID NO:139, or which hybridizes to the complement of this nucleic acid molecule.

If one of the primers' 3'-ends hybridizes to an adenine at a position corresponding to position 4,336 (rather than cytosine) (comparing SEQ ID NO:1 and SEQ ID NO:134) in a particular ANGPTL7 genomic nucleic acid molecule, then the presence of the amplified fragment would indicate the presence of an ANGPTL7 reference genomic nucleic acid molecule. Conversely, if one of the primers' 3'-ends hybridizes to a cytosine at a position corresponding to position 4,336 (rather than adenine) (comparing SEQ ID NO:1 and SEQ ID NO:134) in a particular ANGPTL7 nucleic acid molecule, then the presence of the amplified fragment would indicate the presence of the ANGPTL7 variant genomic nucleic acid molecule. In some embodiments, the nucleotide of the primer complementary to the cytosine at a position corresponding to position 4,336 according to SEQ ID NO:134 can be at the 3' end of the primer. In addition, if one of the primers' 3'-ends hybridizes to an adenine at a position corresponding to position 574 (rather than cytosine) (comparing SEQ ID NO:4 and SEQ ID NO:137) in a particular ANGPTL7 mRNA molecule, then the presence of the amplified fragment would indicate the presence of an ANGPTL7 reference mRNA molecule. Conversely, if one of the primers' 3'-ends hybridizes to a cytosine at a position corresponding to position 574 (rather than adenine) (comparing SEQ ID NO:4 and SEQ ID NO:137) in a particular ANGPTL7 mRNA molecule, then the presence of the amplified fragment would indicate the presence of the ANGPTL7 variant mRNA molecule. In some embodiments, the nucleotide of the primer complementary to the cytosine at a position corresponding to position 574 according to SEQ ID NO:137 can be at the 3' end of the primer. In addition, if one of the primers' 3'-ends hybridizes to an adenine at a position corresponding to position 574 (rather than cytosine) (comparing SEQ ID NO:7 and SEQ ID NO:140) in a particular ANGPTL7 cDNA molecule, then the presence of the amplified fragment would indicate the presence of an ANGPTL7 reference cDNA molecule. Conversely, if one of the primers' 3'-ends hybridizes to a cytosine at a position corresponding to position 574 (rather than adenine) (comparing SEQ ID NO:7 and SEQ ID NO:140) in a particular ANGPTL7 cDNA molecule, then the presence of the amplified fragment would indicate the presence of the ANGPTL7 variant cDNA molecule. In some embodiments, the nucleotide of the primer complementary to the cytosine at a position corresponding to position 574 according to SEQ ID NO:140 can be at the 3' end of the primer.

In some embodiments, the probes or primers comprise a nucleotide sequence which hybridizes to a portion of an ANGPTL7 genomic nucleic acid molecule, wherein the portion comprises a cytosine at a position corresponding to position 4,336 according to SEQ ID NO:134, or which hybridizes to the complement of this nucleic acid molecule. In some embodiments, the probes or primers comprise a nucleotide sequence which hybridizes to an ANGPTL7 genomic nucleic acid molecule comprising SEQ ID NO:134 at a portion comprising a cytosine at a position corresponding to position 4,336 according to SEQ ID NO:134 or which hybridizes to the complement of this nucleic acid molecule. In some embodiments, the probes or primers comprise a nucleotide sequence which hybridizes to a portion of an ANGPTL7 mRNA molecule, wherein the portion comprises a cytosine at a position corresponding to position 574 according to SEQ ID NO:137, or which hybridizes to the complement of this nucleic acid molecule. In some embodiments, the probes or primers comprise a nucleotide sequence which hybridizes to an ANGPTL7 mRNA molecule comprising SEQ ID NO:137 at a portion comprising a cytosine at a position corresponding to position 574 according to SEQ ID NO:137, or which hybridizes to the complement of this nucleic acid molecule. In some embodiments, the probes or primers comprise a nucleotide sequence which hybridizes to a portion of an ANGPTL7 cDNA molecule, wherein the portion comprises a cytosine at a position corresponding to position 574 according to SEQ ID NO:140, or which hybridizes to the complement of this nucleic acid molecule. In some embodiments, the probes or primers comprise a nucleotide sequence which hybridizes to an ANGPTL7 cDNA molecule comprising SEQ ID NO:140 at a portion comprising a cytosine at a position corresponding to position 574 according to SEQ ID NO:140, or which hybridizes to the complement of this nucleic acid molecule.

In the context of the disclosure "specifically hybridizes" means that the probe or primer (such as, for example, the alteration-specific probe or alteration-specific primer) does not hybridize to a nucleic acid sequence encoding an ANGPTL7 reference genomic nucleic acid molecule, an ANGPTL7 reference mRNA molecule, and/or an ANGPTL7 reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The present disclosure also provides molecular complexes comprising or consisting of any of the ANGPTL7 nucleic acid molecules (genomic nucleic acid molecules, mRNA molecules, or cDNA molecules), or complement thereof, described herein and any of the alteration-specific primers or alteration-specific probes described herein. In some embodiments, the ANGPTL7 nucleic acid molecules (genomic nucleic acid molecules, mRNA molecules, or cDNA molecules), or complement thereof, in the molecular complexes are single-stranded. In some embodiments, the ANGPTL7 nucleic acid molecule is any of the genomic nucleic acid molecules described herein. In some embodiments, the ANGPTL7 nucleic acid molecule is any of the mRNA molecules described herein. In some embodiments, the ANGPTL7 nucleic acid molecule is any of the cDNA molecules described herein. In some embodiments, the molecular complex comprises or consists of any of the ANGPTL7 nucleic acid molecules (genomic nucleic acid molecules, mRNA molecules, or cDNA molecules), or complement thereof, described herein and any of the alteration-specific primers described herein. In some embodiments, the molecular complex comprises or consists of any of the ANGPTL7 nucleic acid molecules (genomic nucleic acid molecules, mRNA molecules, or cDNA molecules), or complement thereof, described herein and any of the alteration-specific probes described herein. In some embodiments, the molecular complex comprises an alteration-specific probe or an alteration-specific primer comprising a label. In some embodiments, the label is a fluorescent label, a radiolabel, or biotin. In some embodiments, the molecular complex further comprises a non-human polymerase.

The present disclosure also provides isolated nucleic acid molecules comprising a nucleotide sequence encoding a human ANGPTL7 polypeptide, wherein the polypeptide terminates at a position corresponding to position 176 according to SEQ ID NO:11, or the complement thereof. In some embodiments, the isolated nucleic acid molecule encodes an ANGPTL7 polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:11, and terminates at a position corresponding to position 176 according to SEQ ID NO:11. In some embodiments, the isolated nucleic acid molecule encodes an ANGPTL7 polypeptide having an amino acid sequence that has at least about 90% sequence identity to SEQ ID NO:11, and terminates at a position corresponding to position 176 according to SEQ ID NO:11. In some embodiments, the isolated nucleic acid molecule encodes an ANGPTL7 polypeptide having an amino acid sequence that has at least about 92% sequence identity to SEQ ID NO:11, and terminates at a position corresponding to position 176 according to SEQ ID NO:11. In some embodiments, the isolated nucleic acid molecule encodes an ANGPTL7 polypeptide having an amino acid sequence that has at least about 94% sequence identity to SEQ ID NO:11, and terminates at a position corresponding to position 176 according to SEQ ID NO:11. In some embodiments, the isolated nucleic acid molecule encodes an ANGPTL7 polypeptide having an amino acid sequence that has at least about 96% sequence identity to SEQ ID NO:11, and terminates at a position corresponding to position 176 according to SEQ ID NO:11. In some embodiments, the isolated nucleic acid molecule encodes an ANGPTL7 polypeptide having an amino acid sequence that has at least about 98% sequence identity to SEQ ID NO:11, and terminates at a position corresponding to position 176 according to SEQ ID NO:11.

In some embodiments, the nucleic acid molecule encodes an ANGPTL7 polypeptide comprising SEQ ID NO:11. In some embodiments, the nucleic acid molecule encodes an ANGPTL7 polypeptide consisting of SEQ ID NO:11.

The present disclosure also provides isolated nucleic acid molecules comprising a nucleotide sequence encoding a human ANGPTL7 polypeptide, wherein the polypeptide comprises a histidine at a position corresponding to position 175 according to SEQ ID NO:12, or the complement thereof. In some embodiments, the isolated nucleic acid molecule encodes an ANGPTL7 polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:12, and comprises a histidine at a position corresponding to position 175 according to SEQ ID NO:12. In some embodiments, the isolated nucleic acid molecule encodes an ANGPTL7 polypeptide having an amino acid sequence that has at least about 90% sequence identity to SEQ ID NO:12, and comprises a histidine at a position corresponding to position 175 according to SEQ ID NO:12. In some embodiments, the isolated nucleic acid molecule encodes an ANGPTL7 polypeptide having an amino acid sequence that has at least about 92% sequence identity to SEQ ID NO:12, and comprises a histidine at a position corresponding to position 175 according to SEQ ID NO:12. In some embodiments, the isolated nucleic acid molecule encodes an ANGPTL7 polypeptide having an amino acid sequence that has at least about 94% sequence identity to SEQ ID NO:12, and comprises a histidine at a position corresponding to position 175 according to SEQ ID NO:12. In some embodiments, the isolated nucleic acid molecule encodes an ANGPTL7 polypeptide having an amino acid sequence that has at least about 96% sequence identity to SEQ ID NO:12, and comprises a histidine at a position corresponding to position 175 according to SEQ ID NO:12. In some embodiments, the isolated nucleic acid molecule encodes an ANGPTL7 polypeptide having an amino acid sequence that has at least about 98% sequence identity to SEQ ID NO:12, and comprises a histidine at a position corresponding to position 175 according to SEQ ID NO:12.

In some embodiments, the nucleic acid molecule encodes an ANGPTL7 polypeptide comprising SEQ ID NO:12. In some embodiments, the nucleic acid molecule encodes an ANGPTL7 polypeptide consisting of SEQ ID NO:12.

The present disclosure also provides isolated nucleic acid molecules comprising a nucleotide sequence encoding a human ANGPTL7 polypeptide, wherein the polypeptide comprises an isoleucine at a position corresponding to position 161 according to SEQ ID NO:141, or the complement thereof. In some embodiments, the isolated nucleic acid molecule encodes an ANGPTL7 polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:141, and comprises an isoleucine at a position corresponding to position 161 according to SEQ ID NO:141. In some embodiments, the isolated nucleic acid molecule encodes an ANGPTL7 polypeptide having an amino acid sequence that has at least about 90% sequence identity to SEQ ID NO:141, and comprises an isoleucine at a position corresponding to position 161 according to SEQ ID NO:141. In some embodiments, the isolated nucleic acid molecule encodes an ANGPTL7 polypeptide having an amino acid sequence that has at least about 92% sequence identity to SEQ ID NO:141, and comprises an isoleucine at a position corresponding to position 161 according to SEQ ID NO:141. In some embodiments, the isolated nucleic acid molecule encodes an ANGPTL7 polypeptide having an amino acid sequence that has at least about 94% sequence identity to SEQ ID NO:141, and comprises an isoleucine at a position corresponding to position 161 according to SEQ ID NO:141. In some embodiments, the isolated nucleic acid molecule encodes an ANGPTL7 polypeptide having an amino acid sequence that has at least about 96% sequence identity to SEQ ID NO:141, and comprises an isoleucine at a position corresponding to position 161 according to SEQ ID NO:141. In some embodiments, the isolated nucleic acid molecule encodes an ANGPTL7 polypeptide having an amino acid sequence that has at least about 98% sequence identity to SEQ ID NO:141, and comprises an isoleucine at a position corresponding to position 161 according to SEQ ID NO:141.

In some embodiments, the nucleic acid molecule encodes an ANGPTL7 polypeptide comprising SEQ ID NO:141. In some embodiments, the nucleic acid molecule encodes an ANGPTL7 polypeptide consisting of SEQ ID NO:141.

The present disclosure also provides isolated nucleic acid molecules comprising a nucleotide sequence encoding a human ANGPTL7 polypeptide, wherein the polypeptide terminates at a position corresponding to position 187 according to SEQ ID NO:142, or the complement thereof. In some embodiments, the isolated nucleic acid molecule encodes an ANGPTL7 polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:142, and terminates at a position corresponding to position 187 according to SEQ ID NO:142. In some embodiments, the isolated nucleic acid molecule encodes an ANGPTL7 polypeptide having an amino acid sequence that has at least about 90% sequence identity to SEQ ID NO:142, and terminates at a position corresponding to position 187 according to SEQ ID NO:142. In some embodiments, the isolated nucleic acid molecule encodes an ANGPTL7 polypeptide having an amino acid sequence that has at least about 92% sequence identity to SEQ ID NO:142, and terminates at a position corresponding to position 187 according to SEQ ID NO:142. In some embodiments, the isolated nucleic acid molecule encodes an ANGPTL7 polypeptide having an amino acid sequence that has at least about 94% sequence identity to SEQ ID NO:142, and terminates at a position corresponding to position 187 according to SEQ ID NO:142. In some embodiments, the isolated nucleic acid molecule encodes an ANGPTL7 polypeptide having an amino acid sequence that has at least about 96% sequence identity to SEQ ID NO:142, and terminates at a position corresponding to position 187 according to SEQ ID NO:142. In some embodiments, the isolated nucleic acid molecule encodes an ANGPTL7 polypeptide having an amino acid sequence that has at least about 98% sequence identity to SEQ ID NO:142, and terminates at a position corresponding to position 187 according to SEQ ID NO:142.

In some embodiments, the nucleic acid molecule encodes an ANGPTL7 polypeptide comprising SEQ ID NO:142. In some embodiments, the nucleic acid molecule encodes an ANGPTL7 polypeptide consisting of SEQ ID NO:142.

The present disclosure also provides isolated nucleic acid molecules comprising a nucleotide sequence encoding a human ANGPTL7 polypeptide, wherein the polypeptide comprises a glutamine at a position corresponding to position 192 according to SEQ ID NO:143, or the complement thereof. In some embodiments, the isolated nucleic acid molecule encodes an ANGPTL7 polypeptide having an amino acid sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:143, and comprises a glutamine at a position corresponding to position 192 according to SEQ ID NO:143. In some embodiments, the isolated nucleic acid molecule encodes an ANGPTL7 polypeptide having an amino acid sequence that has at least about 90% sequence identity to SEQ ID NO:143, and comprises a glutamine at a position corresponding to position 192 according to SEQ ID NO:143. In some embodiments, the isolated nucleic acid molecule encodes an ANGPTL7 polypeptide having an amino acid sequence that has at least about 92% sequence identity to SEQ ID NO:143, and comprises a glutamine at a position corresponding to position 192 according to SEQ ID NO:143. In some embodiments, the isolated nucleic acid molecule encodes an ANGPTL7 polypeptide having an amino acid sequence that has at least about 94% sequence identity to SEQ ID NO:143, and comprises a glutamine at a position corresponding to position 192 according to SEQ ID NO:143. In some embodiments, the isolated nucleic acid molecule encodes an ANGPTL7 polypeptide having an amino acid sequence that has at least about 96% sequence identity to SEQ ID NO:143, and comprises a glutamine at a position corresponding to position 192 according to SEQ ID NO:143. In some embodiments, the isolated nucleic acid molecule encodes an ANGPTL7 polypeptide having an amino acid sequence that has at least about 98% sequence identity to SEQ ID NO:143, and comprises a glutamine at a position corresponding to position 192 according to SEQ ID NO:143.

In some embodiments, the nucleic acid molecule encodes an ANGPTL7 polypeptide comprising SEQ ID NO:143. In some embodiments, the nucleic acid molecule encodes an ANGPTL7 polypeptide consisting of SEQ ID NO:143.

The nucleotide sequence of an ANGPTL7 reference genomic nucleic acid molecule is set forth in SEQ ID NO:1. Referring to SEQ ID NO:1, position 4,291 of the ANGPTL7 reference genomic nucleic acid molecule is a cytosine. Referring to SEQ ID NO:1, position 4,287 of the ANGPTL7 reference genomic nucleic acid molecule is a guanine. Referring to SEQ ID NO:1, position 4,243 of the ANGPTL7 reference genomic nucleic acid molecule is a thymine. Referring to SEQ ID NO:1, position 4,325 of the ANGPTL7 reference genomic nucleic acid molecule is a guanine. Referring to SEQ ID NO:1, position 4,336 of the ANGPTL7 reference genomic nucleic acid molecule is an adenine.

A variant genomic nucleic acid molecule of ANGPTL7 exists, wherein the cytosine at position 4,291 (referring to the reference genomic sequence set forth in SEQ ID NO:1) is replaced with a thymine. The nucleotide sequence of this ANGPTL7 variant genomic nucleic acid molecule is set forth in SEQ ID NO:2.

Another variant genomic nucleic acid molecule of ANGPTL7 exists, wherein the guanine at position 4,287 (referring to the reference genomic sequence set forth in SEQ ID NO:1) is replaced with a thymine. The nucleotide sequence of this ANGPTL7 variant genomic nucleic acid molecule is set forth in SEQ ID NO:3.

Another variant genomic nucleic acid molecule of ANGPTL7 exists, wherein the thymine at position 4,243 (referring to the reference genomic sequence set forth in SEQ ID NO:1) is replaced with an adenine. The nucleotide sequence of this ANGPTL7 variant genomic nucleic acid molecule is set forth in SEQ ID NO:132.

Another variant genomic nucleic acid molecule of ANGPTL7 exists, wherein the guanine at position 4,325 (referring to the reference genomic sequence set forth in SEQ ID NO:1) is replaced with an adenine. The nucleotide sequence of this ANGPTL7 variant genomic nucleic acid molecule is set forth in SEQ ID NO:133.

Another variant genomic nucleic acid molecule of ANGPTL7 exists, wherein the adenine at position 4,336 (referring to the reference genomic sequence set forth in SEQ ID NO:1) is replaced with a cytosine. The nucleotide sequence of this ANGPTL7 variant genomic nucleic acid molecule is set forth in SEQ ID NO:134.

The present disclosure provides isolated genomic nucleic acid molecules comprising or consisting of a nucleotide sequence encoding a human ANGPTL7 polypeptide, wherein the nucleotide sequence comprises a thymine at a position corresponding to position 4,291 (C4,291T) according to SEQ ID NO:2, or the complement thereof. In some embodiments, the isolated genomic nucleic acid molecules comprise a nucleotide sequence encoding a human ANGPTL7 polypeptide, wherein the nucleotide sequence comprises a thymine at a position corresponding to position 4,291 (C4,291T) according to SEQ ID NO:2, or the complement thereof. In some embodiments, the isolated genomic nucleic acid molecules consist of a nucleotide sequence encoding a human ANGPTL7 polypeptide, wherein the nucleotide sequence comprises a thymine at a position corresponding to position 4,291 (C4,291T) according to SEQ ID NO:2, or the complement thereof. In some embodiments, the isolated genomic nucleic acid molecules comprise a nucleotide sequence encoding a human ANGPTL7 polypeptide, wherein the nucleotide sequence comprises a TGA codon at positions corresponding to positions 4,289 to 4,291 according to SEQ ID NO:2.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprise a thymine at a position corresponding to position 4,291 according to SEQ ID NO:2, or the complement thereof. In some embodiments, the isolated genomic nucleic acid molecules comprise or consist of a nucleotide sequence that has at least about 90% sequence identity to SEQ ID NO:2, and comprise a thymine at a position corresponding to position 4,291 according to SEQ ID NO:2, or the complement thereof. In some embodiments, the isolated genomic nucleic acid molecules comprise or consist of a nucleotide sequence that has at least about 92% sequence identity to SEQ ID NO:2, and comprise a thymine at a position corresponding to position 4,291 according to SEQ ID NO:2, or the complement thereof. In some embodiments, the isolated genomic nucleic acid molecules comprise or consist of a nucleotide sequence that has at least about 94% sequence identity to SEQ ID NO:2, and comprise a thymine at a position corresponding to position 4,291 according to SEQ ID NO:2, or the complement thereof. In some embodiments, the isolated genomic nucleic acid molecules comprise or consist of a nucleotide sequence that has at least about 96% sequence identity to SEQ ID NO:2, and comprise a thymine at a position corresponding to position 4,291 according to SEQ ID NO:2, or the complement thereof. In some embodiments, the isolated genomic nucleic acid molecules comprise or consist of a nucleotide sequence that has at least about 98% sequence identity to SEQ ID NO:2, and comprise a thymine at a position corresponding to position 4,291 according to SEQ ID NO:2, or the complement thereof. Herein, if reference is made to percent sequence identity, the higher percentages of sequence identity are preferred over the lower ones.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:2, and comprise a TGA codon at positions corresponding to positions 4,289 to 4,291 according to SEQ ID NO:2, or the complement thereof. In some embodiments, the isolated genomic nucleic acid molecules comprise or consist of a nucleotide sequence that has at least about 90% sequence identity to SEQ ID NO:2, and comprise a TGA codon at positions corresponding to positions 4,289 to 4,291 according to SEQ ID NO:2, or the complement thereof. In some embodiments, the isolated genomic nucleic acid molecules comprise or consist of a nucleotide sequence that has at least about 92% sequence identity to SEQ ID NO:2, and comprise a TGA codon at positions corresponding to positions 4,289 to 4,291 according to SEQ ID NO:2, or the complement thereof. In some embodiments, the isolated genomic nucleic acid molecules comprise or consist of a nucleotide sequence that has at least about 94% sequence identity to SEQ ID NO:2, and comprise a TGA codon at positions corresponding to positions 4,289 to 4,291 according to SEQ ID NO:2, or the complement thereof. In some embodiments, the isolated genomic nucleic acid molecules comprise or consist of a nucleotide sequence that has at least about 96% sequence identity to SEQ ID NO:2, and comprise a TGA codon at positions corresponding to positions 4,289 to 4,291 according to SEQ ID NO:2, or the complement thereof. In some embodiments, the isolated genomic nucleic acid molecules comprise or consist of a nucleotide sequence that has at least about 98% sequence identity to SEQ ID NO:2, and comprise a TGA codon at positions corresponding to positions 4,289 to 4,291 according to SEQ ID NO:2, or the complement thereof. Herein, if reference is made to percent sequence identity, the higher percentages of sequence identity are preferred over the lower ones.

In some embodiments, the isolated genomic nucleic acid molecules comprise SEQ ID NO:2. In some embodiments, the isolated genomic nucleic acid molecules consist of SEQ ID NO:2.

The present disclosure also provides isolated genomic nucleic acid molecules comprising or consisting of a nucleotide sequence encoding a human ANGPTL7 polypeptide, wherein the nucleotide sequence comprises a thymine at a position corresponding to position 4,287 (G4,287T) according to SEQ ID NO:3, or the complement thereof. In some embodiments, the isolated genomic nucleic acid molecules comprise a nucleotide sequence encoding a human ANGPTL7 polypeptide, wherein the nucleotide sequence comprises a thymine at a position corresponding to position 4,287 (G4,287T) according to SEQ ID NO:3, or the complement thereof. In some embodiments, the isolated genomic nucleic acid molecules consist of a nucleotide sequence encoding a human ANGPTL7 polypeptide, wherein the nucleotide sequence comprises a thymine at a position corresponding to position 4,287 (G4,287T) according to SEQ ID NO:3, or the complement thereof. In some embodiments, the isolated genomic nucleic acid molecules comprise a nucleotide sequence encoding a human ANGPTL7 polypeptide, wherein the nucleotide sequence comprises a CAT codon at positions corresponding to positions 4,285 to 4,287 according to SEQ ID NO:3.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:3, and comprise a thymine at a position corresponding to position 4,287 according to SEQ ID NO:3, or the complement thereof. In some embodiments, the isolated genomic nucleic acid molecules comprise or consist of a nucleotide sequence that has at least about 90% sequence identity to SEQ ID NO:3, and comprise a thymine at a position corresponding to position 4,287 according to SEQ ID NO:3, or the complement thereof. In some embodiments, the isolated genomic nucleic acid molecules comprise or consist of a nucleotide sequence that has at least about 92% sequence identity to SEQ ID NO:3, and comprise a thymine at a position corresponding to position 4,287 according to SEQ ID NO:3, or the complement thereof. In some embodiments, the isolated genomic nucleic acid molecules comprise or consist of a nucleotide sequence that has at least about 94% sequence identity to SEQ ID NO:3, and comprise a thymine at a position corresponding to position 4,287 according to SEQ ID NO:3, or the complement thereof. In some embodiments, the isolated genomic nucleic acid molecules comprise or consist of a nucleotide sequence that has at least about 96% sequence identity to SEQ ID NO:3, and comprise a thymine at a position corresponding to position 4,287 according to SEQ ID NO:3, or the complement thereof. In some embodiments, the isolated genomic nucleic acid molecules comprise or consist of a nucleotide sequence that has at least about 98% sequence identity to SEQ ID NO:3, and comprise a thymine at a position corresponding to position 4,287 according to SEQ ID NO:3, or the complement thereof. Herein, if reference is made to percent sequence identity, the higher percentages of sequence identity are preferred over the lower ones.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:3, and comprise a CAT codon at positions corresponding to positions 4,285 to 4,287 according to SEQ ID NO:3, or the complement thereof. In some embodiments, the isolated genomic nucleic acid molecules comprise or consist of a nucleotide sequence that has at least about 90% sequence identity to SEQ ID NO:3, and comprise a CAT codon at positions corresponding to positions 4,285 to 4,287 according to SEQ ID NO:3, or the complement thereof. In some embodiments, the isolated genomic nucleic acid molecules comprise or consist of a nucleotide sequence that has at least about 92% sequence identity to SEQ ID NO:3, and comprise a CAT codon at positions corresponding to positions 4,285 to 4,287 according to SEQ ID NO:3, or the complement thereof. In some embodiments, the isolated genomic nucleic acid molecules comprise or consist of a nucleotide sequence that has at least about 94% sequence identity to SEQ ID NO:3, and comprise a CAT codon at positions corresponding to positions 4,285 to 4,287 according to SEQ ID NO:3, or the complement thereof. In some embodiments, the isolated genomic nucleic acid molecules comprise or consist of a nucleotide sequence that has at least about 96% sequence identity to SEQ ID NO:3, and comprise a CAT codon at positions corresponding to positions 4,285 to 4,287 according to SEQ ID NO:3, or the complement thereof. In some embodiments, the isolated genomic nucleic acid molecules comprise or consist of a nucleotide sequence that has at least about 98% sequence identity to SEQ ID NO:3, and comprise a CAT codon at positions corresponding to positions 4,285 to 4,287 according to SEQ ID NO:3, or the complement thereof. Herein, if reference is made to percent sequence identity, the higher percentages of sequence identity are preferred over the lower ones.

In some embodiments, the isolated genomic nucleic acid molecules comprise SEQ ID NO:3. In some embodiments, the isolated genomic nucleic acid molecules consist of SEQ ID NO:3.

The present disclosure also provides isolated genomic nucleic acid molecules comprising or consisting of a nucleotide sequence encoding a human ANGPTL7 polypeptide, wherein the nucleotide sequence comprises an adenine at a position corresponding to position 4,243 (T4,243A) according to SEQ ID NO:132, or the complement thereof. In some embodiments, the isolated genomic nucleic acid molecules comprise a nucleotide sequence encoding a human ANGPTL7 polypeptide, wherein the nucleotide sequence comprises an adenine at a position corresponding to position 4,243 (T4,243A) according to SEQ ID NO:132, or the complement thereof. In some embodiments, the isolated genomic nucleic acid molecules consist of a nucleotide sequence encoding a human ANGPTL7 polypeptide, wherein the nucleotide sequence comprises an adenine at a position corresponding to position 4,243 (T4,243A) according to SEQ ID NO:132, or the complement thereof. In some embodiments, the isolated genomic nucleic acid molecules comprise a nucleotide sequence encoding a human ANGPTL7 polypeptide, wherein the nucleotide sequence comprises an ATC codon at positions corresponding to positions 4,243 to 4,245 according to SEQ ID NO:132.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:132, and comprise an adenine at a position corresponding to position 4,243 according to SEQ ID NO:132, or the complement thereof. In some embodiments, the isolated genomic nucleic acid molecules comprise or consist of a nucleotide sequence that has at least about 90% sequence identity to SEQ ID NO:132, and comprise an adenine at a position corresponding to position 4,243 according to SEQ ID NO:132, or the complement thereof. In some embodiments, the isolated genomic nucleic acid molecules comprise or consist of a nucleotide sequence that has at least about 92% sequence identity to SEQ ID NO:132, and comprise an adenine at a position corresponding to position 4,243 according to SEQ ID NO:132, or the complement thereof. In some embodiments, the isolated genomic nucleic acid molecules comprise or consist of a nucleotide sequence that has at least about 94% sequence identity to SEQ ID NO:132, and comprise an adenine at a position corresponding to position 4,243 according to SEQ ID NO:132, or the complement thereof. In some embodiments, the isolated genomic nucleic acid molecules comprise or consist of a nucleotide sequence that has at least about 96% sequence identity to SEQ ID NO:132, and comprise an adenine at a position corresponding to position 4,243 according to SEQ ID NO:132, or the complement thereof. In some embodiments, the isolated genomic nucleic acid molecules comprise or consist of a nucleotide sequence that has at least about 98% sequence identity to SEQ ID NO:132, and comprise an adenine at a position corresponding to position 4,243 according to SEQ ID NO:132, or the complement thereof. Herein, if reference is made to percent sequence identity, the higher percentages of sequence identity are preferred over the lower ones.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:132, and comprise an ATC codon at positions corresponding to positions 4,243 to 4,245 according to SEQ ID NO:132, or the complement thereof. In some embodiments, the isolated genomic nucleic acid molecules comprise or consist of a nucleotide sequence that has at least about 90% sequence identity to SEQ ID NO:132, and comprise an ATC codon at positions corresponding to positions 4,243 to 4,245 according to SEQ ID NO:132, or the complement thereof. In some embodiments, the isolated genomic nucleic acid molecules comprise or consist of a nucleotide sequence that has at least about 92% sequence identity to SEQ ID NO:132, and comprise an ATC codon at positions corresponding to positions 4,243 to 4,245 according to SEQ ID NO:132, or the complement thereof. In some embodiments, the isolated genomic nucleic acid molecules comprise or consist of a nucleotide sequence that has at least about 94% sequence identity to SEQ ID NO:132, and comprise an ATC codon at positions corresponding to positions 4,243 to 4,245 according to SEQ ID NO:132, or the complement thereof. In some embodiments, the isolated genomic nucleic acid molecules comprise or consist of a nucleotide sequence that has at least about 96% sequence identity to SEQ ID NO:132, and comprise an ATC codon at positions corresponding to positions 4,243 to 4,245 according to SEQ ID NO:132, or the complement thereof. In some embodiments, the isolated genomic nucleic acid molecules comprise or consist of a nucleotide sequence that has at least about 98% sequence identity to SEQ ID NO:132, and comprise an ATC codon at positions corresponding to positions 4,243 to 4,245 according to SEQ ID NO:132, or the complement thereof. Herein, if reference is made to percent sequence identity, the higher percentages of sequence identity are preferred over the lower ones.

In some embodiments, the isolated genomic nucleic acid molecules comprise SEQ ID NO: 132. In some embodiments, the isolated genomic nucleic acid molecules consist of SEQ ID NO:132.

The present disclosure also provides isolated genomic nucleic acid molecules comprising or consisting of a nucleotide sequence encoding a human ANGPTL7 polypeptide, wherein the nucleotide sequence comprises an adenine at a position corresponding to position 4,325 (G4,325A) according to SEQ ID NO:133, or the complement thereof. In some embodiments, the isolated genomic nucleic acid molecules comprise a nucleotide sequence encoding a human ANGPTL7 polypeptide, wherein the nucleotide sequence comprises an adenine at a position corresponding to position 4,325 (G4,325A) according to SEQ ID NO:133, or the complement thereof. In some embodiments, the isolated genomic nucleic acid molecules consist of a nucleotide sequence encoding a human ANGPTL7 polypeptide, wherein the nucleotide sequence comprises an adenine at a position corresponding to position 4,325 (G4,325A) according to SEQ ID NO:133, or the complement thereof. In some embodiments, the isolated genomic nucleic acid molecules comprise a nucleotide sequence encoding a human ANGPTL7 polypeptide, wherein the nucleotide sequence comprises a TAG codon at positions corresponding to positions 4,324 to 4,326 according to SEQ ID NO:133.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:133, and comprise an adenine at a position corresponding to position 4,325 according to SEQ ID NO:133, or the complement thereof. In some embodiments, the isolated genomic nucleic acid molecules comprise or consist of a nucleotide sequence that has at least about 90% sequence identity to SEQ ID NO:133, and comprise an adenine at a position corresponding to position 4,325 according to SEQ ID NO:133, or the complement thereof. In some embodiments, the isolated genomic nucleic acid molecules comprise or consist of a nucleotide sequence that has at least about 92% sequence identity to SEQ ID NO:133, and comprise an adenine at a position corresponding to position 4,325 according to SEQ ID NO:133, or the complement thereof. In some embodiments, the isolated genomic nucleic acid molecules comprise or consist of a nucleotide sequence that has at least about 94% sequence identity to SEQ ID NO:133, and comprise an adenine at a position corresponding to position 4,325 according to SEQ ID NO:133, or the complement thereof. In some embodiments, the isolated genomic nucleic acid molecules comprise or consist of a nucleotide sequence that has at least about 96% sequence identity to SEQ ID NO:133, and comprise an adenine at a position corresponding to position 4,325 according to SEQ ID NO:133, or the complement thereof. In some embodiments, the isolated genomic nucleic acid molecules comprise or consist of a nucleotide sequence that has at least about 98% sequence identity to SEQ ID NO:133, and comprise an adenine at a position corresponding to position 4,325 according to SEQ ID NO:133, or the complement thereof. Herein, if reference is made to percent sequence identity, the higher percentages of sequence identity are preferred over the lower ones.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:133, and comprise a TAG codon at positions corresponding to positions 4,324 to 4,326 according to SEQ ID NO:133, or the complement thereof. In some embodiments, the isolated genomic nucleic acid molecules comprise or consist of a nucleotide sequence that has at least about 90% sequence identity to SEQ ID NO:133, and comprise a TAG codon at positions corresponding to positions 4,324 to 4,326 according to SEQ ID NO:133, or the complement thereof. In some embodiments, the isolated genomic nucleic acid molecules comprise or consist of a nucleotide sequence that has at least about 92% sequence identity to SEQ ID NO:133, and comprise a TAG codon at positions corresponding to positions 4,324 to 4,326 according to SEQ ID NO:133, or the complement thereof. In some embodiments, the isolated genomic nucleic acid molecules comprise or consist of a nucleotide sequence that has at least about 94% sequence identity to SEQ ID NO:133, and comprise a TAG codon at positions corresponding to positions 4,324 to 4,326 according to SEQ ID NO:133, or the complement thereof. In some embodiments, the isolated genomic nucleic acid molecules comprise or consist of a nucleotide sequence that has at least about 96% sequence identity to SEQ ID NO:133, and comprise a TAG codon at positions corresponding to positions 4,324 to 4,326 according to SEQ ID NO:133, or the complement thereof. In some embodiments, the isolated genomic nucleic acid molecules comprise or consist of a nucleotide sequence that has at least about 98% sequence identity to SEQ ID NO:133, and comprise a TAG codon at positions corresponding to positions 4,324 to 4,326 according to SEQ ID NO:133, or the complement thereof. Herein, if reference is made to percent sequence identity, the higher percentages of sequence identity are preferred over the lower ones.

In some embodiments, the isolated genomic nucleic acid molecules comprise SEQ ID NO: 133. In some embodiments, the isolated genomic nucleic acid molecules consist of SEQ ID NO:133.

The present disclosure also provides isolated genomic nucleic acid molecules comprising or consisting of a nucleotide sequence encoding a human ANGPTL7 polypeptide, wherein the nucleotide sequence comprises a cytosine at a position corresponding to position 4,336 (A4,336C) according to SEQ ID NO:134, or the complement thereof. In some embodiments, the isolated genomic nucleic acid molecules comprise a nucleotide sequence encoding a human ANGPTL7 polypeptide, wherein the nucleotide sequence comprises a cytosine at a position corresponding to position 4,336 (A4,336C) according to SEQ ID NO:134, or the complement thereof. In some embodiments, the isolated genomic nucleic acid molecules consist of a nucleotide sequence encoding a human ANGPTL7 polypeptide, wherein the nucleotide sequence comprises a cytosine at a position corresponding to position 4,336 (A4,336C) according to SEQ ID NO:134, or the complement thereof. In some embodiments, the isolated genomic nucleic acid molecules comprise a nucleotide sequence encoding a human ANGPTL7 polypeptide, wherein the nucleotide sequence comprises a CAG codon at positions corresponding to positions 4,336 to 4,338 according to SEQ ID NO:134.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:134, and comprise a cytosine at a position corresponding to position 4,336 according to SEQ ID NO:134, or the complement thereof. In some embodiments, the isolated genomic nucleic acid molecules comprise or consist of a nucleotide sequence that has at least about 90% sequence identity to SEQ ID NO:134, and comprise a cytosine at a position corresponding to position 4,336 according to SEQ ID NO:134, or the complement thereof. In some embodiments, the isolated genomic nucleic acid molecules comprise or consist of a nucleotide sequence that has at least about 92% sequence identity to SEQ ID NO:134, and comprise a cytosine at a position corresponding to position 4,336 according to SEQ ID NO:134, or the complement thereof. In some embodiments, the isolated genomic nucleic acid molecules comprise or consist of a nucleotide sequence that has at least about 94% sequence identity to SEQ ID NO:134, and comprise a cytosine at a position corresponding to position 4,336 according to SEQ ID NO:134, or the complement thereof. In some embodiments, the isolated genomic nucleic acid molecules comprise or consist of a nucleotide sequence that has at least about 96% sequence identity to SEQ ID NO:134, and comprise a cytosine at a position corresponding to position 4,336 according to SEQ ID NO:134, or the complement thereof. In some embodiments, the isolated genomic nucleic acid molecules comprise or consist of a nucleotide sequence that has at least about 98% sequence identity to SEQ ID NO:134, and comprise a cytosine at a position corresponding to position 4,336 according to SEQ ID NO:134, or the complement thereof. Herein, if reference is made to percent sequence identity, the higher percentages of sequence identity are preferred over the lower ones.

In some embodiments, the isolated genomic nucleic acid molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:134, and comprise a CAG codon at positions corresponding to positions 4,336 to 4,338 according to SEQ ID NO:134, or the complement thereof. In some embodiments, the isolated genomic nucleic acid molecules comprise or consist of a nucleotide sequence that has at least about 90% sequence identity to SEQ ID NO:134, and comprise a CAG codon at positions corresponding to positions 4,336 to 4,338 according to SEQ ID NO:134, or the complement thereof. In some embodiments, the isolated genomic nucleic acid molecules comprise or consist of a nucleotide sequence that has at least about 92% sequence identity to SEQ ID NO:134, and comprise a CAG codon at positions corresponding to positions 4,336 to 4,338 according to SEQ ID NO:134, or the complement thereof. In some embodiments, the isolated genomic nucleic acid molecules comprise or consist of a nucleotide sequence that has at least about 94% sequence identity to SEQ ID NO:134, and comprise a CAG codon at positions corresponding to positions 4,336 to 4,338 according to SEQ ID NO:134, or the complement thereof. In some embodiments, the isolated genomic nucleic acid molecules comprise or consist of a nucleotide sequence that has at least about 96% sequence identity to SEQ ID NO:134, and comprise a CAG codon at positions corresponding to positions 4,336 to 4,338 according to SEQ ID NO:134, or the complement thereof. In some embodiments, the isolated genomic nucleic acid molecules comprise or consist of a nucleotide sequence that has at least about 98% sequence identity to SEQ ID NO:134, and comprise a CAG codon at positions corresponding to positions 4,336 to 4,338 according to SEQ ID NO:134, or the complement thereof. Herein, if reference is made to percent sequence identity, the higher percentages of sequence identity are preferred over the lower ones.

In some embodiments, the isolated genomic nucleic acid molecules comprise SEQ ID NO: 134. In some embodiments, the isolated genomic nucleic acid molecules consist of SEQ ID NO:134.

The genomic nucleic acid molecules can be from any organism. For example, the genomic nucleic acid molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

In some embodiments, the isolated genomic nucleic acid molecules comprise less than the entire genomic DNA sequence. In some embodiments, the isolated genomic nucleic acid molecules comprise or consist of at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 contiguous nucleotides of any one or more of SEQ ID NO:2, SEQ ID NO:3, SEQ ID NO:132, SEQ ID NO:133, and/or SEQ ID NO:134. In some embodiments, the isolated genomic nucleic acid molecules comprise or consist of at least about 1000 to at least about 2000 contiguous nucleotides of any one or more of SEQ ID NO:2, SEQ ID NO:3, SEQ ID NO:132, SEQ ID NO:133, and/or SEQ ID NO:134. In some embodiments, these isolated genomic nucleic acid molecules comprise the thymine at a position corresponding to position 4,291 according to SEQ ID NO:2, or comprise the thymine at a position corresponding to position 4,287 according to SEQ ID NO:3, or comprise the adenine at a position corresponding to position 4,243 according to SEQ ID NO:132, or comprise the adenine at a position corresponding to position 4,325 according to SEQ ID NO:133, or comprise the cytosine at a position corresponding to position 4,336 according to SEQ ID NO:134.

The nucleotide sequence of an ANGPTL7 reference mRNA molecule is set forth in SEQ ID NO:4. Referring to SEQ ID NO:4, position 529 of the ANGPTL7 reference mRNA molecule is a cytosine. Referring to SEQ ID NO:4, position 525 of the ANGPTL7 reference mRNA molecule is a guanine. Referring to SEQ ID NO:4, position 481 of the ANGPTL7 reference mRNA molecule is a uracil. Referring to SEQ ID NO:4, position 563 of the ANGPTL7 reference mRNA molecule is a guanine. Referring to SEQ ID NO:4, position 574 of the ANGPTL7 reference mRNA molecule is an adenine.

A variant mRNA molecule of ANGPTL7 exists, wherein the cytosine at position 529 (referring to the reference mRNA sequence set forth in SEQ ID NO:4) is replaced with a uracil. The nucleotide sequence of this ANGPTL7 variant mRNA molecule is set forth in SEQ ID NO:5.

Another variant mRNA molecule of ANGPTL7 exists, wherein the guanine at position 525 (referring to the reference mRNA sequence set forth in SEQ ID NO:4) is replaced with a uracil. The nucleotide sequence of this ANGPTL7 variant mRNA molecule is set forth in SEQ ID NO:6.

Another variant mRNA molecule of ANGPTL7 exists, wherein the uracil at position 481 (referring to the reference mRNA sequence set forth in SEQ ID NO:4) is replaced with an adenine. The nucleotide sequence of this ANGPTL7 variant mRNA molecule is set forth in SEQ ID NO:135.

Another variant mRNA molecule of ANGPTL7 exists, wherein the guanine at position 563 (referring to the reference mRNA sequence set forth in SEQ ID NO:4) is replaced with an adenine. The nucleotide sequence of this ANGPTL7 variant mRNA molecule is set forth in SEQ ID NO:136.

Another variant mRNA molecule of ANGPTL7 exists, wherein the adenine at position 574 (referring to the reference mRNA sequence set forth in SEQ ID NO:4) is replaced with a cytosine. The nucleotide sequence of this ANGPTL7 variant mRNA molecule is set forth in SEQ ID NO:137.

The present disclosure provides isolated mRNA molecules comprising or consisting of a nucleotide sequence encoding a human ANGPTL7 polypeptide, wherein the nucleotide sequence comprises a uracil at a position corresponding to position 529 according to SEQ ID NO:5, or the complement thereof. In some embodiments, the isolated mRNA molecules comprise a nucleotide sequence encoding a human ANGPTL7 polypeptide, wherein the nucleotide sequence comprises a uracil at a position corresponding to position 529 according to SEQ ID NO:5, or the complement thereof. In some embodiments, the isolated mRNA molecules consist of a nucleotide sequence encoding a human ANGPTL7 polypeptide, wherein the nucleotide sequence comprises a uracil at a position corresponding to position 529 according to SEQ ID NO:5, or the complement thereof. In some embodiments, the isolated mRNA molecules comprise or consist of a nucleotide sequence encoding a human ANGPTL7 polypeptide, wherein the nucleotide sequence comprises a UGA codon at positions corresponding to positions 529 to 531 according to SEQ ID NO:5.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:5, and comprise a uracil at a position corresponding to position 529 according to SEQ ID NO:5, or the complement thereof. In some embodiments, the isolated mRNA molecules comprise or consist of a nucleotide sequence that has at least about 90% sequence identity to SEQ ID NO:5, and comprise a uracil at a position corresponding to position 529 according to SEQ ID NO:5, or the complement thereof. In some embodiments, the isolated mRNA molecules comprise or consist of a nucleotide sequence that has at least about 92% sequence identity to SEQ ID NO:5, and comprise a uracil at a position corresponding to position 529 according to SEQ ID NO:5, or the complement thereof. In some embodiments, the isolated mRNA molecules comprise or consist of a nucleotide sequence that has at least about 94% sequence identity to SEQ ID NO:5, and comprise a uracil at a position corresponding to position 529 according to SEQ ID NO:5, or the complement thereof. In some embodiments, the isolated mRNA molecules comprise or consist of a nucleotide sequence that has at least about 96% sequence identity to SEQ ID NO:5, and comprise a uracil at a position corresponding to position 529 according to SEQ ID NO:5, or the complement thereof. In some embodiments, the isolated mRNA molecules comprise or consist of a nucleotide sequence that has at least about 98% sequence identity to SEQ ID NO:5, and comprise a uracil at a position corresponding to position 529 according to SEQ ID NO:5, or the complement thereof. Herein, if reference is made to percent sequence identity, the higher percentages of sequence identity are preferred over the lower ones.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:5, and comprise a UGA codon at positions corresponding to positions 529 to 531 according to SEQ ID NO:5, or the complement thereof. In some embodiments, the isolated mRNA molecules comprise or consist of a nucleotide sequence that has at least about 90% sequence identity to SEQ ID NO:5, and comprise a UGA codon at positions corresponding to positions 529 to 531 according to SEQ ID NO:5, or the complement thereof. In some embodiments, the isolated mRNA molecules comprise or consist of a nucleotide sequence that has at least about 92% sequence identity to SEQ ID NO:5, and comprise a UGA codon at positions corresponding to positions 529 to 531 according to SEQ ID NO:5, or the complement thereof. In some embodiments, the isolated mRNA molecules comprise or consist of a nucleotide sequence that has at least about 94% sequence identity to SEQ ID NO:5, and comprise a UGA codon at positions corresponding to positions 529 to 531 according to SEQ ID NO:5, or the complement thereof. In some embodiments, the isolated mRNA molecules comprise or consist of a nucleotide sequence that has at least about 96% sequence identity to SEQ ID NO:5, and comprise a UGA codon at positions corresponding to positions 529 to 531 according to SEQ ID NO:5, or the complement thereof. In some embodiments, the isolated mRNA molecules comprise or consist of a nucleotide sequence that has at least about 98% sequence identity to SEQ ID NO:5, and comprise a UGA codon at positions corresponding to positions 529 to 531 according to SEQ ID NO:5, or the complement thereof. Herein, if reference is made to percent sequence identity, the higher percentages of sequence identity are preferred over the lower ones.

In some embodiments, the isolated mRNA molecules comprise SEQ ID NO:5. In some embodiments, the isolated mRNA molecules consist of SEQ ID NO:5.

The present disclosure also provides isolated mRNA molecules comprising or consisting of a nucleotide sequence encoding a human ANGPTL7 polypeptide, wherein the nucleotide sequence comprises a uracil at a position corresponding to position 525 according to SEQ ID NO:6, or the complement thereof. In some embodiments, the isolated mRNA molecules comprise a nucleotide sequence encoding a human ANGPTL7 polypeptide, wherein the nucleotide sequence comprises a uracil at a position corresponding to position 525 according to SEQ ID NO:6, or the complement thereof. In some embodiments, the isolated mRNA molecules consist of a nucleotide sequence encoding a human ANGPTL7 polypeptide, wherein the nucleotide sequence comprises a uracil at a position corresponding to position 525 according to SEQ ID NO:6, or the complement thereof. In some embodiments, the isolated mRNA molecules comprise or consist of a nucleotide sequence encoding a human ANGPTL7 polypeptide, wherein the nucleotide sequence comprises a CAU codon at positions corresponding to positions 523 to 525 according to SEQ ID NO:6.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6, and comprise a uracil at a position corresponding to position 525 according to SEQ ID NO:6, or the complement thereof. In some embodiments, the isolated mRNA molecules comprise or consist of a nucleotide sequence that has at least about 90% sequence identity to SEQ ID NO:6, and comprise a uracil at a position corresponding to position 525 according to SEQ ID NO:6, or the complement thereof. In some embodiments, the isolated mRNA molecules comprise or consist of a nucleotide sequence that has at least about 92% sequence identity to SEQ ID NO:6, and comprise a uracil at a position corresponding to position 525 according to SEQ ID NO:6, or the complement thereof. In some embodiments, the isolated mRNA molecules comprise or consist of a nucleotide sequence that has at least about 94% sequence identity to SEQ ID NO:6, and comprise a uracil at a position corresponding to position 525 according to SEQ ID NO:6, or the complement thereof. In some embodiments, the isolated mRNA molecules comprise or consist of a nucleotide sequence that has at least about 96% sequence identity to SEQ ID NO:6, and comprise a uracil at a position corresponding to position 525 according to SEQ ID NO:6, or the complement thereof. In some embodiments, the isolated mRNA molecules comprise or consist of a nucleotide sequence that has at least about 98% sequence identity to SEQ ID NO:6, and comprise a uracil at a position corresponding to position 525 according to SEQ ID NO:6, or the complement thereof. Herein, if reference is made to percent sequence identity, the higher percentages of sequence identity are preferred over the lower ones.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:6, and comprise a CAU codon at positions corresponding to positions 523 to 525 according to SEQ ID NO:6, or the complement thereof. In some embodiments, the isolated mRNA molecules comprise or consist of a nucleotide sequence that has at least about 90% sequence identity to SEQ ID NO:6, and comprise a CAU codon at positions corresponding to positions 523 to 525 according to SEQ ID NO:6, or the complement thereof. In some embodiments, the isolated mRNA molecules comprise or consist of a nucleotide sequence that has at least about 92% sequence identity to SEQ ID NO:6, and comprise a CAU codon at positions corresponding to positions 523 to 525 according to SEQ ID NO:6, or the complement thereof. In some embodiments, the isolated mRNA molecules comprise or consist of a nucleotide sequence that has at least about 94% sequence identity to SEQ ID NO:6, and comprise a CAU codon at positions corresponding to positions 523 to 525 according to SEQ ID NO:6, or the complement thereof. In some embodiments, the isolated mRNA molecules comprise or consist of a nucleotide sequence that has at least about 96% sequence identity to SEQ ID NO:6, and comprise a CAU codon at positions corresponding to positions 523 to 525 according to SEQ ID NO:6, or the complement thereof. In some embodiments, the isolated mRNA molecules comprise or consist of a nucleotide sequence that has at least about 98% sequence identity to SEQ ID NO:6, and comprise a CAU codon at positions corresponding to positions 523 to 525 according to SEQ ID NO:6, or the complement thereof. Herein, if reference is made to percent sequence identity, the higher percentages of sequence identity are preferred over the lower ones.

In some embodiments, the isolated mRNA molecules comprise SEQ ID NO:6. In some embodiments, the isolated mRNA molecules consist of SEQ ID NO:6.

The present disclosure also provides isolated mRNA molecules comprising or consisting of a nucleotide sequence encoding a human ANGPTL7 polypeptide, wherein the nucleotide sequence comprises an adenine at a position corresponding to position 481 according to SEQ ID NO:135, or the complement thereof. In some embodiments, the isolated mRNA molecules comprise a nucleotide sequence encoding a human ANGPTL7 polypeptide, wherein the nucleotide sequence comprises an adenine at a position corresponding to position 481 according to SEQ ID NO:135, or the complement thereof. In some embodiments, the isolated mRNA molecules consist of a nucleotide sequence encoding a human ANGPTL7 polypeptide, wherein the nucleotide sequence comprises an adenine at a position corresponding to position 481 according to SEQ ID NO:135, or the complement thereof. In some embodiments, the isolated mRNA molecules comprise or consist of a nucleotide sequence encoding a human ANGPTL7 polypeptide, wherein the nucleotide sequence comprises an AUC codon at positions corresponding to positions 481 to 483 according to SEQ ID NO:135.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:135, and comprise an adenine at a position corresponding to position 481 according to SEQ ID NO:135, or the complement thereof. In some embodiments, the isolated mRNA molecules comprise or consist of a nucleotide sequence that has at least about 90% sequence identity to SEQ ID NO:135, and comprise an adenine at a position corresponding to position 481 according to SEQ ID NO:135, or the complement thereof. In some embodiments, the isolated mRNA molecules comprise or consist of a nucleotide sequence that has at least about 92% sequence identity to SEQ ID NO:135, and comprise an adenine at a position corresponding to position 481 according to SEQ ID NO:135, or the complement thereof. In some embodiments, the isolated mRNA molecules comprise or consist of a nucleotide sequence that has at least about 94% sequence identity to SEQ ID NO:135, and comprise an adenine at a position corresponding to position 481 according to SEQ ID NO:135, or the complement thereof. In some embodiments, the isolated mRNA molecules comprise or consist of a nucleotide sequence that has at least about 96% sequence identity to SEQ ID NO:135, and comprise an adenine at a position corresponding to position 481 according to SEQ ID NO:135, or the complement thereof. In some embodiments, the isolated mRNA molecules comprise or consist of a nucleotide sequence that has at least about 98% sequence identity to SEQ ID NO:135, and comprise an adenine at a position corresponding to position 481 according to SEQ ID NO:135, or the complement thereof. Herein, if reference is made to percent sequence identity, the higher percentages of sequence identity are preferred over the lower ones.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:135, and comprise an AUC codon at positions corresponding to positions 481 to 483 according to SEQ ID NO:135, or the complement thereof. In some embodiments, the isolated mRNA molecules comprise or consist of a nucleotide sequence that has at least about 90% sequence identity to SEQ ID NO:135, and comprise an AUC codon at positions corresponding to positions 481 to 483 according to SEQ ID NO:135, or the complement thereof. In some embodiments, the isolated mRNA molecules comprise or consist of a nucleotide sequence that has at least about 92% sequence identity to SEQ ID NO:135, and comprise an AUC codon at positions corresponding to positions 481 to 483 according to SEQ ID NO:135, or the complement thereof. In some embodiments, the isolated mRNA molecules comprise or consist of a nucleotide sequence that has at least about 94% sequence identity to SEQ ID NO:135, and comprise an AUC codon at positions corresponding to positions 481 to 483 according to SEQ ID NO:135, or the complement thereof. In some embodiments, the isolated mRNA molecules comprise or consist of a nucleotide sequence that has at least about 96% sequence identity to SEQ ID NO:135, and comprise an AUC codon at positions corresponding to positions 481 to 483 according to SEQ ID NO:135, or the complement thereof. In some embodiments, the isolated mRNA molecules comprise or consist of a nucleotide sequence that has at least about 98% sequence identity to SEQ ID NO:135, and comprise an AUC codon at positions corresponding to positions 481 to 483 according to SEQ ID NO:135, or the complement thereof. Herein, if reference is made to percent sequence identity, the higher percentages of sequence identity are preferred over the lower ones.

In some embodiments, the isolated mRNA molecules comprise SEQ ID NO:135. In some embodiments, the isolated mRNA molecules consist of SEQ ID NO:135.

The present disclosure also provides isolated mRNA molecules comprising or consisting of a nucleotide sequence encoding a human ANGPTL7 polypeptide, wherein the nucleotide sequence comprises an adenine at a position corresponding to position 563 according to SEQ ID NO:136, or the complement thereof. In some embodiments, the isolated mRNA molecules comprise a nucleotide sequence encoding a human ANGPTL7 polypeptide, wherein the nucleotide sequence comprises an adenine at a position corresponding to position 563 according to SEQ ID NO:136, or the complement thereof. In some embodiments, the isolated mRNA molecules consist of a nucleotide sequence encoding a human ANGPTL7 polypeptide, wherein the nucleotide sequence comprises an adenine at a position corresponding to position 563 according to SEQ ID NO:136, or the complement thereof. In some embodiments, the isolated mRNA molecules comprise or consist of a nucleotide sequence encoding a human ANGPTL7 polypeptide, wherein the nucleotide sequence comprises a UAG codon at positions corresponding to positions 562 to 564 according to SEQ ID NO:136.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:136, and comprise an adenine at a position corresponding to position 563 according to SEQ ID NO:136, or the complement thereof. In some embodiments, the isolated mRNA molecules comprise or consist of a nucleotide sequence that has at least about 90% sequence identity to SEQ ID NO:136, and comprise an adenine at a position corresponding to position 563 according to SEQ ID NO:136, or the complement thereof. In some embodiments, the isolated mRNA molecules comprise or consist of a nucleotide sequence that has at least about 92% sequence identity to SEQ ID NO:136, and comprise an adenine at a position corresponding to position 563 according to SEQ ID NO:136, or the complement thereof. In some embodiments, the isolated mRNA molecules comprise or consist of a nucleotide sequence that has at least about 94% sequence identity to SEQ ID NO:136, and comprise an adenine at a position corresponding to position 563 according to SEQ ID NO:136, or the complement thereof. In some embodiments, the isolated mRNA molecules comprise or consist of a nucleotide sequence that has at least about 96% sequence identity to SEQ ID NO:136, and comprise an adenine at a position corresponding to position 563 according to SEQ ID NO:136, or the complement thereof. In some embodiments, the isolated mRNA molecules comprise or consist of a nucleotide sequence that has at least about 98% sequence identity to SEQ ID NO:136, and comprise an adenine at a position corresponding to position 563 according to SEQ ID NO:136, or the complement thereof. Herein, if reference is made to percent sequence identity, the higher percentages of sequence identity are preferred over the lower ones.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:136, and comprise a UAG codon at positions corresponding to positions 562 to 564 according to SEQ ID NO:136, or the complement thereof. In some embodiments, the isolated mRNA molecules comprise or consist of a nucleotide sequence that has at least about 90% sequence identity to SEQ ID NO:136, and comprise a UAG codon at positions corresponding to positions 562 to 564 according to SEQ ID NO:136, or the complement thereof. In some embodiments, the isolated mRNA molecules comprise or consist of a nucleotide sequence that has at least about 92% sequence identity to SEQ ID NO:136, and comprise a UAG codon at positions corresponding to positions 562 to 564 according to SEQ ID NO:136, or the complement thereof. In some embodiments, the isolated mRNA molecules comprise or consist of a nucleotide sequence that has at least about 94% sequence identity to SEQ ID NO:136, and comprise a UAG codon at positions corresponding to positions 562 to 564 according to SEQ ID NO:136, or the complement thereof. In some embodiments, the isolated mRNA molecules comprise or consist of a nucleotide sequence that has at least about 96% sequence identity to SEQ ID NO:136, and comprise a UAG codon at positions corresponding to positions 562 to 564 according to SEQ ID NO:136, or the complement thereof. In some embodiments, the isolated mRNA molecules comprise or consist of a nucleotide sequence that has at least about 98% sequence identity to SEQ ID NO:136, and comprise a UAG codon at positions corresponding to positions 562 to 564 according to SEQ ID NO:136, or the complement thereof. Herein, if reference is made to percent sequence identity, the higher percentages of sequence identity are preferred over the lower ones.

In some embodiments, the isolated mRNA molecules comprise SEQ ID NO:136. In some embodiments, the isolated mRNA molecules consist of SEQ ID NO:136.

The present disclosure also provides isolated mRNA molecules comprising or consisting of a nucleotide sequence encoding a human ANGPTL7 polypeptide, wherein the nucleotide sequence comprises a cytosine at a position corresponding to position 574 according to SEQ ID NO:137, or the complement thereof. In some embodiments, the isolated mRNA molecules comprise a nucleotide sequence encoding a human ANGPTL7 polypeptide, wherein the nucleotide sequence comprises a cytosine at a position corresponding to position 574 according to SEQ ID NO:137, or the complement thereof. In some embodiments, the isolated mRNA molecules consist of a nucleotide sequence encoding a human ANGPTL7 polypeptide, wherein the nucleotide sequence comprises a cytosine at a position corresponding to position 574 according to SEQ ID NO:137, or the complement thereof. In some embodiments, the isolated mRNA molecules comprise or consist of a nucleotide sequence encoding a human ANGPTL7 polypeptide, wherein the nucleotide sequence comprises a CAG codon at positions corresponding to positions 574 to 576 according to SEQ ID NO:137.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:137, and comprise a cytosine at a position corresponding to position 574 according to SEQ ID NO:137, or the complement thereof. In some embodiments, the isolated mRNA molecules comprise or consist of a nucleotide sequence that has at least about 90% sequence identity to SEQ ID NO:137, and comprise a cytosine at a position corresponding to position 574 according to SEQ ID NO:137, or the complement thereof. In some embodiments, the isolated mRNA molecules comprise or consist of a nucleotide sequence that has at least about 92% sequence identity to SEQ ID NO:137, and comprise a cytosine at a position corresponding to position 574 according to SEQ ID NO:137, or the complement thereof. In some embodiments, the isolated mRNA molecules comprise or consist of a nucleotide sequence that has at least about 94% sequence identity to SEQ ID NO:137, and comprise a cytosine at a position corresponding to position 574 according to SEQ ID NO:137, or the complement thereof. In some embodiments, the isolated mRNA molecules comprise or consist of a nucleotide sequence that has at least about 96% sequence identity to SEQ ID NO:137, and comprise a cytosine at a position corresponding to position 574 according to SEQ ID NO:137, or the complement thereof. In some embodiments, the isolated mRNA molecules comprise or consist of a nucleotide sequence that has at least about 98% sequence identity to SEQ ID NO:137, and comprise a cytosine at a position corresponding to position 574 according to SEQ ID NO:137, or the complement thereof. Herein, if reference is made to percent sequence identity, the higher percentages of sequence identity are preferred over the lower ones.

In some embodiments, the isolated mRNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:137, and comprise a CAG codon at positions corresponding to positions 574 to 576 according to SEQ ID NO:137, or the complement thereof. In some embodiments, the isolated mRNA molecules comprise or consist of a nucleotide sequence that has at least about 90% sequence identity to SEQ ID NO:137, and comprise a CAG codon at positions corresponding to positions 574 to 576 according to SEQ ID NO:137, or the complement thereof. In some embodiments, the isolated mRNA molecules comprise or consist of a nucleotide sequence that has at least about 92% sequence identity to SEQ ID NO:137, and comprise a CAG codon at positions corresponding to positions 574 to 576 according to SEQ ID NO:137, or the complement thereof. In some embodiments, the isolated mRNA molecules comprise or consist of a nucleotide sequence that has at least about 94% sequence identity to SEQ ID NO:137, and comprise a CAG codon at positions corresponding to positions 574 to 576 according to SEQ ID NO:137, or the complement thereof. In some embodiments, the isolated mRNA molecules comprise or consist of a nucleotide sequence that has at least about 96% sequence identity to SEQ ID NO:137, and comprise a CAG codon at positions corresponding to positions 574 to 576 according to SEQ ID NO:137, or the complement thereof. In some embodiments, the isolated mRNA molecules comprise or consist of a nucleotide sequence that has at least about 98% sequence identity to SEQ ID NO:137, and comprise a CAG codon at positions corresponding to positions 574 to 576 according to SEQ ID NO:137, or the complement thereof. Herein, if reference is made to percent sequence identity, the higher percentages of sequence identity are preferred over the lower ones.

In some embodiments, the isolated mRNA molecules comprise SEQ ID NO:137. In some embodiments, the isolated mRNA molecules consist of SEQ ID NO:137.

The mRNA molecules can be from any organism. For example, the mRNA molecules can be human or an ortholog from another organism, such as a non-human mammal, a rodent, a mouse, or a rat. It is understood that mRNA sequences within a population can vary due to polymorphisms such as single-nucleotide polymorphisms. The examples provided herein are only exemplary sequences. Other sequences are also possible.

In some embodiments, the isolated mRNA molecules comprise less than the entire mRNA sequence. In some embodiments, the isolated mRNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, or at least about 500 contiguous nucleotides of any one or more of SEQ ID NO:5, SEQ ID NO:6, SEQ ID NO:135, SEQ ID NO:136, and/or SEQ ID NO:137. In some embodiments, the isolated mRNA molecules comprise or consist of at least about 400 to at least about 500 contiguous nucleotides of any one or more of SEQ ID NO:5, SEQ ID NO:6, SEQ ID NO:135, SEQ ID NO:136, and/or SEQ ID NO:137. In some embodiments, these isolated mRNA molecules comprise the uracil at the position corresponding to position 529 according to SEQ ID NO:5, or the uracil at the position corresponding to position 525 according to SEQ ID NO:6, or the adenine at the position corresponding to position 481 according to SEQ ID NO:135, or the adenine at the position corresponding to position 563 according to SEQ ID NO:136, or the cytosine at the position corresponding to position 574 according to SEQ ID NO:137.

The nucleotide sequence of an ANGPTL7 reference cDNA molecule is set forth in SEQ ID NO:7. Referring to SEQ ID NO:7, position 529 of the ANGPTL7 reference cDNA molecule is a cytosine. Referring to SEQ ID NO:7, position 525 of the ANGPTL7 reference cDNA molecule is a guanine. Referring to SEQ ID NO:7, position 481 of the ANGPTL7 reference cDNA molecule is a thymine. Referring to SEQ ID NO:7, position 563 of the ANGPTL7 reference cDNA molecule is a guanine. Referring to SEQ ID NO:7, position 574 of the ANGPTL7 reference cDNA molecule is an adenine.

A variant cDNA molecule of ANGPTL7 exists, wherein the cytosine at position 529 (referring to the reference cDNA sequence set forth in SEQ ID NO:7) is replaced with a thymine. The nucleotide sequence of this ANGPTL7 variant cDNA molecule is set forth in SEQ ID NO:8.

Another variant cDNA molecule of ANGPTL7 exists, wherein the guanine at position 525 (referring to the reference cDNA sequence set forth in SEQ ID NO:7) is replaced with a thymine. The nucleotide sequence of this ANGPTL7 variant cDNA molecule is set forth in SEQ ID NO:9.

Another variant cDNA molecule of ANGPTL7 exists, wherein the thymine at position 481 (referring to the reference cDNA sequence set forth in SEQ ID NO:7) is replaced with an adenine. The nucleotide sequence of this ANGPTL7 variant cDNA molecule is set forth in SEQ ID NO:138.

Another variant cDNA molecule of ANGPTL7 exists, wherein the guanine at position 563 (referring to the reference cDNA sequence set forth in SEQ ID NO:7) is replaced with an adenine. The nucleotide sequence of this ANGPTL7 variant cDNA molecule is set forth in SEQ ID NO:139.

Another variant cDNA molecule of ANGPTL7 exists, wherein the adenine at position 574 (referring to the reference cDNA sequence set forth in SEQ ID NO:7) is replaced with a cytosine. The nucleotide sequence of this ANGPTL7 variant cDNA molecule is set forth in SEQ ID NO:140.

The present disclosure provides isolated cDNA molecules comprising or consisting of a nucleotide sequence encoding a human ANGPTL7 polypeptide, wherein the nucleotide sequence comprises a thymine at a position corresponding to position 529 according to SEQ ID NO:8, or the complement thereof. In some embodiments, the isolated cDNA molecules comprise a nucleotide sequence encoding a human ANGPTL7 polypeptide, wherein the nucleotide sequence comprises a thymine at a position corresponding to position 529 according to SEQ ID NO:8, or the complement thereof. In some embodiments, the isolated cDNA molecules consist of a nucleotide sequence encoding a human ANGPTL7 polypeptide, wherein the nucleotide sequence comprises a thymine at a position corresponding to position 529 according to SEQ ID NO:8, or the complement thereof. In some embodiments, the isolated cDNA molecules comprise a nucleotide sequence encoding a human ANGPTL7 polypeptide, wherein the nucleotide sequence comprises a TGA codon at positions corresponding to positions 529 to 531 according to SEQ ID NO:8.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprise a thymine at a position corresponding to position 529 according to SEQ ID NO:8, or the complement thereof. In some embodiments, the isolated cDNA molecules comprise or consist of a nucleotide sequence that has at least about 90% sequence identity to SEQ ID NO:8, and comprise a thymine at a position corresponding to position 529 according to SEQ ID NO:8, or the complement thereof. In some embodiments, the isolated cDNA molecules comprise or consist of a nucleotide sequence that has at least about 92% sequence identity to SEQ ID NO:8, and comprise a thymine at a position corresponding to position 529 according to SEQ ID NO:8, or the complement thereof. In some embodiments, the isolated cDNA molecules comprise or consist of a nucleotide sequence that has at least about 94% sequence identity to SEQ ID NO:8, and comprise a thymine at a position corresponding to position 529 according to SEQ ID NO:8, or the complement thereof. In some embodiments, the isolated cDNA molecules comprise or consist of a nucleotide sequence that has at least about 96% sequence identity to SEQ ID NO:8, and comprise a thymine at a position corresponding to position 529 according to SEQ ID NO:8, or the complement thereof. In some embodiments, the isolated cDNA molecules comprise or consist of a nucleotide sequence that has at least about 98% sequence identity to SEQ ID NO:8, and comprise a thymine at a position corresponding to position 529 according to SEQ ID NO:8, or the complement thereof. Herein, if reference is made to percent sequence identity, the higher percentages of sequence identity are preferred over the lower ones.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:8, and comprise a TGA codon at positions corresponding to positions 529 to 531 according to SEQ ID NO:8, or the complement thereof. In some embodiments, the isolated cDNA molecules comprise or consist of a nucleotide sequence that has at least about 90% sequence identity to SEQ ID NO:8, and comprise a TGA codon at positions corresponding to positions 529 to 531 according to SEQ ID NO:8, or the complement thereof. In some embodiments, the isolated cDNA molecules comprise or consist of a nucleotide sequence that has at least about 92% sequence identity to SEQ ID NO:8, and comprise a TGA codon at positions corresponding to positions 529 to 531 according to SEQ ID NO:8, or the complement thereof. In some embodiments, the isolated cDNA molecules comprise or consist of a nucleotide sequence that has at least about 94% sequence identity to SEQ ID NO:8, and comprise a TGA codon at positions corresponding to positions 529 to 531 according to SEQ ID NO:8, or the complement thereof. In some embodiments, the isolated cDNA molecules comprise or consist of a nucleotide sequence that has at least about 96% sequence identity to SEQ ID NO:8, and comprise a TGA codon at positions corresponding to positions 529 to 531 according to SEQ ID NO:8, or the complement thereof. In some embodiments, the isolated cDNA molecules comprise or consist of a nucleotide sequence that has at least about 98% sequence identity to SEQ ID NO:8, and comprise a TGA codon at positions corresponding to positions 529 to 531 according to SEQ ID NO:8, or the complement thereof. Herein, if reference is made to percent sequence identity, the higher percentages of sequence identity are preferred over the lower ones.

In some embodiments, the isolated cDNA molecules comprise SEQ ID NO:8. In some embodiments, the isolated cDNA molecules consist of SEQ ID NO:8.

The present disclosure also provides isolated cDNA molecules comprising or consisting of a nucleotide sequence encoding a human ANGPTL7 polypeptide, wherein the nucleotide sequence comprises a thymine at a position corresponding to position 525 according to SEQ ID NO:9, or the complement thereof. In some embodiments, the isolated cDNA molecules comprise a nucleotide sequence encoding a human ANGPTL7 polypeptide, wherein the nucleotide sequence comprises a thymine at a position corresponding to position 525 according to SEQ ID NO:9, or the complement thereof. In some embodiments, the isolated cDNA molecules consist of a nucleotide sequence encoding a human ANGPTL7 polypeptide, wherein the nucleotide sequence comprises a thymine at a position corresponding to position 525 according to SEQ ID NO:9, or the complement thereof. In some embodiments, the isolated cDNA molecules comprise a nucleotide sequence encoding a human ANGPTL7 polypeptide, wherein the nucleotide sequence comprises a CAT codon at positions corresponding to positions 523 to 525 according to SEQ ID NO:9.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:9, and comprise a thymine at a position corresponding to position 525 according to SEQ ID NO:9, or the complement thereof. In some embodiments, the isolated cDNA molecules comprise or consist of a nucleotide sequence that has at least about 90% sequence identity to SEQ ID NO:9, and comprise a thymine at a position corresponding to position 525 according to SEQ ID NO:9, or the complement thereof. In some embodiments, the isolated cDNA molecules comprise or consist of a nucleotide sequence that has at least about 92% sequence identity to SEQ ID NO:9, and comprise a thymine at a position corresponding to position 525 according to SEQ ID NO:9, or the complement thereof. In some embodiments, the isolated cDNA molecules comprise or consist of a nucleotide sequence that has at least about 94% sequence identity to SEQ ID NO:9, and comprise a thymine at a position corresponding to position 525 according to SEQ ID NO:9, or the complement thereof. In some embodiments, the isolated cDNA molecules comprise or consist of a nucleotide sequence that has at least about 96% sequence identity to SEQ ID NO:9, and comprise a thymine at a position corresponding to position 525 according to SEQ ID NO:9, or the complement thereof. In some embodiments, the isolated cDNA molecules comprise or consist of a nucleotide sequence that has at least about 98% sequence identity to SEQ ID NO:9, and comprise a thymine at a position corresponding to position 525 according to SEQ ID NO:9, or the complement thereof. Herein, if reference is made to percent sequence identity, the higher percentages of sequence identity are preferred over the lower ones.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:9, and comprise a CAT codon at positions corresponding to positions 523 to 525 according to SEQ ID NO:9, or the complement thereof. In some embodiments, the isolated cDNA molecules comprise or consist of a nucleotide sequence that has at least about 90% sequence identity to SEQ ID NO:9, and comprise a CAT codon at positions corresponding to positions 523 to 525 according to SEQ ID NO:9, or the complement thereof. In some embodiments, the isolated cDNA molecules comprise or consist of a nucleotide sequence that has at least about 92% sequence identity to SEQ ID NO:9, and comprise a CAT codon at positions corresponding to positions 523 to 525 according to SEQ ID NO:9, or the complement thereof. In some embodiments, the isolated cDNA molecules comprise or consist of a nucleotide sequence that has at least about 94% sequence identity to SEQ ID NO:9, and comprise a CAT codon at positions corresponding to positions 523 to 525 according to SEQ ID NO:9, or the complement thereof. In some embodiments, the isolated cDNA molecules comprise or consist of a nucleotide sequence that has at least about 96% sequence identity to SEQ ID NO:9, and comprise a CAT codon at positions corresponding to positions 523 to 525 according to SEQ ID NO:9, or the complement thereof. In some embodiments, the isolated cDNA molecules comprise or consist of a nucleotide sequence that has at least about 98% sequence identity to SEQ ID NO:9, and comprise a CAT codon at positions corresponding to positions 523 to 525 according to SEQ ID NO:9, or the complement thereof. Herein, if reference is made to percent sequence identity, the higher percentages of sequence identity are preferred over the lower ones.

In some embodiments, the isolated cDNA molecules comprise SEQ ID NO:9. In some embodiments, the isolated cDNA molecules consist of SEQ ID NO:9.

The present disclosure also provides isolated cDNA molecules comprising or consisting of a nucleotide sequence encoding a human ANGPTL7 polypeptide, wherein the nucleotide sequence comprises an adenine at a position corresponding to position 481 according to SEQ ID NO:138, or the complement thereof. In some embodiments, the isolated cDNA molecules comprise a nucleotide sequence encoding a human ANGPTL7 polypeptide, wherein the nucleotide sequence comprises an adenine at a position corresponding to position 481 according to SEQ ID NO:138, or the complement thereof. In some embodiments, the isolated cDNA molecules consist of a nucleotide sequence encoding a human ANGPTL7 polypeptide, wherein the nucleotide sequence comprises an adenine at a position corresponding to position 481 according to SEQ ID NO:138, or the complement thereof. In some embodiments, the isolated cDNA molecules comprise a nucleotide sequence encoding a human ANGPTL7 polypeptide, wherein the nucleotide sequence comprises an ATC codon at positions corresponding to positions 481 to 483 according to SEQ ID NO:138.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:138, and comprise an adenine at a position corresponding to position 481 according to SEQ ID NO:138, or the complement thereof. In some embodiments, the isolated cDNA molecules comprise or consist of a nucleotide sequence that has at least about 90% sequence identity to SEQ ID NO:138, and comprise an adenine at a position corresponding to position 481 according to SEQ ID NO:138, or the complement thereof. In some embodiments, the isolated cDNA molecules comprise or consist of a nucleotide sequence that has at least about 92% sequence identity to SEQ ID NO:138, and comprise an adenine at a position corresponding to position 481 according to SEQ ID NO:138, or the complement thereof. In some embodiments, the isolated cDNA molecules comprise or consist of a nucleotide sequence that has at least about 94% sequence identity to SEQ ID NO:138, and comprise an adenine at a position corresponding to position 481 according to SEQ ID NO:138, or the complement thereof. In some embodiments, the isolated cDNA molecules comprise or consist of a nucleotide sequence that has at least about 96% sequence identity to SEQ ID NO:138, and comprise an adenine at a position corresponding to position 481 according to SEQ ID NO:138, or the complement thereof. In some embodiments, the isolated cDNA molecules comprise or consist of a nucleotide sequence that has at least about 98% sequence identity to SEQ ID NO:138, and comprise an adenine at a position corresponding to position 481 according to SEQ ID NO:138, or the complement thereof. Herein, if reference is made to percent sequence identity, the higher percentages of sequence identity are preferred over the lower ones.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:138, and comprise an ATC codon at positions corresponding to positions 481 to 483 according to SEQ ID NO:138, or the complement thereof. In some embodiments, the isolated cDNA molecules comprise or consist of a nucleotide sequence that has at least about 90% sequence identity to SEQ ID NO:138, and comprise an ATC codon at positions corresponding to positions 481 to 483 according to SEQ ID NO:138, or the complement thereof. In some embodiments, the isolated cDNA molecules comprise or consist of a nucleotide sequence that has at least about 92% sequence identity to SEQ ID NO:138, and comprise an ATC codon at positions corresponding to positions 481 to 483 according to SEQ ID NO:138, or the complement thereof. In some embodiments, the isolated cDNA molecules comprise or consist of a nucleotide sequence that has at least about 94% sequence identity to SEQ ID NO:138, and comprise an ATC codon at positions corresponding to positions 481 to 483 according to SEQ ID NO:138, or the complement thereof. In some embodiments, the isolated cDNA molecules comprise or consist of a nucleotide sequence that has at least about 96% sequence identity to SEQ ID NO:138, and comprise an ATC codon at positions corresponding to positions 481 to 483 according to SEQ ID NO:138, or the complement thereof. In some embodiments, the isolated cDNA molecules comprise or consist of a nucleotide sequence that has at least about 98% sequence identity to SEQ ID NO:138, and comprise an ATC codon at positions corresponding to positions 481 to 483 according to SEQ ID NO:138, or the complement thereof. Herein, if reference is made to percent sequence identity, the higher percentages of sequence identity are preferred over the lower ones.

In some embodiments, the isolated cDNA molecules comprise SEQ ID NO:138. In some embodiments, the isolated cDNA molecules consist of SEQ ID NO:138.

The present disclosure also provides isolated cDNA molecules comprising or consisting of a nucleotide sequence encoding a human ANGPTL7 polypeptide, wherein the nucleotide sequence comprises an adenine at a position corresponding to position 563 according to SEQ ID NO:139, or the complement thereof. In some embodiments, the isolated cDNA molecules comprise a nucleotide sequence encoding a human ANGPTL7 polypeptide, wherein the nucleotide sequence comprises an adenine at a position corresponding to position 563 according to SEQ ID NO:139, or the complement thereof. In some embodiments, the isolated cDNA molecules consist of a nucleotide sequence encoding a human ANGPTL7 polypeptide, wherein the nucleotide sequence comprises an adenine at a position corresponding to position 563 according to SEQ ID NO:139, or the complement thereof. In some embodiments, the isolated cDNA molecules comprise a nucleotide sequence encoding a human ANGPTL7 polypeptide, wherein the nucleotide sequence comprises a TAG codon at positions corresponding to positions 562 to 564 according to SEQ ID NO:139.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:139, and comprise an adenine at a position corresponding to position 563 according to SEQ ID NO:139, or the complement thereof. In some embodiments, the isolated cDNA molecules comprise or consist of a nucleotide sequence that has at least about 90% sequence identity to SEQ ID NO:139, and comprise an adenine at a position corresponding to position 563 according to SEQ ID NO:139, or the complement thereof. In some embodiments, the isolated cDNA molecules comprise or consist of a nucleotide sequence that has at least about 92% sequence identity to SEQ ID NO:139, and comprise an adenine at a position corresponding to position 563 according to SEQ ID NO:139, or the complement thereof. In some embodiments, the isolated cDNA molecules comprise or consist of a nucleotide sequence that has at least about 94% sequence identity to SEQ ID NO:139, and comprise an adenine at a position corresponding to position 563 according to SEQ ID NO:139, or the complement thereof. In some embodiments, the isolated cDNA molecules comprise or consist of a nucleotide sequence that has at least about 96% sequence identity to SEQ ID NO:139, and comprise an adenine at a position corresponding to position 563 according to SEQ ID NO:139, or the complement thereof. In some embodiments, the isolated cDNA molecules comprise or consist of a nucleotide sequence that has at least about 98% sequence identity to SEQ ID NO:139, and comprise an adenine at a position corresponding to position 563 according to SEQ ID NO:139, or the complement thereof. Herein, if reference is made to percent sequence identity, the higher percentages of sequence identity are preferred over the lower ones.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:139, and comprise a TAG codon at positions corresponding to positions 562 to 564 according to SEQ ID NO:139, or the complement thereof. In some embodiments, the isolated cDNA molecules comprise or consist of a nucleotide sequence that has at least about 90% sequence identity to SEQ ID NO:139, and comprise a TAG codon at positions corresponding to positions 562 to 564 according to SEQ ID NO:139, or the complement thereof. In some embodiments, the isolated cDNA molecules comprise or consist of a nucleotide sequence that has at least about 92% sequence identity to SEQ ID NO:139, and comprise a TAG codon at positions corresponding to positions 562 to 564 according to SEQ ID NO:139, or the complement thereof. In some embodiments, the isolated cDNA molecules comprise or consist of a nucleotide sequence that has at least about 94% sequence identity to SEQ ID NO:139, and comprise a TAG codon at positions corresponding to positions 562 to 564 according to SEQ ID NO:139, or the complement thereof. In some embodiments, the isolated cDNA molecules comprise or consist of a nucleotide sequence that has at least about 96% sequence identity to SEQ ID NO:139, and comprise a TAG codon at positions corresponding to positions 562 to 564 according to SEQ ID NO:139, or the complement thereof. In some embodiments, the isolated cDNA molecules comprise or consist of a nucleotide sequence that has at least about 98% sequence identity to SEQ ID NO:139, and comprise a TAG codon at positions corresponding to positions 562 to 564 according to SEQ ID NO:139, or the complement thereof. Herein, if reference is made to percent sequence identity, the higher percentages of sequence identity are preferred over the lower ones.

In some embodiments, the isolated cDNA molecules comprise SEQ ID NO:139. In some embodiments, the isolated cDNA molecules consist of SEQ ID NO:139.

The present disclosure also provides isolated cDNA molecules comprising or consisting of a nucleotide sequence encoding a human ANGPTL7 polypeptide, wherein the nucleotide sequence comprises a cytosine at a position corresponding to position 574 according to SEQ ID NO:140, or the complement thereof. In some embodiments, the isolated cDNA molecules comprise a nucleotide sequence encoding a human ANGPTL7 polypeptide, wherein the nucleotide sequence comprises a cytosine at a position corresponding to position 574 according to SEQ ID NO:140, or the complement thereof. In some embodiments, the isolated cDNA molecules consist of a nucleotide sequence encoding a human ANGPTL7 polypeptide, wherein the nucleotide sequence comprises a cytosine at a position corresponding to position 574 according to SEQ ID NO:140, or the complement thereof. In some embodiments, the isolated cDNA molecules comprise a nucleotide sequence encoding a human ANGPTL7 polypeptide, wherein the nucleotide sequence comprises a CAG codon at positions corresponding to positions 574 to 576 according to SEQ ID NO:140.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:140, and comprise a cytosine at a position corresponding to position 574 according to SEQ ID NO:140, or the complement thereof. In some embodiments, the isolated cDNA molecules comprise or consist of a nucleotide sequence that has at least about 90% sequence identity to SEQ ID NO:140, and comprise a cytosine at a position corresponding to position 574 according to SEQ ID NO:140, or the complement thereof. In some embodiments, the isolated cDNA molecules comprise or consist of a nucleotide sequence that has at least about 92% sequence identity to SEQ ID NO:140, and comprise a cytosine at a position corresponding to position 574 according to SEQ ID NO:140, or the complement thereof. In some embodiments, the isolated cDNA molecules comprise or consist of a nucleotide sequence that has at least about 94% sequence identity to SEQ ID NO:140, and comprise a cytosine at a position corresponding to position 574 according to SEQ ID NO:140, or the complement thereof. In some embodiments, the isolated cDNA molecules comprise or consist of a nucleotide sequence that has at least about 96% sequence identity to SEQ ID NO:140, and comprise a cytosine at a position corresponding to position 574 according to SEQ ID NO:140, or the complement thereof. In some embodiments, the isolated cDNA molecules comprise or consist of a nucleotide sequence that has at least about 98% sequence identity to SEQ ID NO:140, and comprise a cytosine at a position corresponding to position 574 according to SEQ ID NO:140, or the complement thereof. Herein, if reference is made to percent sequence identity, the higher percentages of sequence identity are preferred over the lower ones.

In some embodiments, the isolated cDNA molecules comprise or consist of a nucleotide sequence that has at least about 90%, at least about 91%, at least about 92%, at least about 93%, at least about 94%, at least about 95%, at least about 96%, at least about 97%, at least about 98%, or at least about 99% sequence identity to SEQ ID NO:140, and comprise a CAG codon at positions corresponding to positions 574 to 576 according to SEQ ID NO:140, or the complement thereof. In some embodiments, the isolated cDNA molecules comprise or consist of a nucleotide sequence that has at least about 90% sequence identity to SEQ ID NO:140, and comprise a CAG codon at positions corresponding to positions 574 to 576 according to SEQ ID NO:140, or the complement thereof. In some embodiments, the isolated cDNA molecules comprise or consist of a nucleotide sequence that has at least about 92% sequence identity to SEQ ID NO:140, and comprise a CAG codon at positions corresponding to positions 574 to 576 according to SEQ ID NO:140, or the complement thereof. In some embodiments, the isolated cDNA molecules comprise or consist of a nucleotide sequence that has at least about 94% sequence identity to SEQ ID NO:140, and comprise a CAG codon at positions corresponding to positions 574 to 576 according to SEQ ID NO:140, or the complement thereof. In some embodiments, the isolated cDNA molecules comprise or consist of a nucleotide sequence that has at least about 96% sequence identity to SEQ ID NO:140, and comprise a CAG codon at positions corresponding to positions 574 to 576 according to SEQ ID NO:140, or the complement thereof. In some embodiments, the isolated cDNA molecules comprise or consist of a nucleotide sequence that has at least about 98% sequence identity to SEQ ID NO:140, and comprise a CAG codon at positions corresponding to positions 574 to 576 according to SEQ ID NO:140, or the complement thereof. Herein, if reference is made to percent sequence identity, the higher percentages of sequence identity are preferred over the lower ones.

In some embodiments, the isolated cDNA molecules comprise SEQ ID NO:140. In some embodiments, the isolated cDNA molecules consist of SEQ ID NO:140.

The cDNA molecules can be from any organism. For example, the cDNA molecules can be human or an ortholog from another organism, such as a non-human mammal, a rodent, a mouse, or a rat. It is understood that cDNA sequences within a population can vary due to polymorphisms such as single-nucleotide polymorphisms. The examples provided herein are only exemplary sequences. Other sequences are also possible.

In some embodiments, the isolated cDNA molecules comprise less than the entire cDNA sequence. In some embodiments, the isolated cDNA molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, or at least about 500 contiguous nucleotides of any one or more of SEQ ID NO:8, SEQ ID NO:9, SEQ ID NO:138, SEQ ID NO:139, and/or SEQ ID NO:139. In some embodiments, the isolated cDNA molecules comprise or consist of at least about 400 to at least about 500 contiguous nucleotides of any one or more of SEQ ID NO:8, SEQ ID NO:9, SEQ ID NO:138, SEQ ID NO:139, and/or SEQ ID NO:139. In some embodiments, these isolated cDNA molecules comprise the thymine at the position corresponding to position 529 according to SEQ ID NO:8. In some embodiments, these isolated cDNA molecules comprise the thymine at the position corresponding to position 525 according to SEQ ID NO:9. In some embodiments, these isolated cDNA molecules comprise the adenine at the position corresponding to position 481 according to SEQ ID NO:138. In some embodiments, these isolated cDNA molecules comprise the adenine at the position corresponding to position 563 according to SEQ ID NO:139. In some embodiments, these isolated cDNA molecules comprise the cytosine at the position corresponding to position 574 according to SEQ ID NO:140.

The present disclosure also provides fragments of any of the isolated genomic nucleic acid molecules, mRNA molecules, or cDNA molecules disclosed herein. In some embodiments, the fragments comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 contiguous residues of any of the nucleic acid molecules disclosed herein, or any complement thereof. In this regard, the longer fragments are preferred over the shorter ones.

In some embodiments, the fragments comprise or consist of at least about 20, at least about 25, at least about 30, or at least about 35 contiguous residues of any of the nucleic acid molecules disclosed herein, or any complement thereof. In some embodiments, the fragments comprise or consist of the portion of the nucleic acid molecule that includes a position corresponding to position 4,291 according to SEQ ID NO:2, or includes a position corresponding to position 529 according to SEQ ID NO:5 or SEQ ID NO:8. In some embodiments, the fragments comprise or consist of the portion of the nucleic acid molecule that includes a position corresponding to position 4,287 according to SEQ ID NO:3, or includes a position corresponding to position 525 according to SEQ ID NO:6 or SEQ ID NO:9. In some embodiments, the fragments comprise or consist of the portion of the nucleic acid molecule that includes a position corresponding to position 4,243 according to SEQ ID NO:132, or includes a position corresponding to position 481 according to SEQ ID NO:135 or SEQ ID NO:138. In some embodiments, the fragments comprise or consist of the portion of the nucleic acid molecule that includes a position corresponding to position 4,325 according to SEQ ID NO:133, or includes a position corresponding to position 563 according to SEQ ID NO:136 or SEQ ID NO:139. In some embodiments, the fragments comprise or consist of the portion of the nucleic acid molecule that includes a position corresponding to position 4,336 according to SEQ ID NO:134, or includes a position corresponding to position 574 according to SEQ ID NO:137 or SEQ ID NO:140. Such fragments may be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein.

Also provided herein are functional polynucleotides that can interact with the disclosed nucleic acid molecules. Functional polynucleotides are nucleic acid molecules that have a specific function, such as binding a target molecule or catalyzing a specific reaction. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label, such as a fluorescent label.

The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m are from 1 to about 10. Other modifications at the 2' position include, but are not limited to, $C_{1-10}$ alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

Desired regulatory sequences for mammalian host cell expression can include, for example, viral elements that direct high levels of polypeptide expression in mammalian cells, such as promoters and/or enhancers derived from retroviral LTRs, cytomegalovirus (CMV) (such as, for example, CMV promoter/enhancer), Simian Virus 40 (SV40) (such as, for example, SV40 promoter/enhancer), adenovirus, (such as, for example, the adenovirus major late promoter (AdMLP)), polyoma and strong mammalian promoters such as native immunoglobulin and actin promoters. Methods of expressing polypeptides in bacterial cells or fungal cells (such as, for example, yeast cells) are also well known. A promoter can be, for example, a constitutively active promoter, a conditional promoter, an inducible promoter, a temporally restricted promoter (such as, for example, a developmentally regulated promoter), or a spatially restricted promoter (such as, for example, a cell-specific or tissue-specific promoter).

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the isolated nucleic acid molecules, genomic nucleic acid molecules, mRNA molecules, and/or cDNA molecules disclosed herein. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

The amino acid sequence of an ANGPTL7 reference polypeptide is set forth in SEQ ID NO:10. Referring to SEQ ID NO:10, the ANGPTL7 reference polypeptide is 346 amino acids in length. Referring to SEQ ID NO:10, position 175 is a glutamine. Referring to SEQ ID NO:10, position 177 is an arginine. Referring to SEQ ID NO:10, position 161 is a phenylalanine. Referring to SEQ ID NO:10, position 188 is a tryptophan. Referring to SEQ ID NO:10, position 192 is a lysine.

An ANGPTL7 variant polypeptide exists (p.Arg177Stop or Arg177Stop), the amino acid sequence of which is set forth in SEQ ID NO:11. Referring to SEQ ID NO:11, the ANGPTL7 variant polypeptide is 176 amino acids in length. Referring to SEQ ID NO:11, position 177 does not exist due to a truncation at position 176.

Another ANGPTL7 variant polypeptide exists (Gln175His or Q175H), the amino acid sequence of which is set forth in SEQ ID NO:12. Referring to SEQ ID NO:12, the ANGPTL7 variant polypeptide is 346 amino acids in length. Referring to SEQ ID NO:12, position 175 is a histidine.

Another ANGPTL7 variant polypeptide exists (Phe161Ile or F161I), the amino acid sequence of which is set forth in SEQ ID NO:141. Referring to SEQ ID NO:141, the ANGPTL7 variant polypeptide is 346 amino acids in length. Referring to SEQ ID NO:141, position 161 is an isoleucine.

Another ANGPTL7 variant polypeptide exists (p.Trp188Stop or Trp188Stop), the amino acid sequence of which is set forth in SEQ ID NO:142. Referring to SEQ ID NO:142, the ANGPTL7 variant polypeptide is 187 amino acids in length. Referring to SEQ ID NO:142, position 187 is an aspartic acid. This variant is a result of a replacement of a guanine with an adenine at position 563 of the reference mRNA molecule or cDNA molecule (see, SEQ ID NO:4 and SEQ ID NO:7, respectively, for reference mRNA and cDNA sequences).

Another ANGPTL7 variant polypeptide exists (Lys192Gln or K192Q), the amino acid sequence of which is set forth in SEQ ID NO:143. Referring to SEQ ID NO:143, the ANGPTL7 variant polypeptide is 346 amino acids in length. Referring to SEQ ID NO:143, position 192 is a glutamine.

The present disclosure provides isolated human ANGPTL7 polypeptides having an amino acid sequence at least about 90%, at least about 91%, at least about 92%, at least about 93%, at least about 94%, at least about 95%, at least about 96%, at least about 97%, at least about 98%, or at least about 99% identical to SEQ ID NO:11, and terminating at a position corresponding to position 176 according to SEQ ID NO:11. In some embodiments, the isolated human ANGPTL7 polypeptides have an amino acid sequence at least about 90% identical to SEQ ID NO:11, and terminating at a position corresponding to position 176 according to SEQ ID NO:11. In some embodiments, the isolated human ANGPTL7 polypeptides have an amino acid sequence at least about 92% identical to SEQ ID NO:11, and terminating at a position corresponding to position 176 according to SEQ ID NO:11. In some embodiments, the isolated human ANGPTL7 polypeptides have an amino acid sequence at least about 94% identical to SEQ ID NO:11, and terminating at a position corresponding to position 176 according to SEQ ID NO:11. In some embodiments, the isolated human ANGPTL7 polypeptides have an amino acid sequence at least about 96% identical to SEQ ID NO:11, and terminating at a position corresponding to position 176 according to SEQ ID NO:11. In some embodiments, the isolated human ANGPTL7 polypeptides have an amino acid sequence at least about 98% identical to SEQ ID NO:11, and terminating at a position corresponding to position 176 according to SEQ ID NO:11.

In some embodiments, the amino acid sequence of the isolated human ANGPTL7 polypeptide comprises SEQ ID NO:11. In some embodiments, the amino acid sequence of the isolated human ANGPTL7 polypeptide consists of SEQ ID NO:11.

The present disclosure also provides isolated human ANGPTL7 polypeptides having an amino acid sequence at least about 90%, at least about 91%, at least about 92%, at least about 93%, at least about 94%, at least about 95%, at least about 96%, at least about 97%, at least about 98%, or at least about 99% identical to SEQ ID NO:12, and comprising a histidine at a position corresponding to position 175 according to SEQ ID NO:12. In some embodiments, the isolated human ANGPTL7 polypeptides have an amino acid sequence at least about 90% identical to SEQ ID NO:12, and comprising a histidine at a position corresponding to position 175 according to SEQ ID NO:12. In some embodiments, the isolated human ANGPTL7 polypeptides have an amino acid sequence at least about 92% identical to SEQ ID NO:12, and comprising a histidine at a position corresponding to position 175 according to SEQ ID NO:12. In some embodiments, the isolated human ANGPTL7 polypeptides have an amino acid sequence at least about 94% identical to SEQ ID NO:12, and comprising a histidine at a position corresponding to position 175 according to SEQ ID NO:12. In some embodiments, the isolated human ANGPTL7 polypeptides have an amino acid sequence at least about 96% identical to SEQ ID NO:12, and comprising a histidine at a position corresponding to position 175 according to SEQ ID NO:12. In some embodiments, the isolated human ANGPTL7 polypeptides have an amino acid sequence at least about 98% identical to SEQ ID NO:12, and comprising a histidine at a position corresponding to position 175 according to SEQ ID NO:12.

In some embodiments, the amino acid sequence of the isolated human ANGPTL7 polypeptide comprises SEQ ID NO:12. In some embodiments, the amino acid sequence of the isolated human ANGPTL7 polypeptide consists of SEQ ID NO:12.

The present disclosure also provides isolated human ANGPTL7 polypeptides having an amino acid sequence at least about 90%, at least about 91%, at least about 92%, at least about 93%, at least about 94%, at least about 95%, at least about 96%, at least about 97%, at least about 98%, or at least about 99% identical to SEQ ID NO:141, and comprising an isoleucine at a position corresponding to position 161 according to SEQ ID NO:141. In some embodiments, the isolated human ANGPTL7 polypeptides have an amino acid sequence at least about 90% identical to SEQ ID NO:141, and comprising an isoleucine at a position corresponding to position 161 according to SEQ ID NO:141. In some embodiments, the isolated human ANGPTL7 polypeptides have an amino acid sequence at least about 92% identical to SEQ ID NO:141, and comprising an isoleucine at a position corresponding to position 161 according to SEQ ID NO:141. In some embodiments, the isolated human ANGPTL7 polypeptides have an amino acid sequence at least about 94% identical to SEQ ID NO:141, and comprising an isoleucine at a position corresponding to position 161 according to SEQ ID NO:141. In some embodiments, the isolated human ANGPTL7 polypeptides have an amino acid sequence at least about 96% identical to SEQ ID NO:141, and comprising an isoleucine at a position corresponding to position 161 according to SEQ ID NO:141. In some embodiments, the isolated human ANGPTL7 polypeptides have an amino acid sequence at least about 98% identical to SEQ ID NO:141, and comprising an isoleucine at a position corresponding to position 161 according to SEQ ID NO:141.

In some embodiments, the amino acid sequence of the isolated human ANGPTL7 polypeptide comprises SEQ ID NO:141. In some embodiments, the amino acid sequence of the isolated human ANGPTL7 polypeptide consists of SEQ ID NO:141.

The present disclosure also provides isolated human ANGPTL7 polypeptides having an amino acid sequence at least about 90%, at least about 91%, at least about 92%, at least about 93%, at least about 94%, at least about 95%, at least about 96%, at least about 97%, at least about 98%, or at least about 99% identical to SEQ ID NO:142, and terminating at a position corresponding to position 187 according to SEQ ID NO:142. In some embodiments, the isolated human ANGPTL7 polypeptides have an amino acid sequence at least about 90% identical to SEQ ID NO:142, and terminating at a position corresponding to position 187 according to SEQ ID NO:142. In some embodiments, the isolated human ANGPTL7 polypeptides have an amino acid sequence at least about 92% identical to SEQ ID NO:142, and terminating at a position corresponding to position 187 according to SEQ ID NO:142. In some embodiments, the isolated human ANGPTL7 polypeptides have an amino acid sequence at least about 94% identical to SEQ ID NO:142, and terminating at a position corresponding to position 187 according to SEQ ID NO:142. In some embodiments, the isolated human ANGPTL7 polypeptides have an amino acid sequence at least about 96% identical to SEQ ID NO:142, and terminating at a position corresponding to position 187 according to SEQ ID NO:142. In some embodiments, the isolated human ANGPTL7 polypeptides have an amino acid sequence at least about 98% identical to SEQ ID NO:142, and terminating at a position corresponding to position 187 according to SEQ ID NO:142.

In some embodiments, the amino acid sequence of the isolated human ANGPTL7 polypeptide comprises SEQ ID NO:142. In some embodiments, the amino acid sequence of the isolated human ANGPTL7 polypeptide consists of SEQ ID NO:142.

The present disclosure also provides isolated human ANGPTL7 polypeptides having an amino acid sequence at least about 90%, at least about 91%, at least about 92%, at least about 93%, at least about 94%, at least about 95%, at least about 96%, at least about 97%, at least about 98%, or at least about 99% identical to SEQ ID NO:143, and comprising a glutamine at a position corresponding to position 192 according to SEQ ID NO:143. In some embodiments, the isolated human ANGPTL7 polypeptides have an amino acid sequence at least about 90% identical to SEQ ID NO:143, and comprising a glutamine at a position corresponding to position 192 according to SEQ ID NO:143. In some embodiments, the isolated human ANGPTL7 polypeptides have an amino acid sequence at least about 92% identical to SEQ ID NO:143, and comprising a glutamine at a position corresponding to position 192 according to SEQ ID NO:143. In some embodiments, the isolated human ANGPTL7 polypeptides have an amino acid sequence at least about 94% identical to SEQ ID NO:143, and comprising a glutamine at a position corresponding to position 192 according to SEQ ID NO:143. In some embodiments, the isolated human ANGPTL7 polypeptides have an amino acid sequence at least about 96% identical to SEQ ID NO:143, and comprising a glutamine at a position corresponding to position 192 according to SEQ ID NO:143. In some embodiments, the isolated human ANGPTL7 polypeptides have an amino acid sequence at least about 98% identical to SEQ ID NO:143, and comprising a glutamine at a position corresponding to position 192 according to SEQ ID NO:143.

In some embodiments, the amino acid sequence of the isolated human ANGPTL7 polypeptide comprises SEQ ID NO:143. In some embodiments, the amino acid sequence of the isolated human ANGPTL7 polypeptide consists of SEQ ID NO:143.

In some embodiments, the isolated polypeptides comprise or consist of at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, at least about 350, at least about 400, at least about 450, at least about 500, at least about 550, or at least about 600 contiguous amino acids of any one or more of SEQ ID NO:11, SEQ ID NO:12, SEQ ID NO:141, SEQ ID NO:142, and/or SEQ ID NO:143. In some embodiments, the isolated polypeptides terminate at a position corresponding to position 176 according to SEQ ID NO:11. In some embodiments, the isolated polypeptides comprise a histidine at a position corresponding to position 175 according to SEQ ID NO:12. In some embodiments, the isolated polypeptides comprise an isoleucine at a position corresponding to position 161 according to SEQ ID NO:141. In some embodiments, the isolated polypeptides terminate at a position corresponding to position 187 according to SEQ ID NO:142. In some embodiments, the isolated polypeptides comprise a glutamine at a position corresponding to position 192 according to SEQ ID NO:143.

In some embodiments, the isolated polypeptides comprise or consist of an amino acid sequence at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, at least about 350, at least about 400, at least about 450, at least about 500, at least about 550, or at least about 600 contiguous amino acids of any one or more of SEQ ID NO:11, SEQ ID NO:12, SEQ ID NO:141, SEQ ID NO:142, and/or SEQ ID NO:143. In some embodiments, the isolated polypeptides terminate at a position corresponding to position 176 according to SEQ ID NO:11. In some embodiments, the isolated polypeptides comprise a histidine at a position corresponding to position 175 according to SEQ ID NO:12. In some embodiments, the isolated polypeptides comprise an isoleucine at a position corresponding to position 161 according to SEQ ID NO:141. In some embodiments, the isolated polypeptides terminate at a position corresponding to position 187 according to SEQ ID NO:142. In some embodiments, the isolated polypeptides comprise a glutamine at a position corresponding to position 192 according to SEQ ID NO:143.

In some embodiments, the isolated polypeptides comprise or consist of an amino acid sequence at least about 90%, at least about 91%, at least about 92%, at least about 93%, at least about 94%, at least about 95%, at least about 96%, at least about 97%, at least about 98%, at least about 99%, or 100% identical to at least about 8, at least about 10, at least about 15, at least about 20, at least about 25, at least about 30, at least about 35, at least about 40, at least about 45, at least about 50, at least about 60, at least about 70, at least about 80, at least about 90, at least about 100, at least about 150, at least about 200, at least about 250, at least about 300, at least about 350, at least about 400, at least about 450, at least about 500, at least about 550, or at least about 600 contiguous amino acids of any one or more of SEQ ID NO:11, SEQ ID NO:12, SEQ ID NO:141, SEQ ID NO:142, and/or SEQ ID NO:143. In some embodiments, the isolated polypeptides terminate at a position corresponding to position 176 according to SEQ ID NO:11. In some embodiments, the isolated polypeptides comprise a histidine at a position corresponding to position 175 according to SEQ ID NO:12. In some embodiments, the isolated polypeptides comprise an isoleucine at a position corresponding to position 161 according to SEQ ID NO:141. In some embodiments, the isolated polypeptides terminate at a position corresponding to position 187 according to SEQ ID NO:142. In some embodiments, the isolated polypeptides comprise a glutamine at a position corresponding to position 192 according to SEQ ID NO:143.

The isolated polypeptides disclosed herein can comprise an amino acid sequence of a naturally occurring ANGPTL7 polypeptide, or can comprise a non-naturally occurring sequence. In some embodiments, the naturally occurring sequence can differ from the non-naturally occurring sequence due to conservative amino acid substitutions. For example, the sequence can be identical with the exception of conservative amino acid substitutions.

In some embodiments, the isolated polypeptides comprise non-natural or modified amino acids or peptide analogs. For example, there are numerous D-amino acids or amino acids which have a different functional substituent than the naturally occurring amino acids.

The present disclosure also provides nucleic acid molecules encoding any of the polypeptides disclosed herein. This includes all degenerate sequences related to a specific polypeptide sequence (i.e., all nucleic acids having a sequence that encodes one particular polypeptide sequence as well as all nucleic acids, including degenerate nucleic acids, encoding the disclosed variants and derivatives of the protein sequences). Thus, while each particular nucleic acid sequence may not be written out herein, each and every sequence is in fact disclosed and described herein through the disclosed polypeptide sequences.

The present disclosure also provides compositions comprising any one or more of the nucleic acid molecules and/or any one or more of the polypeptides disclosed herein. In some embodiments, the compositions comprise a carrier. Examples of carriers include, but are not limited to, poly (lactic acid) (PLA) microspheres, poly(D,L-lactic-coglycolic-acid) (PLGA) microspheres, liposomes, micelles, inverse micelles, lipid cochleates, and lipid microtubules.

The present disclosure also provides methods of producing any of the ANGPTL7 polypeptides or fragments thereof disclosed herein. Such ANGPTL7 polypeptides or fragments thereof can be produced by any suitable method.

The present disclosure also provides cells comprising any one or more of the nucleic acid molecules and/or any one or more of the polypeptides disclosed herein. The cells can be in vitro, ex vivo, or in vivo. Nucleic acid molecules can be linked to a promoter and other regulatory sequences so they are expressed to produce an encoded protein.

In some embodiments, the cell is a totipotent cell or a pluripotent cell such as, for example, an embryonic stem (ES) cell such as a rodent ES cell, a mouse ES cell, or a rat ES cell. In some embodiments, the cell is a primary somatic cell, or a cell that is not a primary somatic cell. The cell can be from any source. For example, the cell can be a eukaryotic cell, an animal cell, a plant cell, or a fungal (such as, for example, yeast) cell. Such cells can be fish cells or bird cells, or such cells can be mammalian cells, such as human cells, non-human mammalian cells, rodent cells, mouse cells or rat cells. Mammals include, but are not limited to, humans, non-human primates, monkeys, apes, cats dogs, horses, bulls, deer, bison, sheep, rodents (such as, for example, mice, rats, hamsters, guinea pigs), livestock (such as, for example, bovine species such as cows, steer, etc.; ovine species such as sheep, goats, etc.; and porcine species such as pigs and boars). The term "non-human animal" excludes humans.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1, SEQ ID NO:4, or SEQ ID NO:7). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding a human ANGPTL7 polypeptide, wherein the nucleotide sequence comprises a thymine at a position corresponding to position 4,291 according to SEQ ID NO:2 means that if the nucleotide sequence of the ANGPTL7 genomic nucleic acid molecule is aligned to the sequence of SEQ ID NO:2, the ANGPTL7 sequence has a thymine residue at the position that corresponds to position 4,291 of SEQ ID NO:2. The same applies for mRNA molecules comprising a nucleotide sequence encoding a human ANGPTL7 polypeptide, wherein the nucleotide sequence comprises a uracil at a position corresponding to position 529 according to SEQ ID NO:5, and cDNA molecules comprising a nucleotide sequence encoding a human ANGPTL7 polypeptide, wherein the nucleotide sequence comprises a thymine at a position corresponding to position 529 according to SEQ ID NO:8. In other words, these phrases refer to a nucleic acid molecule encoding an ANGPTL7 polypeptide, wherein the genomic nucleic acid molecule has a nucleotide sequence that comprises a thymine residue that is homologous to the thymine residue at position 4,291 of SEQ ID NO:2 (or wherein the mRNA molecule has a nucleotide sequence that comprises a uracil residue that is homologous to the uracil residue at position 529 of SEQ ID NO:5, or wherein the cDNA molecule has a nucleotide sequence that comprises a thymine residue that is homologous to the thymine residue at position 529 of SEQ ID NO:8). Herein, such a sequence is also referred to as "ANGPTL7 sequence with the C4,291T alteration" or "ANGPTL7 sequence with the C4,291T variation" referring to genomic nucleic acid molecules (or "ANGPTL7 sequence with the C529U alteration" or "ANGPTL7 sequence with the C529U variation" referring to mRNA molecules, and "ANGPTL7 sequence with the C529T alteration" or "ANGPTL7 sequence with the C529T variation" referring to cDNA molecules).

As described herein, a position within an ANGPTL7 genomic nucleic acid molecule that corresponds to position 4,291 according to SEQ ID NO:2 can be identified by performing a sequence alignment between the nucleotide sequence of a particular ANGPTL7 nucleic acid molecule and the nucleotide sequence of SEQ ID NO:2. A variety of computational algorithms exist that can be used for performing a sequence alignment to identify a nucleotide position that corresponds to, for example, position 4,291 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The present disclosure also provides therapeutic agents that treat or inhibit an ophthalmic condition for use in the treatment of an ophthalmic condition in a human subject, wherein the human subject has: a genomic nucleic acid molecule having a nucleotide sequence encoding a human ANGPTL7 polypeptide, wherein the nucleotide sequence comprises a thymine at a position corresponding to position 4,291 according to SEQ ID NO:2, or the complement thereof; an mRNA molecule having a nucleotide sequence encoding a human ANGPTL7 polypeptide, wherein the nucleotide sequence comprises a uracil at a position corresponding to position 529 according to SEQ ID NO:5, or the complement thereof; a cDNA molecule having a nucleotide sequence encoding a human ANGPTL7 polypeptide, wherein the nucleotide sequence comprises a thymine at a position corresponding to position 529 according to SEQ ID NO:8, or the complement thereof; or an ANGPTL7 polypeptide that terminates at a position corresponding to position 176 according to SEQ ID NO:11. The therapeutic agents that treat or inhibit an ophthalmic condition can be any of the therapeutic agents that treat or inhibit an ophthalmic condition described herein.

The present disclosure also provides therapeutic agents that treat or inhibit an ophthalmic condition for use in the preparation of a medicament for treating an ophthalmic condition in a human subject, wherein the human subject has: a genomic nucleic acid molecule having a nucleotide sequence encoding a human ANGPTL7 polypeptide, wherein the nucleotide sequence comprises a thymine at a position corresponding to position 4,291 according to SEQ ID NO:2, or the complement thereof; an mRNA molecule having a nucleotide sequence encoding a human ANGPTL7 polypeptide, wherein the nucleotide sequence comprises a uracil at a position corresponding to position 529 according to SEQ ID NO:5, or the complement thereof; a cDNA molecule having a nucleotide sequence encoding a human ANGPTL7 polypeptide, wherein the nucleotide sequence comprises a thymine at a position corresponding to position 529 according to SEQ ID NO:8, or the complement thereof; or an ANGPTL7 polypeptide that terminates at a position corresponding to position 176 according to SEQ ID NO:11. The therapeutic agents that treat or inhibit an ophthalmic condition can be any of the therapeutic agents that treat or inhibit an ophthalmic condition described herein.

The present disclosure also provides ANGPTL7 inhibitors for use in the treatment of an ophthalmic condition in a human subject, wherein the human subject has: a genomic nucleic acid molecule having a nucleotide sequence encoding a human ANGPTL7 polypeptide, wherein the nucleotide sequence comprises a thymine at a position corresponding to position 4,291 according to SEQ ID NO:2, or the complement thereof; an mRNA molecule having a nucleotide sequence encoding a human ANGPTL7 polypeptide, wherein the nucleotide sequence comprises a uracil at a position corresponding to position 529 according to SEQ ID NO:5, or the complement thereof; a cDNA molecule having a nucleotide sequence encoding a human ANGPTL7 polypeptide, wherein the nucleotide sequence comprises a thymine at a position corresponding to position 529 according to SEQ ID NO:8, or the complement thereof; or an ANGPTL7 polypeptide that terminates at a position corresponding to position 176 according to SEQ ID NO:11. The ANGPTL7 inhibitors can be any of the ANGPTL7 inhibitors described herein.

The present disclosure also provides ANGPTL7 inhibitors for use in the preparation of a medicament for treating an ophthalmic condition in a human subject, wherein the human subject has: a genomic nucleic acid molecule having a nucleotide sequence encoding a human ANGPTL7 polypeptide, wherein the nucleotide sequence comprises a thymine at a position corresponding to position 4,291 according to SEQ ID NO:2, or the complement thereof; an mRNA molecule having a nucleotide sequence encoding a human ANGPTL7 polypeptide, wherein the nucleotide sequence comprises a uracil at a position corresponding to position 529 according to SEQ ID NO:5, or the complement thereof; a cDNA molecule having a nucleotide sequence encoding a human ANGPTL7 polypeptide, wherein the nucleotide sequence comprises a thymine at a position corresponding to position 529 according to SEQ ID NO:8, or the complement thereof; or an ANGPTL7 polypeptide that terminates at a position corresponding to position 176 according to SEQ ID NO:11. The ANGPTL7 inhibitors can be any of the ANGPTL7 inhibitors described herein.

The present disclosure also provides therapeutic agents that treat or inhibit an ophthalmic condition for use in the treatment of an ophthalmic condition in a human subject, wherein the human subject has: a genomic nucleic acid molecule having a nucleotide sequence encoding a human ANGPTL7 polypeptide, wherein the nucleotide sequence comprises a thymine at a position corresponding to position 4,287 according to SEQ ID NO:3, or the complement thereof; an mRNA molecule having a nucleotide sequence encoding a human ANGPTL7 polypeptide, wherein the nucleotide sequence comprises a uracil at a position corresponding to position 525 according to SEQ ID NO:6, or the complement thereof; a cDNA molecule having a nucleotide sequence encoding a human ANGPTL7 polypeptide, wherein the nucleotide sequence comprises a thymine at a position corresponding to position 525 according to SEQ ID NO:9, or the complement thereof; or an ANGPTL7 polypeptide that comprises a histidine at a position corresponding to position 175 according to SEQ ID NO:12. The therapeutic agents that treat or inhibit an ophthalmic condition can be any of the therapeutic agents that treat or inhibit an ophthalmic condition described herein.

The present disclosure also provides therapeutic agents that treat or inhibit an ophthalmic condition for use in the preparation of a medicament for treating an ophthalmic condition in a human subject, wherein the human subject has: a genomic nucleic acid molecule having a nucleotide sequence encoding a human ANGPTL7 polypeptide, wherein the nucleotide sequence comprises a thymine at a position corresponding to position 4,287 according to SEQ ID NO:3, or the complement thereof; an mRNA molecule having a nucleotide sequence encoding a human ANGPTL7 polypeptide, wherein the nucleotide sequence comprises a uracil at a position corresponding to position 525 according to SEQ ID NO:6, or the complement thereof; a cDNA molecule having a nucleotide sequence encoding a human ANGPTL7 polypeptide, wherein the nucleotide sequence comprises a thymine at a position corresponding to position 525 according to SEQ ID NO:9, or the complement thereof; or an ANGPTL7 polypeptide that comprises a histidine at a position corresponding to position 175 according to SEQ ID NO:12. The therapeutic agents that treat or inhibit an ophthalmic condition can be any of the therapeutic agents that treat or inhibit an ophthalmic condition described herein.

The present disclosure also provides ANGPTL7 inhibitors for use in the treatment of an ophthalmic condition in a human subject, wherein the human subject has: a genomic nucleic acid molecule having a nucleotide sequence encoding a human ANGPTL7 polypeptide, wherein the nucleotide sequence comprises a thymine at a position corresponding to position 4,287 according to SEQ ID NO:3, or the complement thereof; an mRNA molecule having a nucleotide sequence encoding a human ANGPTL7 polypeptide, wherein the nucleotide sequence comprises a uracil at a position corresponding to position 525 according to SEQ ID NO:6, or the complement thereof; a cDNA molecule having a nucleotide sequence encoding a human ANGPTL7 polypeptide, wherein the nucleotide sequence comprises a thymine at a position corresponding to position 525 according to SEQ ID NO:9, or the complement thereof; or an ANGPTL7 polypeptide that comprises a histidine at a position corresponding to position 175 according to SEQ ID NO:12. The ANGPTL7 inhibitors can be any of the ANGPTL7 inhibitors described herein.

The present disclosure also provides ANGPTL7 inhibitors for use in the preparation of a medicament for treating an ophthalmic condition in a human subject, wherein the human subject has: a genomic nucleic acid molecule having a nucleotide sequence encoding a human ANGPTL7 polypeptide, wherein the nucleotide sequence comprises a thymine at a position corresponding to position 4,287 according to SEQ ID NO:3, or the complement thereof; an mRNA molecule having a nucleotide sequence encoding a human ANGPTL7 polypeptide, wherein the nucleotide sequence comprises a uracil at a position corresponding to position 525 according to SEQ ID NO:6, or the complement thereof; a cDNA molecule having a nucleotide sequence encoding a human ANGPTL7 polypeptide, wherein the nucleotide sequence comprises a thymine at a position corresponding to position 525 according to SEQ ID NO:9, or the complement thereof; or an ANGPTL7 polypeptide that comprises a histidine at a position corresponding to position 175 according to SEQ ID NO:12. The ANGPTL7 inhibitors can be any of the ANGPTL7 inhibitors described herein.

The present disclosure also provides therapeutic agents that treat or inhibit an ophthalmic condition for use in the treatment of an ophthalmic condition in a human subject, wherein the human subject has: a genomic nucleic acid molecule having a nucleotide sequence encoding a human ANGPTL7 polypeptide, wherein the nucleotide sequence comprises an adenine at a position corresponding to position 4,243 according to SEQ ID NO:132, or the complement thereof; an mRNA molecule having a nucleotide sequence encoding a human ANGPTL7 polypeptide, wherein the nucleotide sequence comprises an adenine at a position corresponding to position 481 according to SEQ ID NO:135, or the complement thereof; a cDNA molecule having a nucleotide sequence encoding a human ANGPTL7 polypeptide, wherein the nucleotide sequence comprises an adenine at a position corresponding to position 481 according to SEQ ID NO:138, or the complement thereof; or an ANGPTL7 polypeptide that comprises an isoleucine at a position corresponding to position 161 according to SEQ ID NO:141. The therapeutic agents that treat or inhibit an ophthalmic condition can be any of the therapeutic agents that treat or inhibit an ophthalmic condition described herein.

The present disclosure also provides therapeutic agents that treat or inhibit an ophthalmic condition for use in the preparation of a medicament for treating an ophthalmic condition in a human subject, wherein the human subject has: a genomic nucleic acid molecule having a nucleotide sequence encoding a human ANGPTL7 polypeptide, wherein the nucleotide sequence comprises an adenine at a position corresponding to position 4,243 according to SEQ ID NO:132, or the complement thereof; an mRNA molecule having a nucleotide sequence encoding a human ANGPTL7 polypeptide, wherein the nucleotide sequence comprises an adenine at a position corresponding to position 481 according to SEQ ID NO:135, or the complement thereof; a cDNA molecule having a nucleotide sequence encoding a human ANGPTL7 polypeptide, wherein the nucleotide sequence comprises an adenine at a position corresponding to position 481 according to SEQ ID NO:138, or the complement thereof; or an ANGPTL7 polypeptide that comprises an isoleucine at a position corresponding to position 161 according to SEQ ID NO:141. The therapeutic agents that treat or inhibit an ophthalmic condition can be any of the therapeutic agents that treat or inhibit an ophthalmic condition described herein.

The present disclosure also provides ANGPTL7 inhibitors for use in the treatment of an ophthalmic condition in a human subject, wherein the human subject has: a genomic nucleic acid molecule having a nucleotide sequence encoding a human ANGPTL7 polypeptide, wherein the nucleotide sequence comprises an adenine at a position corresponding to position 4,243 according to SEQ ID NO:132, or the complement thereof; an mRNA molecule having a nucleotide sequence encoding a human ANGPTL7 polypeptide, wherein the nucleotide sequence comprises an adenine at a position corresponding to position 481 according to SEQ ID NO:135, or the complement thereof; a cDNA molecule having a nucleotide sequence encoding a human ANGPTL7 polypeptide, wherein the nucleotide sequence comprises an adenine at a position corresponding to position 481 according to SEQ ID NO:138, or the complement thereof; or an ANGPTL7 polypeptide that comprises an isoleucine at a position corresponding to position 161 according to SEQ ID NO:141. The ANGPTL7 inhibitors can be any of the ANGPTL7 inhibitors described herein.

The present disclosure also provides ANGPTL7 inhibitors for use in the preparation of a medicament for treating an ophthalmic condition in a human subject, wherein the human subject has: a genomic nucleic acid molecule having a nucleotide sequence encoding a human ANGPTL7 polypeptide, wherein the nucleotide sequence comprises an adenine at a position corresponding to position 4,243 according to SEQ ID NO:132, or the complement thereof; an mRNA molecule having a nucleotide sequence encoding a human ANGPTL7 polypeptide, wherein the nucleotide sequence comprises an adenine at a position corresponding to position 481 according to SEQ ID NO:135, or the complement thereof; a cDNA molecule having a nucleotide sequence encoding a human ANGPTL7 polypeptide, wherein the nucleotide sequence comprises an adenine at a position corresponding to position 481 according to SEQ ID NO:138, or the complement thereof; or an ANGPTL7 polypeptide that comprises an isoleucine at a position corresponding to position 161 according to SEQ ID NO:141. The ANGPTL7 inhibitors can be any of the ANGPTL7 inhibitors described herein.

The present disclosure also provides therapeutic agents that treat or inhibit an ophthalmic condition for use in the treatment of an ophthalmic condition in a human subject, wherein the human subject has: a genomic nucleic acid molecule having a nucleotide sequence encoding a human ANGPTL7 polypeptide, wherein the nucleotide sequence comprises an adenine at a position corresponding to position 4,325 according to SEQ ID NO:133, or the complement thereof; an mRNA molecule having a nucleotide sequence encoding a human ANGPTL7 polypeptide, wherein the nucleotide sequence comprises an adenine at a position corresponding to position 563 according to SEQ ID NO:136, or the complement thereof; a cDNA molecule having a nucleotide sequence encoding a human ANGPTL7 polypeptide, wherein the nucleotide sequence comprises an adenine at a position corresponding to position 563 according to SEQ ID NO:139, or the complement thereof; or an ANGPTL7 polypeptide that terminates at a position corresponding to position 187 according to SEQ ID NO:142. The therapeutic agents that treat or inhibit an ophthalmic condition can be any of the therapeutic agents that treat or inhibit an ophthalmic condition described herein.

The present disclosure also provides therapeutic agents that treat or inhibit an ophthalmic condition for use in the preparation of a medicament for treating an ophthalmic condition in a human subject, wherein the human subject has: a genomic nucleic acid molecule having a nucleotide sequence encoding a human ANGPTL7 polypeptide, wherein the nucleotide sequence comprises an adenine at a position corresponding to position 4,325 according to SEQ ID NO:133, or the complement thereof; an mRNA molecule having a nucleotide sequence encoding a human ANGPTL7 polypeptide, wherein the nucleotide sequence comprises an adenine at a position corresponding to position 563 according to SEQ ID NO:136, or the complement thereof; a cDNA molecule having a nucleotide sequence encoding a human ANGPTL7 polypeptide, wherein the nucleotide sequence comprises an adenine at a position corresponding to position 563 according to SEQ ID NO:139, or the complement thereof; or an ANGPTL7 polypeptide that terminates at a position corresponding to position 187 according to SEQ ID NO:142. The therapeutic agents that treat or inhibit an ophthalmic condition can be any of the therapeutic agents that treat or inhibit an ophthalmic condition described herein.

The present disclosure also provides ANGPTL7 inhibitors for use in the treatment of an ophthalmic condition in a human subject, wherein the human subject has: a genomic nucleic acid molecule having a nucleotide sequence encoding a human ANGPTL7 polypeptide, wherein the nucleotide sequence comprises an adenine at a position corresponding to position 4,325 according to SEQ ID NO:133, or the complement thereof; an mRNA molecule having a nucleotide sequence encoding a human ANGPTL7 polypeptide, wherein the nucleotide sequence comprises an adenine at a position corresponding to position 563 according to SEQ ID NO:136, or the complement thereof; a cDNA molecule having a nucleotide sequence encoding a human ANGPTL7 polypeptide, wherein the nucleotide sequence comprises an adenine at a position corresponding to position 563 according to SEQ ID NO:139, or the complement thereof; or an ANGPTL7 polypeptide that terminates at a position corresponding to position 187 according to SEQ ID NO:142. The ANGPTL7 inhibitors can be any of the ANGPTL7 inhibitors described herein.

The present disclosure also provides ANGPTL7 inhibitors for use in the preparation of a medicament for treating an ophthalmic condition in a human subject, wherein the human subject has: a genomic nucleic acid molecule having a nucleotide sequence encoding a human ANGPTL7 polypeptide, wherein the nucleotide sequence comprises an adenine at a position corresponding to position 4,325 according to SEQ ID NO:133, or the complement thereof; an mRNA molecule having a nucleotide sequence encoding a human ANGPTL7 polypeptide, wherein the nucleotide sequence comprises an adenine at a position corresponding to position 563 according to SEQ ID NO:136, or the complement thereof; a cDNA molecule having a nucleotide sequence encoding a human ANGPTL7 polypeptide, wherein the nucleotide sequence comprises an adenine at a position corresponding to position 563 according to SEQ ID NO:139, or the complement thereof; or an ANGPTL7 polypeptide that terminates at a position corresponding to position 187 according to SEQ ID NO:142. The ANGPTL7 inhibitors can be any of the ANGPTL7 inhibitors described herein.

The present disclosure also provides therapeutic agents that treat or inhibit an ophthalmic condition for use in the treatment of an ophthalmic condition in a human subject, wherein the human subject has: a genomic nucleic acid molecule having a nucleotide sequence encoding a human ANGPTL7 polypeptide, wherein the nucleotide sequence comprises a cytosine at a position corresponding to position 4,336 according to SEQ ID NO:134, or the complement thereof; an mRNA molecule having a nucleotide sequence encoding a human ANGPTL7 polypeptide, wherein the nucleotide sequence comprises a cytosine at a position corresponding to position 574 according to SEQ ID NO:137, or the complement thereof; a cDNA molecule having a nucleotide sequence encoding a human ANGPTL7 polypeptide, wherein the nucleotide sequence comprises a cytosine at a position corresponding to position 574 according to SEQ ID NO:140, or the complement thereof; or an ANGPTL7 polypeptide that comprises a glutamine at a position corresponding to position 192 according to SEQ ID NO:143. The therapeutic agents that treat or inhibit an ophthalmic condition can be any of the therapeutic agents that treat or inhibit an ophthalmic condition described herein.

The present disclosure also provides therapeutic agents that treat or inhibit an ophthalmic condition for use in the preparation of a medicament for treating an ophthalmic condition in a human subject, wherein the human subject has: a genomic nucleic acid molecule having a nucleotide sequence encoding a human ANGPTL7 polypeptide, wherein the nucleotide sequence comprises a cytosine at a position corresponding to position 4,336 according to SEQ ID NO:134, or the complement thereof; an mRNA molecule having a nucleotide sequence encoding a human ANGPTL7 polypeptide, wherein the nucleotide sequence comprises a cytosine at a position corresponding to position 574 according to SEQ ID NO:137, or the complement thereof; a cDNA molecule having a nucleotide sequence encoding a human ANGPTL7 polypeptide, wherein the nucleotide sequence comprises a cytosine at a position corresponding to position 574 according to SEQ ID NO:140, or the complement thereof; or an ANGPTL7 polypeptide that comprises a glutamine at a position corresponding to position 192 according to SEQ ID NO:143. The therapeutic agents that treat or inhibit an ophthalmic condition can be any of the therapeutic agents that treat or inhibit an ophthalmic condition described herein.

The present disclosure also provides ANGPTL7 inhibitors for use in the treatment of an ophthalmic condition in a human subject, wherein the human subject has: a genomic nucleic acid molecule having a nucleotide sequence encoding a human ANGPTL7 polypeptide, wherein the nucleotide sequence comprises a cytosine at a position corresponding to position 4,336 according to SEQ ID NO:134, or the complement thereof; an mRNA molecule having a nucleotide sequence encoding a human ANGPTL7 polypeptide, wherein the nucleotide sequence comprises a cytosine at a position corresponding to position 574 according to SEQ ID NO:137, or the complement thereof; a cDNA molecule having a nucleotide sequence encoding a human ANGPTL7 polypeptide, wherein the nucleotide sequence comprises a cytosine at a position corresponding to position 574 according to SEQ ID NO:140, or the complement thereof; or an ANGPTL7 polypeptide that comprises a glutamine at a position corresponding to position 192 according to SEQ ID NO:143. The ANGPTL7 inhibitors can be any of the ANGPTL7 inhibitors described herein.

The present disclosure also provides ANGPTL7 inhibitors for use in the preparation of a medicament for treating an ophthalmic condition in a human subject, wherein the human subject has: a nucleotide sequence encoding a human ANGPTL7 polypeptide, wherein the nucleotide sequence comprises a cytosine at a position corresponding to position 4,336 according to SEQ ID NO:134, or the complement thereof; an mRNA molecule having a nucleotide sequence encoding a human ANGPTL7 polypeptide, wherein the nucleotide sequence comprises a cytosine at a position corresponding to position 574 according to SEQ ID NO:137, or the complement thereof; a cDNA molecule having a nucleotide sequence encoding a human ANGPTL7 polypeptide, wherein the nucleotide sequence comprises a cytosine at a position corresponding to position 574 according to SEQ ID NO:140, or the complement thereof; or an ANGPTL7 polypeptide that comprises a glutamine at a position corresponding to position 192 according to SEQ ID NO:143. The ANGPTL7 inhibitors can be any of the ANGPTL7 inhibitors described herein.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1

Exome Sequencing Analysis

Exome sequencing and analysis at the Regeneron Genetics Center in conjunction with the UK Biobank (UKB) 50K exome dataset identified that the putative loss-of-function variant, p.Arg177Stop, significantly associates with decreased IOP (Table 10). Table 11 shows the association of the M1 mask, which is an aggregate of all pLOFs (≤1% alt. allele frequency) within ANGPTL7, with IOP. This result supports the single variant pLOF association shown in Table 10 as 27/29 carriers have the p.Arg177Stop variant shown in Table 10.

TABLE 10

| Phenotype | Dataset | Effect (CI) sd | Pvalue | AAF | N RR/RA/AA |
|---|---|---|---|---|---|
| IOPcc | 50k Exome | −0.40 (−0.78, −0.03) | 3.490E−02 | 0.04% | 33,616 33,589/27/0 |
| IOPg | 50k Exome | −0.56 (−0.93, −0.19) | 3.22E−03 | 0.04% | 33,618 33,591/27/0 |

TABLE 11

| Name | Dataset | Phenotype | Effect (CI) sd | Pvalue | AAF | N RR/RA/AA |
|---|---|---|---|---|---|---|
| M1.1 | 50k Exome | IOPcc | −0.38 (−0.74, −0.01) | 4.2E−02 | 0.04% | 33,616 33,587/29/0 |
|  | 50k Exome | IOPg | −0.49 (−0.85, −0.13) | 7.5E−03 | 0.04% | 33,618 33,589/29/0 |

Additional exome sequencing and analysis at the Regeneron Genetics Center in conjunction with the Geisinger Health System 60k (GHS60k), GHS30k and/or UKB were carried out, the results of which are shown in Tables 12-17.

Association of a missense (p.Gln175His) variant in ANGPTL7 with glaucoma in the imputed dataset in GHS60k, GHS30k and UKB, and the meta-analysis of the three cohorts is shown in Table 12. The direction of effect (decreased IOP) of p.Gln175His is the same as the direction of effect of the pLOF p.Arg177Stop variant shown in Tables 10 and 11 suggesting that the Gln175His change acts to reduce the function of ANGPTL7.

TABLE 12

| Phenotype | Dataset | OR (95% CI) | Pval | AAF |
|---|---|---|---|---|
| Glaucoma | META | 0.734 (0.632, 0.853) | 5.59E−05 | 0.0069 |
| Glaucoma | UKB_Imputed_EUR | 0.688 (0.574, 0.825) | 5.35E−05 | 0.0076 |
| Glaucoma | GHS_GSA_Imputed_EUR | 0.612 (0.288, 1.302) | 2.02E−01 | 0.0021 |
| Glaucoma | GHS_Omni_Imputed_EUR | 0.959 (0.681, 1.349) | 8.09E−01 | 0.0028 |

| Phenotype | Dataset | Direction | Ncase RR∣RA∣AA | Nctrl RR∣RA∣AA |
|---|---|---|---|---|
| Glaucoma | META | — | 14,493 14,373∣120∣0 | 528,025 520,720∣7,274∣31 |
| Glaucoma | UKB_Imputed_EUR | — | 8,624 8,537∣87∣0 | 452,880 445,957∣6,892∣31 |
| Glaucoma | GHS_GSA_Imputed_EUR | — | 975 971∣4∣0 | 26,065 25,955∣110∣0 |

TABLE 12-continued

| | | | |
|---|---|---|---|
| Glaucoma | GHS_Omni_Imputed_EUR | — | 4,894 49,080 |
| | | | 4,865\|29\|0  48,808\|272\|0 |

Association of the missense (p.Gln175His) variant with IOPg in the imputed dataset in GHS60k, GHS30k and UKB, and the meta-analysis of the three cohorts is shown in Table 13.

TABLE 13

| Phenotype | Dataset | Effect (95% CI) | Pval |
|---|---|---|---|
| IOPg | META | −0.221 (−0.269, −0.173) | 1.16E−19 |
| IOPg | UKB_Imputed_EUR | −0.234 (−0.284, −0.184) | 6.40E−20 |
| IOPg | GHS_GSA_Imputed_EUR | −0.249 (−0.6, 0.102) | 0.16 |
| IOPg | GHS_Omni_Imputed_EUR | −0.061 (−0.233, 0.111) | 0.48 |

| Phenotype | Data set | AAF | Direction | N RR\|RA\|AA |
|---|---|---|---|---|
| IOPg | META | 0.0069 | — | 111,548 |
| | | | | 110019\|1523\|6 |
| IOPg | UKB_Imputed_EUR | 0.0077 | — | 92,484 |
| | | | | 91,073\|1,405\|6 |
| IOPg | GHS_GSA_Imputed_EUR | 0.0025 | — | 4,135 |
| | | | | 4,114\|21\|0 |
| IOPg | GHS_Omni_Imputed_EUR | 0.0032 | — | 14,929 |
| | | | | 14,832\|97\|0 |

Association of the missense (p.Gln175His) variant with IOPg in the exome dataset in GHS60k, GHS30k and UKB, and the meta-analysis of the three cohorts is shown in Table 14.

TABLE 14

| Phenotype | Dataset | Effect (95% CI) | Pval |
|---|---|---|---|
| IOPg | META | −0.143 (−0.213, −0.073) | 6.77E−05 |
| IOPg | UKB_50K_Exome_EUR | −0.156 (−0.24, −0.072) | 2.70E−04 |
| IOPg | GHS_IDT_Exome_EUR | −0.24 (−0.53, 0.051) | 1.10E−01 |
| IOPg | GHS_VCRome_Exome_EUR | −0.081 (−0.224, 0.062) | 2.70E−01 |

TABLE 14-continued

| Phenotype | Data set | AAF | Direction | N RR\|RA\|AA |
|---|---|---|---|---|
| IOPg | META | 0.0073 | — | 52,925 |
| | | | | 52,159\|762\|4 |
| IOPg | UKB_50K_Exome_EUR | 0.0079 | — | 33,618 |
| | | | | 33,088\|526\|4 |
| IOPg | GHS_IDT_Exome_EUR | 0.0055 | — | 4,187 |
| | | | | 4,141\|46\|0 |
| IOPg | GHS_VCRome_Exome_EUR | 0.0063 | — | 15,120 |
| | | | | 14,930\|190\|0 |

Association of the missense (p.Gln175His) variant with glaucoma in the exome dataset in GHS60k, GHS30k and UKB, and the meta-analysis of the three cohorts is shown in Table 15.

TABLE 15

| Phenotype | Dataset | OR (95% CI) | pval | AAF |
|---|---|---|---|---|
| Glaucoma | META | 0.822 (0.655, 1.032) | 9.16E−02 | 0.0063 |
| Glaucoma | UKB_50K_Exome_EUR | 0.726 (0.436, 1.209) | 2.19E−01 | 0.0077 |
| Glaucoma | GHS_IDT_Exome_EUR | 0.745 (0.388, 1.431) | 3.77E−01 | 0.0050 |
| Glaucoma | GHS_VCRome_Exome_EUR | 0.875 (0.651, 1.176) | 3.76E−01 | 0.0057 |

| Phenotype | Dataset | Direction | Ncase RR\|RA\|AA | Nctrl RR\|RA\|AA |
|---|---|---|---|---|
| Glaucoma | META | — | 6,967 | 121,924 |
| | | | 6,899\|67\|1 | 120,377\|1,539\|8 |
| Glaucoma | UKB_50K_Exome_EUR | — | 1,021 | 45,766 |
| | | | 1,010\|11\|0 | 45,060\|702\|4 |
| Glaucoma | GHS_IDT_Exome_EUR | — | 984 | 26,402 |
| | | | 977\|7\|0 | 26,137\|262\|3 |
| Glaucoma | GHS_VCRome_Exome_EUR | — | 4,962 | 49,756 |
| | | | 4,912\|49\|1 | 49,180\|575\|1 |

Association of the M1.1 (pLOF variants ≤1% AAF) mask in ANGPTL7 with IOPg in burden test is shown in Table 16.

TABLE 16

| Phenotype | Dataset | Effect (95% CI) | Pval | AAF |
|---|---|---|---|---|
| IOPg | META | −0.512 (−0.827, −0.197) | 1.46E-03 | 0.00039 |
| IOPg | UKB_50K_Exome_EUR | −0.49 (−0.85, −0.131) | 7.50E-03 | 0.00043 |
| IOPg | GHS_IDT_Exome_EUR | NA | NA | NA |
| IOPg | GHS_VCRome_Exome_EUR | −0.582 (−1.236, 0.072) | 8.10E-02 | 0.00030 |

| Phenotype | Dataset | Direction | N RR\|RA\|AA |
|---|---|---|---|
| IOPg | META | -?- | 48,738 48,700\|38\|0 |
| IOPg | UKB_50K_Exome_EUR | — | 33,618 33,589\|29\|0 |
| IOPg | GHS_IDT_Exome_EUR | NA | NA |
| IOPg | GHS_VCRome_Exome_EUR | — | 15,120 15,111\|9\|0 |

Association of the missense (p.Gln175His) variant with IOPcc in the exome and genotyped/imputed datasets in UKB is shown in Table H.

TABLE 17

| Phenotype | Dataset | Effect (95% CI) | Pval |
|---|---|---|---|
| IOPcc | UKB_50K_Exome_EUR | −0.13 (−0.214, −0.045) | 2.6E-02 |
| IOPcc | UKB_Imputed_EUR | −0.179 (−0.23, −0.128) | 5.4E-12 |

| Phenotype | Dataset | AAF | N RR\|RA\|AA |
|---|---|---|---|
| IOPcc | UKB_50K_Exome_EUR | 0.0079 | 33,616 33,087\|525\|4 |
| IOPcc | UKB_Imputed_EUR | 0.0077 | 92,629 91,217\|1,406\|6 |

Example 2

Genetic and Functional Studies Identify ANGPTL7 as a Therapeutic Target for Glaucoma Study Design and Participants Association tests using data from 5 cohorts were carried out. The cohorts included: 1) The UK Biobank (UKB) is a large prospective study where >500,000 individuals aged 40 to 69 years were recruited over 4 years, and extensive data on lifestyle, environment, medical history, physical measures and DNA samples, were collected. For genome-wide association conducted on the whole UKB cohort, 92,672 European and 4,179 African ancestry participants with IOP measurements were included in the IOP analyses. In glaucoma association analyses, 8,639 cases and 453,746 controls of European, and 371 cases and 9,361 controls of African ancestry were included. For exome-wide association conducted on about 150,000 UKB participants that have been sequenced, 47,096 European and 1,743 African ancestry individuals were included in the IOP analyses. 2) The DiscovEHR study population (GHS), consisting of a total of about 145,000 sequenced individuals from the MyCode Community Health Initiative of Geisinger, from which 29,395 individuals with IOP measurements and were not diagnosed with glaucoma, 8,154 glaucoma cases and 116,557 controls were included. 3) The Malmö diet and cancer study (MDCS), based in Sweden, includes about 29,000 participants recruited to study the effects of diet on cancer. 1,708 cases of glaucoma and 26,222 controls from MDCS were included. 4) Mount Sinai's BioMe Personalized Medicine Cohort (MSSM) is an electronic health record (EHR)-linked clinical care cohort consisting of about 31,000 participants of diverse ancestries characterized by a broad spectrum of biomedical traits. 424 cases and 8,774 controls of European, and 1,349 cases and 11,258 controls of African ancestry were used for glaucoma analyses. 5) The Primary Open Angle African American Glaucoma Genetics (POAAGG) study is a 5-year, population-based project consisting of self-identified individuals of African descent 35 years of age or older recruited from the Scheie Eye Institute at the University of Pennsylvania and its research affiliates in Philadelphia. For IOP association analyses in POAAGG, 3,097 individuals with IOP measurements who also did not have a POAG diagnosis were included, and 2,474 POAG cases and 4,092 controls were included in the glaucoma association analyses.

Phenotype Definitions

IOP in UKB was measured in each eye using the Ocular Response Analyzer (ORA, Reichert Corp., Buffalo, N.Y.). Participants were excluded from this test if they reported having eye surgery in the preceding 4 weeks or having an eye infection. The ORA calculates two forms of IOP, a Goldmann-correlated IOP (IOPg) and a corneal compensated IOP (IOPcc). IOPg most closely approximates the IOP measured by the Goldmann applanation tonometer, which has been the gold standard for measuring IOP, while IOPcc provides a measure of IOP that is adjusted to remove the influence of corneal biomechanics. For this study, IOPg was focused on, as this measurement was the most comparable to IOP measurements in other cohorts, and herein IOPg will be referred to as IOP. For association analyses of IOP, the following individuals were excluded: 1) with a glaucoma diagnosis (N=1,932), 2) with IOP measures that were more than 5 standard deviations away from the mean, and 3) with more than a 10-mmHg difference between both eyes. A mean IOP measure between both eyes was developed for each individual. IOP of only one eye was used in instances where IOP measures for both eyes were not available. As for UKB, the mean IOP between left and right eyes for GHS (the most recent IOP measure in the EHR was used) and POAAGG were analyzed, applying the same exclusions and criteria outlined above.

Glaucoma ICD-based definitions of cases in UKB required one primary diagnosis or secondary diagnoses of ICD10-H40 in the in-patient Health Episode Statistics (HES) records. ICD-based glaucoma case definition in GHS, MDCS and MSSM required an in-patient diagnosis or outpatient diagnoses of ICD10-H40 in the EHR. ICD-based excludes had ≥primary or ≥secondary diagnoses in the code range (H40-H42). ICD-based controls for glaucoma were defined as individuals who were not cases or excluded.

For UKB, ICD-based and self-reported glaucoma were combined in the case definition where individuals were considered cases if they: identified 'glaucoma' from the eye problems or disorders list in the touchscreen questionnaire or, stated they had glaucoma in the verbal interview or, were a case for ICD10 H40 glaucoma. Normal controls for glaucoma in UKB were defined as individuals who did not report having glaucoma in the touchscreen or the verbal interview, and were defined as controls for ICD-based glaucoma as described above (Van Hout, 2019, BioRxiv. https at "//doi.org/10.1101/572347").

A detailed description of criteria used to define glaucoma cases in POAAGG is provided elsewhere (Charlson, Ophthalmology, 2015, 122, 711-20). In brief, POAG cases were defined as having an open iridocorneal angle and characteristic glaucomatous optic nerve findings in one or both eyes, characteristic visual field defects and all secondary causes of glaucoma excluded. Controls in POAAGG defined as subjects older than 35, without high myopia (greater than −8.00 diopters) or presbyopia (+8.00 diopters), a family history of POAG, abnormal visual field, IOP greater than 21 mmHg, neuroretinal rim thinning, excavation, notching or nerve fiber layer defects, optic nerves asymmetry or a cup to disc ratio between eyes greater than 0.2. Additional controls for POAAGG were identified from the Penn Medicine Biobank as individuals without ICD9 diagnoses for glaucoma.

Sample Preparation, Sequencing and Genotyping

Sample preparation and whole-exome sequencing for UKB, GHS, MDCS, MSSM, and POAAGG were performed as described (Dewey, Science, 2016, 354, 6319; and Van Hout, 2019, BioRxiv. https at "//doi.org/10.1101/572347"). Details on DNA extraction and genotyping for UK Biobank participants are described in Bycroft (Bycroft, Nature, 2019, 562, 203-209).

Statistical Analysis

Statistical analysis included burden test description, rare variant analysis, and meta-analysis methods.

Human Trabecular Meshwork (TM) Cell Culture and Dexamethasone Treatment

Human TM cells were obtained from the Stamer laboratory at Duke University, NC, and characterized using previously developed methodology. Human TM cells were cultured and maintained in Dulbecco's modified Eagle's medium (DMEM) (Invitrogen-Gibco Life Technologies, Grand Island, N.Y., USA) supplemented with 10% fetal bovine serum (FBS; Atlas Biologicals, Fort Collins, Colo., USA), penicillin (100 units/mL), streptomycin (0.1 mg/mL), and L-glutamine (0.292 mg/mL) (Thermo Fisher Scientific, Rockford, Ill., USA). Human TM cells were cultured on six-well plates until confluent and then treated with vehicle control (0.1% ethanol) or dexamethasone (DEX, 100 nM) for another 72 hours.

IOP Measurements

Isoflurane anesthetized IOPs were measured as previously described. For IOP measurements, mice were anesthetized before IOP was measured in both eyes using a TonoLab rebound tonometer (Colonial Medical Supply, Franconia, N.H.). IOP measurements for both eyes were completed in 3-5 minutes. IOP in each eye was measured before start of Angptl7 injections and every day afterwards for six days.

Intravitreal Injection of ANGPTL7 Protein

A 33-gauge needle with a glass microsyringe (5-µL volume; Hamilton Company) was used. The eye was proposed, and the needle was inserted through the equatorial sclera and inserted into the vitreous chamber at an angle of approximately 45 degrees, taking care to avoid touching the posterior part of the lens or the retina. ANGPTL7 protein (catalog #4960-AN-025; R&D Systems, Minneapolis, Minn.) or PBS (1 µL) was injected into the vitreous over the course of 1 minute. The needle was then left in place for a further 45 seconds (to facilitate mixing), before being rapidly withdrawn. Only one injection was administered at day 0.

Intracameral Injection of ANGPTL7 Protein

A 33-gauge needle with a glass microsyringe (5-4 volume) (Hamilton Company) was used. Before and during injection, mice were anesthetized with isoflurane (2.5%) containing oxygen (0.8 L/min). For topical anesthesia, both eyes received one to two drops of 0.5% proparacaine HCl (Akorn, Inc.). Each eye was proposed and the needle was inserted through the cornea just above the limbal region and into the anterior chamber at an angle parallel to the cornea, taking care to avoid touching the iris, anterior lens capsule epithelium, or corneal endothelium. Up to 1 µL of ANGPTL7 protein (catalog #4960-AN-025; R&D Systems, Minneapolis, Minn.) or PBS was injected slowly (over a 30-second period). The needle was then withdrawn. The procedure was performed on both eyes of each animal. Only one injection was administered at day 0.

In Situ Hybridization Using RNAScope

The expression pattern of TM single cell cluster specific gene expression in the human donor eye was determined by in situ hybridization using RNAScope® according to manufacturer's specifications (Advanced Cell Diagnostics). Briefly, 10% NBF fixed and paraffin embedded human donor eye cups were cut into 5 to 10 µm sections and mounted on SUPERFROST® Plus glass slides. For RNAScope, slides were baked on slide warmer for 1 hour at 60° C. and deparaffinized for 20 minutes. Tissue sections then underwent 10 minutes of Pretreat 1-RNAScope hydrogen peroxide treatment at room temperature, followed by 20 minutes of boiling at 90° C. in Pretreat 2-target retrieval treatment in Oster Steamer (IHC World, LLC, Model 5709) and 30 minutes of Pretreat 3-RNAScope protease plus treatment at 40° C. in a HybEZ Oven. Tissue sections were then incubated with DNase I for 10 minutes at 40° C. to reduce potential background from probes binding to genomic DNA. Tissue sections were then washed five times with water, hybridized with RNAScope probes for 2 hours at 40° C. and the remainder of the manufacturer's assay protocol was implemented from Amplified 1 to Amplified 6. The slides were washed twice (two minutes each at room temperature) with RNAScope wash buffer. Signal was detected by incubation with Red working solution (1:60 ratio of Red B to Red A) at room temperature for 10 minutes in the absence of light, followed by washing the slides in water several times and viewing under microscope. In some experiments, fluorescent signals were visualized and captured using an open-field Nikon Eclipse Ti-E microscope.

Cell Culture.

HEK293 cell line was cultured in DMEM media (4.5 g/L D-Glucose, (+) L-Glutamine, (−) Sodium Phosphate, (−) Sodium Pyruvate supplemented with 10% FBS and 1% Penicillin-Streptomycin-Glutamine (BRAND), at 37° C. in a humidified atmosphere under 5% CO2.

Transfection.

The day before transfection, HEK293 cells were seeded in OptiMEM supplemented with 10% FBS. After 24 hours, the cells were transfected with FuGENE 6, and 10 ug of pcDNA 3.1(+) encoding the following proteins: ANGPTL7 wild type, Gln175His, and Arg177*. After 24 hours, the media was changed with 2% FBS OptiMEM. The following day, the cells were collected in RIPA buffer, supplemented with protease and phosphatase inhibitors (BRAND) or TRIzol reagent (Invitrogen) for protein and RNA analysis, respectively. The supernatants were transferred to an Eppendorf tube and immediately flash frozen for downstream protein analysis.

RNA Extraction and Taqman Analysis.

Total RNA was extracted using TRIzol reagent (Invitrogen) and RNeasy kit (Qiagen) according to manufacturer's instructions and treated with RNase-free DNase I (Promega). cDNA was synthesized using Superscript VILO cDNA synthesis kit (Invitrogen). Taqman analysis was performed using TaqMan Fast Advanced Master Mix (Applied Biosystems) in a QuantStudio 6 Flex (Applied Biosystems) and commercially available primers and probes for ANGPTL7 (Hs00221727—Applied Biosystem) and GAPDH (Hs02786624_g1—Applied Biosystem).

Western Blot.

Western blot analysis was performed using a rabbit polyclonal antibody against ANGPTL7 at 1:1,000 dilution (10396-1-AP ProteinTech), using standard procedures.

ELISA Assay.

ANGPTL7 was quantified by ELISA according to manufacturer's instructions (LS-F50425 Life Sciences). The cell lysates were diluted 1:1,000. The supernatants were diluted 1:10,000. The ELISA plate was read at 450 nm via SpectraMax M4 plate reader (Molecular Devices).

Results

Coding Variants in ANGPTL7 are Associated With IOP and Glaucoma

Figure 2A:
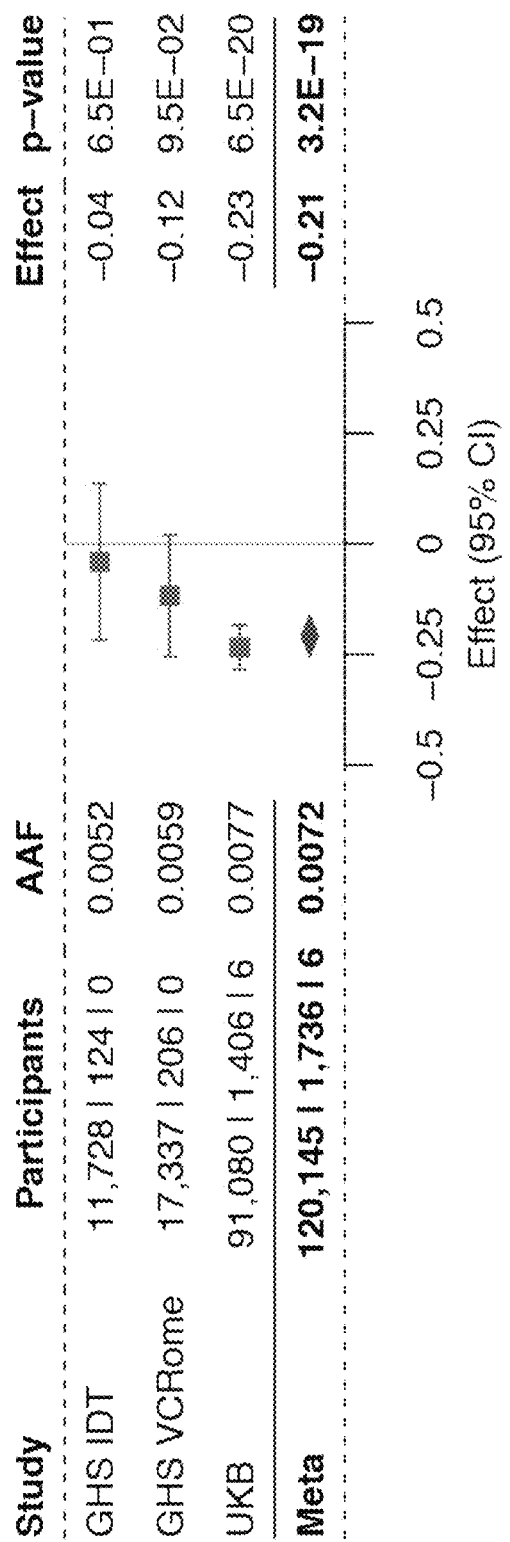
FIGS. 2A-2F show the association of Gln175His (FIGS. 2A, 2C, and 2E) and Arg177* (FIG. 2B, FIG. 2D, and FIG. 2F) variants in ANGPTL7 with IOP and glaucoma in individuals of European descent; the effect for association with IOP is measured in standard deviation units; association p-values were calculated using BOLT-LMM adjusted for age, age squared, sex, top principal components and, for UKB, genotyping array and assessment center (FIGS. 2A and 2B); boxplots representing Goldmann-correlated (IOPg) in the UK Biobank across genotypes (FIGS. 2C and 2D); Gln175His heterozygous and homozygous carriers have a 0.8-mmHg and 4.1-mmHg lower median IOPg, respectively, compared to non-carriers (FIG. 2C); Arg177* heterozygous carriers have a 1.4-mmHg lower IOPg compared to non-carriers (FIG. 2D); association with glaucoma was conducted across four series for Gln175His and Arg177*. GHS VCRome: Geisinger ~60,000 individuals, captured with VCRome; GHS IDT: ~85,000 individuals, captured with IDT; UKB: UK Biobank; MSSM: Mt. Sinai Medical School BioMe Biobank; MDCS: Malmo Diet and Cancer Study (FIGS. 2E and 2F); AAF=alternative allele frequency.

The effect of rare coding variation on IOP was studied across two large cohorts, UK Biobank (UKB) and Geisinger DiscovEHR (GHS) (FIG. 1), on 120,145 individuals of European descent after exclusion of cases with a glaucoma diagnosis. 1,368,641 protein-altering variants (including splice variants) with a minor allele frequency (MAF) <1% for association with IOP were examined. Two rare coding variants were significantly associated (p-value<5E-08) with decreased IOP (FIG. 1): a missense variant (p.Pro191Arg; MAF=about 1.0%) in son of seven less 2 (SOS2) associated with reduced IOP (beta$_{allelic}$–0.11 standard deviations (SD); p-value=3.39E-08), and a missense variant (p.Gln175His, MAF=about 0.7%) in Angiopoietin-like 7 (ANGPTL7) also associated with reduced IOP (beta$_{allelic}$=–0.21 SD, p-value=3.2E-19, FIG. 2A).

Figure 2B:
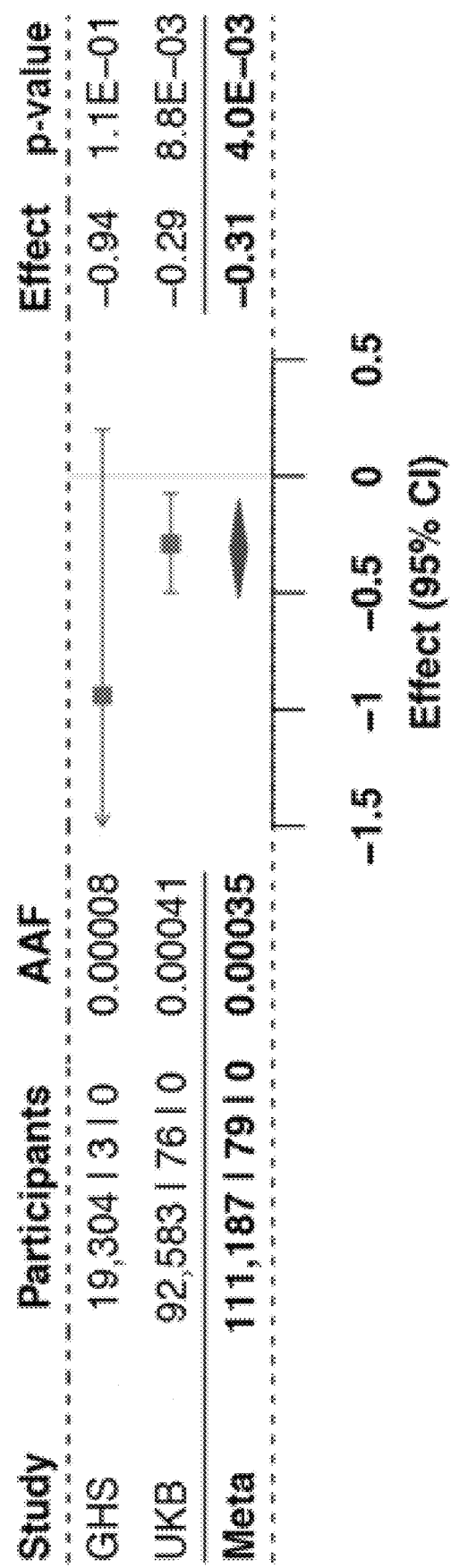
Figure 2C:
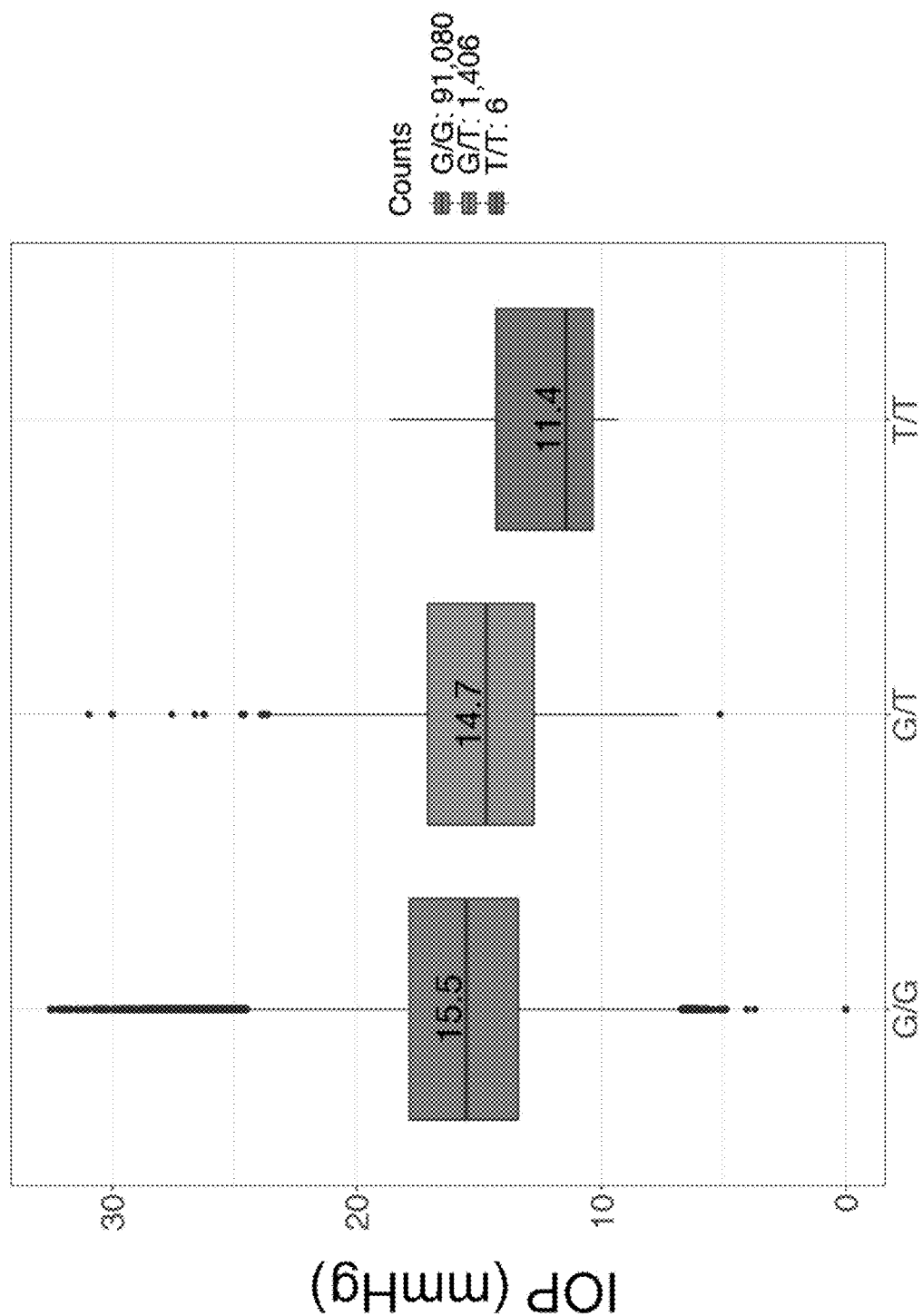
Figure 2D:
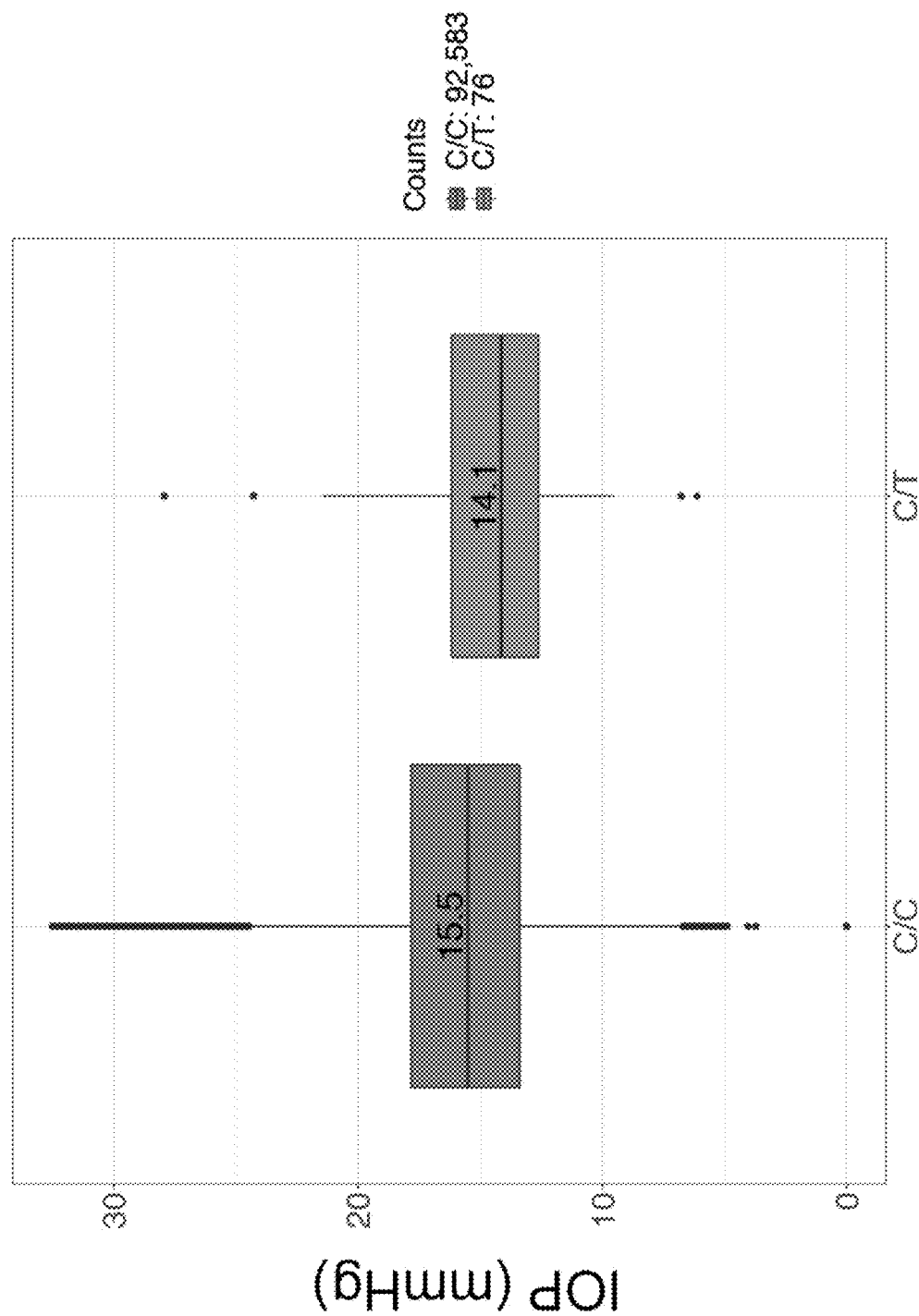
Figure 2E:
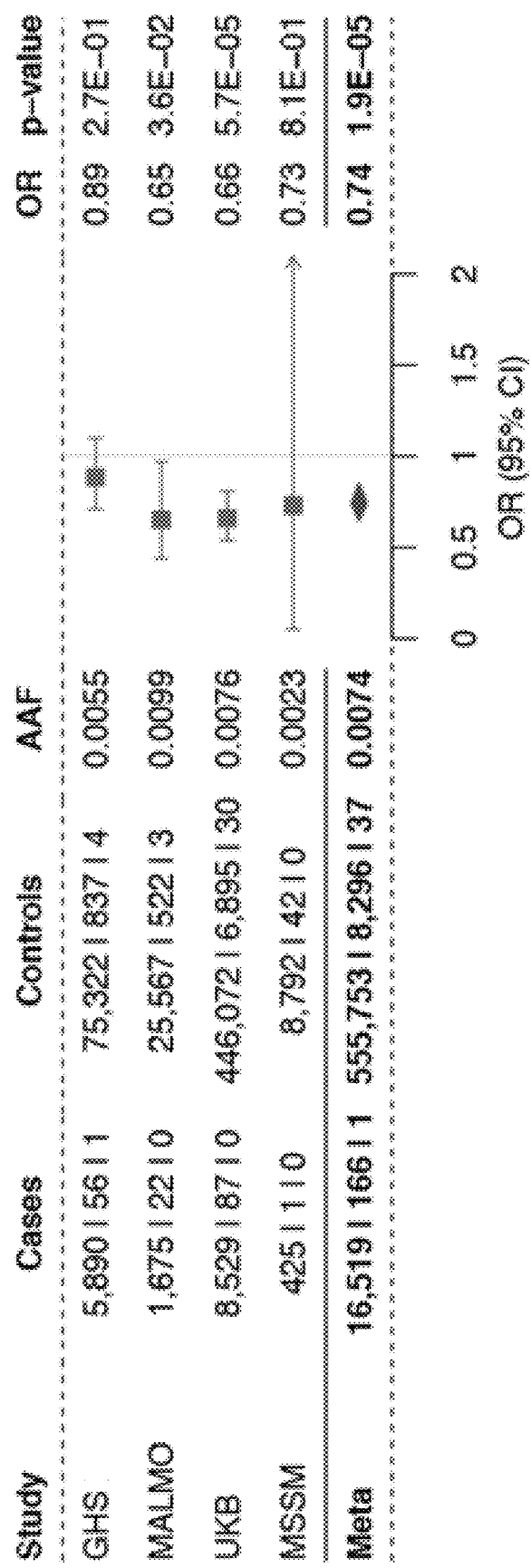
Figure 2F:
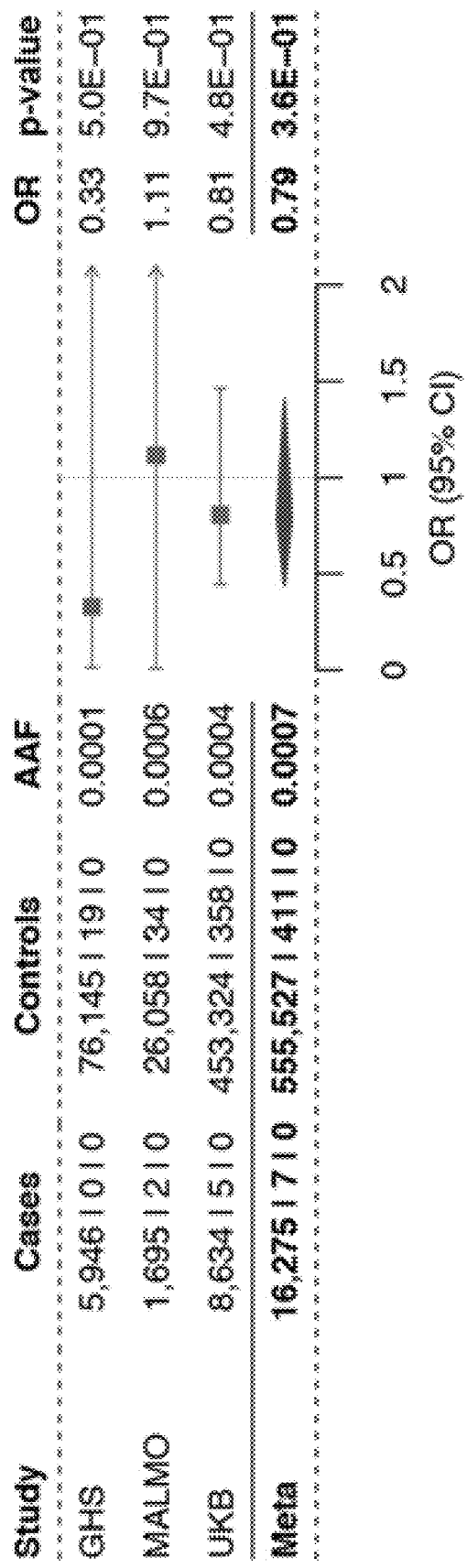

A sub-threshold association of a rare, predicted loss-of-function (pLOF) variant (Arg177*, AAF=about 0.03%) in ANGPTL7 with reduced IOP (beta$_{allelic}$=–0.31 SD, p-value=4.0E-03, FIG. 2B) was also noted. Heterozygous and homozygous carriers of Gln175His in ANGPTL7 have a 5.1% (0.8 mmHg) and 26.5% (4.1 mmHg) reduction in median IOP, respectively (FIG. 2C), and the Arg177* variant conferred a median IOP decrease of 9% (1.4 mmHg) in heterozygous carriers (FIG. 2D). To understand the biological significance of the decrease in IOP, the effect of ANGPTL7 variants on glaucoma risk in UKB, GHS and two additional series collected at Mount Sinai School of Medicine (MSSM, n=31,203) and a Malmö (MDCS, n=29,483) were examined. Meta-analysis across these cohorts showed a significant reduction in glaucoma risk in Gln175His carriers (odds ratio (OR$_{allelic}$)=0.74, p-value=1.9E-05, FIG. 2E), and a subthreshold but consistent reduction in risk in carriers of the rarer Arg177* variant (OR$_{allelic}$=0.79, p-value=3.6E-01, FIG. 2F). Taken together, the associations of missense and pLOF variants in ANGPTL7 with reduced IOP and reduced glaucoma risk support the hypothesis that loss or reduced function of ANGPTL7 results in lower IOP, and protection from glaucoma.

Figure 3:
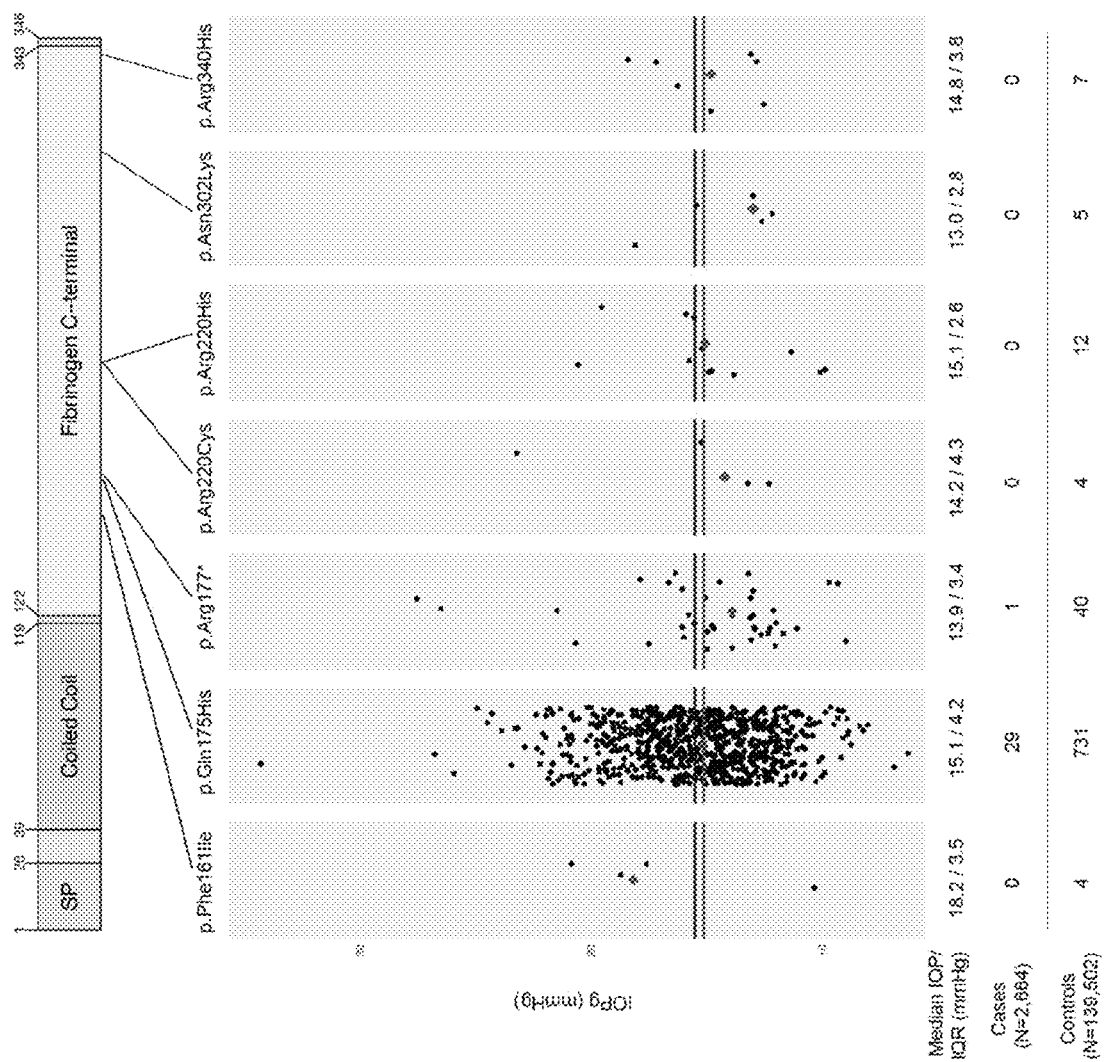
FIG. 3 shows missense and predicted loss-of-function (pLOF) variants in ANGPTL7 and IOP levels in individuals of European descent. The plots represent Goldmann-correlated IOP (mean of both eyes) levels in carriers of 1 pLOF and 6 missense variants in ANGPTL7 that are predicted deleterious by five different algorithms and have at least 4 carriers with IOP measurements in about 150,000 individuals in the UK Biobank for whom exome sequence data are available. The median IOP level across carriers of all 34 pLOF and predicted-deleterious missense ANGPTL7 variants (15.11 mmHg) is indicated by the red line, and the median IOP in non-variant carriers (15.51 mmHg) is indicated by the blue line. Magenta diamonds mark the median IOP in carriers of each variant. Beneath the plots is the median and interquartile range of IOP and the numbers of carriers that are glaucoma cases and controls for each variant.

Gene burden tests were performed to assess whether ultra-rare variants in ANGPTL7 had, in aggregate, an effect on IOP. The association between IOP and a set of 30 pLOF and missense variants predicted deleterious by five algorithms, excluding Gln175His and Arg177* was examined. A burden test showed a sub-threshold association with reduced IOP (beta=–0.31, p-value=8.40E-03) suggesting that additional variants in ANGPTL7 could confer protection from glaucoma by lowering IOP. However, at the current sample sizes these associations do not reach statistical significance. FIG. 3 shows the distribution of IOP in carriers of Gln175His, Arg177* and other ultra-rare variants with at least 4 carriers.

ANGPTL7 Variants in Individuals of African Descent

Figure 7A:
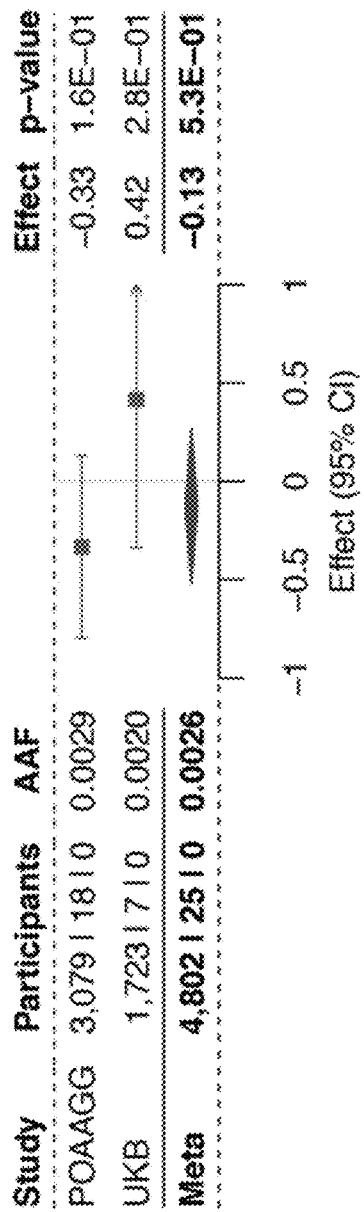
FIG. 7A shows association of Trp188* in ANGPTL7 with IOP in individuals of African ancestry across two cohorts.
Figure 7B:
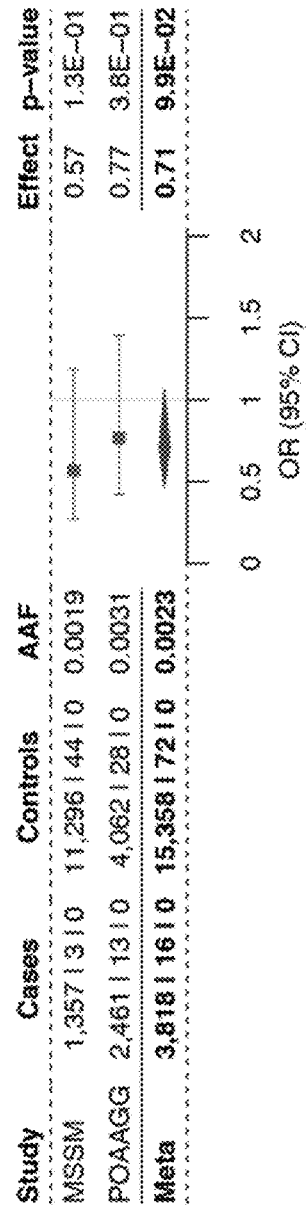
FIG. 7B shows association of Trp188* in ANGPTL7 with glaucoma in individuals of African ancestry across two cohorts.
Figure 7C:
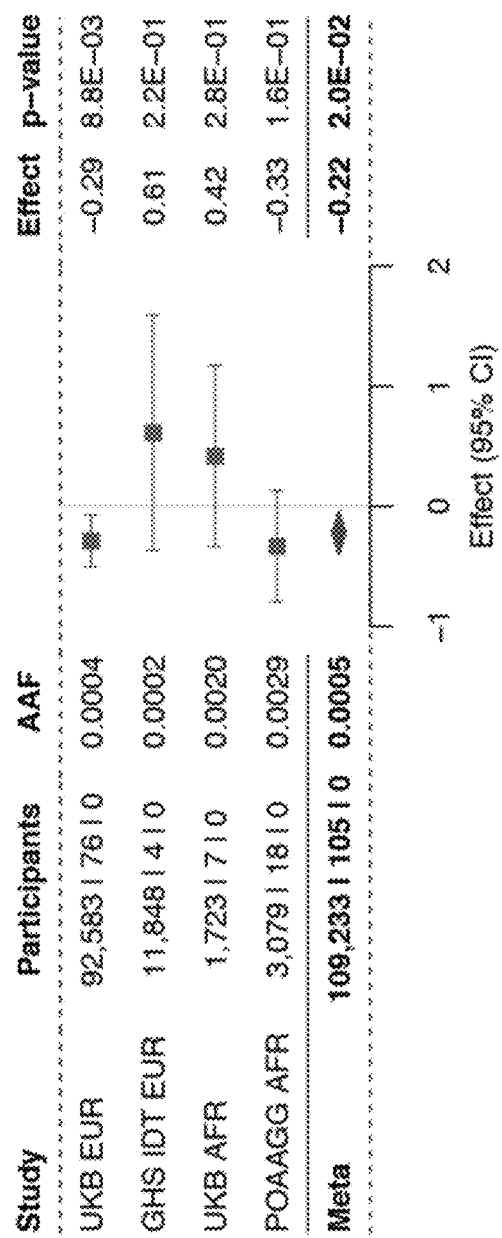
FIG. 7C shows Meta-analysis of the European-enriched Arg177*, and the African-enriched Trp188*, pLOF variants in ANGPTL7 for IOP. The Arg177* variant is represented by the cohorts labeled 'EUR', which include only European ancestry individuals. The Trp188* variant is represented by the cohorts labeled 'AFR', which include only African ancestry individuals.
Figure 7D:
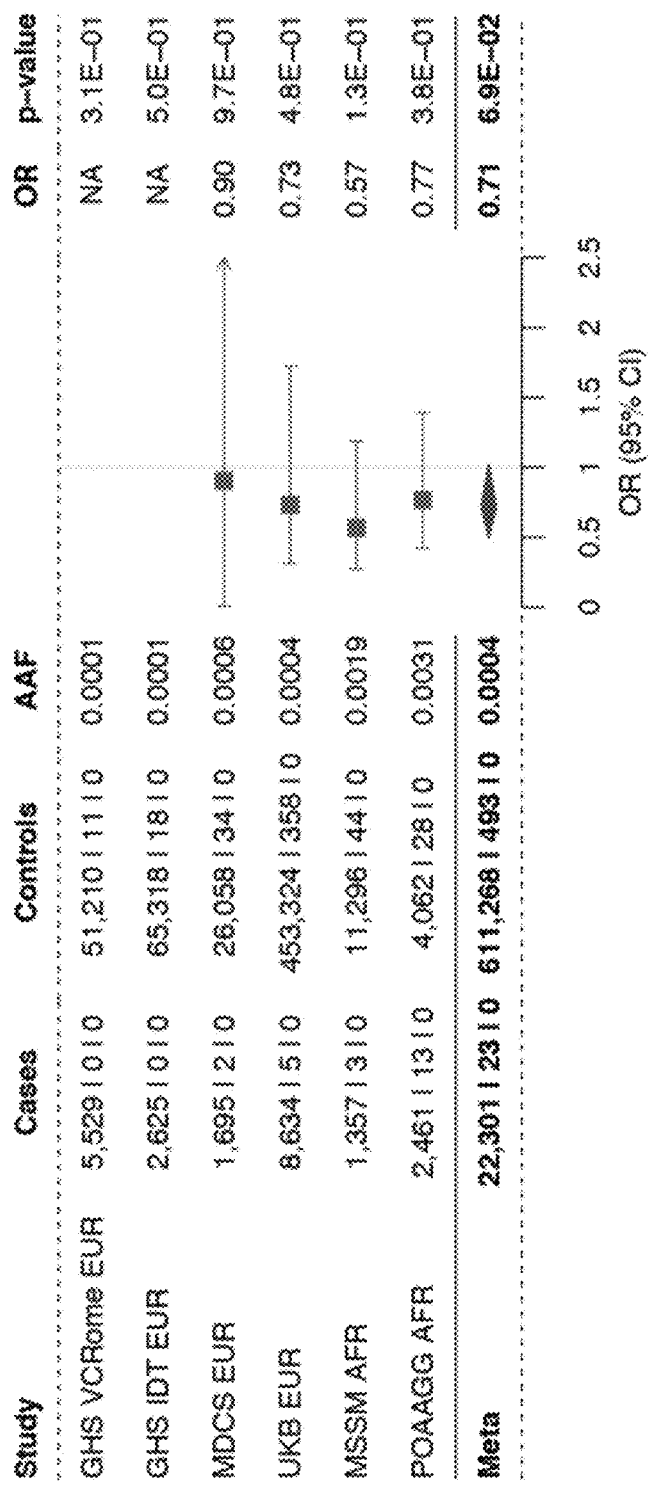
FIG. 7D shows Meta-analysis of the European-enriched Arg177*, and the African-enriched Trp188*, pLOF variants in ANGPTL7 for glaucoma. The Arg177* variant is represented by the cohorts labeled 'EUR', which include only European ancestry individuals. The Trp188* variant is represented by the cohorts labeled 'AFR', which include only African ancestry individuals.

The association between IOP (and glaucoma) and ANGPTL7 variants in individuals of African ancestry in UKB, MSSM, and the Primary Open Angle African American Glaucoma Genetics (POAAGG) study was also analyzed. A pLOF variant (Trp188*) in ANGPTL7 was identified, more prevalent in individuals of African ancestry (MAF=about 0.27%) compared to Europeans (MAF=about 0.0013%), which trends towards a decrease in IOP (betaallelic=–0.13, p-value=5.3E-01; FIG. 7A), and decrease in risk for glaucoma (ORallelic=0.71, p-value=9.9E-02; FIG. 7B) in a meta-analysis across two cohorts). A meta-analysis including both Arg177* and Trp188* pLOF variants decreased the p-value for association with glaucoma from 1.9E-01 (Arg177* alone) and 9.8E-02 (Trp188* alone) to 6.9E-02 (FIG. 7D). Similar results were obtained in regard to IOP (FIG. 7C).

ANGPTL7 Expression in Ocular Tissues Across Species

Figure 4A:
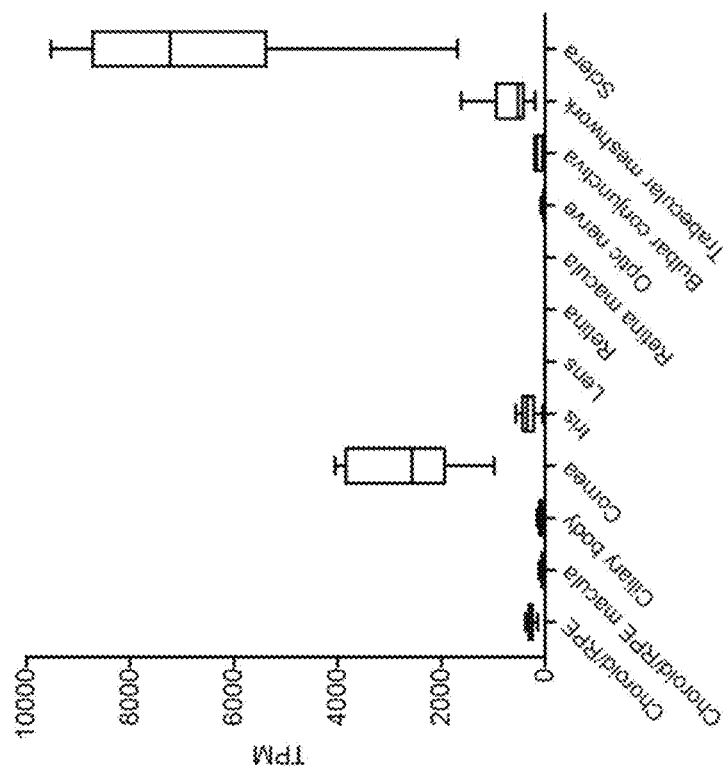
FIGS. 4A-4E show ANGPTL7 expression in ocular tissues across species; RNA-sequencing-based expression levels (measured in transcripts per million, TPM) are highest in cornea, trabecular meshwork (TM), and sclera in human (FIG. 4A), and African green monkey (FIG. 4B) eyes, and in cornea, TM, sclera, optic nerve, and choroid/RPE in C57BL/6J mice (FIG. 4C). In situ hybridization (RNAScope) shows ANGPTL7/Angptl7 (red) expression in TM, cornea and sclera in human (FIG. 4D) and murine (FIG. 4E) eyes. DAPI staining (blue) counterstains cell nuclei. RPE: retinal pigmented epithelium; CB: ciliary body; SC: Schlemm's canal; CM: ciliary muscle; AC: anterior chamber; TM: trabecular meshwork; RGC: retinal ganglion cell; INL: inner nuclear layer; ONL: outer nuclear layer.
Figure 4B:
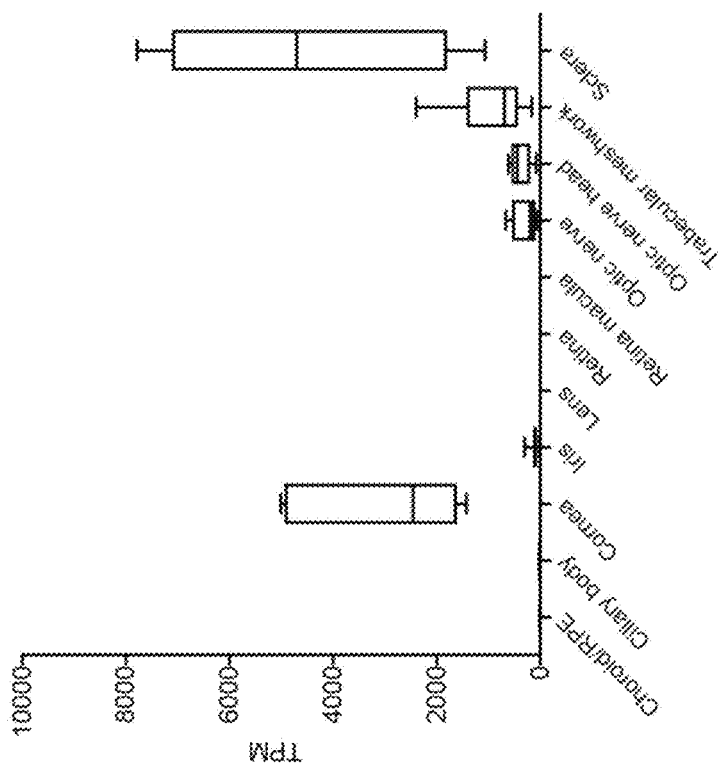
Figure 4C:
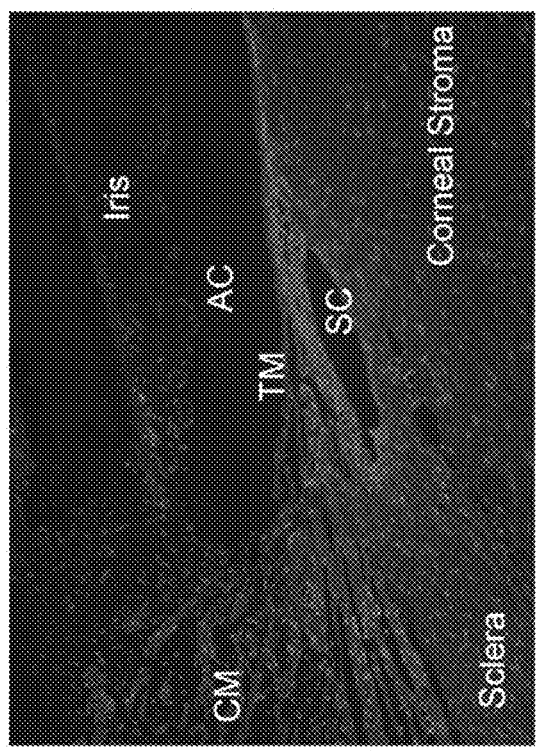
Figure 4D:
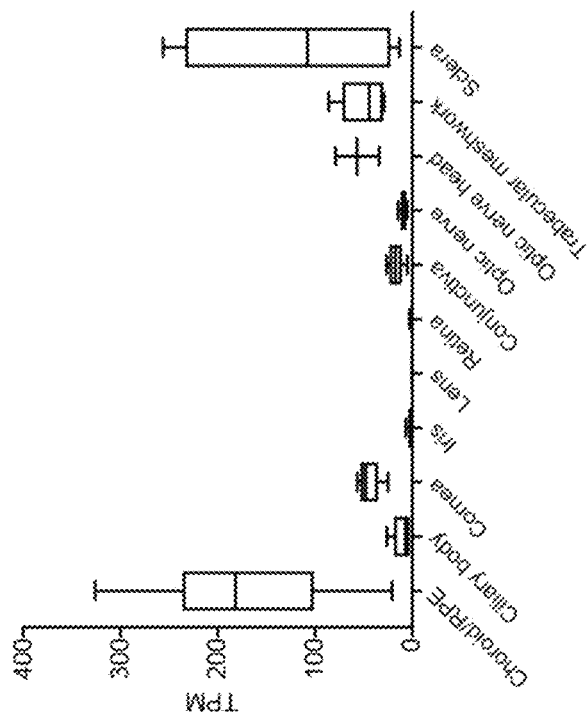
Figure 4E:
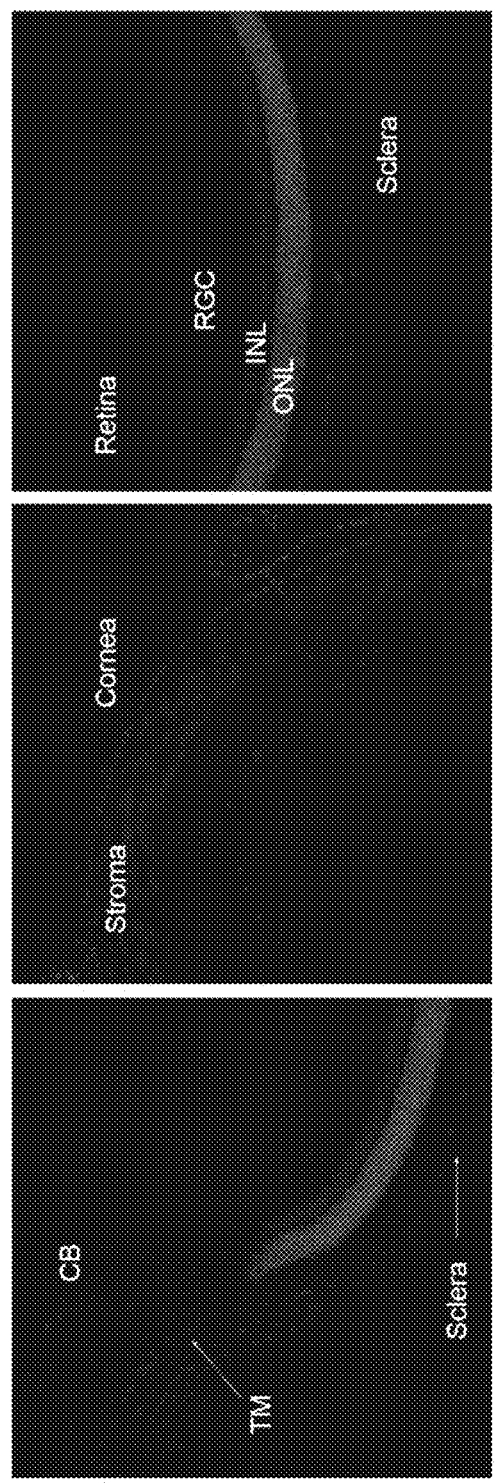

To identify expression of ANGPTL7 in ocular tissues across different species, transcriptome profiles from different parts of eye were generated. High ANGPTL7 expression was observed in cornea, trabecular meshwork (TM), and sclera in human and African green monkey eyes (FIGS. 4A and 4B). High Angptl7 expression was also observed in cornea, TM, sclera, optic nerve, and choroid/RPE in eyes of C57BL/6J mice (FIG. 4C). In situ hybridization on human donor and mouse eyes using RNAScope probes for human ANGPTL7 and mouse Angptl7 showed ANGPTL7/Angptl7 expression in TM, cornea stroma, and sclera (FIGS. 4D and 4E).

Gene Expression Changes in Human TM Cells Upon Dexamethasone Treatment

Figure 5:
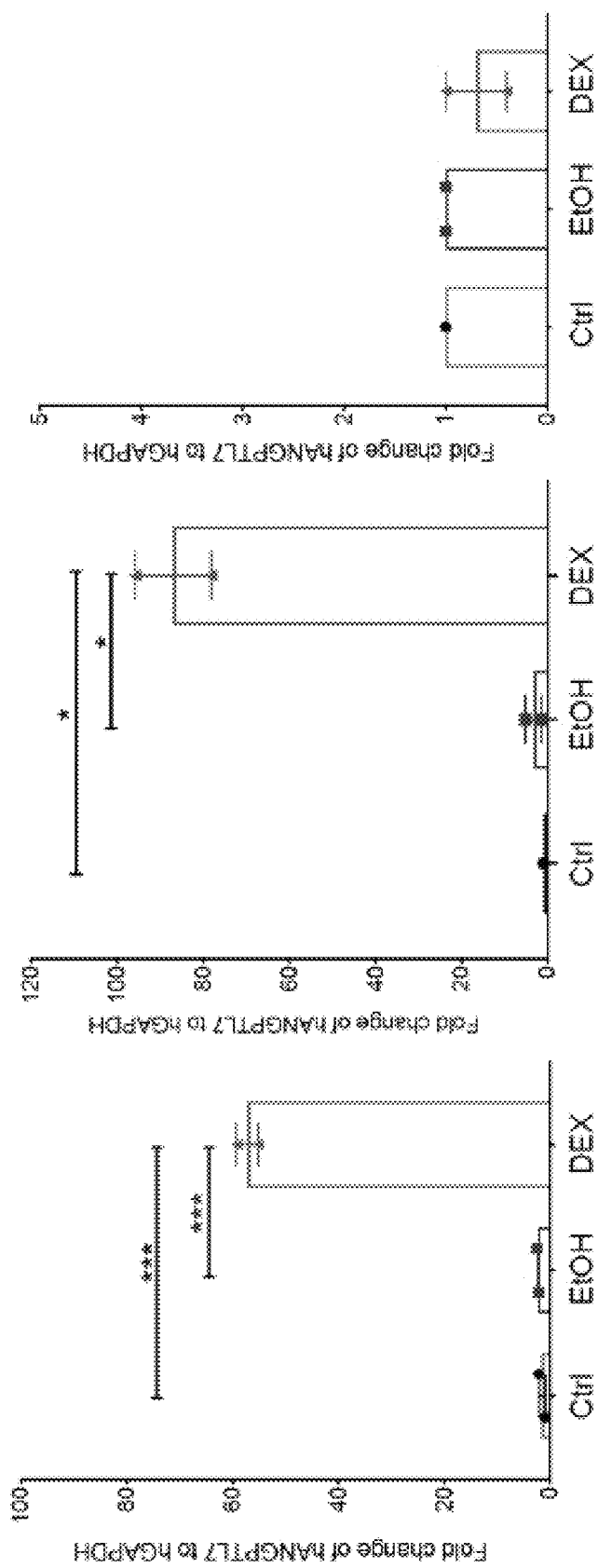
FIG. 5 shows dexamethasone (DEX)-induced gene expression changes in three human trabecular meshwork (hTM) primary cell lines from three independent human eyes, measured with quantitative PCR (qPCR); hTM cells were treated with DEX for 72 hours followed by qPCR analysis; DEX treatment increased ANGPTL7 expression in two out of three HTM cell lines; Ctrl represents untreated cells and EtOH represents ethanol treatment; ata are presented as means±standard error across two replicates, one-way ANOVA, *p=0.01, p=0.001, *p=0.0001.

Dexamethasone (DEX) treatment is known to lead to many biochemical changes at the gene expression level in the TM, including upregulation ANGPTL7. To further characterize these previous findings, quantitative PCR (qPCR) was performed on three human TM primary cell lines from three independent human eyes treated with vehicle (0.1% ethanol) or DEX (100 nM) for 72 hours. qPCR analysis revealed increased expression of ANGPTL7 expression in two out of three (FIG. 5), suggesting some degree of variability in the DEX-induced upregulation of ANGTPL7, consistent with the observed variation in response to steroid treatment in the general population.

Angptl7 Increases IOP in Mouse Eyes

Figure 6B:
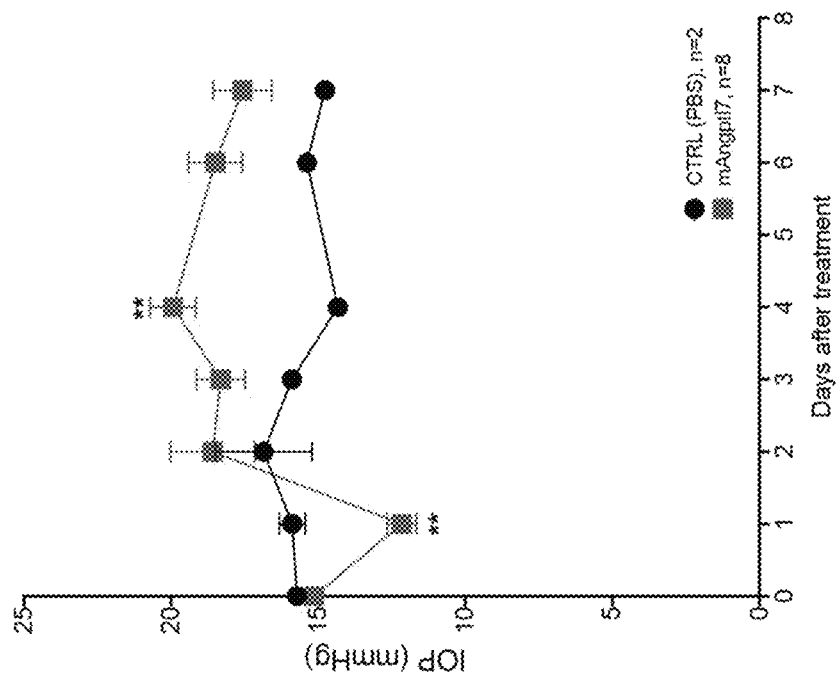
FIG. 6B shows Increasing mAngptl7 levels in mouse eyes increases IOP. Murine Angptl7 (mAngptl7) protein was injected into mouse eyes via intracameral route and IOP was measured over time. After an initial drop, IOP was elevated in Angptl7-treated eyes compared to control eyes. Data are presented as means±SEM.
Figure 6A:
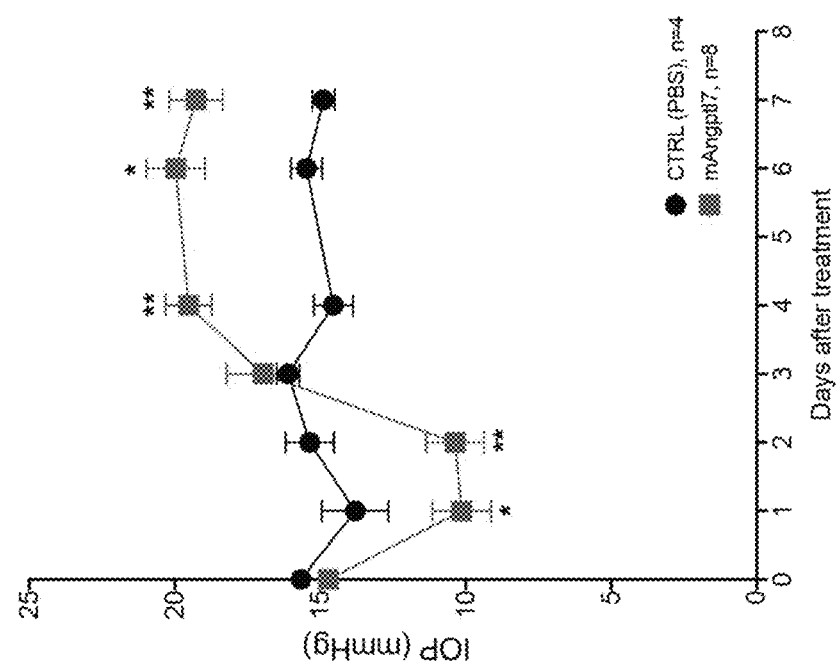
FIG. 6A shows increasing mAngptl7 levels in mouse eyes increases IOP. Murine Angptl7 (mAngptl7) protein was injected into mouse eyes via intravitreal route and IOP was measured over time. After an initial drop, IOP was elevated in Angptl7-treated eyes compared to control eyes. Data are presented as means±SEM.

Previous studies showed that overexpression of ANGPTL7 in TM cells leads to changes in extracellular matrix deposition and reorganization (Comes et al., Genes to Cells: Devoted to Molecular & Cellular Mechanisms, 2011, 16, 243-259; and Kuchtey, Invest. Ophthalmol. & Visual Sci., 2008, 49, 3438-48) and that ANGPTL7 is increased in aqueous humor of glaucoma patients (Kuchtey, Invest. Ophthalmol. & Visual Sci., 2008, 49, 3438-48), however, the role of ANGPTL7 in IOP regulation is not clear. To investigate the role of ANGPTL7 in IOP regulation, ANGPTL7 protein was injected in mice via intravitreal and intracameral routes and measured IOP over time. Intravitreal injection of ANGPTL7 protein in mice led to an initial drop in IOP and then, starting on day 4, to an elevation of IOP of 4-5 mmHg (22-25% compared to baseline) that lasted until the end of the experiment on day 7 (FIG. 6A). Similarly, intracameral injection of ANGPTL7 protein in mice led to an initial drop and subsequent elevation (by 2-5 mmHg) of IOP, starting on day 3 until the end of the experiment on day 7 (FIG. 6B).

Vehicle-injected mice did not show an increase in IOP in either route of administration.

Figure 8A:
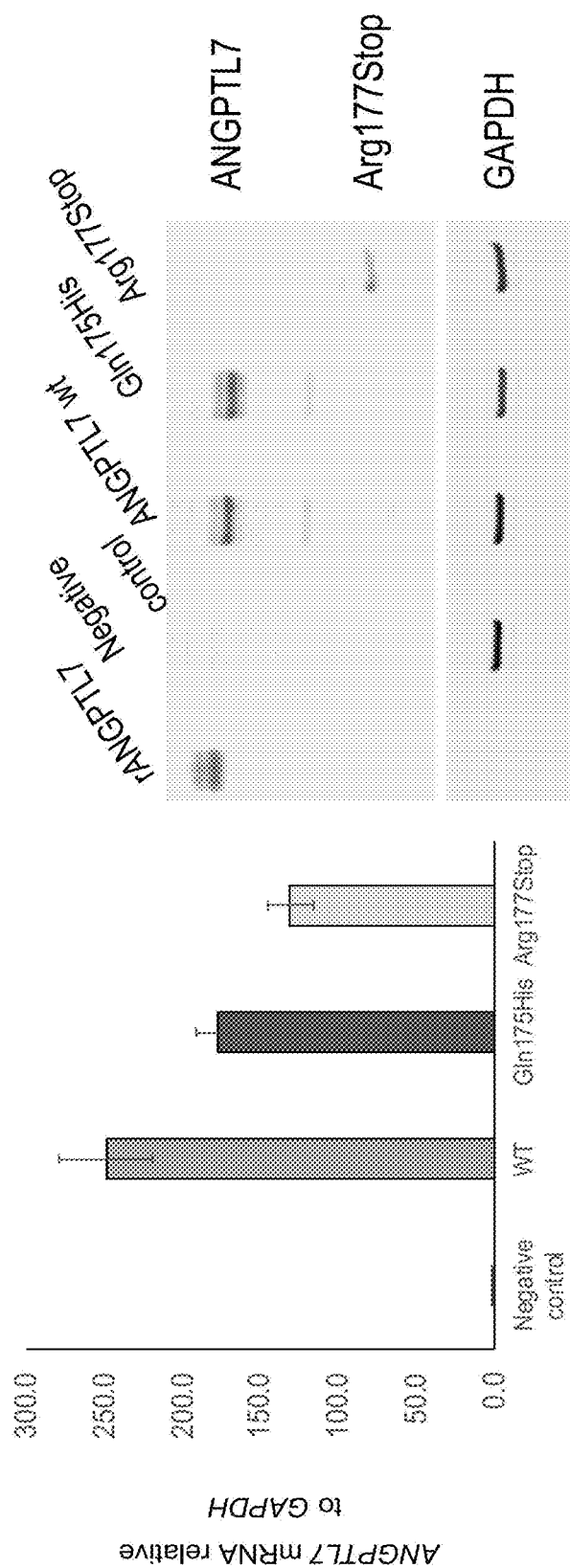
FIGS. 8A and 8B show the expression of two variants of ANGPTL7 (Gln175His and Arg177Stop) in HEK 293 whole cell lysates.
Figure 8B:
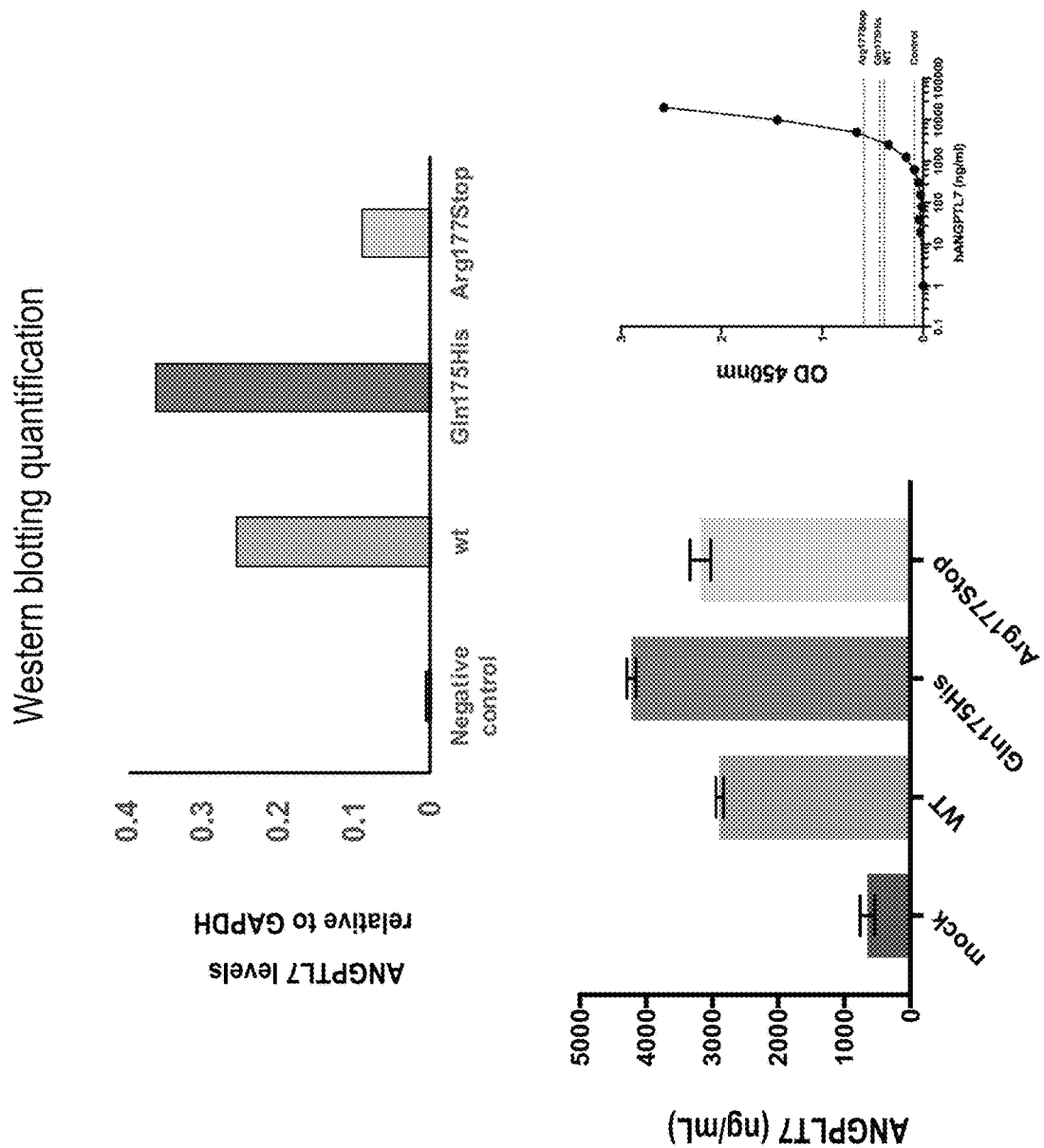
Figure 8C:
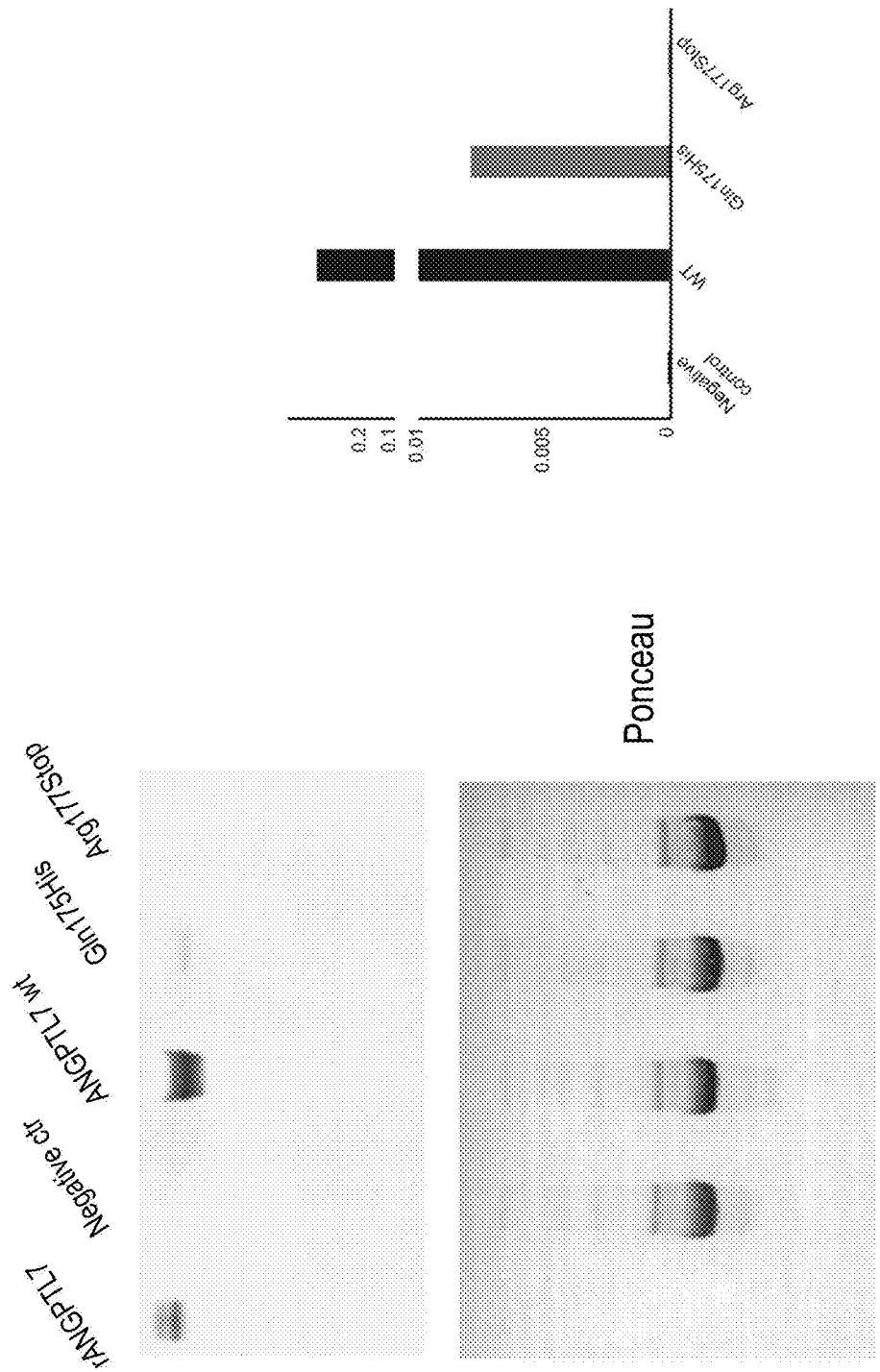
FIG. 8C and FIG. 8D shows a drastic decrease of the Gln175His variant observed in the cell supernatant compared to the wild type ANGPTL7.
Figure 8D:
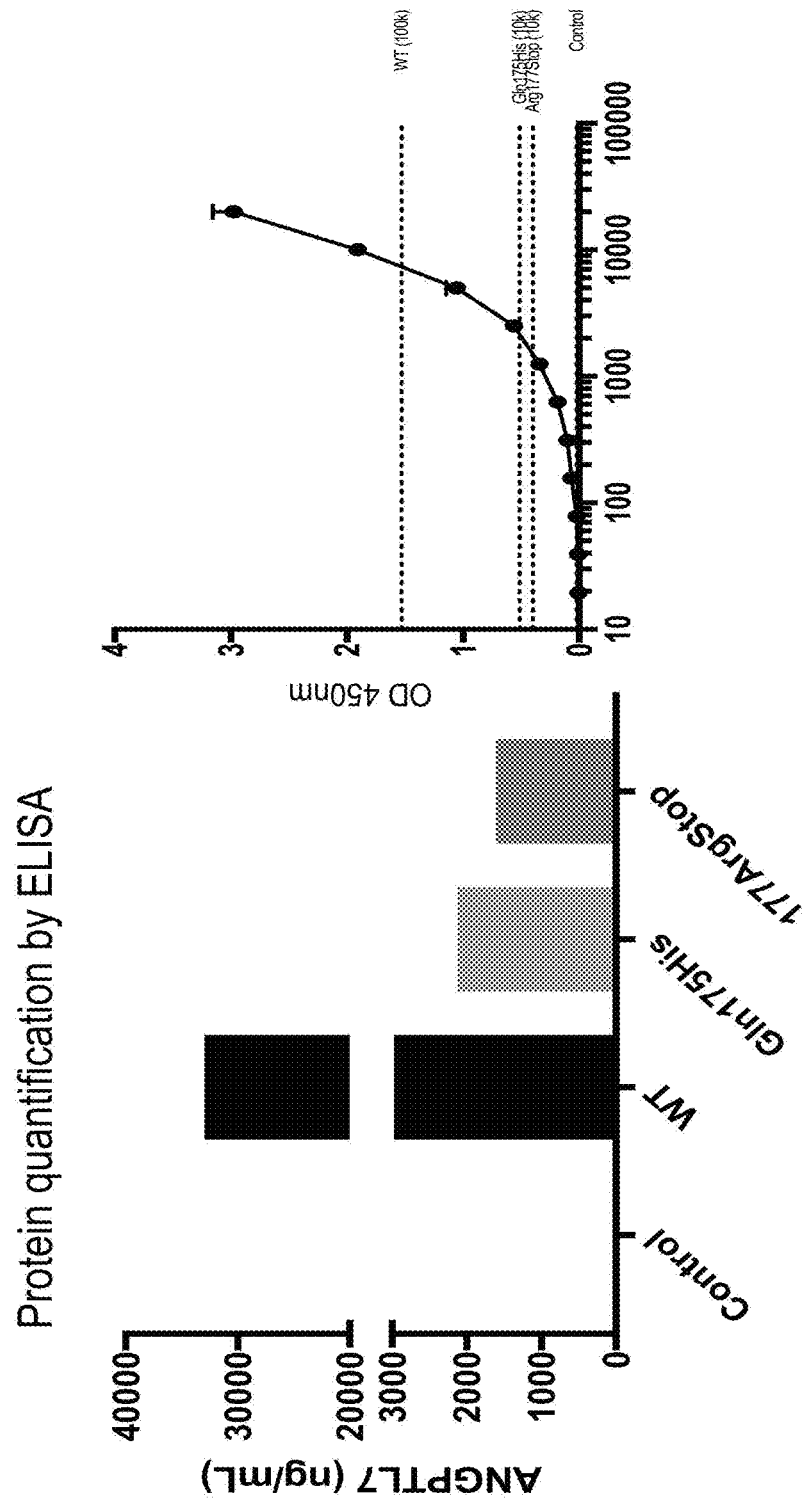
Figure 8E:
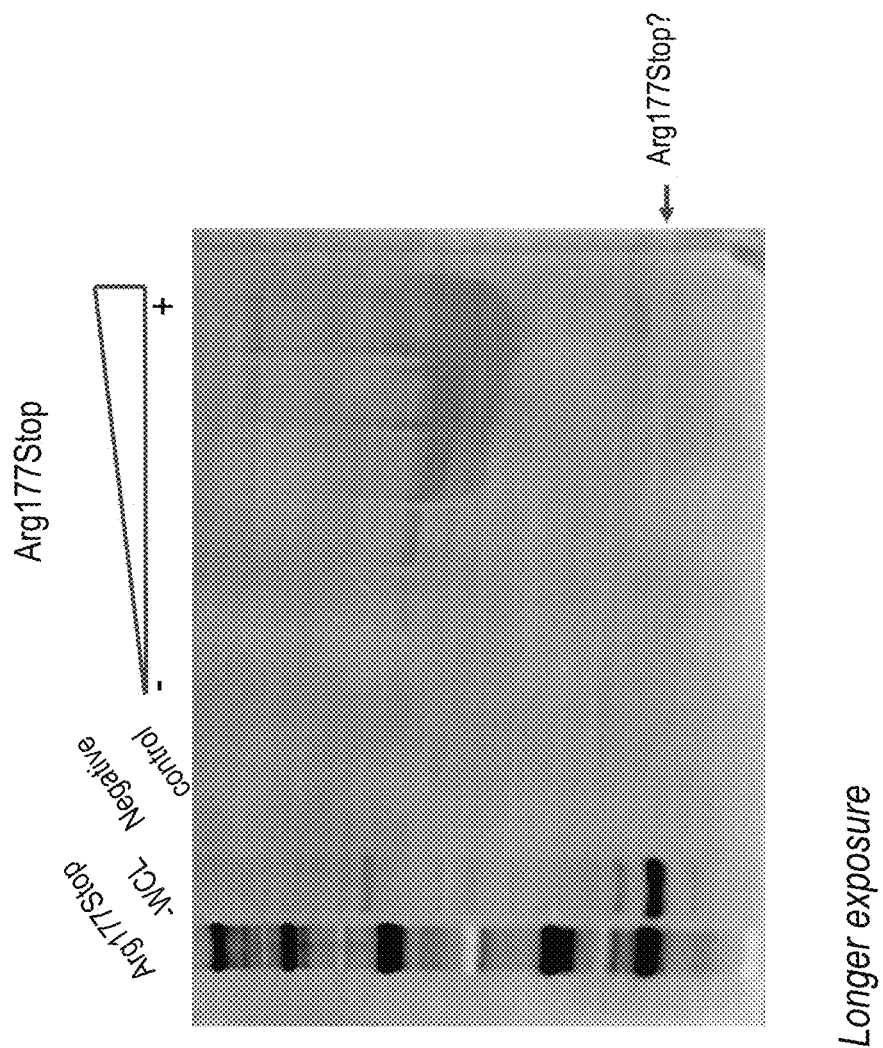
FIG. 8E shows Arg177Stop variant unable to be secreted in the supernatant.

ANGPTL7 Gln175His and Arg177Stop Exogenous Expression in HEK 293 Whole Cell Lysates Studies were conducted to show the expression of two variants of ANGPTL7 (Gln175His and Arg177Stop) in HEK 293 whole cell lysates (FIG. 8A and FIG. 8B). A drastic decrease of the Gln175His variant was observed in the cell supernatant compared to the wild type ANGPTL7 (FIG. 8C and FIG. 8D). In addition, a study was performed to determine whether the Arg177Stop variant was able to be secreted in the supernatant (FIG. 8E). Exogenous expression of ANGPTL7 wild type and Gln175His variant in HEK293 showed a comparable intracellular protein level, but a drastic decrease of secreted Gln175His compared to the wild type ANGPTL7. Expression of Arg177Stop in HEK293 cells showed reduced intracellular protein level. The Arg177Stop variant was not able to be secreted.

Figure 9E:
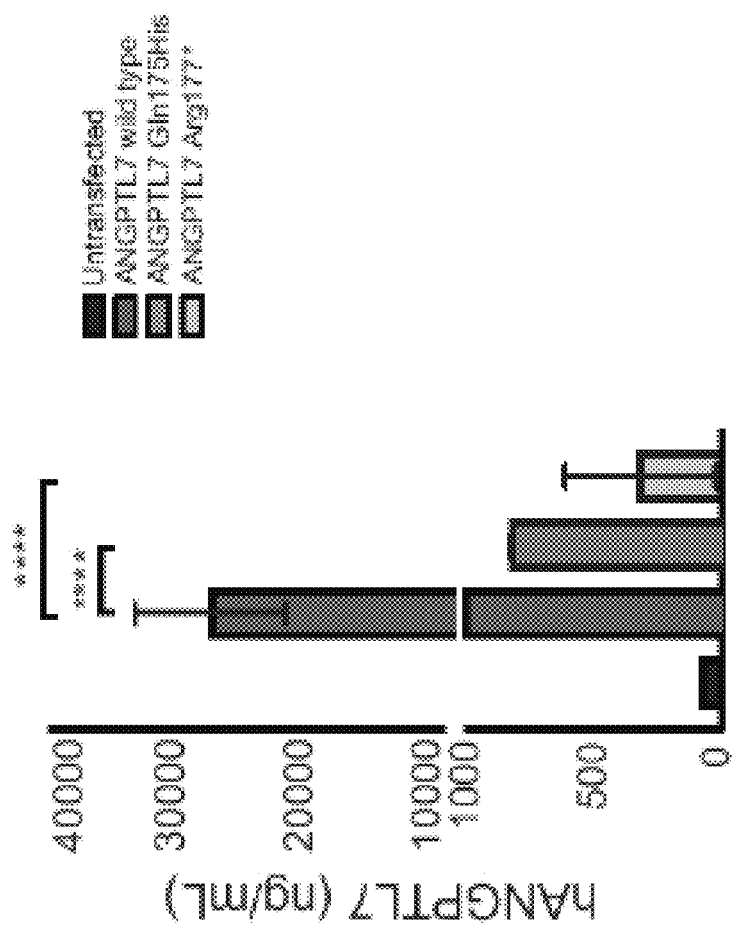
FIG. 9E shows ELISA assay showing extracellular protein levels of ANGPTL7 wild type, ANGPTL7 Gln175His and ANGPTL7 Arg177*. For quantification each supernatant was diluted 1:10,000. Western blotting and ELISA analysis were repeated on three independent biological replicates. Technical replicates (n=3) were run for RT-PCR and ELISA analysis.

Expression Analysis of ANGPTL7 Gln175His and ANGPTL7 Arg177* in a HEK293 Cell Line In vitro experiments were conducted to assess the expression and secretion of two variants of ANGPTL7 (Gln175His and Arg177Stop) that were identified in genetic association analyses, in HEK293T cells. Plasmids carrying either the 'wild type' (non-mutant) ANGPTL7 coding region or the variations that lead to Gln175His and Arg177Stop mutant forms were introduced into HEK293T. The levels of mRNA of each the wild type, Gln175His and Arg177Stop ANGPTL7 were measured, and it was observed that the Gln175His and Arg177Stop mRNAs were reduced compared to the wild type (FIG. 9A). Whole cell lysate (FIG. 9B) and the cell supernatant (FIG. 9D) was probed with an anti-ANGPTL7 polyclonal antibody to determine the levels of the wild type ANGPTL7 and the two mutant proteins. An ELISA assay was performed to quantify the levels of each protein in the whole cell lysate (FIG. 9C) and the supernatant (FIG. 9E). The results indicate that the levels of wild type, Gln175His and Arg177Stop proteins are not significantly different in the whole cell lysate (FIGS. 9B and 9C), however, there is a drastic reduction in the amount of Gln175His and Arg177Stop in the supernatant of the cells when compared to the wild type protein (FIGS. 9D and 9E). These data suggest that the Gln175His and Arg177Stop mutations cause ANGPTL7 to be secreted inefficiently in this in vitro system, and are consistent with the genetic hypothesis that loss or reduction of ANGPTL7 function results in reduced intraocular pressure, and protection from glaucoma.

In this study, genetic and functional evidence highlighting inhibition of ANGPTL7 as a potential strategy for glaucoma therapy are demonstrated. Through genetic association analyses in Europeans, a rare, missense variant, Gln175His (rs28991009), in ANGPTL7 was identified that associated with a decrease in IOP, and with decreased risk for glaucoma. A pLOF variant in ANGPTL7, Arg177* (rs143435072), was also identified that also associated with a decrease in IOP, suggesting that Gln175His carriers are protected from glaucoma through a loss or reduction in ANGPTL7 activity. Consistent with this hypothesis, several ultra-rare variants in ANGPTL7 were associated, in aggregate, with decreased IOP, and an additional ANGPTL7 pLOF variant, Trp188*, was enriched in individuals of African descent, who also showed a trend towards protection from glaucoma. Taken together, the genetic data strongly imply a causal relationship between downregulation of ANGPTL7 and protection from glaucoma. The RNA sequencing and in situ hybridization data in ocular tissues across mice, humans and the African Green monkey showed strongest expression of ANGPTL7 in the cornea and trabecular meshwork.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

What is claimed is:

1. A method of treating a patient having glaucoma or increased intraocular pressure (IOP), the method comprising administering an angiopoietin like 7 (ANGPTL7) inhibitor to the patient, wherein the patient lacks an ANGPTL7 predicted loss-of-function variant nucleic acid molecule or is heterozygous for an ANGPTL7 predicted loss-of-function variant nucleic acid molecule, wherein the ANGPTL7 predicted loss-of-function variant nucleic acid molecule encodes ANGPTL7 Arg177Stop or Trp188Stop.

2. The method according to claim 1, wherein the ANGPTL7 inhibitor comprises an antisense nucleic acid molecule, a small interfering RNA (siRNA), or a short hairpin RNA (shRNA) that hybridizes to an ANGPTL7 mRNA.

3. The method according to claim 1, further comprising detecting the presence or absence of the ANGPTL7 predicted loss-of-function variant nucleic acid molecule in a biological sample from the patient.

4. The method according to claim 1, the method further comprising administering to the patient a second therapeutic agent that treats or inhibits glaucoma or IOP, wherein the second therapeutic agent does not comprise an ANGPTL7 inhibitor.

5. The method according to claim 1, wherein the ANGPTL7 predicted loss-of-function variant nucleic acid molecule is:

a genomic nucleic acid molecule having a nucleotide sequence comprising a thymine at a position corresponding to position 4,291 according to SEQ ID NO:2, or a genomic nucleic acid molecule having a nucleotide sequence comprising an adenine at a position corresponding to position 4,325 according to SEQ ID NO: 133;

an mRNA molecule having a nucleotide sequence comprising a uracil at a position corresponding to position 529 according to SEQ ID NO:5, or an mRNA molecule having a nucleotide sequence comprising an adenine at a position corresponding to position 563 according to SEQ ID NO:136; or a cDNA molecule produced from an mRNA molecule, wherein the cDNA molecule has a nucleotide sequence comprising a thymine at a position corresponding to position 529 according to SEQ ID NO:8, or a cDNA molecule produced from an mRNA molecule, wherein the cDNA molecule has a nucleotide sequence comprising an adenine at a position corresponding to position 563 according to SEQ ID NO:139.

6. The method according to claim 4, wherein the second therapeutic agent comprises a prostaglandin, a beta blocker, an alpha-adrenergic agonist, a carbonic anhydrase inhibitor, a rho kinase inhibitor, a miotic agent, or a cholinergic agent.

7. A method of treating a patient suffering from an ophthalmic condition, the method comprising:
   determining whether the patient has an angiopoietin like 7 (ANGPTL7) predicted loss-of-function variant nucleic acid molecule encoding a human ANGPTL7 polypeptide by:
      performing or having performed a genotyping assay on a biological sample from the patient to determine if the patient has a genotype comprising the ANGPTL7 predicted loss-of-function variant nucleic acid molecule; and
   administering or continuing to administer to a patient that is ANGPTL7 reference a second therapeutic agent that treats or inhibits the ophthalmic condition in a standard dosage amount, and administering to the patient an ANGPTL7 inhibitor, wherein the second therapeutic agent is not an ANGPTL7 inhibitor; and
   administering or continuing to administer to a patient that is heterozygous for the ANGPTL7 predicted loss-of-function variant a second therapeutic agent that treats or inhibits the ophthalmic condition in an amount that is the same as or lower than a standard dosage amount, and administering to the patient an ANGPTL7 inhibitor, wherein the second therapeutic agent is not an ANGPTL7 inhibitor;
   wherein the presence of a genotype having the ANGPTL7 predicted loss-of-function variant nucleic acid molecule encoding the human ANGPTL7 polypeptide indicates the patient has a reduced risk of developing the ophthalmic condition;
   wherein the ANGPTL7 predicted loss-of-function variant nucleic acid molecule is a nucleic acid molecule encoding ANGPTL7 Arg177Stop or Trp188Stop.

8. The method according to claim 7, wherein the ANGPTL7 predicted loss-of-function variant nucleic acid molecule is:
   a genomic nucleic acid molecule having a nucleotide sequence comprising a thymine at a position corresponding to position 4,291 according to SEQ ID NO:2, or a genomic nucleic acid molecule having a nucleotide sequence comprising an adenine at a position corresponding to position 4,325 according to SEQ ID NO:133;
   an mRNA molecule having a nucleotide sequence comprising a uracil at a position corresponding to position 529 according to SEQ ID NO:5, or an mRNA molecule having a nucleotide sequence comprising an adenine at a position corresponding to position 563 according to SEQ ID NO:136; or
   a cDNA molecule produced from an mRNA molecule, wherein the cDNA molecule has a nucleotide sequence comprising a thymine at a position corresponding to position 529 according to SEQ ID NO:8, or a cDNA molecule produced from an mRNA molecule, wherein the cDNA molecule has a nucleotide sequence comprising an adenine at a position corresponding to position 563 according to SEQ ID NO:139.

9. The method according to claim 7, wherein the nucleic acid molecule is present within a cell obtained from the human subject.

10. The method according to claim 7, wherein the ANGPTL7 inhibitor comprises an antisense nucleic acid molecule, a small interfering RNA (siRNA), or a short hairpin RNA (shRNA) that hybridizes to an ANGPTL7 mRNA.

11. The method according to claim 7, wherein the second therapeutic agent comprises a prostaglandin, a beta blocker, an alpha-adrenergic agonist, a carbonic anhydrase inhibitor, a rho kinase inhibitor, a miotic agent, or a cholinergic agent.

* * * * *

SEQUENCE LISTING

```
<160> NUMBER OF SEQ ID NOS: 165

<210> SEQ ID NO 1
<211> LENGTH: 6641
<212> TYPE: DNA
<213> ORGANISM: homo sapien

<400> SEQUENCE: 1
cttgtggagc attcgggctt ggaaggaaag ctataggcta cccattcagc tcccctgtca      60
gagactcaag ctttgagaaa ggctagcaaa gagcaaggaa agagagaaaa caacaaagtg     120
gcgaggccct cagagtgaaa gcgtaaggtt cagtcagcct gctgcagctt tgcagacctc     180
agctgggcat ctccagactc ccctgaagga agagccttcc tcacccaaac ccacaaaaga     240
tgctgaaaaa gcctctctca gctgtgacct ggctctgcat tttcatcgtg gcctttgtca     300
gccacccagc gtggctgcag aagctctcta agcacaagac accagcacag ccacagctca     360
aagcggccaa ctgctgtgag gaggtgaagg agctcaaggc ccaagttgcc aaccttagca     420
gcctgctgag tgaactgaac aagaagcagg agagggactg ggtcagcgtg gtcatgcagg     480
tgatggagct ggagagcaac agcaagcgca tggagtcgcg gctcacagat gctgagagca     540
```

```
agtactccga gatgaacaac caaattgaca tcatgcagct gcaggcagca cagacggtca    600
ctcagacctc cgcaggtaag gagaccagtc ccctgaggga gcgtggagtg cctccccatc    660
tacagcactg cttctacata tcctggtcat cagaaccact actggggcct cttttgtggg    720
tacactttcc ctttagtaaa ggcttatgca gtatttcctt tgacttctaa tgctatgtaa    780
gtttacctaa caccttcacg ggtctctttt atccacacag tgtttcagcc taccatcttg    840
gagtgctgag atactacatg gtttgcccaa agtcacccag caagtcttag aagcagggtt    900
caagtcttcc tgattggtgt agctctgcta cttcctcacc aagagctgac aggctatatc    960
tcaagaaatt ccaaggaagc accaaactgt aacagctgtt cctctggaag caaagttttg   1020
ccagaaacag ttctctggtg ttcctaagat ttaccaggaa tgagcattaa tggaattttg   1080
tgtcctctct ctgtaaacgt aactcttctc attggctcag agttaagtgt agagacacat   1140
aaccatgtga agagtcccct tgtgttcagg aaggatgcgg ctccttaagg ttcctcaatt   1200
gtgatacgtc tattttttc catggtctta aatgaatttc tccgaataca ggatttttta    1260
aatgcaatgc tgaaatatag acttaatagg ccaaaaataa gataaattta atctttcttt   1320
tgcaaaataa cttttatttc tggttagctc agctcaggtg ggccaacatg aatttacggt   1380
ttagagataa aaatttggtt ttctgaaatt atcaggaaaa tattagttgt aaggagcata   1440
tcctatagac atgtcatttc ttgctgatat aaaaaccatt ggtcccatta taaactacat   1500
gaagaacaaa gacatgatca gcttctactg actaagtcaa tggttaacct cagctcaaat   1560
taagaaaaag ttttaacatg aaaccaagct tgaaaattct gttacctgaa ccaacatgta   1620
tcaatcactt tctaagcatg gacttccggg ccctcagttt gggattagaa aggtattctc   1680
aggccatttt ccagacaagt gagtcctgat ttggtctgtg agatgaaacc agacatgcgg   1740
aagaccaggc cagacagagg aatctgaccg tgccacttcc tgctcatcca acaggaggc    1800
tttctcacca tcctgcaagg aggttcttgg ggtcaagtgc agctctccca ccaggtctct   1860
tgctcttctt gcccaggaca tcattcctta ttttttcttct ctatgaccaa gtgctcagtt   1920
acccttatat tctataagta ggtagtccct tagaggaagc agtaagttgg tgctttcacc   1980
actaagacga aatgaagaat agtgatggcg aaggcacacg tactctacct cccttttccca   2040
aggtgctctg caagagaacc tatgtgcctc agacaactcc catctgccat cttggtgctc   2100
ctctctaagg tcccagtgca gtggtcacca agaaaagcac cccgagacat agcaggcagg   2160
aagcttctct tggatagtaa gggccgcagt ctctgaatcc tatcagaaaa ggctgtctct   2220
tccactatgc tctttgatat ttagaataca gagcttaaat cctgcataaa gtagcagctc   2280
catggcccta gagtaaaaaa actggccagt ctgatgctct catttcattg ttttaacaaa   2340
acttctggga ggaaggcctc aaaggttctt ctgagtgttt tgaggtgcta gctggatgga   2400
agggggaaaat atgtgataat aaaatctatc tcccttaatt atggtctcag gtggcagtag   2460
ccaccatctc tgaacaacaa caaaaacaac caaccaggaa acatcaacaa aaccagactc   2520
tatgagatat tcacgactga tttgttatag tggcggctgt ctaagaagtc tgaatctatc   2580
tgacaggagt atctgttacg tggccctcat acactgtaac atttctagaa ttcatggccc   2640
agctatagca gaataattta tttcagagtt aacctgaaac cacctgttgg aacgtcccac   2700
taatgctatc caggtgaagg gcttccctac ccctctgctc caccgctagt aaagccaaaa   2760
tacaccccct ctggatctcc ccatatccac ctcccaaa tgcagacact gatgggtaat     2820
taacaccact gagaatccca gggtagaaat aaaggctcag tctctaaaca ctcaactcag   2880
atggagccac tgggtctaaa tgctcaccct gtggtttgtt ctcttgtaga tgccatctac   2940
```

```
gactgctctt ccctctacca gaagaactac cgcatctctg gagtgtataa gcttcctcct     3000
gatgacttcc tgggcagccc tgaactggag gtgaggtcat tacagtcact ggccatgccc     3060
taatacctgt ccttcacccc ctcaaggggga ctacaacaac agggccattc acagtttaaa    3120
gaaaggaaaa ttcggctggg cgcagtggct cacacctgta atcccagcac tatgggaggc     3180
cgaggcaggt ggatcacttc aggtcaggag tttaagacca gcctggccaa catggtgaaa     3240
ccctgtctct actaaaaata caaaaaaatt agccaggcat ggtggtgggc acctgtaatc     3300
cctgctacac aggaggattg cttgaactca ggaggcagag gttgcagtga gccgagatca     3360
cgccactgca ctataatctg ggagacaaag tgagactcca tttcaattaa aaaaaaaaa     3420 aaaaaaagg aaaactcaaa cacaagcaaa cacaccaaac accacagagc tatgcaaaca      3480
ctcagtttat gccctgcact ccaaacccag gcatctgttt ggcccccttca aatcattatc    3540 agtcaaacaa caagccttct aacatagatc agatcattct tataaccacc acataactta    3600
gtttaaatct cttgccatgt cctagaacag ctattccttg ggggaggaga aaagaaaaca    3660
cgaaggcagc atcaaattat ctggattttc acccaggcat ggtggctcac acctgtaatc    3720
ccaagttttt tgggaggtga ggtgggcgga acaatcacct gaggtcagga ctttgagacc    3780
agcctggcca acatgctgaa acccagtctc tactaaaaat acaaaaatta gcccagtgtg    3840
gtgacaggca ctctggtccc agctactagg aaggcaggag aatcactgga actcaggagg    3900
tggaggttgc agtgagccga gattgcacca ctgtactcta gcctgggcaa caagagtgaa    3960
attctgcttc aaaaaaaaaa aaagtatctg gattttccc tccaagcttc atgtgcactc      4020 accccgggc ccaatttgca tcgttcttcc agagcaatgc accacccacc ccagctcacc      4080
agcagtgggg cagcatcact gcccgagtga gccagtgtga ctgcgggagt gcacacatct     4140
actggctctg cagggacagg aacaggttgg gaagcctgcc ctcttgctcc tgccttctgc     4200
ccctgcaagt ccctcaccag agtatcccct ctgcttcagg tgttctgtga catggagact    4260
tcaggcggag gctggaccat catccagaga cgaaaaagtg gccttgtctc cttctaccgg    4320
gactggaagc agtacaagca gggctttggc agcatccgtg gggacttctg gctggggaac    4380
gaacacatcc accggctctc cagacagcca acccggctgc gtgtagagat ggaggtaagc    4440
acaaggccag gggccccatg actggaccag tgccaccaca catgaccgcg tacaactccg    4500
ggggtgccat tcctattctg attcaagaca aatctgtata ttcattgtga tggttttcct    4560
gcaagttgta atggagttga ggaaaaatag gtattttttc tttctgcaac ccccccaacc    4620 cccgacaaa agtggggctg caggtgggac aggaagaggc cagacccagg ccagagtaga     4680
gcaaattcaa cagtcagctg tgccgaacac tagtctctgc tctggccgag catgaggtcc    4740
tttaggtgca aatcttactg atactgtttg ggacccttg ctgaaggtct gaaagcactc     4800
actatatcct catgtttctc ttacagcagc tctgtgtggg attcagcaaa aacatagctg    4860
caccttataa gcaggaaagt gaggaatata gaaagagaga ctaatcaagg ccatatggtg    4920
aatcaggaaa gaagttcgag ccttgttttc tgattcccag gttaacacag taaactggag    4980
gtaaacaagt aataaagtct tattagattc acacctataa aaagatgttt ggctatggga    5040
ctgtcaggag agaaggggta tagagacagc atgaaatgga gcctgctgca ctttcttaa    5100 ggctctgctc ctcctgacag gactgggagg gcaacctgcg ctacgctgag tatagccact    5160
ttgttttggg caatgaactc aacagctatc gcctcttcct ggggaactac actggcaatg   5220
tggggaacga cgccctccag tatcataaca acacagcctt cagcaccaag gacaaggaca    5280
```

```
atgacaactg cttggacaag tgtgcacagc tccgcaaagg tgagatttgg ggggaccgga    5340
aaggagaagt tcaggtacaa gctcataatc ccacttgagg agaaagagtg aattataact    5400
gtacagttga tattccggtt tggtattct ttctgaccct ggctctaact ccttacctga     5460
tgtctggtct atcacagtca acttactagc actgggtctg tttctcatgc caggtggcta    5520
ctggtacaac tgctgcacag actccaacct caatggagtg tactaccgcc tgggtgagca    5580
caataagcac ctggatggca tcacctggta tggctggcat ggatctacct actccctcaa    5640
acgggtggag atgaaaatcc gcccagaaga cttcaagcct aaaaggagg  ctgccgtgga    5700 gcacggatac agaaactgag acacgtggag actggatgag gcagatgag  acaggaaga    5760 gagtgttaga aagggtagga ctgagaaaca gcctataatc tccaaagaaa gaataagtct    5820
ccaaggagca caaaaaaatc atatgtacca aggatgttac agtaaacagg atgaactatt    5880
taaacccact gggtcctgcc acatccttct caaggtggta gactgagtgg ggtctctctg    5940
cccaagatcc ctgacatagc agtagcttgt cttttccaca tgatttgtct gtgaaagaaa    6000
ataattttga gatcgtttta tctattttct ctacggctta ggctatgtga gggcaaaaca    6060
caaatccctt tgctaaaaag aaccatatta ttttgattct caaaggatag gcctttgagt    6120
gttagagaaa ggagtgaagg aggcaggtgg gaaatgtat  ttctattttt aaatccagtg    6180
aaattatctt gagtctacac attattttta aaacacaaaa attgttcggc tggaactgac    6240
ccaggctgga cttgcgggga ggaaactcca gggcactgca tctggcgatc agactctgag    6300
cactgcccct gctcgccttg gtcatgtaca gcactgaaag gaatgaagca ccagcaggag    6360
gtggacagag tctctcatgg atgccggcac aaaactgcct taaatattc atagttaata    6420 caggtatatc tatttttatt tactttgtaa gaaacaagct caaggagctt cctttaaat     6480 tttgtctgta ggaaatggtt gaaaactgaa ggtagatggt gttatagtta ataataaatg    6540
ctgtaaataa gcatctcact ttgtaaaaat aaaatattgt ggttttgttt taaacattca    6600
acgtttcttt tccttctaca ataaacactt tcaaaatgtg a                        6641
```

<210> SEQ ID NO 2
<211> LENGTH: 6641
<212> TYPE: DNA
<213> ORGANISM: homo sapien

<400> SEQUENCE: 2

```
cttgtggagc attcgggctt ggaaggaaag ctataggcta cccattcagc tcccctgtca     60
gagactcaag ctttgagaaa ggctagcaaa gagcaaggaa agagagaaaa caacaaagtg    120
gcgaggccct cagagtgaaa gcgtaaggtt cagtcagcct gctgcagctt tgcagacctc    180
agctgggcat ctccagactc ccctgaagga agagccttcc tcacccaaac ccacaaaaga    240
tgctgaaaaa gcctctctca gctgtgacct ggctctgcat tttcatcgtg gcctttgtca    300
gccacccagc gtggctgcag aagctctcta agcacaagac accagcacag ccacagctca    360
aagcggccaa ctgctgtgag gaggtgaagg agctcaaggc ccaagttgcc aaccttagca    420
gcctgctgag tgaactgaac aagaagcagg agagggactg ggtcagcgtg gtcatgcagg    480
tgatggagct ggagagcaac agcaagcgca tggagtcgcg gctcacagat gctgagagca    540
agtactccga gatgaacaac caaattgaca tcatgcagct gcaggcagca cagacggtca    600
ctcagacctc cgcaggtaag gagaccagtc cctgaggga gcgtggagtg cctccccatc    660
tacagcactg cttctacata tcctggtcat cagaaccact actggggcct cttttgtggg    720
tacactttcc ctttagtaaa ggcttatgca gtatttcctt tgacttctaa tgctatgtaa    780
```

```
gtttacctaa caccttcacg ggtctctttt atccacacag tgtttcagcc taccatcttg    840
gagtgctgag atactacatg gtttgcccaa agtcacccca caagtcttag aagcagggtt    900
caagtcttcc tgattggtgt agctctgcta cttcctcacc aagagctgac aggctatatc    960
tcaagaaatt ccaaggaagc accaaactgt aacagctgtt cctctggaag caaagttttg   1020
ccagaaacag ttctctggtg ttcctaagat ttaccaggaa tgagcattaa tggaattttg   1080
tgtcctctct ctgtaaacgt aactcttctc attggctcag agttaagtgt agagacacat   1140
aaccatgtga agagtccctt tgtgttcagg aaggatgcgg ctccttaagg ttcctcaatt   1200
gtgatacgtc tattttttc catggtctta aatgaatttc tccgaataca ggatttttta   1260
aatgcaatgc tgaaatatag acttaatagg ccaaaaataa gataaattta atctttcttt   1320
tgcaaaataa cttttatttc tggttagctc agctcaggtg ggccaacatg aatttacggt   1380
ttagagataa aaatttggtt ttctgaaatt atcaggaaaa tattagttgt aaggagcata   1440
tcctatagac atgtcatttc ttgctgatat aaaaaccatt ggtcccatta taaactacat   1500
gaagaacaaa gacatgatca gcttctactg actaagtcaa tggttaacct cagctcaaat   1560
taagaaaaag ttttaacatg aaaccaagct tgaaaattct gttacctgaa ccaacatgta   1620
tcaatcactt tctaagcatg gacttccggg ccctcagttt gggattagaa aggtattctc   1680
aggccatttt ccagacaagt gagtcctgat ttggtctgtg agatgaaacc agacatgcgg   1740
aagaccaggc cagacagagg aatctgaccg tgccacttcc tgctcatcca acaggaggc    1800 tttctcacca tcctgcaagg aggttcttgg ggtcaagtgc agctctccca ccaggtctct   1860
tgctcttctt gcccaggaca tcattcctta tttttcttct ctatgaccaa gtgctcagtt   1920
acccttatat tctataagta ggtagtccct tagaggaagc agtaagttgg tgctttcacc   1980
actaagacga aatgaagaat agtgatggcg aaggcacacg tactctacct ccctttccca   2040
aggtgctctg caagagaacc tatgtgcctc agacaactcc catctgccat cttggtgctc   2100
ctctctaagg tcccagtgca gtggtcacca agaaaagcac cccgagacat agcaggcagg   2160
aagcttctct tggatagtaa gggccgcagt ctctgaatcc tatcagaaaa ggctgtctct   2220
tccactatgc tctttgatat ttagaataca gagcttaaat cctgcataaa gtagcagctc   2280
catggcccta gagtaaaaaa actggccagt ctgatgctct catttcattg ttttaacaaa   2340
acttctggga ggaaggcctc aaaggttctt ctgagtgttt tgaggtgcta gctggatgga   2400 agggaaaat atgtgataat aaaatctatc tcccttaatt atggtctcag gtggcagtag    2460
ccaccatctc tgaacaacaa caaaaacaac caaccaggaa acatcaacaa aaccagactc   2520
tatgagatat tcacgactga tttgttatag tggcggctgt ctaagaagtc tgaatctatc   2580
tgacaggagt atctgttacg tggccctcat acactgtaac atttctagaa ttcatggccc   2640
agctatagca gaataattta tttcagagtt aacctgaaac cacctgttgg aacgtcccac   2700
taatgctatc caggtgaagg gcttccctac ccctctgctc caccgctagt aaagccaaaa   2760
tacaccccct ctggatctcc ccatatccac ctctcccaaa tgcagacact gatgggtaat   2820
taacaccact gagaatccca gggtagaaat aaaggctcag tctctaaaca ctcaactcag   2880
atggagccac tgggtctaaa tgctcaccct gtggtttgtt ctcttgtaga tgccatctac   2940
gactgctctt ccctctacca gaagaactac cgcatctctg gagtgtataa gcttcctcct   3000
gatgacttcc tgggcagccc tgaactggag gtgaggtcat tacagtcact ggccatgccc   3060
taatacctgt ccttcacccc ctcaaggga ctacaacaac agggccattc acagtttaaa    3120
```

-continued

```
gaaaggaaaa ttcggctggg cgcagtggct cacacctgta atcccagcac tatgggaggc   3180
cgaggcaggt ggatcacttc aggtcaggag tttaagacca gcctggccaa catggtgaaa   3240
ccctgtctct actaaaaata caaaaaatt agccaggcat ggtggtgggc acctgtaatc    3300
cctgctacac aggaggattg cttgaactca ggaggcagag gttgcagtga gccgagatca   3360
cgccactgca ctataatctg ggagacaaag tgagactcca tttcaattaa aaaaaaaaa    3420 aaaaaaagg aaaactcaaa cacaagcaaa cacaccaaac accacagagc tatgcaaaca    3480
ctcagtttat gccctgcact ccaaacccag gcatctgttt ggccccttca aatcattatc   3540
agtcaaacaa caagccttct aacatagatc agatcattct tataaccacc acataactta   3600
gtttaaatct cttgccatgt cctagaacag ctattccttg ggggaggaga aaagaaaaca   3660
cgaaggcagc atcaaattat ctggattttc acccaggcat ggtggctcac acctgtaatc   3720
ccaagttttt tgggaggtga ggtgggcgga acaatcacct gaggtcagga ctttgagacc   3780
agcctggcca acatgctgaa acccagtctc tactaaaaat acaaaaatta gcccagtgtg   3840
gtgacaggca ctctggtccc agctactagg aaggcaggag aatcactgga actcaggagg   3900
tggaggttgc agtgagccga gattgcacca ctgtactcta gcctgggcaa caagagtgaa   3960
attctgcttc aaaaaaaaa aaagtatctg gattttccc tccaagcttc atgtgcactc     4020 accccgggc caatttgca tcgttcttcc agagcaatgc accacccacc ccagctcacc     4080
agcagtgggg cagcatcact gcccgagtga gccagtgtga ctgcgggagt gcacacatct   4140
actggctctg cagggacagg aacaggttgg gaagcctgcc ctcttgctcc tgccttctgc   4200
ccctgcaagt ccctcaccag agtatcccct ctgcttcagg tgttctgtga catggagact   4260
tcaggcggag gctggaccat catccagaga tgaaaaagtg gccttgtctc cttctaccgg   4320
gactggaagc agtacaagca gggctttggc agcatccgtg gggacttctg gctggggaac   4380
gaacacatcc accggctctc cagacagcca acccggctgc gtgtagagat ggaggtaagc   4440
acaaggccag gggcccatg actggaccag tgccaccaca catgaccgcg tacaactccg    4500
ggggtgccat tcctattctg attcaagaca aatctgtata ttcattgtga tggttttcct   4560
gcaagttgta atggagttga ggaaaaatag gtattttcc tttctgcaac cccccaacc     4620 ccccgacaaa agtggggctg caggtgggac aggaagaggc cagacccagg ccagagtaga   4680
gcaaattcaa cagtcagctg tgccgaacac tagtctctgc tctggccgag catgaggtcc   4740
tttaggtgca aatcttactg atactgtttg gggacccttg ctgaaggtct gaaagcactc   4800
actatatcct catgtttctc ttacagcagc tctgtgtggg attcagcaaa acatagctg    4860 caccttataa gcaggaaagt gaggaatata gaaagagaga ctaatcaagg ccatatggtg   4920
aatcaggaaa gaagttcgag ccttgttttc tgattcccag gttaacacag taaactggag   4980
gtaaacaagt aataaagtct tattagattc acacctataa aaagatgttt ggctatggga   5040
ctgtcaggag agaaggggta tagagacagc atgaaatgga gcctgctgca ctttctttaa   5100
ggctctgctc ctcctgacag gactgggagg gcaacctgcg ctacgctgag tatagccact   5160
ttgttttggg caatgaactc aacagctatc gcctcttcct ggggaactac actggcaatg   5220
tggggaacga cgccctccag tatcataaca acacagcctt cagcaccaag gacaaggaca   5280
atgacaactg cttggacaag tgtgcacagc tccgcaaagg tgagatttgg ggggaccgga   5340
aaggagaagt tcaggtacaa gctcataatc ccacttgagg agaaagagtg aattataact   5400
gtacagttga tattccggtt ttggtattct ttctgaccct ggctctaact ccttacctga   5460
tgtctggtct atcacagtca acttactagc actgggtctg tttctcatgc caggtggcta   5520
```

```
ctggtacaac tgctgcacag actccaacct caatggagtg tactaccgcc tgggtgagca      5580
caataagcac ctggatggca tcacctggta tggctggcat ggatctacct actccctcaa      5640
acgggtggag atgaaaatcc gcccagaaga cttcaagcct aaaaggagg  ctgccgtgga      5700 gcacggatac agaaactgag acacgtggag actggatgag ggcagatgag gacaggaaga      5760
gagtgttaga aagggtagga ctgagaaaca gcctataatc tccaaagaaa gaataagtct      5820
ccaaggagca caaaaaatc  atatgtacca aggatgttac agtaaacagg atgaactatt      5880
taaacccact gggtcctgcc acatccttct caaggtggta gactgagtgg ggtctctctg      5940
cccaagatcc ctgacatagc agtagcttgt cttttccaca tgatttgtct gtgaaagaaa      6000
ataattttga gatcgtttta tctattttct ctacggctta ggctatgtga gggcaaaaca      6060
caaatccctt tgctaaaaag aaccatatta ttttgattct caaggatag  gcctttgagt      6120 gttagagaaa ggagtgaagg aggcaggtgg gaaatggtat ttctattttt aaatccagtg      6180
aaattatctt gagtctacac attattttta aaacacaaaa attgttcggc tggaactgac      6240
ccaggctgga cttgcgggga ggaaactcca gggcactgca tctggcgatc agactctgag      6300
cactgcccct gctcgccttg gtcatgtaca gcactgaaag gaatgaagca ccagcaggag      6360
gtggacagag tctctcatgg atgccggcac aaaactgcct taaaatattc atagttaata      6420
caggtatatc tattttat   tactttgtaa gaaacaagct caaggagctt ccttttaaat      6480
tttgtctgta ggaaatggtt gaaaactgaa ggtagatggt gttatagtta ataataaatg      6540
ctgtaaataa gcatctcact ttgtaaaaat aaaatattgt ggttttgttt taaacattca      6600
acgtttcttt tccttctaca ataaacactt tcaaaatgtg a                          6641

<210> SEQ ID NO 3
<211> LENGTH: 6641
<212> TYPE: DNA
<213> ORGANISM: homo sapien

<400> SEQUENCE: 3
cttgtggagc attcgggctt ggaaggaaag ctataggcta cccattcagc tcccctgtca        60
gagactcaag ctttgagaaa ggctagcaaa gagcaaggaa agagagaaaa caacaaagtg       120
gcgaggccct cagagtgaaa gcgtaaggtt cagtcagcct gctgcagctt gcagacctc        180 agctgggcat ctccagactc ccctgaagga agagccttcc tcacccaaac ccacaaaaga       240
tgctgaaaaa gcctctctca gctgtgacct ggctctgcat tttcatcgtg gcctttgtca       300
gccacccagc gtggctgcag aagctctcta agcacaagac accagcacag ccacagctca       360
aagcggccaa ctgctgtgag gaggtgaagg agctcaaggc ccaagttgcc aaccttagca       420
gcctgctgag tgaactgaac aagaagcagg agagggactg ggtcagcgtg gtcatgcagg       480
tgatggagct ggagagcaac agcaagcgca tggagtcgcg gctcacagat gctgagagca       540
agtactccga tgaacaac   caaattgaca tcatgcagct gcaggcagca cagacggtca       600
ctcagacctc cgcaggtaag gagaccagtc ccctgaggga gcgtggagtg cctccccatc       660
tacagcactg cttctacata tcctggtcat cagaaccact actggggcct cttttgtggg       720
tacactttcc ctttagtaaa ggcttatgca gtatttcctt tgacttctaa tgctatgtaa       780
gtttacctaa caccttcacg ggtctctttt atccacacag tgtttcagcc taccatcttg       840
gagtgctgag atactacatg gtttgcccaa agtcacccag caagtcttag aagcagggtt       900
caagtcttcc tgattggtgt agctctgcta cttcctcacc aagagctgac aggctatatc       960
```

```
tcaagaaatt ccaaggaagc accaaactgt aacagctgtt cctctggaag caaagttttg    1020
ccagaaacag ttctctggtg ttcctaagat ttaccaggaa tgagcattaa tggaattttg    1080
tgtcctctct ctgtaaacgt aactcttctc attggctcag agttaagtgt agagacacat    1140
aaccatgtga agagtccctt tgtgttcagg aaggatgcgg ctccttaagg ttcctcaatt    1200
gtgatacgtc tattttttc catggtctta aatgaatttc tccgaataca ggattttta    1260 aatgcaatgc tgaaatatag acttaatagg ccaaaaataa gataaattta atctttcttt    1320
tgcaaaataa cttttatttc tggttagctc agctcaggtg ggccaacatg aatttacggt    1380
ttagagataa aaatttggtt ttctgaaatt atcaggaaaa tattagttgt aaggagcata    1440
tcctatagac atgtcatttc ttgctgatat aaaaaccatt ggtcccatta taaactacat    1500
gaagaacaaa gacatgatca gcttctactg actaagtcaa tggttaacct cagctcaaat    1560
taagaaaaag ttttaacatg aaaccaagct tgaaaattct gttacctgaa ccaacatgta    1620
tcaatcactt tctaagcatg gacttccggg ccctcagttt gggattagaa aggtattctc    1680
aggccatttt ccagacaagt gagtcctgat ttggtctgtg agatgaaacc agacatgcgg    1740
aagaccaggc cagacagagg aatctgaccg tgccacttcc tgctcatcca acaggaggc    1800 tttctcacca tcctgcaagg aggttcttgg ggtcaagtgc agctctccca ccaggtctct    1860
tgctcttctt gcccaggaca tcattcctta tttttcttct ctatgaccaa gtgctcagtt    1920
acccttatat tctataagta ggtagtccct tagaggaagc agtaagttgg tgctttcacc    1980
actaagacga aatgaagaat agtgatggcg aaggcacacg tactctacct cccttttccca   2040 aggtgctctg caagagaacc tatgtgcctc agacaactcc catctgccat cttggtgctc    2100
ctctctaagg tcccagtgca gtggtcacca agaaaagcac cccgagacat agcaggcagg    2160
aagcttctct tggatagtaa gggccgcagt ctctgaatcc tatcagaaaa ggctgtctct    2220
tccactatgc tctttgatat ttagaataca gagcttaaat cctgcataaa gtagcagctc    2280
catgccccta gagtaaaaaa actggccagt ctgatgctct catttcattg ttttaacaaa    2340
acttctggga ggaaggcctc aaaggttctt ctgagtgttt tgaggtgcta gctggatgga    2400 agggaaaat atgtgataat aaaatctatc tcccttaatt atggtctcag gtggcagtag    2460
ccaccatctc tgaacaacaa caaaaacaac caaccaggaa acatcaacaa aaccagactc    2520
tatgagatat tcacgactga tttgttatag tggcggctgt ctaagaagtc tgaatctatc    2580
tgacaggagt atctgttacg tggccctcat acactgtaac atttctagaa ttcatggccc    2640
agctatagca gaataattta tttcagagtt aacctgaaac cacctgttgg aacgtcccac    2700
taatgctatc caggtgaagg gcttccctac ccctctgctc caccgctagt aaagccaaaa    2760
tacaccccct ctggatctcc ccatatccac ctctcccaaa tgcagacact gatgggtaat    2820
taacaccact gagaatccca gggtagaaat aaaggctcag tctctaaaca ctcaactcag    2880
atggagccac tgggtctaaa tgctcaccct gtggtttgtt ctcttgtaga tgccatctac    2940
gactgctctt ccctctacca gaagaactac cgcatctctg gagtgtataa gcttcctcct    3000
gatgacttcc tgggcagccc tgaactggag gtgaggtcat acagtcact ggccatgccc    3060 taatacctgt ccttcacccc ctcaagggga ctacaacaac agggccattc acagtttaaa    3120
gaaaggaaaa ttcggctggg cgcagtggct cacacctgta atcccagcac tatgggaggc    3180
cgaggcaggt ggatcacttc aggtcaggag tttaagacca gcctggccaa catggtgaaa    3240
ccctgtctct actaaaaata caaaaaatt agccaggcat ggtggtgggc acctgtaatc    3300
cctgctacac aggaggattg cttgaactca ggaggcagag gttgcagtga gccgagatca    3360
```

```
cgccactgca ctataatctg ggagacaaag tgagactcca tttcaattaa aaaaaaaaaa    3420
aaaaaaaagg aaaactcaaa cacaagcaaa cacaccaaac accacagagc tatgcaaaca    3480
ctcagtttat gccctgcact ccaaacccag gcatctgttt ggccccttca aatcattatc    3540
agtcaaacaa caagccttct aacatagatc agatcattct tataaccacc acataactta    3600
gtttaaatct cttgccatgt cctagaacag ctattccttg ggggaggaga aaagaaaaca    3660
cgaaggcagc atcaaattat ctggatttc acccaggcat ggtggctcac acctgtaatc    3720
ccaagttttt tgggaggtga ggtgggcgga acaatcacct gaggtcagga ctttgagacc    3780
agcctggcca acatgctgaa acccagtctc tactaaaaat acaaaaatta gcccagtgtg    3840
gtgacaggca ctctggtccc agctactagg aaggcaggag aatcactgga actcaggagg    3900
tggaggttgc agtgagccga gattgcacca ctgtactcta gcctgggcaa caagagtgaa    3960
attctgcttc aaaaaaaaaa aaagtatctg gattttccc tccaagcttc atgtgcactc    4020
accccccggc ccaatttgca tcgttcttcc agagcaatgc accacccacc ccagctcacc    4080
agcagtgggg cagcatcact gcccgagtga gccagtgtga ctgcgggagt gcacacatct    4140
actggctctg cagggacagg aacaggttgg gaagcctgcc ctcttgctcc tgccttctgc    4200
ccctgcaagt ccctcaccag agtatcccct ctgcttcagg tgttctgtga catggagact    4260
tcaggcggag gctggaccat catccataga cgaaaaagtg gccttgtctc cttctaccgg    4320
gactggaagc agtacaagca gggctttggc agcatccgtg gggacttctg gctggggaac    4380
gaacacatcc accggctctc cagacagcca acccggctgc gtgtagagat ggaggtaagc    4440
acaaggccag gggcccatg actggaccag tgccaccaca catgaccgcg tacaactccg    4500
ggggtgccat tcctattctg attcaagaca aatctgtata ttcattgtga tggttttcct    4560
gcaagttgta atggagttga ggaaaaatag gtatttttcc tttctgcaac cccccaacc    4620 ccccgacaaa agtggggctg caggtgggac aggaagaggc cagacccagg ccagagtaga    4680
gcaaattcaa cagtcagctg tgccgaacac tagtctctgc tctggccgag catgaggtcc    4740
tttaggtgca aatcttactg atactgtttg gggaccttg ctgaaggtct gaaagcactc    4800
actatatcct catgtttctc ttacagcagc tctgtgtggg attcagcaaa acatagctg    4860 caccttataa gcaggaaagt gaggaatata gaaagagaga ctaatcaagg ccatatggtg    4920
aatcaggaaa gaagttcgag ccttgttttc tgattcccag gttaacacag taaactggag    4980
gtaaacaagt aataaagtct tattagattc acacctataa aaagatgttt ggctatggga    5040
ctgtcaggag agaaggggta tagagacagc atgaaatgga gcctgctgca ctttctttaa    5100
ggctctgctc ctcctgacag gactgggagg gcaacctgcg ctacgctgag tatagccact    5160 ttgtttggg caatgaactc aacagctatc gcctcttcct ggggaactac actggcaatg    5220
tggggaacga cgccctccag tatcataaca acacagcctt cagcaccaag gacaaggaca    5280
atgacaactg cttggacaag tgtgcacagc tccgcaaagg tgagatttgg ggggaccgga    5340
aaggagaagt tcaggtacaa gctcataatc ccacttgagg agaaagagtg aattataact    5400
gtacagttga tattccggtt ttggtattct ttctgaccct ggctctaact ccttacctga    5460
tgtctggtct atcacagtca acttactagc actgggtctg tttctcatgc caggtggcta    5520
ctggtacaac tgctgcacag actccaacct caatggagtg tactaccgcc tgggtgagca    5580
caataagcac ctgatggca tcacctggta tggctggcat ggatctacct actccctcaa    5640
acgggtggag atgaaaatcc gcccagaaga cttcaagcct taaaaggagg ctgccgtgga    5700
```

```
gcacggatac agaaactgag acacgtggag actggatgag ggcagatgag gacaggaaga    5760
gagtgttaga aagggtagga ctgagaaaca gcctataatc tccaaagaaa gaataagtct    5820
ccaaggagca caaaaaaatc atatgtacca aggatgttac agtaaacagg atgaactatt    5880
taaacccact gggtcctgcc acatccttct caaggtggta gactgagtgg ggtctctctg    5940
cccaagatcc ctgacatagc agtagcttgt cttttccaca tgatttgtct gtgaaagaaa    6000
ataattttga gatcgtttta tctattttct ctacggctta ggctatgtga gggcaaaaca    6060
caaatccctt tgctaaaaag aaccatatta ttttgattct caaaggatag gcctttgagt    6120
gttagagaaa ggagtgaagg aggcaggtgg gaaatggtat ttctattttt aaatccagtg    6180
aaattatctt gagtctacac attatttta aaacacaaaa attgttcggc tggaactgac    6240
ccaggctgga cttgcgggga ggaaactcca gggcactgca tctggcgatc agactctgag    6300
cactgcccct gctcgccttg gtcatgtaca gcactgaaag gaatgaagca ccagcaggag    6360
gtggacagag tctctcatgg atgccggcac aaaactgcct taaaatattc atagttaata    6420
caggtatatc tatttttatt tactttgtaa gaaacaagct caaggagctt ccttttaaat    6480
tttgtctgta ggaaatggtt gaaaactgaa ggtagatggt gttatagtta ataataaatg    6540
ctgtaaataa gcatctcact ttgtaaaaat aaaatattgt ggttttgttt taaacattca    6600
acgtttcttt tccttctaca ataaacactt tcaaaatgtg a                        6641

<210> SEQ ID NO 4
<211> LENGTH: 1041
<212> TYPE: DNA
<213> ORGANISM: homo sapien

<400> SEQUENCE: 4
augcugaaaa agcccucucuc agcugugacc uggcucugca uuuucaucgu ggccuuuguc      60
agccacccag cguggcugca gaagcucucu aagcacaaga caccagcaca gccacagcuc     120
aaagcggcca acugcuguga ggaggugaag gagcucaagg cccaaguugc caaccuuagc     180
agccugcuga gugaacugaa caagaagcag agagggacu gggucagcgu ggucaugcag     240
gugauggagc uggagagcaa cagcaagcgc auggagucgc ggcucacaga ugcugagagc     300
aaguacuccg agaugaacaa ccaaauugac aucaugcagc ugcaggcagc acagacgguc     360
acucagaccu ccgcagaugc caucuacgac ugcucuuccc ucuaccagaa gaacuaccgc     420
aucucuggag uguauaagcu uccuccugau gacuuccugg gcagcccuga acuggaggug     480
uucugugaca uggagacuuc aggcggaggc uggaccauca uccagagacg aaaaagugc     540 cuugucuccu ucuaccggga cuggaagcag uacaagcagg gcuuuggcag caauccguggg     600 gacuucuggc uggggaacga acacauccac cggcucucca gacaagccaac ccggcugcgu     660 guagagaugg aggacuggga gggcaaccug cgcuacgcug aguauagcca cuuuguuuug     720
ggcaaugaac ucaacagcua ucgccucuuc cuggggaacu acacuggcaa ugugggggaac     780 gacgcccucc aguaucauaa caacacagcc uucagccacca aggacaagga caaugacaac     840
ugcuuggaca gugugcaca gcuccgcaaa ggugcuacu gguacaacug cugcacagac     900
uccaaccuca auggagugua cuaccgccug gugagcaca auaagcaccu ggauggcauc     960
accugguaug gcuggcaugg aucuaccuac ucccucaaac ggguggagau gaaaauccgc    1020
ccagaagacu ucaagccuua a                                              1041

<210> SEQ ID NO 5
<211> LENGTH: 531
```

```
<212> TYPE: DNA
<213> ORGANISM: homo sapien

<400> SEQUENCE: 5
augcugaaaa agccucucuc agcugugacc uggcucugca uuucaucgu ggccuuuguc      60 agccacccag cguggcugca gaagcucucu aagcacaaga caccagcaca gccacagcuc    120
aaagcggcca acugcuguga ggaggugaag gagcucaagg cccaaguugc caaccuuagc    180
agccugcuga gugaacugaa caagaagcag gagagggacu ggucagcgu ggucaugcag     240 gugauggagc uggagagcaa cagcaagcgc auggagucgc ggcucacaga ugcugagagc    300
aaguacuccg augaacaa ccaaauugac aucaugcagc ugcaggcagc acagacgguc      360
acucagaccu ccgcagaugc caucuacgac ugcucuuccc ucuaccagaa gaacuaccgc    420
aucucuggag uguauaagcu uccuccugau gacuuccugg gcagcccuga acuggaggug    480
uucugugaca uggagacuuc aggcggaggc uggaccauca uccagagaug a             531

<210> SEQ ID NO 6
<211> LENGTH: 1041
<212> TYPE: DNA
<213> ORGANISM: homo sapien

<400> SEQUENCE: 6
augcugaaaa agccucucuc agcugugacc uggcucugca uuucaucgu ggccuuuguc      60 agccacccag cguggcugca gaagcucucu aagcacaaga caccagcaca gccacagcuc    120
aaagcggcca acugcuguga ggaggugaag gagcucaagg cccaaguugc caaccuuagc    180
agccugcuga gugaacugaa caagaagcag gagagggacu ggucagcgu ggucaugcag     240 gugauggagc uggagagcaa cagcaagcgc auggagucgc ggcucacaga ugcugagagc    300
aaguacuccg augaacaa ccaaauugac aucaugcagc ugcaggcagc acagacgguc      360
acucagaccu ccgcagaugc caucuacgac ugcucuuccc ucuaccagaa gaacuaccgc    420
aucucuggag uguauaagcu uccuccugau gacuuccugg gcagcccuga acuggaggug    480
uucugugaca uggagacuuc aggcggaggc uggaccauca uccauagacg aaaaaguggc    540
cuugucuccu ucuaccggga cuggaagcag uacaagcagg gcuuuggcag cauccguggg    600
gacuucuggc uggggaacga acacauccac cggcucucca gacagccaac ccggcugcgu    660
guagagaugg aggacuggga gggcaaccug cgcuacgcug aguauagcca cuuuguuug     720 ggcaaugaac ucaacagcua ucgccucuuc cuggggaacu acacuggcaa uguggggaac    780
gacgcccucc aguaucauaa caacacagcc uucagcacca aggacaagga caaugacaac    840
ugcuuggaca agugugcaca gcuccgcaaa gguggcuacu gguacaacug cugcacagac    900
uccaaccuca auggaguguc cuaccgccug ggugagcaca auaagcaccu ggauggcauc    960
accugguaug gcuggcaugg aucuaccuac ucccucaaac gguggagau gaaaauccgc     1020 ccagaagacu ucaagccuua a                                              1041

<210> SEQ ID NO 7
<211> LENGTH: 1041
<212> TYPE: DNA
<213> ORGANISM: homo sapien

<400> SEQUENCE: 7
atgctgaaaa agcctctctc agctgtgacc tggctctgca ttttcatcgt ggcctttgtc      60
agccacccag cgtggctgca gaagctctct aagcacaaga caccagcaca gccacagctc    120
```

| | |
|---|---|
| aaagcggcca actgctgtga ggaggtgaag gagctcaagg cccaagttgc caaccttagc | 180 |
| agcctgctga gtgaactgaa caagaagcag gagagggact gggtcagcgt ggtcatgcag | 240 |
| gtgatggagc tggagagcaa cagcaagcgc atggagtcgc ggctcacaga tgctgagagc | 300 |
| aagtactccg agatgaacaa ccaaattgac atcatgcagc tgcaggcagc acagacggtc | 360 |
| actcagacct ccgcagatgc catctacgac tgctcttccc tctaccagaa gaactaccgc | 420 |
| atctctggag tgtataagct tcctcctgat gacttcctgg gcagccctga actggaggtg | 480 |
| ttctgtgaca tggagacttc aggcggaggc tggaccatca tccagagacg aaaaagtggc | 540 |
| cttgtctcct tctaccggga ctggaagcag tacaagcagg gctttggcag catccgtggg | 600 |
| gacttctggc tggggaacga acacatccac cggctctcca gacagccaac ccggctgcgt | 660 |
| gtagagatgg aggactggga gggcaacctg cgctacgctg agtatagcca ctttgttttg | 720 |
| ggcaatgaac tcaacagcta tcgcctcttc ctggggaact acactggcaa tgtggggaac | 780 |
| gacgccctcc agtatcataa caacacagcc ttcagcacca aggacaagga caatgacaac | 840 |
| tgcttggaca gtgtgcaca gctccgcaaa ggtggctact ggtacaactg ctgcacagac | 900 |
| tccaacctca tggagtgta ctaccgcctg ggtgagcaca ataagcacct ggatggcatc | 960 |
| acctggtatg gctggcatgg atctacctac tccctcaaac gggtggagat gaaaatccgc | 1020 |
| ccagaagact tcaagcctta a | 1041 |

<210> SEQ ID NO 8
<211> LENGTH: 531
<212> TYPE: DNA
<213> ORGANISM: homo sapien

<400> SEQUENCE: 8

| | |
|---|---|
| atgctgaaaa agcctctctc agctgtgacc tggctctgca ttttcatcgt ggcctttgtc | 60 |
| agccacccag cgtggctgca gaagctctct aagcacaaga caccagcaca gccacagctc | 120 |
| aaagcggcca actgctgtga ggaggtgaag gagctcaagg cccaagttgc caaccttagc | 180 |
| agcctgctga gtgaactgaa caagaagcag gagagggact gggtcagcgt ggtcatgcag | 240 |
| gtgatggagc tggagagcaa cagcaagcgc atggagtcgc ggctcacaga tgctgagagc | 300 |
| aagtactccg agatgaacaa ccaaattgac atcatgcagc tgcaggcagc acagacggtc | 360 |
| actcagacct ccgcagatgc catctacgac tgctcttccc tctaccagaa gaactaccgc | 420 |
| atctctggag tgtataagct tcctcctgat gacttcctgg gcagccctga actggaggtg | 480 |
| ttctgtgaca tggagacttc aggcggaggc tggaccatca tccagagatg a | 531 |

<210> SEQ ID NO 9
<211> LENGTH: 1041
<212> TYPE: DNA
<213> ORGANISM: homo sapien

<400> SEQUENCE: 9

| | |
|---|---|
| atgctgaaaa agcctctctc agctgtgacc tggctctgca ttttcatcgt ggcctttgtc | 60 |
| agccacccag cgtggctgca gaagctctct aagcacaaga caccagcaca gccacagctc | 120 |
| aaagcggcca actgctgtga ggaggtgaag gagctcaagg cccaagttgc caaccttagc | 180 |
| agcctgctga gtgaactgaa caagaagcag gagagggact gggtcagcgt ggtcatgcag | 240 |
| gtgatggagc tggagagcaa cagcaagcgc atggagtcgc ggctcacaga tgctgagagc | 300 |
| aagtactccg agatgaacaa ccaaattgac atcatgcagc tgcaggcagc acagacggtc | 360 |
| actcagacct ccgcagatgc catctacgac tgctcttccc tctaccagaa gaactaccgc | 420 |

```
atctctggag tgtataagct tcctcctgat gacttcctgg gcagccctga actggaggtg      480
ttctgtgaca tggagacttc aggcggaggc tggaccatca tccatagacg aaaaagtggc      540
cttgtctcct tctaccggga ctggaagcag tacaagcagg gctttggcag catccgtggg      600
gacttctggc tggggaacga acacatccac cggctctcca gacagccaac ccggctgcgt      660
gtagagatgg aggactggga gggcaacctg cgctacgctg agtatagcca ctttgttttg      720
ggcaatgaac tcaacagcta tcgcctcttc ctggggaact acactggcaa tgtggggaac      780
gacgccctcc agtatcataa caacacagcc ttcagcacca aggacaagga caatgacaac      840
tgcttggaca gtgtgcaca gctccgcaaa ggtggctact ggtacaactg ctgcacagac       900
tccaacctca atggagtgta ctaccgcctg ggtgagcaca ataagcacct ggatggcatc      960
acctggtatg gctggcatgg atctacctac tccctcaaac gggtggagat gaaaatccgc     1020
ccagaagact tcaagcctta a                                               1041
```

<210> SEQ ID NO 10
<211> LENGTH: 346
<212> TYPE: PRT
<213> ORGANISM: homo sapien

<400> SEQUENCE: 10

```
Met Leu Lys Lys Pro Leu Ser Ala Val Thr Trp Leu Cys Ile Phe Ile
1               5                   10                  15

Val Ala Phe Val Ser His Pro Ala Trp Leu Gln Lys Leu Ser Lys His
            20                  25                  30

Lys Thr Pro Ala Gln Pro Gln Leu Lys Ala Ala Asn Cys Cys Glu Glu
        35                  40                  45

Val Lys Glu Leu Lys Ala Gln Val Ala Asn Leu Ser Ser Leu Leu Ser
    50                  55                  60

Glu Leu Asn Lys Lys Gln Glu Arg Asp Trp Val Ser Val Met Gln
65                  70                  75                  80

Val Met Glu Leu Glu Ser Asn Ser Lys Arg Met Glu Ser Arg Leu Thr
                85                  90                  95

Asp Ala Glu Ser Lys Tyr Ser Glu Met Asn Asn Gln Ile Asp Ile Met
            100                 105                 110

Gln Leu Gln Ala Ala Gln Thr Val Thr Gln Thr Ser Ala Asp Ala Ile
        115                 120                 125

Tyr Asp Cys Ser Ser Leu Tyr Gln Lys Asn Tyr Arg Ile Ser Gly Val
    130                 135                 140

Tyr Lys Leu Pro Pro Asp Asp Phe Leu Gly Ser Pro Glu Leu Glu Val
145                 150                 155                 160

Phe Cys Asp Met Glu Thr Ser Gly Gly Gly Trp Thr Ile Ile Gln Arg
                165                 170                 175

Arg Lys Ser Gly Leu Val Ser Phe Tyr Arg Asp Trp Lys Gln Tyr Lys
            180                 185                 190

Gln Gly Phe Gly Ser Ile Arg Gly Asp Phe Trp Leu Gly Asn Glu His
        195                 200                 205

Ile His Arg Leu Ser Arg Gln Pro Thr Arg Leu Arg Val Glu Met Glu
    210                 215                 220

Asp Trp Glu Gly Asn Leu Arg Tyr Ala Glu Tyr Ser His Phe Val Leu
225                 230                 235                 240

Gly Asn Glu Leu Asn Ser Tyr Arg Leu Phe Leu Gly Asn Tyr Thr Gly
                245                 250                 255
```

```
Asn Val Gly Asn Asp Ala Leu Gln Tyr His Asn Asn Thr Ala Phe Ser
            260                 265                 270

Thr Lys Asp Lys Asp Asn Asp Asn Cys Leu Asp Lys Cys Ala Gln Leu
        275                 280                 285

Arg Lys Gly Gly Tyr Trp Tyr Asn Cys Cys Thr Asp Ser Asn Leu Asn
        290                 295                 300

Gly Val Tyr Tyr Arg Leu Gly Glu His Asn Lys His Leu Asp Gly Ile
305                 310                 315                 320

Thr Trp Tyr Gly Trp His Gly Ser Thr Tyr Ser Leu Lys Arg Val Glu
                325                 330                 335

Met Lys Ile Arg Pro Glu Asp Phe Lys Pro
        340                 345
```

<210> SEQ ID NO 11
<211> LENGTH: 176
<212> TYPE: PRT
<213> ORGANISM: homo sapien

<400> SEQUENCE: 11

```
Met Leu Lys Lys Pro Leu Ser Ala Val Thr Trp Leu Cys Ile Phe Ile
1               5                   10                  15

Val Ala Phe Val Ser His Pro Ala Trp Leu Gln Lys Leu Ser Lys His
                20                  25                  30

Lys Thr Pro Ala Gln Pro Gln Leu Lys Ala Ala Asn Cys Cys Glu Glu
            35                  40                  45

Val Lys Glu Leu Lys Ala Gln Val Ala Asn Leu Ser Ser Leu Leu Ser
    50                  55                  60

Glu Leu Asn Lys Lys Gln Glu Arg Asp Trp Val Ser Val Val Met Gln
65                  70                  75                  80

Val Met Glu Leu Glu Ser Asn Ser Lys Arg Met Glu Ser Arg Leu Thr
                85                  90                  95

Asp Ala Glu Ser Lys Tyr Ser Glu Met Asn Asn Gln Ile Asp Ile Met
            100                 105                 110

Gln Leu Gln Ala Ala Gln Thr Val Thr Gln Thr Ser Ala Asp Ala Ile
        115                 120                 125

Tyr Asp Cys Ser Ser Leu Tyr Gln Lys Asn Tyr Arg Ile Ser Gly Val
130                 135                 140

Tyr Lys Leu Pro Pro Asp Asp Phe Leu Gly Ser Pro Glu Leu Glu Val
145                 150                 155                 160

Phe Cys Asp Met Glu Thr Ser Gly Gly Gly Trp Thr Ile Ile Gln Arg
                165                 170                 175
```

<210> SEQ ID NO 12
<211> LENGTH: 346
<212> TYPE: PRT
<213> ORGANISM: homo sapien

<400> SEQUENCE: 12

```
Met Leu Lys Lys Pro Leu Ser Ala Val Thr Trp Leu Cys Ile Phe Ile
1               5                   10                  15

Val Ala Phe Val Ser His Pro Ala Trp Leu Gln Lys Leu Ser Lys His
                20                  25                  30

Lys Thr Pro Ala Gln Pro Gln Leu Lys Ala Ala Asn Cys Cys Glu Glu
            35                  40                  45

Val Lys Glu Leu Lys Ala Gln Val Ala Asn Leu Ser Ser Leu Leu Ser
    50                  55                  60
```

-continued

```
Glu Leu Asn Lys Lys Gln Glu Arg Asp Trp Val Ser Val Val Met Gln
 65                  70                  75                  80

Val Met Glu Leu Glu Ser Asn Ser Lys Arg Met Glu Ser Arg Leu Thr
                 85                  90                  95

Asp Ala Glu Ser Lys Tyr Ser Glu Met Asn Asn Gln Ile Asp Ile Met
            100                 105                 110

Gln Leu Gln Ala Ala Gln Thr Val Thr Gln Thr Ser Ala Asp Ala Ile
        115                 120                 125

Tyr Asp Cys Ser Ser Leu Tyr Gln Lys Asn Tyr Arg Ile Ser Gly Val
    130                 135                 140

Tyr Lys Leu Pro Pro Asp Asp Phe Leu Gly Ser Pro Glu Leu Glu Val
145                 150                 155                 160

Phe Cys Asp Met Glu Thr Ser Gly Gly Gly Trp Thr Ile Ile His Arg
                165                 170                 175

Arg Lys Ser Gly Leu Val Ser Phe Tyr Arg Asp Trp Lys Gln Tyr Lys
            180                 185                 190

Gln Gly Phe Gly Ser Ile Arg Gly Asp Phe Trp Leu Gly Asn Glu His
        195                 200                 205

Ile His Arg Leu Ser Arg Gln Pro Thr Arg Leu Arg Val Glu Met Glu
    210                 215                 220

Asp Trp Glu Gly Asn Leu Arg Tyr Ala Glu Tyr Ser His Phe Val Leu
225                 230                 235                 240

Gly Asn Glu Leu Asn Ser Tyr Arg Leu Phe Leu Gly Asn Tyr Thr Gly
                245                 250                 255

Asn Val Gly Asn Asp Ala Leu Gln Tyr His Asn Asn Thr Ala Phe Ser
            260                 265                 270

Thr Lys Asp Lys Asp Asn Asp Asn Cys Leu Asp Lys Cys Ala Gln Leu
        275                 280                 285

Arg Lys Gly Gly Tyr Trp Tyr Asn Cys Cys Thr Asp Ser Asn Leu Asn
    290                 295                 300

Gly Val Tyr Tyr Arg Leu Gly Glu His Asn Lys His Leu Asp Gly Ile
305                 310                 315                 320

Thr Trp Tyr Gly Trp His Gly Ser Thr Tyr Ser Leu Lys Arg Val Glu
                325                 330                 335

Met Lys Ile Arg Pro Glu Asp Phe Lys Pro
            340                 345

<210> SEQ ID NO 13
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 13
ctgcagggac aggaacaggt tgg                                          23

<210> SEQ ID NO 14
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 14
cagagtatcc cctctgcttc agg                                          23
```

```
<210> SEQ ID NO 15
<211> LENGTH: 23
<212> TYPE: DNA
<213> ORGANISM: artificial sequence
<220> FEATURE:
<223> OTHER INFORMATION: GGCTCTGCAGGGACAGGAACAGG

<400> SEQUENCE: 15
ggctctgcag ggacaggaac agg                                          23

<210> SEQ ID NO 16
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 16
gcttcaggtg ttctgtgaca tgg                                          23

<210> SEQ ID NO 17
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 17
tgcagggaca ggaacaggtt ggg                                          23

<210> SEQ ID NO 18
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 18
tctactggct ctgcagggac agg                                          23

<210> SEQ ID NO 19
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 19
ccttctaccg ggactggaag cag                                          23

<210> SEQ ID NO 20
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 20
ccgtggggac ttctggctgg gga                                          23

<210> SEQ ID NO 21
<211> LENGTH: 23
<212> TYPE: DNA
<213> ORGANISM: artificial sequence
<220> FEATURE:
<223> OTHER INFORMATION: Guide RNA Recognition Sequence
```

<400> SEQUENCE: 21
ccgggactgg aagcagtaca agc                                                    23

<210> SEQ ID NO 22
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 22
ccttgtctcc ttctaccggg act                                                    23

<210> SEQ ID NO 23
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 23
ccaccggctc tccagacagc caa                                                    23

<210> SEQ ID NO 24
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 24
ccggctctcc agacagccaa ccc                                                    23

<210> SEQ ID NO 25
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 25
tggagacttc aggcggaggc tgg                                                    23

<210> SEQ ID NO 26
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 26
tgtgacatgg agacttcagg cgg                                                    23

<210> SEQ ID NO 27
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 27
ttctgtgaca tggagacttc agg                                                    23

<210> SEQ ID NO 28
<211> LENGTH: 23

```
<212> TYPE: DNA
<213> ORGANISM: artificial sequence
<220> FEATURE:
<223> OTHER INFORMATION: Guide RNA Recognition Sequence

<400> SEQUENCE: 28
gacatggaga cttcaggcgg agg                                              23

<210> SEQ ID NO 29
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 29
ccatgactgg accagtgcca cca                                              23

<210> SEQ ID NO 30
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 30
cccggctgcg tgtagagatg gag                                              23

<210> SEQ ID NO 31
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 31
ccggctgcgt gtagagatgg agg                                              23

<210> SEQ ID NO 32
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 32
ccaacccggc tgcgtgtaga gat                                              23

<210> SEQ ID NO 33
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 33
ccaggggccc catgactgga cca                                              23

<210> SEQ ID NO 34
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 34
```
ccccatgact ggaccagtgc cac                                              23

<210> SEQ ID NO 35
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 35
ctgcttccag tcccggtaga agg                                              23

<210> SEQ ID NO 36
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 36
ttgtctcctt ctaccgggac tgg                                              23

<210> SEQ ID NO 37
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 37
gcgggagtgc acacatctac tgg                                              23

<210> SEQ ID NO 38
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 38
ggactggaag cagtacaagc agg                                              23

<210> SEQ ID NO 39
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 39
gtggccttgt ctccttctac cgg                                              23

<210> SEQ ID NO 40
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 40
tactctggtg agggacttgc agg                                              23

<210> SEQ ID NO 41
<211> LENGTH: 23
<212> TYPE: DNA
<213> ORGANISM: artificial sequence

```
<220> FEATURE:
<223> OTHER INFORMATION: Guide RNA Recognition Sequence

<400> SEQUENCE: 41
actctggtga gggacttgca ggg                                              23

<210> SEQ ID NO 42
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 42
gcttgtactg cttccagtcc cgg                                              23

<210> SEQ ID NO 43
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 43
agtcccggta gaaggagaca agg                                              23

<210> SEQ ID NO 44
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 44
cacacatcta ctggctctgc agg                                              23

<210> SEQ ID NO 45
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 45
caaggccact ttttcgtcta tgg                                              23

<210> SEQ ID NO 46
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 46
gactggaagc agtacaagca ggg                                              23

<210> SEQ ID NO 47
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 47
gcagagggga tactctggtg agg                                              23
```

```
<210> SEQ ID NO 48
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 48
ctctggtgag ggacttgcag ggg                                            23

<210> SEQ ID NO 49
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 49
cagaggggat actctggtga ggg                                            23

<210> SEQ ID NO 50
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 50
actttttcgt ctatggatga tgg                                            23

<210> SEQ ID NO 51
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 51
tggccttgtc tccttctacc ggg                                            23

<210> SEQ ID NO 52
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 52
aagcagtaca agcagggctt tgg                                            23

<210> SEQ ID NO 53
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 53
ctgaagcaga ggggatactc tgg                                            23

<210> SEQ ID NO 54
<211> LENGTH: 23
<212> TYPE: DNA
<213> ORGANISM: artificial sequence
<220> FEATURE:
<223> OTHER INFORMATION: Guide RNA Recognition Sequence
```

<400> SEQUENCE: 54
tcacagaaca cctgaagcag agg                                                    23

<210> SEQ ID NO 55
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 55
acacatctac tggctctgca ggg                                                    23

<210> SEQ ID NO 56
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 56
atcatccata gacgaaaaag tgg                                                    23

<210> SEQ ID NO 57
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 57
atgaccgcgt acaactccgg ggg                                                    23

<210> SEQ ID NO 58
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 58
catgaccgcg tacaactccg ggg                                                    23

<210> SEQ ID NO 59
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 59 ggcaccccccg gagttgtacg cgg                                                   23

<210> SEQ ID NO 60
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 60
gagttgtacg cggtcatgtg tgg                                                    23

<210> SEQ ID NO 61

```
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 61
acatgaccgc gtacaactcc ggg                                          23

<210> SEQ ID NO 62
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 62
cacatgaccg cgtacaactc cgg                                          23

<210> SEQ ID NO 63
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 63
ttgtacgcgg tcatgtgtgg tgg                                          23

<210> SEQ ID NO 64
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 64
tggggaacga acacatccac cgg                                          23

<210> SEQ ID NO 65
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 65
ggtggcactg gtccagtcat ggg                                          23

<210> SEQ ID NO 66
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 66
cagaatagga atggcacccc cgg                                          23

<210> SEQ ID NO 67
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 67
```
gtggcactgg tccagtcatg ggg                                                    23

<210> SEQ ID NO 68
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 68
gcggtcatgt gtggtggcac tgg                                                    23

<210> SEQ ID NO 69
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 69
tggtggcact ggtccagtca tgg                                                    23

<210> SEQ ID NO 70
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 70
gcagcatccg tggggacttc tgg                                                    23

<210> SEQ ID NO 71
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 71
catccgtggg gacttctggc tgg                                                    23

<210> SEQ ID NO 72
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 72
ggctctccag acagccaacc cgg                                                    23

<210> SEQ ID NO 73
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 73
atccgtgggg acttctggct ggg                                                    23

<210> SEQ ID NO 74
<211> LENGTH: 23
<212> TYPE: DNA

```
<213> ORGANISM: artificial sequence
<220> FEATURE:
<223> OTHER INFORMATION: Guide RNA Recognition Sequence

<400> SEQUENCE: 74
ttggctgtct ggagagccgg tgg                                              23

<210> SEQ ID NO 75
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 75
tggtccagtc atggggcccc tgg                                              23

<210> SEQ ID NO 76
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 76
gatttgtctt gaatcagaat agg                                              23

<210> SEQ ID NO 77
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 77
aacccggctg catgtagaga tgg                                              23

<210> SEQ ID NO 78
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 78
ctccatctct acatgcagcc ggg                                              23

<210> SEQ ID NO 79
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 79
tagagatgga ggtaagcaca agg                                              23

<210> SEQ ID NO 80
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 80
tccgtgggga cttctggctg ggg                                              23
```

<210> SEQ ID NO 81
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 81
atctctacac acagccgggt tgg                                             23

<210> SEQ ID NO 82
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 82
aacccggctg tgtgtagaga tgg                                             23

<210> SEQ ID NO 83
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 83
cctccatctc tacacacagc cgg                                             23

<210> SEQ ID NO 84
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 84
caatggagtg tactaccgcc tgg                                             23

<210> SEQ ID NO 85
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 85
aatggagtgt actaccgcct ggg                                             23

<210> SEQ ID NO 86
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 86
tacctactcc ctcaaacggg tgg                                             23

<210> SEQ ID NO 87
<211> LENGTH: 23
<212> TYPE: DNA
<213> ORGANISM: artificial sequence
<220> FEATURE:

```
<223> OTHER INFORMATION: Guide RNA Recognition Sequence

<400> SEQUENCE: 87
tttcatctcc acccgtttga ggg                                              23

<210> SEQ ID NO 88
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 88
acagtcaact tactagcact ggg                                              23

<210> SEQ ID NO 89
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 89
ttttcatctc cacccgtttg agg                                              23

<210> SEQ ID NO 90
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 90
gggtgagcac aataagcacc tgg                                              23

<210> SEQ ID NO 91
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 91
atggcatcac ctggtatggc tgg                                              23

<210> SEQ ID NO 92
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 92
ctccacccgt ttgagggagt agg                                              23

<210> SEQ ID NO 93
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 93
ggtgcttatt gtgctcaccc agg                                              23
```

```
<210> SEQ ID NO 94
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 94
ctaactcctt acctgatgtc tgg                                              23

<210> SEQ ID NO 95
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 95
cacagtcaac ttactagcac tgg                                              23

<210> SEQ ID NO 96
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 96
cagttgtacc agtagccacc tgg                                              23

<210> SEQ ID NO 97
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 97
gatagaccag acatcaggta agg                                              23

<210> SEQ ID NO 98
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 98
tcaggtaagg agttagagcc agg                                              23

<210> SEQ ID NO 99
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 99
gatctaccta ctccctcaaa cgg                                              23

<210> SEQ ID NO 100
<211> LENGTH: 23
<212> TYPE: DNA
<213> ORGANISM: artificial sequence
<220> FEATURE:
<223> OTHER INFORMATION: Guide RNA Recognition Sequence
```

```
<400> SEQUENCE: 100
agatccatgc cagccatacc agg                                              23

<210> SEQ ID NO 101
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 101
gcttattgtg ctcacccagg cgg                                              23

<210> SEQ ID NO 102
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 102
cataccaggt gatgccatcc agg                                              23

<210> SEQ ID NO 103
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 103
atctacctac tccctcaaac ggg                                              23

<210> SEQ ID NO 104
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 104
actgtgatag accagacatc agg                                              23

<210> SEQ ID NO 105
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 105
ttctcatgcc aggtggctac tgg                                              23

<210> SEQ ID NO 106
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 106
ctggatggca tcacctggta tgg                                              23

<210> SEQ ID NO 107
<211> LENGTH: 23
```

```
<212> TYPE: DNA
<213> ORGANISM: artificial sequence
<220> FEATURE:
<223> OTHER INFORMATION: Guide RNA Recognition Sequence

<400> SEQUENCE: 107
agcacctgga tggcatcacc tgg                                              23

<210> SEQ ID NO 108
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 108
atcacctggt atggctggca tgg                                              23

<210> SEQ ID NO 109
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 109
gtagtacact ccattgagtt tgg                                              23

<210> SEQ ID NO 110
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 110
gagcacaata agcacctgga tgg                                              23

<210> SEQ ID NO 111
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 111
caggtaagga gttagagcca ggg                                              23

<210> SEQ ID NO 112
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 112
ctgggtctgt ttctcatgcc agg                                              23

<210> SEQ ID NO 113
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 113
```
tttggtattc tttctgaccc tgg                                          23

<210> SEQ ID NO 114
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 114
gtcagaaaga ataccaaaac cgg                                          23

<210> SEQ ID NO 115
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 115
ggtctgtttc tcatgccagg tgg                                          23

<210> SEQ ID NO 116
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 116
ggcggtagta cactccattg agg                                          23

<210> SEQ ID NO 117
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 117
gtagtacact ccattgaggt tgg                                          23

<210> SEQ ID NO 118
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 118
gtttctgtat ccgtgctcca cgg                                          23

<210> SEQ ID NO 119
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 119
aaactgagac acgtggagac tgg                                          23

<210> SEQ ID NO 120
<211> LENGTH: 23
<212> TYPE: DNA
<213> ORGANISM: artificial sequence

```
<220> FEATURE:
<223> OTHER INFORMATION: Guide RNA Recognition Sequence

<400> SEQUENCE: 120
gccttaaaag gaggctgccg tgg                                              23

<210> SEQ ID NO 121
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 121
gacacgtgga gactggatga ggg                                              23

<210> SEQ ID NO 122
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 122
tccacggcag cctcctttta agg                                              23

<210> SEQ ID NO 123
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 123
tgcacagact ccaacctcaa tgg                                              23

<210> SEQ ID NO 124
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 124
agacacgtgg agactggatg agg                                              23

<210> SEQ ID NO 125
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 125
agacttcaag ccttaaaagg agg                                              23

<210> SEQ ID NO 126
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 126
tttaaggctt gaagtcttct ggg                                              23
```

```
<210> SEQ ID NO 127
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 127
aaggcttgaa gtcttctggg tgg                                              23

<210> SEQ ID NO 128
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 128
ttttaaggct tgaagtcttc tgg                                              23

<210> SEQ ID NO 129
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 129
gatacagaaa ctgagacacg tgg                                              23

<210> SEQ ID NO 130
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 130
aaggaggctg ccgtggagca cgg                                              23

<210> SEQ ID NO 131
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 131
agaagacttc aagccttaaa agg                                              23

<210> SEQ ID NO 132
<211> LENGTH: 6641
<212> TYPE: DNA
<213> ORGANISM: homo sapien

<400> SEQUENCE: 132
cttgtggagc attcgggctt ggaaggaaag ctataggcta cccattcagc tcccctgtca      60
gagactcaag ctttgagaaa ggctagcaaa gagcaaggaa agagagaaaa caacaaagtg     120
gcgaggccct cagagtgaaa gcgtaaggtt cagtcagcct gctgcagctt tgcagacctc     180
agctgggcat ctccagactc ccctgaagga agagccttcc tcacccaaac ccacaaaaga     240
tgctgaaaaa gcctctctca gctgtgacct ggctctgcat tttcatcgtg gcctttgtca     300
gccacccagc gtggctgcag aagctctcta agcacaagac caagcacagc ccacagctca     360
```

```
aagcggccaa ctgctgtgag gaggtgaagg agctcaaggc ccaagttgcc aaccttagca    420
gcctgctgag tgaactgaac aagaagcagg agagggactg ggtcagcgtg gtcatgcagg    480
tgatggagct ggagagcaac agcaagcgca tggagtcgcg gctcacagat gctgagagca    540
agtactccga gatgaacaac caaattgaca tcatgcagct gcaggcagca cagacggtca    600
ctcagacctc cgcaggtaag gagaccagtc ccctgaggga gcgtggagtg cctccccatc    660
tacagcactg cttctacata tcctggtcat cagaaccact actggggcct cttttgtggg    720
tacactttcc ctttagtaaa ggcttatgca gtatttcctt tgacttctaa tgctatgtaa    780
gtttacctaa caccttcacg ggtctctttt atccacacag tgtttcagcc taccatcttg    840
gagtgctgag atactacatg gtttgcccaa agtcacccag caagtcttag aagcagggtt    900
caagtcttcc tgattggtgt agctctgcta cttcctcacc aagagctgac aggctatatc    960
tcaagaaatt ccaaggaagc accaaactgt aacagctgtt cctctggaag caaagttttg   1020
ccagaaacag ttctctggtg ttcctaagat ttaccaggaa tgagcattaa tggaattttg   1080
tgtcctctct ctgtaaacgt aactcttctc attggctcag agttaagtgt agagacacat   1140
aaccatgtga agagtccctt tgtgttcagg aaggatgcgg ctccttaagg ttcctcaatt   1200
gtgatacgtc tatttttttc catggtctta aatgaatttc tccgaataca ggattttta    1260 aatgcaatgc tgaaatatag acttaatagg ccaaaaataa gataaattta atctttcttt   1320
tgcaaaataa cttttatttc tggttagctc agctcaggtg ggccaacatg aatttacggt   1380
ttagagataa aaatttggtt ttctgaaatt atcaggaaaa tattagttgt aaggagcata   1440
tcctatagac atgtcatttc ttgctgatat aaaaaccatt ggtcccatta taaactacat   1500
gaagaacaaa gacatgatca gcttctactg actaagtcaa tggttaacct cagctcaaat   1560
taagaaaaag ttttaacatg aaaccaagct tgaaaattct gttacctgaa ccaacatgta   1620
tcaatcactt tctaagcatg gacttccggg ccctcagttt gggattagaa aggtattctc   1680
aggccatttt ccagacaagt gagtcctgat ttggtctgtg agatgaaacc agacatgcgg   1740
aagaccaggc cagacagagg aatctgaccg tgccacttcc tgctcatcca aacaggaggc   1800
tttctcacca tcctgcaagg aggttcttgg ggtcaagtgc agctctccca ccaggtctct   1860
tgctcttctt gcccaggaca tcattcctta ttttcttct ctatgaccaa gtgctcagtt    1920
acccttatat tctataagta ggtagtccct tagaggaagc agtaagttgg tgctttcacc   1980
actaagacga aatgaagaat agtgatggcg aaggcacacg tactctacct cccttccca    2040 aggtgctctg caagagaacc tatgtgcctc agacaactcc catctgccat cttggtgctc   2100
ctctctaagg tcccagtgca gtggtcacca agaaaagcac cccgagacat agcaggcagg   2160
aagcttctct tggatagtaa gggccgcagt ctctgaatcc tatcagaaaa ggctgtctct   2220
tccactatgc tctttgatat ttagaataca gagcttaaat cctgcataaa gtagcagctc   2280
catgccccta gagtaaaaaa actggccagt ctgatgctct catttcattg ttttaacaaa   2340
acttctggga ggaaggcctc aaaggttctt ctgagtgttt tgaggtgcta gctggatgga   2400 agggaaaat atgtgataat aaaatctatc tcccttaatt atggtctcag gtggcagtag    2460
ccaccatctc tgaacaacaa caaaacaac caaccaggaa acatcaacaa aaccagactc    2520
tatgagatat tcacgactga tttgttatag tggcggctgt ctaagaagtc tgaatctatc   2580
tgacaggagt atctgttacg tggccctcat acactgtaac atttctagaa ttcatggccc   2640
agctatagca gaataattta tttcagagtt aacctgaaac cacctgttgg aacgtcccac   2700
```

```
taatgctatc caggtgaagg gcttccctac ccctctgctc caccgctagt aaagccaaaa    2760
tacaccccct ctggatctcc ccatatccac ctctcccaaa tgcagacact gatgggtaat    2820
taacaccact gagaatccca gggtagaaat aaaggctcag tctctaaaca ctcaactcag    2880
atggagccac tgggtctaaa tgctcaccct gtggtttgtt ctcttgtaga tgccatctac    2940
gactgctctt ccctctacca gaagaactac cgcatctctg gagtgtataa gcttcctcct    3000
gatgacttcc tgggcagccc tgaactggag gtgaggtcat tacagtcact ggccatgccc    3060
taatacctgt ccttcacccc ctcaagggga ctacaacaac agggccattc acagtttaaa    3120
gaaaggaaaa ttcggctggg cgcagtggct cacacctgta atcccagcac tatgggaggc    3180
cgaggcaggt ggatcacttc aggtcaggag tttaagacca gcctggccaa catggtgaaa    3240
ccctgtctct actaaaaata caaaaaaatt agccaggcat ggtggtgggc acctgtaatc    3300
cctgctacac aggaggattg cttgaactca ggaggcagag gttgcagtga gccgagatca    3360
cgccactgca ctataatctg ggagacaaag tgagactcca tttcaattaa aaaaaaaaa    3420
aaaaaaagg aaaactcaaa cacaagcaaa cacaccaaac accacagagc tatgcaaaca    3480
ctcagtttat gccctgcact ccaaacccag gcatctgttt ggccccttca aatcattatc    3540
agtcaaacaa caagccttct aacatagatc agatcattct tataaccacc acataactta    3600
gtttaaatct cttgccatgt cctagaacag ctattccttg ggggaggaga aagaaaaca    3660
cgaaggcagc atcaaattat ctggattttc acccaggcat ggtggctcac acctgtaatc    3720
ccaagttttt tgggaggtga ggtgggcgga acaatcacct gaggtcagga ctttgagacc    3780
agcctggcca acatgctgaa acccagtctc tactaaaaat acaaaaatta gcccagtgtg    3840
gtgacaggca ctctggtccc agctactagg aaggcaggag aatcactgga actcaggagg    3900
tggaggttgc agtgagccga gattgcacca ctgtactcta gcctgggcaa caagagtgaa    3960
attctgcttc aaaaaaaaaa aaagtatctg gattttccc tccaagcttc atgtgcactc    4020
acccccgggc ccaatttgca tcgttcttcc agagcaatgc accacccacc ccagctcacc    4080
agcagtgggg cagcatcact gcccgagtga gccagtgtga ctgcgggagt gcacacatct    4140
actggctctg cagggacagg aacaggttgg gaagcctgcc ctcttgctcc tgccttctgc    4200
ccctgcaagt ccctcaccag agtatcccct ctgcttcagg tgatctgtga catggagact    4260
tcaggcggag gctggaccat catccagaga cgaaaaagtg gccttgtctc cttctaccgg    4320
gactggaagc agtacaagca gggctttggc agcatccgtg gggacttctg gctggggaac    4380
gaacacatcc accggctctc cagacagcca cccggctgc gtgtagagat ggaggtaagc    4440
acaaggccag gggcccatg actggaccag tgccaccaca catgaccgcg tacaactccg    4500
ggggtgccat tcctattctg attcaagaca aatctgtata ttcattgtga tggttttcct    4560
gcaagttgta atggagttga ggaaaaatag gtattttttcc tttctgcaac cccccaacc    4620
ccccgacaaa agtggggctg caggtggac aggaagaggc cagacccagg ccagagtaga    4680
gcaaattcaa cagtcagctg tgccgaacac tagtctctgc tctggccgag catgaggtcc    4740
tttaggtgca aatcttactg atactgtttg gggaccttg ctgaaggtct gaaagcactc    4800
actatatcct catgtttctc ttacagcagc tctgtgtggg attcagcaaa acatagctg    4860
caccttataa gcaggaaagt gaggaatata gaaagagaga ctaatcaagg ccatatggtg    4920
aatcaggaaa gaagttcgag ccttgttttc tgattcccag ttaacacag taaactggag    4980
gtaaacaagt aataaagtct tattagattc acacctataa aaagatgttt ggctatggga    5040
ctgtcaggag agaaggggta tagagacagc atgaaatgga gcctgctgca ctttctttaa    5100
```

| | |
|---|---|
| ggctctgctc ctcctgacag gactgggagg gcaacctgcg ctacgctgag tatagccact | 5160 |
| ttgttttggg caatgaactc aacagctatc gcctcttcct ggggaactac actggcaatg | 5220 |
| tggggaacga cgccctccag tatcataaca acacagcctt cagcaccaag gacaaggaca | 5280 |
| atgacaactg cttggacaag tgtgcacagc tccgcaaagg tgagatttgg ggggaccgga | 5340 |
| aaggagaagt tcaggtacaa gctcataatc ccacttgagg agaaagagtg aattataact | 5400 |
| gtacagttga tattccggtt ttggtattct ttctgaccct ggctctaact ccttacctga | 5460 |
| tgtctggtct atcacagtca acttactagc actgggtctg tttctcatgc caggtggcta | 5520 |
| ctggtacaac tgctgcacag actccaacct caatggagtg tactaccgcc tgggtgagca | 5580 |
| caataagcac ctggatggca tcacctggta tggctggcat ggatctacct actccctcaa | 5640 |
| acgggtggag atgaaaatcc gcccagaaga cttcaagcct taaaaggagg ctgccgtgga | 5700 |
| gcacggatac agaaactgag acacgtggag actggatgag ggcagatgag gacaggaaga | 5760 |
| gagtgttaga aagggtagga ctgagaaaca gcctataatc tccaaagaaa gaataagtct | 5820 |
| ccaaggagca caaaaaaatc atatgtacca aggatgttac agtaaacagg atgaactatt | 5880 |
| taaacccact gggtcctgcc acatccttct caaggtggta gactgagtgg ggtctctctg | 5940 |
| cccaagatcc ctgacatagc agtagcttgt cttttccaca tgatttgtct gtgaaagaaa | 6000 |
| ataattttga gatcgtttta tctattttct ctacggctta ggctatgtga gggcaaaaca | 6060 |
| caaatccctt tgctaaaaag aaccatatta ttttgattct caaaggatag gcctttgagt | 6120 |
| gttagagaaa ggagtgaagg aggcaggtgg gaaatggtat ttctattttt aaatccagtg | 6180 |
| aaattatctt gagtctacac attattttta aaacacaaaa attgttcggc tggaactgac | 6240 |
| ccaggctgga cttgcgggga ggaaactcca gggcactgca tctggcgatc agactctgag | 6300 |
| cactgcccct gctcgccttg gtcatgtaca gcactgaaag gaatgaagca ccagcaggag | 6360 |
| gtggacagag tctctcatgg atgccggcac aaaactgcct taaaatattc atagttaata | 6420 |
| caggtatatc tatttttatt tactttgtaa gaaacaagct caaggagctt ccttttaaat | 6480 |
| tttgtctgta ggaaatggtt gaaaactgaa ggtagatggt gttatagtta ataataaatg | 6540 |
| ctgtaaataa gcatctcact ttgtaaaaat aaaatattgt ggttttgttt taaacattca | 6600 |
| acgtttcttt tccttctaca ataaacactt tcaaaatgtg a | 6641 |

<210> SEQ ID NO 133
<211> LENGTH: 6641
<212> TYPE: DNA
<213> ORGANISM: homo sapien

<400> SEQUENCE: 133

| | |
|---|---|
| cttgtggagc attcgggctt ggaaggaaag ctataggcta cccattcagc tcccctgtca | 60 |
| gagactcaag ctttgagaaa ggctagcaaa gagcaaggaa agagagaaaa caacaaagtg | 120 |
| gcgaggccct cagagtgaaa gcgtaaggtt cagtcagcct gctgcagctt tgcagacctc | 180 |
| agctgggcat ctccagactc ccctgaagga agagccttcc tcacccaaac ccacaaaaga | 240 |
| tgctgaaaaa gcctctctca gctgtgacct ggctctgcat tttcatcgtg gcctttgtca | 300 |
| gccacccagc gtggctgcag aagctctcta agcacaagac accagcacag ccacagctca | 360 |
| aagcggccaa ctgctgtgag gaggtgaagg agctcaaggc ccaagttgcc aaccttagca | 420 |
| gcctgctgag tgaactgaac aagaagcagg agagggactg ggtcagcgtg gtcatgcagg | 480 |
| tgatggagct ggagagcaac agcaagcgca tggagtcgcg gctcacagat gctgagagca | 540 |

```
agtactccga gatgaacaac caaattgaca tcatgcagct gcaggcagca cagacggtca    600
ctcagacctc cgcaggtaag gagaccagtc ccctgaggga gcgtggagtg cctccccatc    660
tacagcactg cttctacata tcctggtcat cagaaccact actggggcct cttttgtggg    720
tacactttcc ctttagtaaa ggcttatgca gtatttcctt tgacttctaa tgctatgtaa    780
gtttacctaa caccttcacg ggtctctttt atccacacag tgtttcagcc taccatcttg    840
gagtgctgag atactacatg gtttgcccaa agtcacccag caagtcttag aagcagggtt    900
caagtcttcc tgattggtgt agctctgcta cttcctcacc aagagctgac aggctatatc    960
tcaagaaatt ccaaggaagc accaaactgt aacagctgtt cctctggaag caaagttttg    1020
ccagaaacag ttctctggtg ttcctaagat ttaccaggaa tgagcattaa tggaattttg    1080
tgtcctctct ctgtaaacgt aactcttctc attggctcag agttaagtgt agagacacat    1140
aaccatgtga agagtccctt tgtgttcagg aaggatgcgg ctccttaagg ttcctcaatt    1200
gtgatacgtc tatttttttc catggtctta aatgaatttc tccgaataca ggatttttta    1260
aatgcaatgc tgaaatatag acttaatagg ccaaaaataa gataaattta atctttcttt    1320
tgcaaaataa cttttatttc tggttagctc agctcaggtg ggccaacatg aatttacggt    1380
ttagagataa aaatttggtt ttctgaaatt atcaggaaaa tattagttgt aaggagcata    1440
tcctatagac atgtcatttc ttgctgatat aaaaaccatt ggtcccatta taaactacat    1500
gaagaacaaa gacatgatca gcttctactg actaagtcaa tggttaacct cagctcaaat    1560
taagaaaaag ttttaacatg aaaccaagct tgaaaattct gttacctgaa ccaacatgta    1620
tcaatcactt tctaagcatg gacttccggg ccctcagttt gggattagaa aggtattctc    1680
aggccatttt ccagacaagt gagtcctgat ttggtctgtg agatgaaacc agacatgcgg    1740
aagaccaggc cagacagagg aatctgaccg tgccacttcc tgctcatcca acaggaggc    1800 tttctcacca tcctgcaagg aggttcttgg ggtcaagtgc agctctccca ccaggtctct    1860
tgctcttctt gcccaggaca tcattcctta ttttcttct ctatgaccaa gtgctcagtt    1920
acccttatat tctataagta ggtagtccct tagaggaagc agtaagttgg tgctttcacc    1980
actaagacga aatgaagaat agtgatggcg aaggcacacg tactctacct cccttttccca    2040 aggtgctctg caagagaacc tatgtgcctc agacaactcc catctgccat cttggtgctc    2100
ctctctaagg tcccagtgca gtggtcacca agaaaagcac cccgagacat agcaggcagg    2160
aagcttctct tggatagtaa gggccgcagt ctctgaatcc tatcagaaaa ggctgtctct    2220
tccactatgc tctttgatat ttagaataca gagcttaaat cctgcataaa gtagcagctc    2280
catggcccta gagtaaaaaa actggccagt ctgatgctct catttcattg ttttaacaaa    2340
acttctggga ggaaggcctc aaaggttctt ctgagtgttt tgaggtgcta gctggatgga    2400
aggggaaaat atgtgataat aaaatctatc tcccttaatt atggtctcag gtggcagtag    2460
ccaccatctc tgaacaacaa caaaaacaac caaccaggaa acatcaacaa aaccagactc    2520
tatgagatat tcacgactga tttgttatag tggcggctgt ctaagaagtc tgaatctatc    2580
tgacaggagt atctgttacg tggccctcat acactgtaac atttctagaa ttcatggccc    2640
agctatagca gaataattta tttcagagtt aacctgaaac cacctgttgg aacgtcccac    2700
taatgctatc caggtgaagg gcttccctac ccctctgctc caccgctagt aaagccaaaa    2760 tacacccccct ctggatctcc ccatatccac ctctcccaaa tgcagacact gatgggtaat    2820
taacaccact gagaatccca gggtagaaat aaaggctcag tctctaaaca ctcaactcag    2880
atggagccac tgggtctaaa tgctcaccct gtggtttgtt ctcttgtaga tgccatctac    2940
```

```
gactgctctt ccctctacca gaagaactac cgcatctctg gagtgtataa gcttcctcct    3000
gatgacttcc tgggcagccc tgaactggag gtgaggtcat tacagtcact ggccatgccc    3060
taatacctgt ccttcacccc ctcaaggga ctacaacaac agggccattc acagtttaaa    3120
gaaaggaaaa ttcggctggg cgcagtggct cacacctgta atcccagcac tatgggaggc    3180
cgaggcaggt ggatcacttc aggtcaggag tttaagacca gcctggccaa catggtgaaa    3240
ccctgtctct actaaaaata caaaaaatt agccaggcat ggtggtgggc acctgtaatc    3300
cctgctacac aggaggattg cttgaactca ggaggcagag gttgcagtga gccgagatca    3360
cgccactgca ctataatctg ggagacaaag tgagactcca tttcaattaa aaaaaaaaa    3420
aaaaaaagg aaaactcaaa cacaagcaaa cacccaaac accacagagc tatgcaaaca    3480
ctcagtttat gccctgcact ccaaacccag gcatctgttt ggcccttca aatcattatc    3540
agtcaaacaa caagccttct aacatagatc agatcattct tataaccacc ataactta    3600
gtttaaatct cttgccatgt cctagaacag ctattccttg ggggaggaga aaagaaaaca    3660
cgaaggcagc atcaaattat ctggattttc acccaggcat ggtggctcac acctgtaatc    3720
ccaagttttt tgggaggtga ggtgggcgga acaatcacct gaggtcagga ctttgagacc    3780
agcctggcca acatgctgaa acccagtctc tactaaaaat acaaaaatta gcccagtgtg    3840
gtgacaggca ctctggtccc agctactagg aaggcaggag aatcactgga actcaggagg    3900
tggaggttgc agtgagccga gattgcacca ctgtactcta gcctgggcaa caagagtgaa    3960
attctgcttc aaaaaaaaaa aagtatctg gatttttccc tccaagcttc atgtgcactc    4020
acccccgggc ccaatttgca tcgttcttcc agagcaatgc accacccacc ccagctcacc    4080
agcagtgggg cagcatcact gcccgagtga gccagtgtga ctgcgggagt gcacacatct    4140
actggctctg cagggacagg aacaggttgg gaagcctgcc ctcttgctcc tgccttctgc    4200
ccctgcaagt ccctcaccag agtatcccct ctgcttcagg tgttctgtga catggagact    4260
tcaggcggag gctggaccat catccagaga cgaaaaagtg gccttgtctc cttctaccgg    4320
gactagaagc agtacaagca gggctttggc agcatccgtg gggacttctg gctggggaac    4380
gaacacatcc accggctctc cagacagcca acccggctgc gtgtagagat ggaggtaagc    4440
acaaggccag gggccccatg actggaccag tgccaccaca catgaccgcg tacaactccg    4500
ggggtgccat tcctattctg attcaagaca aatctgtata ttcattgtga tggttttcct    4560
gcaagttgta atggagttga ggaaaaatag gtattttcc tttctgcaac cccccaacc    4620
ccccgacaaa gtggggctg caggtgggac aggaagaggc cagacccagg ccagagtaga    4680
gcaaattcaa cagtcagctg tgccgaacac tagtctctgc tctggccgag catgaggtcc    4740
tttaggtgca aatcttactg atactgtttg ggacccttg ctgaaggtct gaaagcactc    4800
actatatcct catgtttctc ttacagcagc tctgtgtggg attcagcaaa acatagctg    4860
caccttataa gcaggaaagt gaggaatata gaaagagaga ctaatcaagg ccatatggtg    4920
aatcaggaaa gaagttcgag ccttgttttc tgattcccag gttaacacag taaactggag    4980
gtaaacaagt aataaagtct tattagattc acacctataa aaagatgttt ggctatggga    5040
ctgtcaggag agaaggggta tagagacagc atgaaatgga gcctgctgca ctttcttaa    5100
ggctctgctc ctcctgacag gactgggagg gcaacctgcg ctacgctgag tatagccact    5160
ttgtttttggg caatgaactc aacagctatc gcctcttcct ggggaactac actggcaatg    5220
tggggaacga cgccctccag tatcataaca acacagcctt cagcaccaag gacaaggaca    5280
```

| | |
|---|---|
| atgacaactg cttggacaag tgtgcacagc tccgcaaagg tgagatttgg ggggaccgga | 5340 |
| aaggagaagt tcaggtacaa gctcataatc ccacttgagg agaaagagtg aattataact | 5400 |
| gtacagttga tattccggtt ttggtattct ttctgaccct ggctctaact ccttacctga | 5460 |
| tgtctggtct atcacagtca acttactagc actgggtctg tttctcatgc caggtggcta | 5520 |
| ctggtacaac tgctgcacag actccaacct caatggagtg tactaccgcc tgggtgagca | 5580 |
| caataagcac ctggatggca tcacctggta tggctggcat ggatctacct actccctcaa | 5640 |
| acgggtggag atgaaaatcc gcccagaaga cttcaagcct aaaaggagg ctgccgtgga | 5700 |
| gcacggatac agaaactgag acacgtggag actggatgag ggcagatgag gacaggaaga | 5760 |
| gagtgttaga aagggtagga ctgagaaaca gcctataatc tccaaagaaa gaataagtct | 5820 |
| ccaaggagca caaaaaaatc atatgtacca aggatgttac agtaaacagg atgaactatt | 5880 |
| taaacccact gggtcctgcc acatccttct caaggtggta gactgagtgg ggtctctctg | 5940 |
| cccaagatcc ctgacatagc agtagcttgt cttttccaca tgatttgtct gtgaaagaaa | 6000 |
| ataattttga gatcgtttta tctatttct ctacggctta ggctatgtga gggcaaaaca | 6060 |
| caaatccctt tgctaaaaag aaccatatta ttttgattct caaaggatag gcctttgagt | 6120 |
| gttagagaaa ggagtgaagg aggcaggtgg gaaatgtat ttctattttt aaatccagtg | 6180 |
| aaattatctt gagtctacac attatttta aaacacaaaa attgttcggc tggaactgac | 6240 |
| ccaggctgga cttgcgggga ggaaactcca gggcactgca tctggcgatc agactctgag | 6300 |
| cactgcccct gctcgccttg gtcatgtaca gcactgaaag gaatgaagca ccagcaggag | 6360 |
| gtggacagag tctctcatgg atgccggcac aaaactgcct taaatattc atagttaata | 6420 |
| caggtatatc tattttattt tactttgtaa gaaacaagct caaggagctt ccttttaaat | 6480 |
| tttgtctgta ggaaatggtt gaaaactgaa ggtagatggt gttatagtta ataataaatg | 6540 |
| ctgtaaataa gcatctcact ttgtaaaaat aaaatattgt ggttttgttt taaacattca | 6600 |
| acgtttcttt tccttctaca ataaacactt tcaaaatgtg a | 6641 |

<210> SEQ ID NO 134
<211> LENGTH: 6641
<212> TYPE: DNA
<213> ORGANISM: homo sapien

<400> SEQUENCE: 134

| | |
|---|---|
| cttgtggagc attcgggctt ggaaggaaag ctataggcta cccattcagc tcccctgtca | 60 |
| gagactcaag ctttgagaaa ggctagcaaa gagcaaggaa agagagaaaa caacaaagtg | 120 |
| gcgaggccct cagagtgaaa gcgtaaggtt cagtcagcct gctgcagctt tgcagacctc | 180 |
| agctgggcat ctccagactc ccctgaagga agagccttcc tcacccaaac ccacaaaaga | 240 |
| tgctgaaaaa gcctctctca gctgtgacct ggctctgcat tttcatcgtg gcctttgtca | 300 |
| gccacccagc gtggctgcag aagctctcta agcacaagac accagcacag ccacagctca | 360 |
| aagcggccaa ctgctgtgag gaggtgaagg agctcaaggc ccaagttgcc aaccttagca | 420 |
| gcctgctgag tgaactgaac aagaagcagg agagggactg ggtcagcgtg gtcatgcagg | 480 |
| tgatggagct ggagagcaac agcaagcgca tggagtcgcg gctcacagat gctgagagca | 540 |
| agtactccga gatgaacaac caaattgaca tcatgcagct gcaggcagca cagacggtca | 600 |
| ctcagacctc cgcaggtaag gagaccagtc cctgaggga gcgtggagtg cctccccatc | 660 |
| tacagcactg cttctacata tcctggtcat cagaaccact actggggcct cttttgtggg | 720 |
| tacactttcc ctttagtaaa ggcttatgca gtatttcctt tgacttctaa tgctatgtaa | 780 |

```
gtttacctaa caccttcacg ggtctctttt atccacacag tgtttcagcc taccatcttg    840
gagtgctgag atactacatg gtttgcccaa agtcacccga caagtcttag aagcagggtt    900
caagtcttcc tgattggtgt agctctgcta cttcctcacc aagagctgac aggctatatc    960
tcaagaaatt ccaaggaagc accaaactgt aacagctgtt cctctggaag caaagttttg   1020
ccagaaacag ttctctggtg ttcctaagat ttaccaggaa tgagcattaa tggaattttg   1080
tgtcctctct ctgtaaacgt aactcttctc attggctcag agttaagtgt agagacacat   1140
aaccatgtga agagtccctt tgtgttcagg aaggatgcgg ctccttaagg ttcctcaatt   1200
gtgatacgtc tattttttc catggtctta aatgaatttc tccgaataca ggattttta    1260 aatgcaatgc tgaaatatag acttaatagg ccaaaaataa gataaattta atctttcttt   1320
tgcaaaataa ctttttattc tggttagctc agctcaggtg ggccaacatg aatttacggt   1380
ttagagataa aaatttggtt ttctgaaatt atcaggaaaa tattagttgt aaggagcata   1440
tcctatagac atgtcatttc ttgctgatat aaaaaccatt ggtcccatta taaactacat   1500
gaagaacaaa gacatgatca gcttctactg actaagtcaa tggttaacct cagctcaaat   1560
taagaaaaag ttttaacatg aaaccaagct tgaaaattct gttacctgaa ccaacatgta   1620
tcaatcactt tctaagcatg gacttccggg ccctcagttt gggattagaa aggtattctc   1680
aggccatttt ccagacaagt gagtcctgat ttggtctgtg agatgaaacc agacatgcgg   1740
aagaccaggc cagacagagg aatctgaccg tgccacttcc tgctcatcca acaggaggc    1800 tttctcacca tcctgcaagg aggttcttgg ggtcaagtgc agctctccca ccaggtctct   1860
tgctcttctt gcccaggaca tcattcctta tttttcttct ctatgaccaa gtgctcagtt   1920
acccttatat tctataagta ggtagtccct tagaggaagc agtaagttgg tgctttcacc   1980
actaagacga aatgaagaat agtgatggcg aaggcacacg tactctacct cccttttccca  2040 aggtgctctg caagagaacc tatgtgcctc agacaactcc catctgccat cttggtgctc   2100
ctctctaagg tcccagtgca gtggtcacca agaaaagcac cccgagacat agcaggcagg   2160
aagcttctct tggatagtaa gggccgcagt ctctgaatcc tatcagaaaa ggctgtctct   2220
tccactatgc tctttgatat ttagaataca gagcttaaat cctgcataaa gtagcagctc   2280
catggcccta gagtaaaaaa actggccagt ctgatgctct catttcattg ttttaacaaa   2340
acttctggga ggaaggcctc aaaggttctt ctgagtgttt tgaggtgcta gctggatgga   2400 agggggaaaat atgtgataat aaaatctatc tcccttaatt atggtctcag gtggcagtag   2460
ccaccatctc tgaacaacaa caaaaacaac caaccaggaa acatcaacaa aaccagactc   2520
tatgagatat tcacgactga tttgttatag tggcggctgt ctaagaagtc tgaatctatc   2580
tgacaggagt atctgttacg tggccctcat acactgtaac atttctagaa ttcatggccc   2640
agctatagca gaataattta tttcagagtt aacctgaaac cacctgttgg aacgtcccac   2700
taatgctatc caggtgaagg gcttccctac ccctctgctc caccgctagt aaagccaaaa   2760
tacaccccct ctggatctcc ccatatccac ctctcccaaa tgcagacact gatgggtaat   2820
taacaccact gagaatccca gggtagaaat aaaggctcag tctctaaaca ctcaactcag   2880
atggagccac tgggtctaaa tgctcaccct gtggtttgtt ctcttgtaga tgccatctac   2940
gactgctctt ccctctacca gaagaactac cgcatctctg gagtgtataa gcttcctcct   3000
gatgacttcc tgggcagccc tgaactggag gtgaggtcat tacagtcact ggccatgccc   3060
taatacctgt ccttcacccc ctcaagggga ctacaacaac agggccattc acagtttaaa   3120
```

```
gaaaggaaaa ttcggctggg cgcagtggct cacacctgta atcccagcac tatgggaggc    3180
cgaggcaggt ggatcacttc aggtcaggag tttaagacca gcctggccaa catggtgaaa    3240
ccctgtctct actaaaaata caaaaaatt agccaggcat ggtggtgggc acctgtaatc     3300
cctgctacac aggaggattg cttgaactca ggaggcagag gttgcagtga gccgagatca    3360
cgccactgca ctataatctg ggagacaaag tgagactcca tttcaattaa aaaaaaaaaa    3420 aaaaaaagg aaaactcaaa cacaagcaaa cacaccaaac accacagagc tatgcaaaca     3480
ctcagtttat gccctgcact ccaaacccag gcatctgttt ggccccttca aatcattatc    3540
agtcaaacaa caagccttct aacatagatc agatcattct tataaccacc acataactta    3600
gtttaaatct cttgccatgt cctagaacag ctattccttg ggggaggaga aagaaaaca     3660 cgaaggcagc atcaaattat ctggattttc acccaggcat ggtggctcac acctgtaatc    3720
ccaagttttt tgggaggtga ggtgggcgga acaatcacct gaggtcagga ctttgagacc    3780
agcctggcca acatgctgaa acccagtctc tactaaaaat acaaaaatta gcccagtgtg    3840
gtgacaggca ctctggtccc agctactagg aaggcaggag aatcactgga actcaggagg    3900
tggaggttgc agtgagccga gattgcacca ctgtactcta gcctgggcaa caagagtgaa    3960
attctgcttc aaaaaaaaaa aaagtatctg gattttccc tccaagcttc atgtgcactc     4020 accccgggc caatttgca tcgttcttcc agagcaatgc accacccacc ccagctcacc      4080
agcagtgggg cagcatcact gcccgagtga gccagtgtga ctgcgggagt gcacacatct    4140
actggctctg cagggacagg aacaggttgg gaagcctgcc ctcttgctcc tgccttctgc    4200
ccctgcaagt ccctcaccag agtatcccct ctgcttcagg tgttctgtga catggagact    4260
tcaggcggag gctggaccat catccagaga cgaaaaagtg gccttgtctc cttctaccgg    4320
gactggaagc agtaccagca gggctttggc agcatccgtg gggacttctg gctggggaac    4380
gaacacatcc accggctctc cagacagcca accggctgc gtgtagagat ggaggtaagc     4440
acaaggccag gggcccatg actggaccag tgccaccaca catgaccgcg tacaactccg     4500
ggggtgccat tcctattctg attcaagaca aatctgtata ttcattgtga tggttttcct    4560
gcaagttgta atggagttga ggaaaaatag gtatttttcc tttctgcaac cccccaacc    4620 ccccgacaaa agtgggctg caggtgggac aggaagaggc cagacccagg ccagagtaga     4680
gcaaattcaa cagtcagctg tgccgaacac tagtctctgc tctggccgag catgaggtcc    4740
tttaggtgca aatcttactg atactgtttg gggaccttg ctgaaggtct gaaagcactc     4800
actatatcct catgtttctc ttacagcagc tctgtgtggg attcagcaaa acatagctg     4860 caccttataa gcaggaaagt gaggaatata gaaagagaga ctaatcaagg ccatatggtg    4920
aatcaggaaa gaagttcgag ccttgttttc tgattcccag gttaacacag taaactggag    4980
gtaaacaagt aataaagtct tattagattc acacctataa aaagatgttt ggctatggga    5040
ctgtcaggag agaaggggta tagagacagc atgaaatgga gcctgctgca cttctcttaa   5100
ggctctgctc ctcctgacag gactgggagg gcaacctgcg ctacgctgag tatagccact    5160
ttgttttggg caatgaactc aacagctatc gcctcttcct ggggaactac actggcaatg    5220
tggggaacga cgccctccag tatcataaca acacagcctt cagcaccaag gacaaggaca    5280
atgacaactg cttggacaag tgtgcacagc tccgcaaagg tgagatttgg ggggaccgga    5340
aaggagaagt tcaggtacaa gctcataatc ccacttgagg agaaagagtg aattataact    5400
gtacagttga tattccggtt ttggtattct ttctgaccct ggctctaact ccttacctga    5460
tgtctggtct atcacagtca acttactagc actgggtctg tttctcatgc caggtggcta    5520
```

-continued

```
ctggtacaac tgctgcacag actccaacct caatggagtg tactaccgcc tgggtgagca    5580
caataagcac ctggatggca tcacctggta tggctggcat ggatctacct actccctcaa    5640
acgggtggag atgaaaatcc gcccagaaga cttcaagcct aaaaggagg ctgccgtgga     5700 gcacggatac agaaactgag acacgtggag actggatgag ggcagatgag gacaggaaga    5760
gagtgttaga aagggtagga ctgagaaaca gcctataatc tccaaagaaa gaataagtct    5820
ccaaggagca caaaaaatc atatgtacca aggatgttac agtaaacagg atgaactatt     5880
taaacccact gggtcctgcc acatccttct caaggtggta gactgagtgg ggtctctctg    5940
cccaagatcc ctgacatagc agtagcttgt cttttccaca tgatttgtct gtgaaagaaa    6000
ataattttga gatcgtttta tctattttct ctacggctta ggctatgtga gggcaaaaca    6060
caaatccctt tgctaaaaag aaccatatta ttttgattct caaggatag gcctttgagt     6120 gttagagaaa ggagtgaagg aggcaggtgg gaaatggtat ttctattttt aaatccagtg    6180
aaattatctt gagtctacac attatttta aaacacaaaa attgttcggc tggaactgac      6240
ccaggctgga cttgcgggga ggaaactcca gggcactgca tctggcgatc agactctgag    6300 cactgccct gctcgccttg gtcatgtaca gcactgaaag gaatgaagca ccagcaggag     6360
gtggacagag tctctcatgg atgccggcac aaaactgcct taaaatattc atagttaata    6420
caggtatatc tatttttatt tactttgtaa gaaacaagct caaggagctt cctttttaaat    6480 tttgtctgta ggaaatggtt gaaaactgaa ggtagatggt gttatagtta ataataaatg    6540
ctgtaaataa gcatctcact ttgtaaaaat aaaatattgt ggttttgttt taaacattca    6600
acgtttcttt tccttctaca ataaacactt tcaaaatgtg a                         6641
```

<210> SEQ ID NO 135
<211> LENGTH: 1041
<212> TYPE: DNA
<213> ORGANISM: homo sapien

<400> SEQUENCE: 135

```
augcugaaaa agccucucuc agcugugacc uggcucugca uuucaucgu ggccuuuguc      60 agccacccag cguggcugca gaagcucucu aagcacaaga caccagcaca gccacagcuc    120
aaagcggcca acugcuguga ggaggugaag gagcucaagg cccaaguugc caaccuuagc    180
agccugcuga gugaacugaa caagaagcag gagagggacu ggucagcgu ggucaugcag     240 gugauggagc uggagagcaa cagcaagcgc augagucgc ggcucacaga ugcugagagc      300
aaguacuccg agaugaacaa ccaaauugac aucaugcagc ugcaggcagc acagacgguc    360
acucagaccu ccgcagaugc caucuacgac ugcucuuccc ucuaccagaa gaacuaccgc    420
aucucuggag uguauaagcu uccuccugau gacuuccugg gcagcccuga acuggaggug    480
aucugugaca uggagacuuc aggcggaggc uggaccauca uccagagacg aaaaagugc     540 cuugucuccu ucuaccggga cuggaagcag uacaagcagg gcuuuggcag cauccgugggg    600 gacuucuggc uggggaacga acacauccac cggcucucca gacagccaac ccggcugcgu    660
guagagaugg aggacuggga gggcaaccug cgcuacgcug aguauagcca cuuuguuuug    720
ggcaaugaac ucaacagcua ucgccucuuc cuggggaacu acacuggcaa uguggggaac    780
gacgcccucc aguaucauaa caacacagcc uucagcacca aggacaagga caaugacaac    840
ugcuuggaca agugugcaca gccucgcaaa ggugcucuacu ggacaacug cugcacagac    900 uccaaccuca auggagugua cuaccgccug ggugagcaca auaagcaccu ggauggcauc    960
```

| | |
|---|---|
| accugguaug gcuggcaugg aucuaccuac ucccucaaac ggguggagau gaaaauccgc | 1020 |
| ccagaagacu ucaagccuua a | 1041 |

<210> SEQ ID NO 136
<211> LENGTH: 1041
<212> TYPE: DNA
<213> ORGANISM: homo sapien

<400> SEQUENCE: 136

| | |
|---|---|
| augcugaaaa agccucucuc agcugugacc uggcucugca uuucaucgu ggccuuuguc | 60 |
| agccacccag cguggcugca gaagcucucu aagcacaaga caccagcaca gccacagcuc | 120 |
| aaagcggcca acugcuguga ggaggugaag gagcucaagg cccaaguugc caaccuuagc | 180 |
| agccugcuga gugaacugaa caagaagcag gagagggacu gggucagcgu ggucaugcag | 240 |
| gugauggagc uggagagcaa cagcaagcgc auggagucgc ggcucacaga ugcugagagc | 300 |
| aaguacuccg agaugaacaa ccaaauugac aucaugcagc ugcaggcagc acagacgguc | 360 |
| acucagaccu ccgcagaugc caucuacgac ugcucuuccc ucuaccagaa gaacuaccgc | 420 |
| aucucuggag uguauaagcu uccuccugau gacuuccugg gcagcccuga acuggaggug | 480 |
| uucgugaca uggagacuuc aggcggaggc uggaccauca uccagagacg aaaaagugc | 540 |
| cuugucuccu ucuaccggga cuagaagcag uacaagcagg gcuuuggcag cauccguggg | 600 |
| gacuucuggc ugggaacga acacauccac cggcucucca dacagccaac ccggcugcgu | 660 |
| guagagaugg aggacuggga gggcaaccug cgcuacgcug aguauagcca cuuuguuug | 720 |
| ggcaaugaac ucaacagcua ucgccucuuc cuggggaacu acacuggcaa uguggggaac | 780 |
| gacgcccucc aguaucauaa caacacagcc uucagcacca aggacaagga caaugacaac | 840 |
| ugcuuggaca agugugaca gcuccgcaaa gguggcuacu gguacaacug cugcacagac | 900 |
| uccaaccuca auggagugua cuaccgccug ggugagcaca auaagcaccu ggauggcauc | 960 |
| accugguaug gcuggcaugg aucuaccuac ucccucaaac ggguggagau gaaaauccgc | 1020 |
| ccagaagacu ucaagccuua a | 1041 |

<210> SEQ ID NO 137
<211> LENGTH: 1041
<212> TYPE: DNA
<213> ORGANISM: homo sapien

<400> SEQUENCE: 137

| | |
|---|---|
| augcugaaaa agccucucuc agcugugacc uggcucugca uuucaucgu ggccuuuguc | 60 |
| agccacccag cguggcugca gaagcucucu aagcacaaga caccagcaca gccacagcuc | 120 |
| aaagcggcca acugcuguga ggaggugaag gagcucaagg cccaaguugc caaccuuagc | 180 |
| agccugcuga gugaacugaa caagaagcag gagagggacu gggucagcgu ggucaugcag | 240 |
| gugauggagc uggagagcaa cagcaagcgc auggagucgc ggcucacaga ugcugagagc | 300 |
| aaguacuccg agaugaacaa ccaaauugac aucaugcagc ugcaggcagc acagacgguc | 360 |
| acucagaccu ccgcagaugc caucuacgac ugcucuuccc ucuaccagaa gaacuaccgc | 420 |
| aucucuggag uguauaagcu uccuccugau gacuuccugg gcagcccuga acuggaggug | 480 |
| uucgugaca uggagacuuc aggcggaggc uggaccauca uccagagacg aaaaagugc | 540 |
| cuugucuccu ucuaccggga cuggaagcag uaccagcagg gcuuuggcag cauccguggg | 600 |
| gacuucuggc ugggaacga acacauccac cggcucucca dacagccaac ccggcugcgu | 660 |
| guagagaugg aggacuggga gggcaaccug cgcuacgcug aguauagcca cuuuguuug | 720 |

```
ggcaaugaac ucaacagcua ucgccucuuc cugggggaacu acacuggcaa uguggggaac      780
gacgcccucc aguaucauaa caacacagcc uucagcacca aggacaagga caaugacaac      840
ugcuuggaca agugugcaca gcuccgcaaa ggugguacu gguacaacug cugcacagac       900
uccaaccuca auggagugua cuaccgccug ggugagcaca auaagcaccu ggauggcauc      960
accugguaug gcuggcaugg aucuaccuac ucccucaaac ggguggagau gaaaauccgc     1020
ccagaagacu ucaagccuua a                                                1041

<210> SEQ ID NO 138
<211> LENGTH: 1041
<212> TYPE: DNA
<213> ORGANISM: homo sapien

<400> SEQUENCE: 138
atgctgaaaa agcctctctc agctgtgacc tggctctgca ttttcatcgt ggcctttgtc       60
agccacccag cgtggctgca gaagctctct aagcacaaga caccagcaca gccacagctc      120
aaagcggcca actgctgtga ggaggtgaag gagctcaagg cccaagttgc caaccttagc      180
agcctgctga gtgaactgaa caagaagcag gagagggact gggtcagcgt ggtcatgcag      240
gtgatggagc tggagagcaa cagcaagcgc atggagtcgc ggctcacaga tgctgagagc      300
aagtactccg agatgaacaa ccaaattgac atcatgcagc tgcaggcagc acagacggtc      360
actcagacct ccgcagatgc catctacgac tgctcttccc tctaccagaa gaactaccgc      420
atctctggag tgtataagct tcctcctgat gacttcctgg gcagccctga actggaggtg      480
atctgtgaca tggagacttc aggcggaggc tggaccatca tccagagacg aaaaagtggc      540
cttgtctcct tctaccggga ctggaagcag tacaagcagg gctttggcag catccgtggg      600
gacttctggc tggggaacga acacatccac cggctctcca gacagccaac ccggctgcgt      660
gtagagatgg aggactggga gggcaacctg cgctacgctg agtataggcca ctttgttttg      720 ggcaatgaac tcaacagcta tcgcctcttc ctggggaact acactggcaa tgtggggaac      780
gacgccctcc agtatcataa caacacagcc ttcagcacca aggacaagga caatgacaac      840
tgcttggaca agtgtgcaca gctccgcaaa ggtggctact ggtacaactg ctgcacagac      900
tccaacctca atggagtgta ctaccgcctg ggtgagcaca ataagcacct ggatggcatc      960
acctggtatg gctggcatgg atctacctac tccctcaaac gggtggagat gaaaatccgc     1020
ccagaagact tcaagcctta a                                                1041

<210> SEQ ID NO 139
<211> LENGTH: 1041
<212> TYPE: DNA
<213> ORGANISM: homo sapien

<400> SEQUENCE: 139
atgctgaaaa agcctctctc agctgtgacc tggctctgca ttttcatcgt ggcctttgtc       60
agccacccag cgtggctgca gaagctctct aagcacaaga caccagcaca gccacagctc      120
aaagcggcca actgctgtga ggaggtgaag gagctcaagg cccaagttgc caaccttagc      180
agcctgctga gtgaactgaa caagaagcag gagagggact gggtcagcgt ggtcatgcag      240
gtgatggagc tggagagcaa cagcaagcgc atggagtcgc ggctcacaga tgctgagagc      300
aagtactccg agatgaacaa ccaaattgac atcatgcagc tgcaggcagc acagacggtc      360
actcagacct ccgcagatgc catctacgac tgctcttccc tctaccagaa gaactaccgc      420
```

```
atctctggag tgtataagct tcctcctgat gacttcctgg gcagccctga actggaggtg      480
ttctgtgaca tggagacttc aggcggaggc tggaccatca tccagagacg aaaaagtggc      540
cttgtctcct tctaccggga ctagaagcag tacaagcagg gctttggcag catccgtggg      600
gacttctggc tggggaacga acacatccac cggctctcca gacagccaac ccggctgcgt      660
gtagagatgg aggactggga gggcaacctg cgctacgctg agtatagcca ctttgttttg      720
ggcaatgaac tcaacagcta tcgcctcttc ctggggaact acactggcaa tgtggggaac      780
gacgccctcc agtatcataa caacacagcc ttcagcacca aggacaagga caatgacaac      840
tgcttggaca gtgtgcaca gctccgcaaa ggtggctact ggtacaactg ctgcacagac      900
tccaacctca atggagtgta ctaccgcctg ggtgagcaca ataagcacct ggatggcatc      960
acctggtatg gctggcatgg atctacctac tccctcaaac gggtggagat gaaaatccgc     1020
ccagaagact tcaagcctta a                                               1041

<210> SEQ ID NO 140
<211> LENGTH: 1041
<212> TYPE: DNA
<213> ORGANISM: homo sapien

<400> SEQUENCE: 140
atgctgaaaa agcctctctc agctgtgacc tggctctgca ttttcatcgt ggcctttgtc       60
agccacccag cgtggctgca gaagctctct aagcacaaga caccagcaca gccacagctc      120
aaagcggcca actgctgtga ggaggtgaag gagctcaagg cccaagttgc caaccttagc      180
agcctgctga gtgaactgaa caagaagcag gagagggact gggtcagcgt ggtcatgcag      240
gtgatggagc tggagagcaa cagcaagcgc atggagtcgc ggctcacaga tgctgagagc      300
aagtactccg agatgaacaa ccaaattgac atcatgcagc tgcaggcagc acagacggtc      360
actcagacct ccgcagatgc catctacgac tgctcttccc tctaccagaa gaactaccgc      420
atctctggag tgtataagct tcctcctgat gacttcctgg gcagccctga actggaggtg      480
ttctgtgaca tggagacttc aggcggaggc tggaccatca tccagagacg aaaaagtggc      540
cttgtctcct tctaccggga ctggaagcag taccagcagg gctttggcag catccgtggg      600
gacttctggc tggggaacga acacatccac cggctctcca gacagccaac ccggctgcgt      660
gtagagatgg aggactggga gggcaacctg cgctacgctg agtatagcca ctttgttttg      720
ggcaatgaac tcaacagcta tcgcctcttc ctggggaact acactggcaa tgtggggaac      780
gacgccctcc agtatcataa caacacagcc ttcagcacca aggacaagga caatgacaac      840
tgcttggaca gtgtgcaca gctccgcaaa ggtggctact ggtacaactg ctgcacagac      900
tccaacctca atggagtgta ctaccgcctg ggtgagcaca ataagcacct ggatggcatc      960
acctggtatg gctggcatgg atctacctac tccctcaaac gggtggagat gaaaatccgc     1020
ccagaagact tcaagcctta a                                               1041

<210> SEQ ID NO 141
<211> LENGTH: 346
<212> TYPE: PRT
<213> ORGANISM: homo sapien

<400> SEQUENCE: 141

Met Leu Lys Lys Pro Leu Ser Ala Val Thr Trp Leu Cys Ile Phe Ile
1               5                   10                  15

Val Ala Phe Val Ser His Pro Ala Trp Leu Gln Lys Leu Ser Lys His
            20                  25                  30
```

-continued

```
Lys Thr Pro Ala Gln Pro Gln Leu Lys Ala Ala Asn Cys Cys Glu Glu
            35                  40                  45

Val Lys Glu Leu Lys Ala Gln Val Ala Asn Leu Ser Ser Leu Leu Ser
 50                  55                  60

Glu Leu Asn Lys Lys Gln Glu Arg Asp Trp Val Ser Val Val Met Gln
 65                  70                  75                  80

Val Met Glu Leu Glu Ser Asn Ser Lys Arg Met Glu Ser Arg Leu Thr
                85                  90                  95

Asp Ala Glu Ser Lys Tyr Ser Glu Met Asn Asn Gln Ile Asp Ile Met
                100                 105                 110

Gln Leu Gln Ala Ala Gln Thr Val Thr Gln Thr Ser Ala Asp Ala Ile
            115                 120                 125

Tyr Asp Cys Ser Ser Leu Tyr Gln Lys Asn Tyr Arg Ile Ser Gly Val
130                 135                 140

Tyr Lys Leu Pro Pro Asp Asp Phe Leu Gly Ser Pro Glu Leu Glu Val
145                 150                 155                 160

Ile Cys Asp Met Glu Thr Ser Gly Gly Gly Trp Thr Ile Ile Gln Arg
                165                 170                 175

Arg Lys Ser Gly Leu Val Ser Phe Tyr Arg Asp Trp Lys Gln Tyr Lys
            180                 185                 190

Gln Gly Phe Gly Ser Ile Arg Gly Asp Phe Trp Leu Gly Asn Glu His
            195                 200                 205

Ile His Arg Leu Ser Arg Gln Pro Thr Arg Leu Arg Val Glu Met Glu
        210                 215                 220

Asp Trp Glu Gly Asn Leu Arg Tyr Ala Glu Tyr Ser His Phe Val Leu
225                 230                 235                 240

Gly Asn Glu Leu Asn Ser Tyr Arg Leu Phe Leu Gly Asn Tyr Thr Gly
                245                 250                 255

Asn Val Gly Asn Asp Ala Leu Gln Tyr His Asn Asn Thr Ala Phe Ser
            260                 265                 270

Thr Lys Asp Lys Asp Asn Asp Asn Cys Leu Asp Lys Cys Ala Gln Leu
        275                 280                 285

Arg Lys Gly Gly Tyr Trp Tyr Asn Cys Cys Thr Asp Ser Asn Leu Asn
    290                 295                 300

Gly Val Tyr Tyr Arg Leu Gly Glu His Asn Lys His Leu Asp Gly Ile
305                 310                 315                 320

Thr Trp Tyr Gly Trp His Gly Ser Thr Tyr Ser Leu Lys Arg Val Glu
                325                 330                 335

Met Lys Ile Arg Pro Glu Asp Phe Lys Pro
            340                 345

<210> SEQ ID NO 142
<211> LENGTH: 187
<212> TYPE: PRT
<213> ORGANISM: homo sapien

<400> SEQUENCE: 142

Met Leu Lys Lys Pro Leu Ser Ala Val Thr Trp Leu Cys Ile Phe Ile
1               5                   10                  15

Val Ala Phe Val Ser His Pro Ala Trp Leu Gln Lys Leu Ser Lys His
                20                  25                  30

Lys Thr Pro Ala Gln Pro Gln Leu Lys Ala Ala Asn Cys Cys Glu Glu
            35                  40                  45

Val Lys Glu Leu Lys Ala Gln Val Ala Asn Leu Ser Ser Leu Leu Ser
 50                  55                  60
```

```
            50                  55                  60
Glu Leu Asn Lys Lys Gln Glu Arg Asp Trp Val Ser Val Val Met Gln
 65                  70                  75                  80

Val Met Glu Leu Glu Ser Asn Ser Lys Arg Met Glu Ser Arg Leu Thr
                 85                  90                  95

Asp Ala Glu Ser Lys Tyr Ser Glu Met Asn Asn Gln Ile Asp Ile Met
                100                 105                 110

Gln Leu Gln Ala Ala Gln Thr Val Thr Gln Thr Ser Ala Asp Ala Ile
                115                 120                 125

Tyr Asp Cys Ser Ser Leu Tyr Gln Lys Asn Tyr Arg Ile Ser Gly Val
                130                 135                 140

Tyr Lys Leu Pro Pro Asp Asp Phe Leu Gly Ser Pro Glu Leu Glu Val
145                 150                 155                 160

Phe Cys Asp Met Glu Thr Ser Gly Gly Gly Trp Thr Ile Ile Gln Arg
                165                 170                 175

Arg Lys Ser Gly Leu Val Ser Phe Tyr Arg Asp
                180                 185

<210> SEQ ID NO 143
<211> LENGTH: 346
<212> TYPE: PRT
<213> ORGANISM: homo sapien

<400> SEQUENCE: 143

Met Leu Lys Lys Pro Leu Ser Ala Val Thr Trp Leu Cys Ile Phe Ile
 1               5                  10                  15

Val Ala Phe Val Ser His Pro Ala Trp Leu Gln Lys Leu Ser Lys His
                 20                  25                  30

Lys Thr Pro Ala Gln Pro Gln Leu Lys Ala Ala Asn Cys Cys Glu Glu
                 35                  40                  45

Val Lys Glu Leu Lys Ala Gln Val Ala Asn Leu Ser Ser Leu Leu Ser
                 50                  55                  60

Glu Leu Asn Lys Lys Gln Glu Arg Asp Trp Val Ser Val Val Met Gln
 65                  70                  75                  80

Val Met Glu Leu Glu Ser Asn Ser Lys Arg Met Glu Ser Arg Leu Thr
                 85                  90                  95

Asp Ala Glu Ser Lys Tyr Ser Glu Met Asn Asn Gln Ile Asp Ile Met
                100                 105                 110

Gln Leu Gln Ala Ala Gln Thr Val Thr Gln Thr Ser Ala Asp Ala Ile
                115                 120                 125

Tyr Asp Cys Ser Ser Leu Tyr Gln Lys Asn Tyr Arg Ile Ser Gly Val
                130                 135                 140

Tyr Lys Leu Pro Pro Asp Asp Phe Leu Gly Ser Pro Glu Leu Glu Val
145                 150                 155                 160

Phe Cys Asp Met Glu Thr Ser Gly Gly Gly Trp Thr Ile Ile Gln Arg
                165                 170                 175

Arg Lys Ser Gly Leu Val Ser Phe Tyr Arg Asp Trp Lys Gln Tyr Gln
                180                 185                 190

Gln Gly Phe Gly Ser Ile Arg Gly Asp Phe Trp Leu Gly Asn Glu His
                195                 200                 205

Ile His Arg Leu Ser Arg Gln Pro Thr Arg Leu Arg Val Glu Met Glu
                210                 215                 220

Asp Trp Glu Gly Asn Leu Arg Tyr Ala Glu Tyr Ser His Phe Val Leu
225                 230                 235                 240
```

-continued

```
Gly Asn Glu Leu Asn Ser Tyr Arg Leu Phe Leu Gly Asn Tyr Thr Gly
                245                 250                 255

Asn Val Gly Asn Asp Ala Leu Gln Tyr His Asn Asn Thr Ala Phe Ser
            260                 265                 270

Thr Lys Asp Lys Asp Asn Asp Asn Cys Leu Asp Lys Cys Ala Gln Leu
        275                 280                 285

Arg Lys Gly Gly Tyr Trp Tyr Asn Cys Cys Thr Asp Ser Asn Leu Asn
    290                 295                 300

Gly Val Tyr Tyr Arg Leu Gly Glu His Asn Lys His Leu Asp Gly Ile
305                 310                 315                 320

Thr Trp Tyr Gly Trp His Gly Ser Thr Tyr Ser Leu Lys Arg Val Glu
                325                 330                 335

Met Lys Ile Arg Pro Glu Asp Phe Lys Pro
                340                 345
```

<210> SEQ ID NO 144
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 144
acagaacacc tgaagcagag ggg                                        23

<210> SEQ ID NO 145
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 145
acagaacacc tgaagcagag ggg                                        23

<210> SEQ ID NO 146
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 146
cacagaacac ctgaagcaga ggg                                        23

<210> SEQ ID NO 147
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 147
cagagtatcc cctctgcttc agg                                        23

<210> SEQ ID NO 148
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 148
actctggtga gggacttgca ggg                                          23

<210> SEQ ID NO 149
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 149
tactctggtg agggacttgc agg                                          23

<210> SEQ ID NO 150
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 150
gcagagggga tactctggtg agg                                          23

<210> SEQ ID NO 151
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 151
gcttcaggtg ttctgtgaca tgg                                          23

<210> SEQ ID NO 152
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 152
cagaggggat actctggtga ggg                                          23

<210> SEQ ID NO 153
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 153
ttgtctcctt ctaccgggac tgg                                          23

<210> SEQ ID NO 154
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 154
gtggccttgt ctccttctac cgg                                          23

<210> SEQ ID NO 155
<211> LENGTH: 23
<212> TYPE: DNA
<213> ORGANISM: artificial sequence

```
<220> FEATURE:
<223> OTHER INFORMATION: Guide RNA Recognition Sequence

<400> SEQUENCE: 155
tggccttgtc tccttctacc ggg                                              23

<210> SEQ ID NO 156
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 156
gactggaagc agtacaagca ggg                                              23

<210> SEQ ID NO 157
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 157
ggactggaag cagtacaagc agg                                              23

<210> SEQ ID NO 158
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 158
ctgcttccag tcccggtaga agg                                              23

<210> SEQ ID NO 159
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 159
gcttgtactg cttccagtcc cgg                                              23

<210> SEQ ID NO 160
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 160
agtcccggta gaaggagaca agg                                              23

<210> SEQ ID NO 161
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 161
aagcagtaca agcagggctt tgg                                              23
```

```
<210> SEQ ID NO 162
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 162
cagggctttg gcagcatccg tgg                                          23

<210> SEQ ID NO 163
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 163
agggctttgg cagcatccgt ggg                                          23

<210> SEQ ID NO 164
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 164
gggctttggc agcatccgtg ggg                                          23

<210> SEQ ID NO 165
<211> LENGTH: 23
<212> TYPE: DNA
<213> ORGANISM: artificial sequence
<220> FEATURE:
<223> OTHER INFORMATION: Guide RNA Recognition Sequence

<400> SEQUENCE: 165
tccccagcca gaagtcccca cgg                                          23
```